(12) United States Patent
Johnson

(10) Patent No.: US 6,333,170 B1
(45) Date of Patent: Dec. 25, 2001

(54) METHOD AND PRODUCT FOR REGULATING CELL RESPONSIVENESS TO EXTERNAL SIGNALS

(75) Inventor: Gary L. Johnson, Boulder, CO (US)

(73) Assignee: National Jewish Center for Immunology and Respiratory Medicine, Denver, CO (US)

( * ) Notice: Subject to any disclaimer, the term of this patent is extended or adjusted under 35 U.S.C. 154(b) by 0 days.

(21) Appl. No.: 08/628,829

(22) Filed: Apr. 5, 1996

Related U.S. Application Data

(63) Continuation-in-part of application No. 08/440,421, filed on May 12, 1995, now abandoned, which is a continuation-in-part of application No. 08/323,460, filed on Oct. 14, 1994, now Pat. No. 5,854,043, which is a continuation-in-part of application No. 08/049,254, filed on Apr. 15, 1993, now Pat. No. 5,405,941, said application No. 08/440,421, is a continuation-in-part of application No.08/049,254, filed on Apr. 15, 1993, now Pat. No. 5,405,941, said application No. 08/628,829, is a continuation-in-part of application No.08/410,602, filed on Mar. 24, 1995, now abandoned, and a continuation-in-part of application No. 08/472,934, filed on Jun. 6, 1995, now Pat. No. 5,753,446.

(51) Int. Cl.[7] .......................... C07H 21/04; C12N 15/12; C12N 16/63

(52) U.S. Cl. ................. 435/69.1; 435/252.3; 435/320.1; 536/23.1; 536/24.31

(58) Field of Search ................................. 435/69.1, 252.3, 435/320.1, 194; 530/300, 350; 536/23.1, 23.5

(56) References Cited

U.S. PATENT DOCUMENTS 5,405,941 * 4/1995 Johnson .............................. 530/350

FOREIGN PATENT DOCUMENTS

| WO 94/24159 | 10/1994 | (WO) . |
| WO 95/28421 | 10/1995 | (WO) . |

* cited by examiner

*Primary Examiner*—Elizabeth Kemmerer
*Assistant Examiner*—Nirmal S. Basi
(74) *Attorney, Agent, or Firm*—Lahive & Cockfield, LLP; Guilio A. DeConti, Jr., Esq.; Peter C. Lauro, Esq.

(57) ABSTRACT

The present invention relates to isolated MEKK proteins, nucleic acid molecules having sequences that encode such proteins, and antibodies raised against such proteins. The present invention also includes methods to use such proteins to regulate signal transduction in a cell. The present invention also includes therapeutic compositions comprising such proteins or nucleic acid molecules that encode such proteins and their use to treat animals having medical disorders including cancer, inflammation, neurological disorders, autoimmune diseases, allergic reactions, and hormone-related diseases. When MEKK is expressed, it phosphorylates and activates MKKs 1–4 (also referred to as MEK-1, MEK-2 and JNKK1 and JNKK2).

16 Claims, 30 Drawing Sheets

Inhibitory N17Ras expression inhibits growth factor activation of MEKK

Myc-Gal 4 fusion protein:

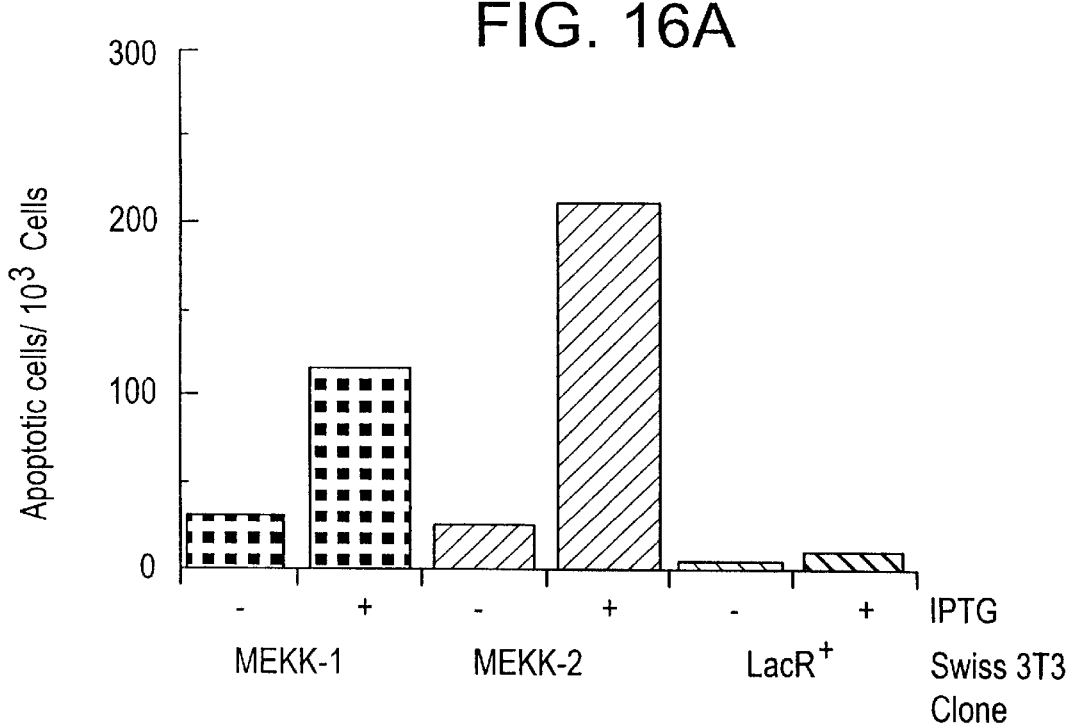
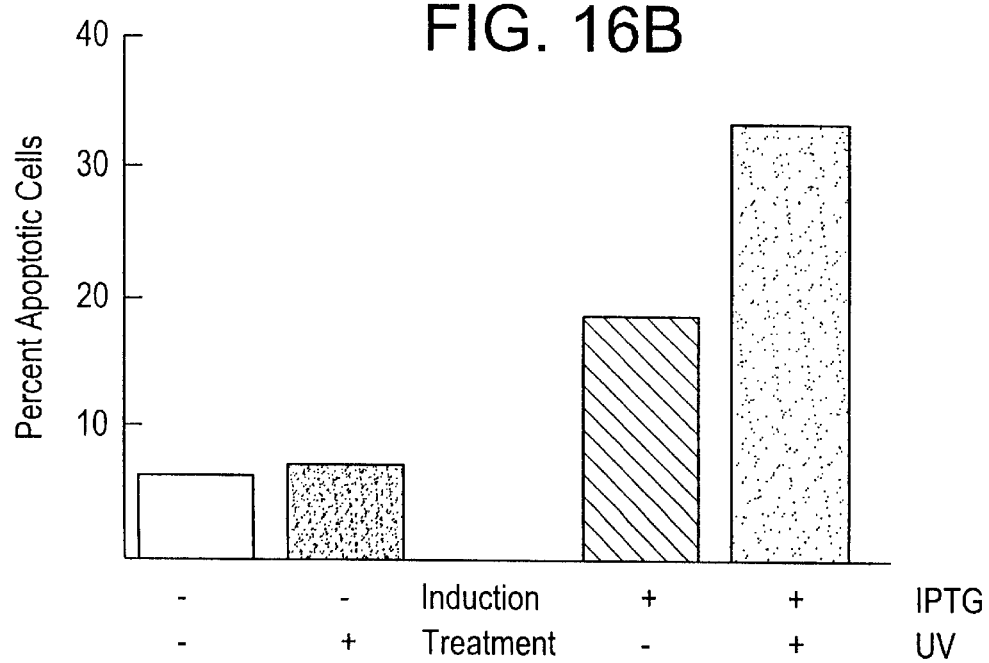

METHOD AND PRODUCT FOR REGULATING CELL RESPONSIVENESS TO EXTERNAL SIGNALS

CROSS-REFERENCE TO RELATED APPLICATIONS

The present application is a continuation-in-part of U.S. patent application Ser. No. 08/440,421 filed May 12, 1995, and now abandoned, which is a CIP of U.S. patent application Ser. No. 08/323,460 filed Oct. 14, 1994, and now U.S. Pat. No. 5,854,043 both of which applications are continuations in part of U.S. Ser. No. 08/049,254, filed Apr. 15, 1993, and now U.S. Pat. No. 5,405,941. The present application is also a continuation-in-part of U.S. Ser. No. 08/410, 602, filed Mar. 24, 1995, now abandoned, and of U.S. Ser. No. 08/472,934, filed Jun. 6, 1995, now U.S. Pat. No. 5,753,446. The above-referenced patents and patent applications are incorporated herein by this reference in their entirety.

GOVERNMENT FUNDING

This invention was made in part with government support under USPHS Grant DK37871 and USPHS Grant GM30324, both awarded by the National Institutes of Health. The government has certain rights to this invention.

FIELD OF THE INVENTION

This invention relates to isolated nucleic acid molecules encoding MEKK proteins, substantially pure MEKK proteins, and products and methods for regulating signal transduction in a cell.

BACKGROUND OF THE INVENTION

Mitogen-activated protein kinase (MAPKs) (also called extracellular signal-regulated kinases or ERKs) are rapidly activated in response to ligand binding by both growth factor receptors that are tyrosine kinases (such as the epidermal growth factor (EGF) receptor) and receptors that are coupled to heterotrimeric guanine nucleotide binding proteins (G proteins) such as the thrombin receptor. In addition, receptors like the T cell (TCR) and B cell (BCR) receptors are non-covalently associated with src family tyrosine kinases which activate MAPK pathways. Specific cytokines like tumor necrosis factor (TNFα) can also regulate MAPK pathways. The MAPKs appear to integrate multiple intracellular signals transmitted by various second messengers. MAPKs phosphorylate and regulate the activity of enzymes and transcription factors including the EGF receptor, Rsk 90, phospholipase $A_2$, c-Myc, c-Jun and Elk-1/TCF. Although the rapid activation of MAPKs by receptors that are tyrosine kinases is dependent on Ras, G protein-mediated activation of MAPK appears to occur through pathways dependent and independent of Ras.

Complementation analysis of the pheromone-induced signaling pathway in yeast has defined a protein kinase system that controls the activity of Spk1 and Fus3-Kss1, the *Schizosaccharomyces pombe* and *Saccharomyces cerevisiae* homologs of MAPK (see for example, B. R. Cairns et al., *Genes and Dev.* 6, 1305 (1992); B. J. Stevenson et al., *Genes and Dev.* 6, 1293 (1992); S. A. Nadin-Davis et al., *EMBO J* 7, 985 (1988); Y. Wang et al., *Mol. Cell. Biol.* 11, 3554 (1991). In *S. cerevisiae*, the protein kinase Ste7 is the upstream regulator of Fus3-Kss1 activity; the protein kinase Ste11 regulates Ste7. The *S. pombe* gene products Byr1 and Byr2 are homologous to Ste7 and Ste11, respectively. The MEK (MAPK Kinase or ERK Kinase) or MKK (MAP Kinase kinase) enzymes are similar in sequence to Ste7 and Byr1. The MEKs phosphorylate MAPKs on both tyrosine and threonine residues which results in activation of MAPK. The mammalian serine-threonine protein kinase Raf phosphorylates and activates MEK, which leads to activation of MAPK. Raf is activated in response to growth factor receptor tyrosine kinase activity and therefore Raf may activate MAPK in response to stimulation of membrane-associated tyrosine kinases. Raf is unrelated in sequence to Ste11 and Byr2. Thus, Raf may represent a divergence in mammalian cells from the pheromone-responsive protein kinase system defined in yeast. Cell and receptor specific differences in the regulation of MAPKs suggest that other Raf independent regulators of mammalian MEKs exist.

Certain biological functions, such as growth and differentiation, are tightly regulated by signal transduction pathways within cells. Signal transduction pathways maintain the balanced steady state functioning of a cell. Disease states can arise when signal transduction in a cell breaks down, thereby removing the tight control that typically exists over cellular functions. For example, tumors develop when regulation of cell growth is disrupted enabling a clone of cells to expand indefinitely. Because signal transduction networks regulate a multitude of cellular functions depending upon the cell type, a wide variety of diseases can result from abnormalities in such networks. Devastating diseases such as cancer, autoimmune diseases, allergic reactions, inflammation, neurological disorders and hormone-related diseases can result from abnormal signal transduction.

SUMMARY OF THE INVENTION

The present invention relates to a substantially pure MEKK protein capable of regulating a MEK kinase dependent pathway. In certain embodiments a MEK kinase comprises a catalytic domain and is capable of phosphorylating MKK proteins. In preferred embidiments the MEKK substrate is seleted from the group of MAP kinase kinases consisting of MEKK1, MKK2, (also called MEK1 and MEK2 respectively) MKK3, or MKK4 (also called JNKK1 and JNKK2 or SEK respectively). The present invention includes a substantially pure MEKK protein capable of regulating signals initiated from a growth factor receptor on the surface of a cell by regulating the activity of MAPK protein. Exemplary MAP kinases include p42, p44, ERK1, ERK2, JNK1, JNK2, or p38 SAPK. In preferred embodiments a MEK kinase can activate at least one of the group c myc, cJun, cPLA2, Rsk 90, TCF, Elk-1, or ATF-2.

In certain embodiments the MEKK protein of the present invention is regulates the activity of a MAPK protein independently of Raf. In preferred embodiments the MEKK proteins described herein are capable of binding members of the Ras superfamily. Exemplary polypeptides which bind to MEKK proteins include Ras, Rac/Cdc42, or Rho.

In particular, the substantially pure MEKK proteins of the present invention comprise at least a portion of an amino acid sequence shown in one of SEQ ID NOS:2, 4, 6, 8, 10, 12, or 14. In other embodiments, proteins at least 50% homologous, at least 75% homologous, preferably at least 85% homologous, or more preferably 95% homologous to one of SEQ ID NOS: 2, 4, 6, 8, 10, 12, or 14 are also contemplated.

In certain embodiments MEKK proteins have homology to the kinase catalytic domain of one of SEQ ID NOS: 2, 4, 6, 8, 10, 12, or 14. In other embodiments proteins having at least 50% homology, at least 75% homology, preferably at least 85% homology, or more preferably at least 95% homology to the kinase catalytic domain of one of SEQ ID NOS: 2, 4, 6, 8, 10, 12, or 14 are contemplated. In more preferred embodiements the kinase domain of a MEKK protein is capable of phosphorylating a MAP kinase kinase protein and binding to a member of the ras superfamily, such as ras or rac or cdc42 protein.

In another embodiment the MEKK protein of the present invention comprises a NH2 regulatory domain represented in one of SEQ ID NOS: 2, 4, 6, 8, 10, 12, or 14. In other embodiments MEKK proteins which comprise regions of at least 50% homology, at least 75% homology, preferrably 85% homology, or more preferably at least 95% homology to the NH2 regulatory domain of one of SEQ ID NOS: 2, 4, 6, 8, 10, 12, or 14 are contemplated.

In a further embodiment MEKK proteins which have molecular weights ranging from 60 to 190 are contemplated. Preferred molecular weights are 98 kD for MEKK1, 69.5 kD for MEKK2, 71 kD for MEKK3, and 95–98 kD for MEKK 4. In other embodiments MEKK 4 migrates with an apparent molecular weight of 185 kD.

MEKK proteins of the present invention lack an SH2 or SH3 domain. In preferred embodiments exemplary MEKK proteins comprise a proline rich SH3 binding motif. In certain embodiments, MEKK proteins of the instant invention comprise a Pleckstrin homology domain.

In a particularly preferred embodiment, exemplary MEKK proteins can competitively inhibit the activity of a MEKK designated in one or more of SEQ ID NOS: 2, 4, 6, 8, 10, or 12, or 14.

Fragments of MEKK proteins are also contemplated by the present invention. In preferred embodiments exemplary MEKK proteins lack a MEKK regulatory domain. In particularly preferred embodiments MEKK protein fragments lack the scrine/threonine rich regulatory domain shown in one of SEQ ID NOS: 2, 4, 6, 8, 10, 12, or 14. In another embodiment the fragement of a MEKK protein lacks the serine/threonine kinase domain of a MEKK protein. In preferred embodiments MEKK protein fragments lack the serine/threonine kinase domain shown in one of SEQ ID NOS: 2, 4, 6, 8, 10, 12, or 14.

In another embodiment the MEKK protein of the present invention is a fusion protein further comprising, in addition to the MEKK polypeptide, a second polypeptide sequence having an amino acid sequence unrelated to MEKK polypeptide sequence. In a preferred embodiment the fusion protein includes as a second polypeptide sequence, a polypeptide which functions as a detectable label for detecting the presence of said fusion protein or as a matrix-binding domain for immobilizing said fusion protein.

In another embodiment a MEKK protein or a portion of a MEKK protein which is encoded by a nucleic acid sequence that is capable of hybridizing under stringent conditions with a nucleic acid molecule encoding an amino acid sequence including SEQ ID NOS: 2, 4, 6, 8, 10, 12, or 14. The substantially pure MEKK protein capable of regulating the activity of a MEKK dependent pathway, said protein having an amino acid sequence distinct from Raf protein.

In a particularly preferred embodiment the MEKK protein of the present invention is capable of regulating apoptosis in a cell.

One aspect of the present invention includes an isolated nucleic acid molecule having a sequence encoding a protein capable of regulating a MEKK dependent pathway. In preferred embodiements the nucleic acid of the present invention encodes a protein which phosphorylates a MAP kinase kinase independently of Raf protein and is capable of regulating the activity of MAPK protein. In particular, the present invention includes an isolated nucleic acid molecule shown in one of SEQ ID NOS: 1, 3, 5, 7, 9, 11, or 13. In another embodiment nucleic acids capable of hybridizing under stringent conditions with a nucleic acid sequence selected from the group consisting of SEQ ID NOS: 1, 3, 5, 7, 9, 11, or 13 are also contemplated.

In certain embodiments the nucleic acid of the present invention encodes a protein which regulates a MAP kinase kinase selected from the group consisting of p42, p44, ERK1, ERK2, JNK1, JNK2, or p38 SAPK.

In another embodiment nucleic acids at least 50%, at least 75%, more preferably at least 85%, or most preferably 95% homologous to one of SEQ ID NOS: 1, 3, 5, 7, 9, 11, or 13 are also contemplated.

In another embodiment the nucleic acid of the present invention encodes a polypeptide, wherein said polypeptide i)phosphorylates a MAP kinase kinase protein and ii) binds to a ras superfamily protein. In certain embodiments the ras superfamily member is ras and said binding is mediated by the carboxy terminus of said polypeptide. In another embodiment the nucleic acid encodes a protein with a cdc42/rac binding site.

In another embodiment the nucleic acid of the present invention encodes a polypeptide which comprises a MKK consensus binding site. In another embodiment the nucleic acid of the present invention encodes a polypeptide which comprises a proline rich SH3 binding motif.

In another embodiment the nucleic acid of the present invention is capable of hybridizing under stringent conditions to a nucleic acid probe having a sequence represented by at least 60 consecutive nucleotides of sense of antisense of one or more of SEQ ID NOS: 1, 3, 5, 7, 9, 1 1, or 13. Oligonucleotide probes which hybridize to one of SEQ ID NOS: 1, 3, 5, 7, 9, 11, or 13 are also contemplated.

Another aspect of the present invention includes a recombinant molecule, comprising a nucleic acid molecule capable of hybridizing under stringent conditions with a nucleic acid sequence including SEQ ID NOS: 1, 3, 5, 7, 9, 11, or 13 in which the nucleic acid molecule is operatively linked to an expression vector.

In another embodiment a nucleic acid of the present invention is poerably linked to a transcriptional regulatory sequence and said gene construct is delivedable to a cell and causes the cell to be transfected with said gene construct.

Yet another aspect of the present invention is a recombinant cell transformed with a recombinant molecule, comprising a nucleic acid molecule operatively linked to an expression vector, the nucleic acid molecule comprising a nucleic acid sequence capable of hybridizing under stringent conditions with a nucleic acid sequence selected from the group consisting of SEQ ID NOS: 1, 3, 5, 7, 9, 1 1, or 13.

In another embodiment the present invention comprises a host cell transfected with the expression vector comprising one of SEQ ID NOS: 1, 3, 5, 7, 9, 11, or 13. Another embodiment of the present invention comprises a method for producing recombinant MEKK polypeptide by culturing a host cell transfected with such an expression vector.

Also contemplated by the present invention are transgenic animals having cells which harbor a transgene encoding a MEKK polypeptide or in which a gene for a MEKK is disrupted.

One embodiment of the invention provides for drug screening assays that can be used to identify compounds which inhibit the interaction of MEKK with a MEKK binding protein, said binding protein including a substrate or upstream activator of MEKK as described herein. The invention further contemplates the development of peptides or mimetics or nucleic acids which can block MEKK activation in a similar manner. In a preferred embodiment a peptide which blocks the interaction of a MEKK protein with Rac or Cdc42 is provided. In a further preferred embodiment a peptide whcih blocks the interaction of a MEKK protein with Ras is also provided.

The present invention also includes a method for regulating the homeostasis of a cell comprising regulating the activity of a MEKK-dependent pathway relative to the activity of a Raf-dependent pathway in the cell. In particular, the method comprises regulating the apoptosis of the cell. Such a method is useful for the treatment of a medical disorder. In particular, the method is useful for inhibiting tumorigenesis and autoimmunity.

According to the present invention, the method for treatment of a disease, comprises administering to a patient an effective amount of a therapeutic compound comprising at least one regulatory molecule including a molecule capable of decreasing the activity of a Raf-dependent pathway, a molecule capable of increasing the activity of a MEKK-dependent pathway, and combinations thereof, in which the effective amount comprises an amount which results in the depletion of harmful cells involved in the disease.

Also included in the present invention is a therapeutic compound capable of regulating the activity of a MEKK-dependent pathway in a cell identified by a process, comprising: (a) contacting a cell with a putative regulatory molecule; and (b)determining the ability of the putative regulatory compound to regulate the activity of a MEKK-dependent pathway in the cell by measuring the activation of at least one member of said MEKK-dependent pathway.

One embodiment of the present invention includes a substantially pure protein, in which the protein is isolated using an antibody capable of selectively binding to a MEKK protein capable of phosphorylating mammalian MKK proteins and capable of regulating the activity of MAPK proteins independent of Raf protein, the antibody capable of being produced by a method comprising: (a) administering to an animal an effective amount of a substantially pure MEKK protein of the present invention; and (b) recovering an antibody capable of selectively binding to the MEKK protein.

Another embodiment of the present invention includes an isolated antibody capable of selectively binding to a MEKK protein, the antibody capable of being produced by a method comprising administering to an animal an effective amount of a substantially pure protein of the present invention, and recovering an antibody capable of selectively binding to the MEKK protein. Also contemplated by the present invention is a MEKK polypeptide bound by an antibody which specifically binds to a MEKK protein shown in one of SEQ ID NOS: 2, 4, 6, 8, 10, or 12.

This invention further relates to biological responses modulated by the MAPK pathway, which is regulated by signaling through interactions of Ras protein and MEK kinase (MEKK) protein. These biological responses include activation of immune responses, especially in B cells and in T cells; other biological responses regulated by the Ras protein; MEK kinase (MEKK) interactions including activation, proliferation and immunoglobulin class switching. Methods herein disclosed may be used to specifically modulate the interaction of Ras protein and MEK kinase (MEKK) protein, or to identify compounds which specifically act to alter the interaction of Ras protein and MEK kinase protein. Alternatively, such biological responses regulated by the interaction of Ras protein and MEK kinase (MEKK) protein may be manipulated to achieve therapeutic results in vivo by methods of the present invention.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I–IV (D. M. Weir and C. C. Blackwell, eds., 1986); *Manipulating the Mouse Embryo,* (Cold Spring Harbor Laboratory Press, Cold Spring Harbor, N.Y., 1986).

BRIEF DESCRIPTION OF THE FIGURES

FIGS. 16A and B Induction of MEKKCOOH expression by IPTG in Swiss 3T3 cells increases the number of condensed cells and stimulates c-Myc transactivation. In panel A, cells were incubated in the presence or absence of 5 mM IPTG for forty eight hours. Cells were stained with acrodine orange and condensed cells quantitated per 1000 cells counted per coverslip. In panel B Swiss 3T3 cells with inducible MEKKCOOH were incubated in the presence or absence of IPTG. The indicated cells were then exposed to UV-C irradiation and then fixed and stained with propidium iodide. The percentage of apoptotic cells was enumerated.

DETAILED DESCRIPTION OF THE INVENTION

Figure 1:
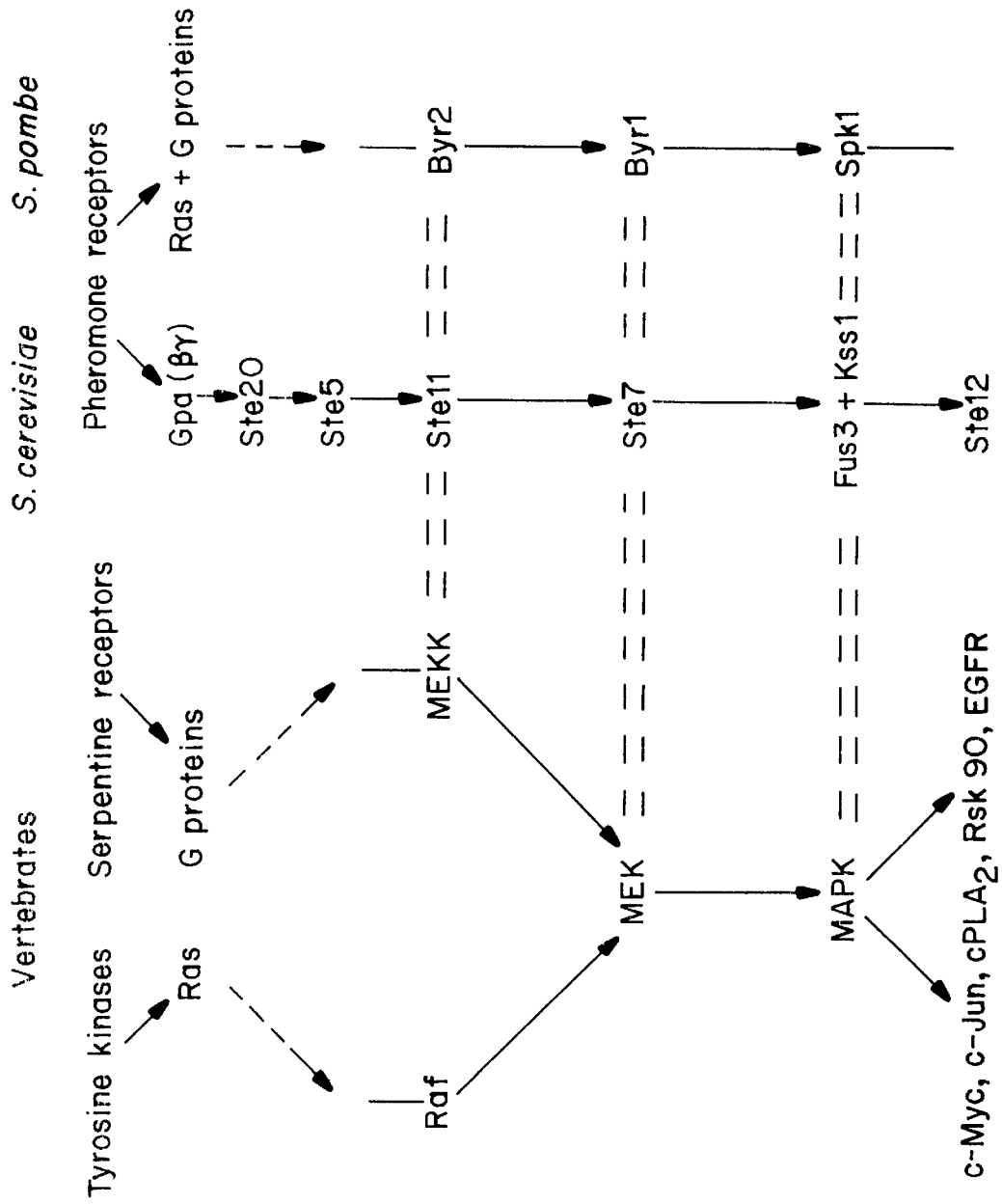
FIG. 1 is a schematic representation of the signal pathways of vertebrates and yeast.

Through a series of inducible and reversible protein-protein interactions and phosphorylation-mediated enzymatic activities, regulatory proteins are recruited to relay signals throughout the cell. Such interactions are involved in all stages of the intracellular signal transduction process—at the plasma membrane, where the signal is initiated; in the cytoplasm, where the signals are disseminated to different cellular locations; and in the nucleus, where other proteins involved in transcriptional control form complexes to regulate transcription of particular genes. The structural nature of protein interactions and control of enzymatic activities in signal transduction is emerging through the identification of the individual proteins that participate in each signal transduction pathway, the elucidation of the temporal order in which these proteins interact, and the definition of the sites of contact between the proteins. The understanding gained in intracellular signaling pathways of cells will be advantageous in developing the next generation of pharmaceuticals. In particular, the pleiotropic richness of intracellular signaling pathways in cells represents a means for developing more selective pharmacological activity in a therapeutic agent than may be possible in the present generation of drugs.

The present invention concerns the discovery of a family of novel mitogen ERK kinase kinase proteins (referred to herein as "MEK kinases", "MEKKs" or "MEKK proteins") which function in intracellular signal transduction pathways in a variety of cells, and accordingly have a role in determining cell/tissue fate and maintenance. The family of MEKK genes or gene products provided by the present invention apparently consists of at least six different members (MEKK 4.2 is a splicing varient of MEKK4.1 and MEKK 2.2 is a sequencing varient of MEKK2) with ample evidence indicating that yet other members of the family exist.

A salient feature of the MEKK gene products deriving from this discovery not only implicates these proteins in intracellular signaling, but also strongly suggests that the diversity of the MEKK family is important to providing a diversity of responses to different environmental cues. That is, the ability of a cell to respond to a particular growth factor, morphogen, or even stress cue, and the type of response the cell undegoes is dependent at least in part upon which MEKK gene products are expressed in the cell and/or engaged by signals propagated upstream of the kinase.

Still another important feature of the present invention is the discovery of the involvment of MEKK proteins in certain apoptotic pathways.

Accordingly, certain aspects of the present invention relate to nucleic acids encoding vertebrate MEKK proteins, the MEKK proteins themselves, antibodies immunoreactive with MEKK proteins, and preparations of such compositions. Moreover, the present invention provides diagnostic and therapeutic assays and reagents for detecting and treating disorders involving, for example, aberrant expression or activaition of the MEKK gene products. In addition, drug discovery assays are provided for identifying agents which can modulate the biological function of MEKK proteins, such as by altering the binding of the protein to either downstream or upstream elements in a signal transduction pathway, or which inhibit the kinase activity of the MEKK protein. Such agents can be useful therapeutically to alter the growth and/or differentiation of a cell. Other aspects of the invention are described below or will be apparent to those skilled in the art in light of the present disclosure.

Intial cloning of a member of the mammalian MEKK family was accomplished using primers based on sequences for the yeast protein kinases Byr2 (from *S pombe*) and Ste11 (from *S. cerevisiae*). Using the sequence obtained for the mammalian MEKK cDNA, other MEKK transcripts have been detected and several subsequently cloned to reveal a family of mammalian MEKK proteins.

TABLE 1

Guide to MEKK sequences in Sequence Listing

|  | Nucleotide | Amino Acid |
|---|---|---|
| MEKK1.1 | SEQ ID NO. 1 | SEQ ID NO. 2 |
| MEKK1.2 | SEQ ID NO. 3 | SEQ ID NO. 4 |
| MEKK2.1 | SEQ ID NO. 5 | SEQ ID NO. 6 |
| MEKK2.2 | SEQ ID NO. 7 | SEQ ID NO. 8 |
| MEKK3 | SEQ ID NO. 9 | SEQ ID NO. 10 |
| MEKK4.1 | SEQ ID NO. 11 | SEQ ID NO. 12 |
| MEKK4.2 | SEQ ID NO. 13 | SEQ ID NO. 14 |

The foregoing SEQ ID NO's represent sequences deduced according to methods disclosed in the Examples. It should be noted that since nucleic acid and amino acid sequencing technology is not entirely error-free, the foregoing SEQ ID NO's, at best, represent apparent nucleic acid and amino acid sequences of MEKK proteins of the present invention. For convenience, we will use the term MEKK1 to refer to both MEKK1.1 and MEKK 1.2, MEKK 2 to refer to both MEKK2.1 and MEKK 2.2, and MEKK4 to refer to both MEKK4.1 and MEKK 4.2 herein.

The primary sequence of the MEKK proteins suggests two functional domains, an amino-terminal moiety rich in serine and threonine that apparently serves a regulatory role, and a carboxy-terminal protein kinase catalytic domain. The catalytic domain of, for example, MEKK1 shows approximately 35 percent identity with the amino acid sequences of the catalytic domains of Byr2 and Ste11. The amino-terminal moieties of each of the mammalian MEKKs show little similarity with Ste11 or Byr2.

Furthermore, the MEKK family is apparently encoded by several genes, at least some of which are able to produce different transcripts by differential splicing. For example, the divergence in sequence amongst the catalytic domains of each of MEKK1 to MEKK4 indicated that seperate genomic genes encode each paralog. However, MEKK2 and MEKK4 genes can give rise to at least two different transcripts, presumably be differential splicing. Expression data suggests that MEKKs 1–4 are ubiquitously expressed.

By use of overexpression and/or constitutively activated MEKKs, a variety of cellular substrates for each MEKK protein have been identified. In general, the proteins of the MAP kinase kinases (MEK) family are each targets for one or more of the MEKKs. Moreover, the data set out below demonstrate that MEKK-dependent signal propagation can result in the phosphorylation/activation of members of the MAP kinase family, such as p42MAPK, p44MAPK, p38MAPK, and the Jun $NH_2$-terminal kinases (JNKs).

Certain of the MEKK proteins have been shown to be activated, e.g., as kinases, in response to growth factors and cytokines (such as TNFα and chemoattractants like FMLP and IL-8) and other environmental cues, including stress, as well as expression of activated Ras or other members of the Ras Superfamily, including Rac and Cdc 42. It is demonstrated below that the kinase domain of at least MEKK1 binds to activated Ras in a GTP-dependent manner, implicating that interaction as a a potential therapeutic target. Moreover, a Ras effector domain peptide blocks the binding of the MEKK catalytic domain with the GTP-bound form of Ras. In addition, it is shown in the appended Examples that MEKK4 binds to Rac, a low molecular weight GTP binding protein of the Ras superfamily. The sequence of MEKK4 which binds to Cdc42 and Rac has been identified. This sequence IIGQVCDTPKSYDNVMHVGLR occurrs around residue 1306–1326 of MEKK4.2 or 599–619 of MEKK4 and peptides from this region can be used to block the binding of the MEKK catalytic domain with Cdc42 and Rac.

Yet another set of experimental data provided in the appended examples indicates that activation of certain MEKK pathways can lead to apoptosis. The integration of signal transduction pathways regulated by growth factor and cytokine receptors commits a cell either to proliferation or apoptosis (Sumimoto, S. L. et al. (1994) J. Immunol. 153:2488–2496). Specific cytokines and stresses to cells, such as DNA damage, appear to preferentially acitvate the JNK/SAPK pathway which leads to apoptosis. Several checkpoints exist in the pathways leading to apoptosis that involve proteins such as Bcl2 and p58, which can both inhibit apoptosis. The MEKK proteins are therefore, important to the dynamic balance between growth factor-activated ERK and stress-activated JNK/p38 pathways and accordingly important in determining whether a cell survives or undergoes apoptosis. To date candidate molecules involved in signaling apoptosis include ceramide, Ras, Rho, c-myc, c-Jun, and the proteins associated with the TNFα receptor and Fas.

One aspect of the present invention relates to isolated MEKK proteins. As used herein protein, peptide, and polypeptide are meant to be synonomous. According to the present invention, an isolated protein is a protein that has been removed from its natural milieu. It will be understood that "isolated", with respect to MEKK polypeptides, is meant to include formulations of the polypeptides which are isolated from, or otherwise substantially free of other cellular proteins ("contaminating proteins"), especially other cellular signal transduction factors, normally associated with the MEKK polypeptide. Thus, isolated MEKK protein preparations include preparations having less than 20% (by dry weight) contaminating protein, and preferably having less than 5% contaminating protein (but water, buffers, and other small molecules, especially molecules having a molecular weight of less than 5000, can be present). Functional forms of the subject MEKK polypeptides can be prepared, for the first time, as purified preparations by using a cloned gene as described herein. Alternatively, the subject MEKK polypeptides can be isolated by affinity purification using, for example, a catalytically inactive MEK. "Isolated" does not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions.

An isolated MEKK protein can, for example, be obtained from its natural source, be produced using recombinant DNA technology, or be synthesized chemically. As used herein, an isolated MEKK protein can be a full-length MEKK protein or any homologue of such a protein, such as a MEKK protein in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycosylphosphatidyl inositol), wherein the modified protein is capable of phosphorylating MAP kinase kinases, such as mitogen ERK kinases (MEKs (MKK1 and MKK2)) and/or Jun kinase kinases (JNKKs (MKK3 and MKK4)).

As used herein, the term "gene" or "recombinant gene" refers to a nucleic acid comprising an open reading frame encoding one of the MEKK polypeptides of the present invention, including both exon and (optionally) intron sequences. A "recombinant gene" refers to nucleic acid encoding a vertebrate MEKK polypeptide and comprising vertebrate MEKK-encoding exon sequences, though it may optionally include intron sequences which are either derived from a chromosomal vertebrate MEKK gene or from an unrelated chromosomal gene. Exemplary recombinant genes encoding the subject vertebrate MEKK polypeptide are represented in the appended Sequence Listing. The term "intron" refers to a DNA sequence present in a given vertebrate MEKK gene which is not translated into protein and is generally found between exons.

A homologue of a MEKK protein is a protein having an amino acid sequence that is sufficiently similar to a natural MEKK protein amino acid sequence that a nucleic acid sequence encoding the homologue is capable of hybridizing under stringent conditions to (i.e., with) a nucleic acid sequence encoding the natural MEKK protein amino acid sequence. As used herein, stringent hybridization conditions refer to standard hybridization conditions under which nucleic acid molecules, including oligonucleotides, are used to identify similar nucleic acid molecules. Such standard conditions are disclosed, for example, in Sambrook et al., *Molecular Cloning: A Laboratory Manual*, Cold Spring Harbor Labs Press, 1989. A homologue of a MEKK protein also includes a protein having an amino acid sequence that is sufficiently cross-reactive such that the homologue has the ability to elicit an immune response against at least one epitope of a naturally-occurring MEKK protein.

The minimal size of a protein homologue of the present invention is a size sufficient to be encoded by a nucleic acid molecule capable of forming a stable hybrid with the complementary sequence of a nucleic acid molecule encoding the corresponding natural protein. As such, the size of the nucleic acid molecule encoding such a protein homologue is dependent on nucleic acid composition, percent homology between the nucleic acid molecule and complementary sequence, as well as upon hybridization conditions per se (e.g., temperature, salt concentration, and formamide concentration). The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode a MEKK protein homologue of the present invention is from about 12 to about 18 nucleotides in length. There is no limit, other than a practical limit, on the maximal size of such a nucleic acid molecule in that the nucleic acid molecule can include a portion of a gene, an entire gene, or multiple genes, or portions thereof. Similarly, the minimal size of a MEKK protein homologue of the present invention is from about 4 to about 6 amino acids in length, with preferred sizes depending on whether a full-length, multivalent protein (i.e., fusion protein having more than one domain each of which has a function), or a functional portion of such a protein is desired.

MEKK protein homologues can be the result of allelic variation of a natural gene encoding a MEKK protein. A natural gene refers to the form of the gene found most often in nature. MEKK protein homologues can be produced using techniques known in the art including, but not limited to, direct modifications to a gene encoding a protein using, for example, classic or recombinant DNA techniques to effect random or targeted mutagenesis. As will be understood, mutagenesis includes point mutations, as well as deletions and truncations of the MEKK polypeptide sequence. The ability of a MEKK protein homologue to phosphorylate MEK and/or JNKK protein can be tested using techniques known to those skilled in the art. Such techniques include phosphorylation assays described in detail in the Examples section.

With respect to homologues, it will also be possible to modify the structure of the subject MEKK polypeptides for such purposes as enhancing therapeutic or prophylactic efficacy, or stability (e.g., ex vivo shelf life and resistance to proteolytic degradation in vivo). Such modified polypeptides, when designed to retain at least one activity of the naturally-occurring form of the protein, are considered functional equivalents of the MEKK polypeptide described in more detail herein. Such modified peptide can be produced, for instance, by amino acid substitution, deletion, or addition.

In one embodiment, a MEKK protein of the present invention is capable of regulating a MEKK-dependent pathway. According to the present invention, a MEKK-dependent pathway refers generally to a pathway in which a MEKK protein regulates a pathway substantially independent of Raf, though the pathway including the MEKK protein may converge with common members of a pathway involving Raf protein, such as a MEK protein (see FIG. 1).

In certain preferred embodiments, the MEKK protein will be involved in a pathway controlling the phosphorylation of a mitogen-activiated protein (MAP) kinase. The mammalian MAP kinase family includes, for example, the extracellular signal-regulated protein kinases (ERK1 and ERK2), p42 or p44 MAPKs. In another preferred embodiment the MEKK protein will be involved in the pathway controlling c-Jun NH2-terminal kinases (JNKs, or SAPKs), and the so-called "p38 subgroup" kinases (p38 and Hog-1 kinases). For example, it is contemplated that the MEKK proteins of the present invention interact with, and directly phosphorylate members of the MAP kinase kinase family (MEKs or MKKs), as MEK1, MEK2, MKK1, MKK2, or the stress-activated kinases (SEKs), and the Jun kinase kinases (JNKK1, JNKK2, MKK3, MKK4), or the like.

An exemplary MEKK-dependent pathway includes a pathway involving a MEKK protein and a MKK protein. One of skill in the art can determine whether or not the regulation of a pathway by a MEKK protein is substantially independent of a Raf protein by comparing the ability of a MEKK protein and a Raf protein to regulate the phosphorylation of a downstream member of such pathway using, for example, the general method described in Example 16. For instance, a MEKK protein can regulate a pathway substantially independently of a Raf protein if the MEKK protein induces phosphorylation of a member of the pathway downstream of MEKK (e.g., proteins including JEK, Jun kinase, Jun and/or ATF-2) by an amount significantly greater than that seen when Raf protein is utilized. Raf-1 and B-Raf kinases selectively regulate MEK1 and MEK2 and do not recognize the JNKK proteins, thus Raf proteins appear to be highly selective for the regulation of p42/p44 MAPK pathways. MEKK proteins, in contrast, are capable of regulating both JNK and p42/p44 MAPK pathways.

For example, MEKK induction of phosphorylation of a JNK protein is preferably at least about 10-fold, more preferably at least about 20-fold and even more preferably at least about 30-fold than the phosphorylation of the ANK protein induced when using a Raf protein. If MEKK induction of phosphorylation is similar to Raf protein induction of phosphorylation, then one of skill in the art can conclude that regulation of a pathway by a MEKK protein includes members of a signal transduction pathway that could also include Raf protein. For example, MEKK induction of phosphorylation of MAPK is of a similar magnitude as induction of phosphorylation with Raf protein.

A "Raf-dependent pathway" refers to a signal transduction pathway in which a Raf protein regulates a signal transduction pathway substantially independently of a MEKK protein, and a pathway in which Raf protein regulation converges with common members of a pathway involving MEKK protein. The independence of regulation of a pathway by a Raf protein from regulation of a pathway by a MEKK protein can be determined using methods similar to those used to determine MEKK independence.

In another embodiment, a MEKK protein is capable of regulating the activity of signal transduction proteins including, but not limited to, mitogen activated ERK kinases (MEKs), mitogen activated protein kinases (MAPKs), transcription control factor (TCF), Ets-like-1 transcription factor (Elk-1), Jun ERK kinases (JNKKs), Jun kinases (JNK; which is equivalent to SAPK), stress activated MAPK proteins, Jun, activating transcription factor-2 (ATF-2) and/or Myc protein. As used herein, the "activity" of a protein can be directly correlated with the phosphorylation state of the protein and/or the ability of the protein to perform a particular function (e.g., phosphorylate another protein or regulate transcription). Preferred MEK proteins regulated by a MEKK protein of the present invention include MEK-1 and/or MEK-2 (MKK1 or MKK2). Preferred MAPK proteins regulated by a MEKK protein of the present invention include p38/hog-1 MAPK, p42 MAPK and/or p44 MAPK. Preferred stress activated MAPK proteins regulated by a MEKK protein of the present invention include Jun kinase (JNK), stress activated MAPK-α and/or stress activated MAPK-β. A preferred MEKK protein that is capable of activating p42/44 MAPK proteins includes a protein encoded by the nucleic acid sequence represented by SEQ ID NO:9 with a protein having the amino acid sequence represented by SEQ ID NO:10 being more preferred. A preferred MEKK protein that is capable of activating JNK MAPK is encoded by the nucleic acid sequence represented by one of SEQ ID NOS: 5 or 7, with a protein having the amino acid sequence represented by one of SEQ ID NOS: 6 or 8 being more preferred.

A MEKK protein of the present invention is capable of increasing the activity of an MEK protein over basal levels of MEK (i.e., levels found in nature when not stimulated). For example, a MEKK protein is preferably capable of increasing the phosphorylation of an MEK protein (such as MEK1 or MEK2, also known as MKK1 and MKK2 respectively) by at least about 2-fold, more preferably at least about 3-fold, and even more preferably at least about 4-fold over basal levels when measured under conditions described in Example 9. In another embodiment, a preferred MEKK protien is capable of increasing the phosphorylation of a JNKK protein (such as JNKK1 or JNKK2, also known as MKK3 and MKK4 respecitvely).

A preferred MEKK protein of the present invention is also capable of increasing the activity of an MAPK protein over basal levels of MAPK (i.e., levels found in nature when not stimulated). For example, a MEKK protein of the present invention is preferably capable of increasing MAPK activity at least about 2-fold, more preferably at least about 3-fold, and even more preferably at least about 4-fold over basal activity when measured under the conditions described in Example 3.

Moreover, a MEKK protein of the present invention is capable of increasing the activity of a JNK protein. JNK regulates the activity of the transcription factor JTJN which is involved in controlling the growth and differentiation of different cell types, such as T cells, neural cells or fibroblasts. JNK also regulates Elk-1, an Ets family member. JNK shows structural and regulatory homologies with MAPK. For example, a MEKK protein of the present invention is preferably capable of inducing the phosphorylation of JNK protein at least about 30 times more than Raf, more preferably at least about 40 times more than Raf, and even more preferably at least about 50 times more than Raf, when measured under conditions described in Example 16.

In addition, a MEKK protein of the present invention is capable of specific binding to a Ras superfamily protein. In particular, a MEKK protein is capable of binding to a Ras protein that is associated with GTP. According to the present invention, a MEKK protein binds to Ras via the COOH terminal region of the MEKK protein, e.g., a ras-binding domain. A preferred MEKK protein that is capable of binding to Ras or a member of the ras superfamily is endocoded by the nucleic acid shown in SEQ ID NO: 1, 3, 5, 7, 9, 11, or 13 with a protein having the amino acid sequence shown in SEQ ID NO:2, 4, 6, 8, 10, 12, or 14 being more preferred. In certain embodiments a MEKK protein is capable of binding to Rac-GTP. A preferred MEKK protein that is capable of binding to Rac or Cdc42 includes a protein encoded by the nucleic acid sequence shown in one of SEQ ID NOS: 11 or 13 with a protein having the amino acid sequence represented by one of SEQ ID NOS: 12 or 14 being more preferred.

In a preferred embodiment, a MEKK protein of the present invention is capable of phosphorylating a MEK or MKK, Jun kinase kinase (JNKK) and/or stress activated ERK kinase (SEK), in particular MEK1, MEK2, MKK1, MKK2, MKK3, MKK4, JNKK1, JNKK2, SEK1 and/or SEK2 proteins. As described herein, MEK1 and MEK2 are equivalent to MKK1 and MKK2, respectively. In addition, JNKK1 and JNKK2 are equivalent to MKK3 and MKK4, which are equivalent to SEK1 and SEK2.

A preferred MEKK protein of the present invention is additionally capable of inducing the phosphorylation of a Myc protein, particularly a transcriptional transactivation domain of Myc, in such a manner that the phosphorylated Myc protein is capable of regulating gene transcription. For example, according to Example 17, a MEKK protein of the present invention is preferably capable of inducing luciferase gene transcription by a phosphorylated Myc at least about 25-fold, more preferably at least about 35-fold, and even more preferably at least about 45-fold, over Raf induction when measured under the conditions described in Example 17.

Another aspect of the present invention relates to the ability of a MEKK activity to be stimulated by growth factors including, but not limited to, epidermal growth factor (EGF), neuronal growth factor (NGF), tumor necrosis factor (TNF), C5A, interleukin-8 (IL-8), interleukin-5 (IL-5), monocyte chemotactic protein I (MIP1α), monocyte chemoattractant protein I (MCP-1), platelet activating factor (PAF), N-Formyl-methionyl-leucylphenylalanine (FMLP), leukotriene $B_4$ ($LTB_4R$), gastrin releasing peptide (GRP), IgE, major histocompatibility protein (MHC), peptide, superantigen, antigen, vasopressin, thrombin, bradykinin and acetylcholine. In addition, the activity of a MEKK protein of the present invention is capable of being stimulated by compounds including phorbol esters such as TPA. A preferred MEKK protein is also capable of being stimulated by EGF, NGF and/or TNF (especially TNFα).

Preferably, the activity of certain of the MEKK proteins of the present invention is capable of being stimulated at least 2-fold over basal levels (i.e., levels found in nature when not stimulated), more preferably at least about 4-fold over basal levels and even more preferably at least about 6-fold over basal levels, when a cell producing the MEKK protein is contacted with EGF under the conditions described in Example 3.

Similarly, the activity of certain of the MEKK proteins of the present invention are capable of being stimulated at least 1-fold over basal levels, more preferably at least about 2-fold over basal levels and even more preferably at least about 3-fold over basal levels by NGF stimulation, when a cell producing the MEKK protein is contacted with NGF under the conditions described in the appended examples. MEKK proteins which are stimulated by NGF may subsequently cause the activation of one or more ERKs.

On the other hand, as demonstrated below, certain of the MEKK proteins of the present invention are capable of being stimulated by removal of NGF stimulation. MEKK proteins which are stimulated by NGF removal may subsequently cause the activation of one or more p38 kinases and/or JNKs.

In yet another embodiment, a MEKK protein of the present invention is capable of being stimulated at least 0.5-fold over basal levels, more preferably at least about 1-fold over basal levels and even more preferably at least about 2-fold over basal levels by TPA stimulation when a cell producing the MEKK protein is contacted with TPA under the conditions described in Example 9.

TNF is capable of regulating cell death and other functions in different cell types. Another aspect of the present invention relates to the discovery that MEKK stimulation by TNF can be independent of Raf. Similarly, the present invention demonstrates that the kinase activity of certain of the subject MEKK proteins can be stimulated by ultraviolet light (UV) damage of cells. It has been observed that both TNF and UV stimulate MEKK activity without substantially activating Raf. In addition, both UV and TNF activation of MEKK is apparently Ras dependent. In certain embodiments FGF is capable of preventing TNF induced apoptosis.

Another aspect of the present invention is the recognition that a MEKK protein of the present invention is capable of regulating the apoptosis of a cell As used herein, apoptosis refers to the form of cell death that comprises: progressive contraction of cell volume with the preservation of the integrity of cytoplasmic organelles; condensation of chromatin, as viewed by light or electron microscopy; and DNA cleavage, as electrophoresis or labeling of DNA fragments using terminal deoxytransferase (TDT). Cell death occurs when the membrane integrity of the cell is lost and cell lysis occurs. Apoptosis differs from necrosis in which cells swell and eventually rupture.

A preferred MEKK protein of the present invention is capable of inducing the apoptosis of cells, such that the cells have characteristics substantially similar to cytoplasmic shrinkage and/or nuclear condensation as described in the apended Examples. The appended examples also illustrate that TNF and MEKK can synergize to induce apoptosis in cells.

Figure 2:
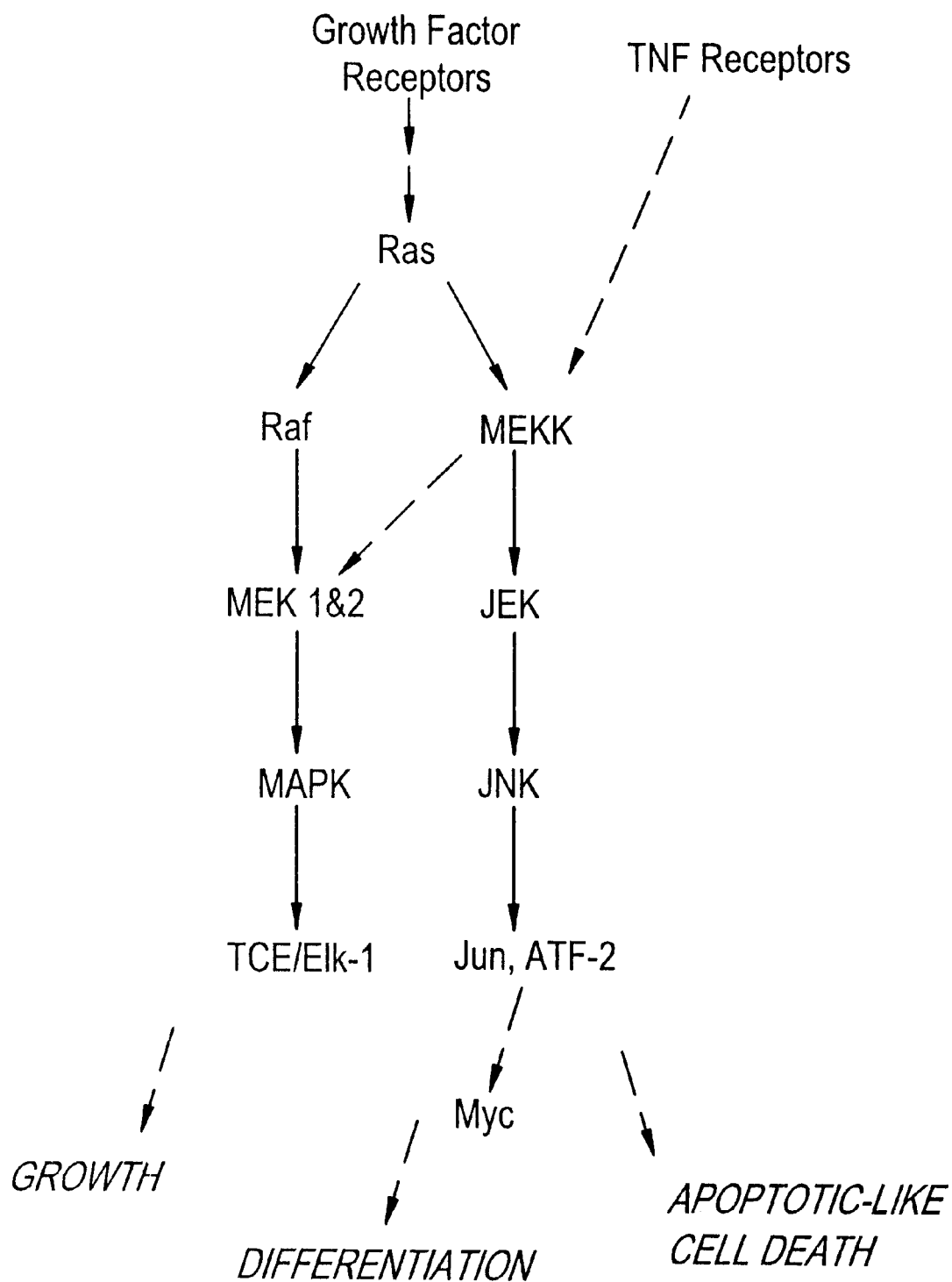
FIG. 2 is a schematic representation of the dual MEKK and Raf pathways divergent from Ras protein pathway.

A schematic representation of an exemplary cell growth regulatory signal transduction pathway that is MEKK dependent is shown in FIG. 2. Preferred MEKK proteins of the present invention are capable of regulating the activity of a JNKK protein, JNK protein, Jun protein and/or ATF-2 protein, and Myc protein, such regulation being substantially, if not entirely, independent of Raf protein. Such Raf-independent regulation can regulate the growth characteristics of a cell, including the apoptosis of a cell. In addition, a MEKK protein of the present invention is capable of regulating the activity of MEK protein, which is also capable of being regulated by Raf protein. As such, a MEKK protein of the present invention is capable of regulating the activity of MAPK protein and members of the Ets family of transcription factors, such as TCF protein, also referred to as Elk-1 protein.

Referring to FIG. 2, a MEKK protein of the present invention is capable of being activated by a variety of growth factors and environmental cues capable of activating Ras superfamily protein. In addition, a MEKK protein is capable of activating JNK protein which is also activated by Ras protein, but which is not activated by Raf protein. As such, a MEKK protein of the present invention comprises a protein kinase at a divergence point in a signal transduction pathway initiated by different cell surface receptors. A MEKK protein is also capable of being regulated by TNF protein independent of Raf, thereby indicating an association of MEKK protein to a novel signal transduction pathway which is independent of Ras protein and Raf protein.

Thus, a MEKK protein is capable of performing numerous unique functions independent of or by-passing Raf protein in one or more signal transduction pathways. A MEKK protein is capable of regulating the activity of MEK and/or JNKK activity. As such, a MEKK protein is capable of regulating the activity of members of a signal transduction pathway that does not substantially include Raf activity. Such members include, but are not limited to, JNK, Jun, ATF and Myc protein. In addition, a MEKK protein is capable of regulating the members of a signal transduction pathway that does involve Raf, such members including, but are not limited to, MEK, MAPK and TCF. A MEKK protein of the present invention is thus capable of regulating the apoptosis of a cell independent of significant involvement by Raf protein.

In addition to the numerous functional characteristics of a MEKK protein, a MEKK protein of the present invention comprises numerous unique structural characteristics. For example, in one embodiment, a MEKK protein of the present invention includes at least one of two different structural domains having particular functional characteristics. Such structural domains include an $NH_2$-terminal regulatory domain that serves to regulate a second structural domain comprising a COOH-terminal protein kinase catalytic domain that is capable of phosphorylating an MKK protein.

According to the present invention, a MEKK protein of the present invention includes a full-length MEKK protein, as well as at least a portion of a MEKK protein capable of performing at least one of the functions defined above. The phrase "at least a portion of a MEKK protein" refers to a portion of a MEKK protein encoded by a nucleic acid molecule that is capable of hybridizing, under stringent conditions, with a nucleic acid encoding a full-length MEKK protein of the present invention. Preferred portions of MEKK proteins are useful for regulating apoptosis in a cell. Additional preferred portions have activities useful for regulating MEKK kinase activity. Suitable sizes for portions of a MEKK protein of the present invention are as disclosed for MEKK protein homologues of the present invention.

In another embodiment, a MEKK protein of the present invention includes at least a portion of a MEKK protein having molecular weights ranging from about 70 kD to about 250 kD as determined by Tris-glycine SDS-PAGE, preferably using an 8% polyacrylamide SDS gel (SDS-PAGE) and resolved using methods standard in the art. A preferred MEKK protein has a molecular weight ranging from about 65 kD to about 190 kD and even more preferably from about 69 kD to about 98 kD. In particularly preferred embodiments MEKK2 and MEKK3 proteins of the present invention have a molecular weight of about 65–75 kD. Preferred MEKK4 proteins have molecular weights about 180–190 kD. Most preferred molecular weights for the subject MEKKs are: >175 kD (MEKK1), 69.5 kD (MEKK2 or MEKK2.2), 71 kD (MEKK3), 185 kD (MEKK4). It is noted that experimental conditions used when running gels to determine the molecular size of putative MEKK proteins will cause variations in results. Moreover, it has become apparent to the Applicant that, relative to predicted molecular weights, shorter apparently related polypeptides can be observed. Whether these are the result of proteolytic processing, alternative splicing or start codon usage or the like is unclear, but other preferred MEKK1 polypeptides (e.g. MEKK 1.2) have apparent molecular weights of about 95–100 kD; and other preferred MEKK4 polypeptides (e.g., MEKK 4.2) have apparent molecular weights of about 90–100 kD, more preferably 95–98 kD.

In another embodiment, an $NH_2$-terminal regulatory domain of the present invention includes an $NH_2$-terminal comprising about 400 amino acids having at least about 10% serine and/or threonine residues, more preferably about 400 amino acids having at least about 15% serine and/or threonine residues, and even more preferably about 400 amino acids having at least about 20% serine and/or threonine residues.

In another embodiment an $NH_2$-terminal regulatory domain of the present invention includes an $NH_2$-terminal comprising about 600 amino acids having at least about 10% serine and/or threonine residues, more preferably about 600 amino acids having at least about 15% serine and/or threonine residues, and even more preferably about 600 amino acids having at least about 20% serine and/or threonine residues.

Another preferred an $NH_2$-terminal regulatory domain of the present invention includes an $NH_2$-terminal comprising about 1300 amino acids having at least about 10% serine and/or threonine residues, more preferably about 1300 amino acids having at least about 15% serine and/or threonine residues, and even more preferably about 1300 amino acids having at least about 20% serine and/or threonine residues.

In one embodiment, a MEKK protein of the present invention is devoid of SH2 and SH3 domains.

A MEKK homologue has at least about 50%, more preferably 75%, more preferably 85%, and more preferably 95% homology with one of SEQ ID NOs: 2, 4, 6, 8, 10, 12, or 14. In preferred embodiments the homolog has 50%, more preferably at least about 75% and more preferably at least about 85%, or most preferably at least about 95% amino acid homology with the kinase catalytic domain of a MEKK protein having an amino acid sequence represented by one or more of amino acids 409–672 of SEQ ID NO:2, 1329–1594 of SEQ ID NO:4, amino acids 361–620 of SEQ ID NOs:6 or 8, amino acids 366–626 of SEQ ID NO:10, amino acids, amino acids 631–890 of SEQ ID NO:12, or amino acids 1338–1597 of SEQ ID NO:14. Another preferred MEKK homologue has at least about 50%, more preferably at least about 75%, more preferably at least about 85% and even more preferably about 95% amino acid homology with the $NH_2$-terminal regulatory domain of a MEKK protein having an amino acid sequence represented by amino acids 1–408 of SEQ ID NO:2, amino acids 1–1328 of SEQ ID NO:4, amino acids 1–360 of SEQ ID NO:6 or 8. amino acids 1–365 of SEQ ID NO:10, amino acids 1–630 of SEQ ID NO:12, or amino acids 1–1337 of SEQ ID NO: 14.

In another embodiment, a MEKK protein of the present invention includes at least a portion of a MEKK protein homologue preferably has at least about 50%, more preferably 75%, more preferably 85%, and more preferably 95% homology with one of SEQ ID NOS:2, 4, 6, 8, 10, 12, or 14. In other embodiments the homolog is 50%, more preferably 75%, more preferably at least about 85%, and even more preferably at least about 95% amino acid homology (identity within comparable regions) with the kinase catalytic domain of a naturally occurring MEKK protein. Another MEKK protein of the present invention also includes at least a portion of a MEKK homologue of the present invention has at least about 50%, more preferably at least about 75%, or most preferably at least about 85% amino acid homology with the $NH_2$-terminal regulatory domain of a MEKK protein of a naturally occurring MEKK protein.

In certain embodiements MEKK proteins have proline rich sequences that are src homology 3 (SH3) binding motifs. Proline rich regions, specifically the sequence PXXP is thought to be critical in all SH3 ligands (Alexandropoulous and Cheng (1995) *Proc. Natal. Acad. Sci* 92:3110–3114). Preferred MEKK proteins that have proline rich sequences are encoded by nucleic acids shown in one of SEQ ID NOS:3 or 13. In particularly preferred embodiments MEKK proteins comprising SH3 binding motifs are shown in one of SEQ ID NOS:4 or 14. Particularly preferred proline rich sequences are exemplified by the sequences shown in amino acids 26–37 of SEQ ID NO:14 or in amino acids 41–51, 70–90, 186–191, 211–219 of SEQ ID NO:4.

In other embodiments certain MEKK proteins comprise pleckstrin homology domains The 'pleckstrin homology' (PH) domain is an approximately 100-residue protein module that is thought to be involved in interactions with GTP-binding proteins (Musacchio et al (1993) TIBS 28:343–348). Pleckstrin homology domains are very divergent and do not occupy a specific positions in molecules; alignments of PH domains show six conserved blocks which all contain several conserved hydrophobic residues which are thought to form a folded structure comprising seven to eight β-strands, most likely in one or two β-sheets, and just a single helix (Musacchio et al. supra). PH domains have been identified in kinases and also in Vav, Dbl, Bcr, yeast cdc24, Ras-GAP, DM GAP, Ras-GRF, and Sos, all of which are regulators of small GTP-binding proteins. Interestingly, three of the four proteins that have been identified as being capable of binding to SH3 domains (dynamin, 3BP2, and Sos) also contain PH domains (Musacchio et al. supra). The PH domain of β adrenergic receptor kinase may be involved in binding to G protein βγ complexes (Koch et al. (1993) J. Biol. Chem. 268:8256–8260). Preferred MEKK proteins that have PH domains are encoded by nucleic acids shown in one of SEQ ID NOS:3 or 13. In particularly preferred embodiments MEKK proteins comprising PH domains are shown in one of SEQ ID NOS:4 or 14. Particularly preferred PH domains are exemplified by the amino acids 262–665 of SEQ ID NO:4 or amino acids 233–397 of SEQ ID NO: 14.

In another embodiment the MEKK proteins of the present invention bind to MKK substrates. Preferred MEKK proteins comprise consensus MKK binding domains as encoded by the nucleic acid sequences shown in one of SEQ ID NOS: 1, 3, 5, 7, 9, 11, or 13. Preferred MKK consensus binding regions are illustrated by amino acids 658–672 of SEQ ID NO:2, amino acids 1579–1593 of SEQ ID NO:4, amino acids 605–620 of SEQ ID NOS: 6 or 8, amino acids 611–626 of SEQ ID NO:10, amino acids 872–890 of SEQ ID NO:12, or amino acids 1579–1597 of SEQ ID NO: 14.

The sequences comprising the catalytic domain of a MEKK protein are involved in phosphotransferase activity, and therefore display a relatively conserved amino acid sequence. The $NH_2$-terminal regulatory domain of a MEKK protein, however, can be substantially divergent. The lack of significant homology between MEKK protein $NH_2$-terminal regulatory domains is related to the regulation of each of such domains by different upstream regulatory proteins. For example, a MEKK protein can be regulated by the protein Ras, while others can be regulated independent of Ras. In addition, some MEKK proteins can be regulated by the growth factor TNFα, while others cannot. As such, the $NH_2$-terminal regulatory domain of a MEKK protein provides selectivity for upstream signal transduction regulation, while the catalytic domain provides for MEKK substrate selectivity function.

In a preferred embodiment, a MEKK protein of the present invention includes at least a portion of a MEKK protein homologue of the present invention that is encoded by a nucleic acid molecule preferably has at least about 50%, more preferably 75%, more preferably 85%, and more preferably 95% homology with one of SEQ ID NOS: 2, 4, 6, 8, 10,12, or 14. Preferred fragments of MEKK proteins include those in which at least a portion of a MEKK regulatory domain is deleted to form a constitutively active molecule, or those in which at least a portion of a MEKK catalytic domain is deleted to form a catalyticly inactive molecule.

Still another preferred MEKK homologue is encoded by a nucleic acid molecule having at least about 50%, more preferably 75%, more preferably 85%, and more preferably 95% homology with one of SEQ ID NOS: 1, 3, 5, 7, 9, 11, or 13. In other embodiments the nucleic acid has at least about 50%, more preferably at least about 75%, more preferably at least about 85%, or most preferably at least about 95% homologous with the kinase catalytic domain of a MEKK protein encoded by a nucleic acid sequence represented by SEQ ID NOS: 1, 3, 5, 7, 9, 11, or 13. A MEKK homologue also includes those encoded by a nucleic acid molecule having at least about 50%, more preferably at least about 75%, more preferably at least about 85%, and even more preferably at least about 95% amino acid homology with the $NH_2$-terminal regulatory domain of a MEKK protein encoded by a nucleic acid sequence represented by SEQ ID NOS: 1, 3, 5, 7, 9, 11, or 13.

In another embodiment, the subject MEKK proteins are provided as fusion proteins. It is widely appreciated that fusion proteins can also facilitate the expression of proteins, and accordingly, can be used in the expression of the MEKK polypeptides of the present invention. For example, MEKK polypeptides can be generated as glutathione-S-transferase (GST-fusion) proteins. Such GST-fusion proteins can enable easy purification of the MEKK polypeptide, as for example by the use of glutathione-derivatized matrices (see, for example, *Current Protocols in Molecular Biology*, eds. Ausubel et al. (N.Y.: John Wiley & Sons, 1991)).

In another embodiment, a fusion gene coding for a purification leader sequence, such as a poly-(His)/ enterokinase cleavage site sequence at the N-terminus of the desired portion of the recombinant protein, can allow purification of the expressed fusion protein by affinity chromatography using a Ni2+ metal resin. The purification leader sequence can then be subsequently removed by treatment with enterokinase to provide the purified protein (e.g., see Hochuli et al. (1987) *J. Chromatography* 411:177; and Janknecht et al. *PNAS* 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al. John Wiley & Sons: 1992).

According to the present invention, a MEKK protein of the present invention can include MEKK proteins that have undergone post-translational modification. Such modification can include, for example, phosphorylation or among other post-translational modifications including conformational changes or post-translational deletions.

This invention further contemplates a method for generating sets of combinatorial mutants of the subject MEKK proteins as well as truncation mutants, and is especially useful for identifying potential variant sequences (e.g. homologs) that are functional in modulating signal transduction. The purpose of screening such combinatorial libraries is to generate, for example, novel MEKK homologs which can act as either agonists or antagonist of the wildtype MEKK proteins, or alternatively, which possess novel activities all together. To illustrate, MEKK homologs can be engineered by the present method to provide selective, constitutive activation of a pathway, so as mimic induction by a factor when the MEKK homolog is expressed in a cell capable of responding to the factor. Thus, combinatorially-derived homologs can be generated to have an increased potency relative to a naturally occurring form of the protein.

Likewise, MEKK homologs can be generated by the present combinatorial approach to selectively inhibit (antagonize) induction by a growth or other factor. For instance, mutagenesis can provide MEKK homologs which are able to bind other signal pathway proteins (e.g., MEKs) yet prevent propagation of the signal, e.g. the homologs can be dominant negative mutants. Moreover, manipulation of certain domains of MEKK by the present method can provide domains more suitable for use in fusion proteins.

In one aspect of this method, the amino acid sequences for a population of MEKK homologs or other related proteins are aligned, preferably to promote the highest homology possible. Such a population of variants can include, for example, MEKK homologs from one or more species. Amino acids which appear at each position of the aligned sequences are selected to create a degenerate set of combinatorial sequences. In a preferred embodiment, the variegated library of MEKK variants is generated by combinatorial mutagenesis at the nucleic acid level, and is encoded by a variegated gene library. For instance, a mixture of synthetic oligonucleotides can be enzymatically ligated into gene sequences such that the degenerate set of potential MEKK sequences are expressible as individual polypeptides, or alternatively, as a set of larger fusion proteins (e.g. for phage display) containing the set of MEKK sequences therein.

There are many ways by which such libraries of potential MEKK homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential MEKK sequences. The synthesis of degenerate oligonucleotides is well known in the art (see for example, Narang, SA (1983) *Tetrahedron* 39:3; Itakura et al. (1981) *Recombinant DNA, Proc 3rd Cleveland Sympos. Macromolecules*, ed. AG Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

Likewise, a library of coding sequence fragments can be provided for a MEKK clone in order to generate a variegated population of MEKK fragments for screening and subsequent selection of bioactive fragments. A variety of techniques are known in the art for generating such libraries, including chemical synthesis. In one embodiment, a library of coding sequence fragments can be generated by (i) treating a double stranded PCR fragment of a MEKK coding sequence with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of MEKK homologs. The most widely used techniques for screening large gene libraries typically comprise cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate MEKK sequences created by combinatorial mutagenesis techniques.

In an illustrative embodiment of a screening assay, the gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical *E. coli* filamentous phages M13, fd, and f1 are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) *J. Biol. Chem.* 267:16007–16010; Griffths et al. (1993) *EMBO J* 12:725–734; Clackson et al. (1991) *Nature* 352:624–628; and Barbas et al. (1992) *PNAS* 89:4457–4461). The resulting phage libraries with the fusion tail proteins may be panned, e.g. using a fluorescently labeled MEK protein, e.g. FITC-MEK, to score for MEKK homologs which retain the ability to bind to the MEK protein. Individual phage which encode a MEKK homolog which retains MEK binding can be isolated, the MEKK homolog gene recovered from the isolate, and further tested to discern between active and antagonistic mutants.

In another embodiment, the REF52 cells of Example 18 or 19 can be exploited to analyze the variegated MEKK library. For instance, the library of expression vectors can be transfected into a population of REF52 cells which also inducibly overexpress a MEKK protein (e.g., and which overexpression causes apoptosis). Expression of WT-MEKK is then induced. and the effect of the MEKK mutant on induction of apoptosis can be detected. Plasmid DNA can then be recovered from the cells which score for inhibition, or alternatively, potentiation of apoptosis, and the individual clones further characterized.

The invention also provides for reduction of the MEKK proteins to generate mimetics, e.g. peptide or non-peptide agents, which are able to disrupt binding of a MEKK polypeptide of the present invention with either upstream or downstream components of its signaling cascade. Thus, such mutagenic techniques as described above are also useful to map the determinants of the MEKK proteins which participate in protein-protein interactions involved in, for example, binding of the subject MEKK polypeptide to proteins which may function upstream (including both activators and repressors of its activity) or to proteins which may function downstream of the MEKK polypeptide, whether they are positively or negatively regulated by it. To illustrate, the critical residues of a subject MEKK polypeptide which are involved in molecular recognition of an upstream or downstream MEKK component can be determined and used to generate MEKK-derived peptidomimetics which competitively inhibit binding of the authentic protein with that moiety. By employing, for example, scanning mutagenesis to map the amino acid residues of each of the subject MEKK proteins which are involved in binding other cellular proteins, peptidomimetic compounds can be generated which mimic those residues of the MEKK protein which facilitate the interaction. Such mimetics may then be used to interfere with the normal function of a MEKK protein. For instance, non-hydrolyzable peptide analogs of such residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gamma lactam rings (Garvey et al. in *Peptides: Chemistry and Biology*, G. R. Marshall ed., ESCOM Publisher: Leiden, Netherlands, 1988), ketomethylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), (β-turn dipeptide cores (Nagai et al. (1985) *Tetrahedron Lett* 26:647; and Sato et al. (1986) *J Chem Soc Perkin Trans* 1:1231), and β-aminoalcohols (Gordon et al. (1985) *Biochem Biophys Res Commun* 126:419; and Dann et al. (1986) *Biochem Biophys Res Commun* 134:71).

Another aspect of the present invention is an isolated nucleic acid molecule capable of hybridizing, under stringent conditions, with a MEKK protein gene encoding a MEKK protein of the present invention. In accordance with the present invention, an isolated nucleic acid molecule is a nucleic acid molecule that has been removed from its natural milieu (i.e., that has been subject to human manipulation). As such, "isolated" does not reflect the extent to which the nucleic acid molecule has been purified. To this end, the term "isolated" as used herein with respect to nucleic acids, such as DNA or RNA, refers to molecules separated from other DNAs, or RNAs, respectively, that are present in the natural source of the macromolecule. For example, an isolated nucleic acid encoding one of the subject MEKK polypeptides preferably includes no more than 10 kilobases (kb) of nucleic acid sequence which naturally immediately flanks the MEKK gene in genomic DNA, more preferably no more than 5 kb of such naturally occurring flanking sequences, and most preferably less than 1.5 kb of such naturally occurring flanking sequence. The term isolated as used herein will also be understood to include nucleic acid that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

An isolated nucleic acid molecule can include DNA, RNA, or derivatives of either DNA or RNA. Accordingly, as used herein, the term "nucleic acid" includes polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "gene" or "recombinant gene" includes nucleic acid comprising an open reading frame encoding one of the MEKK polypeptides of the present invention, including both exon and (optionally) intron sequences. A "recombinant gene" refers to nucleic acid encoding a MEKK polypeptide and comprising MEKK-encoding exon sequences, though it may optionally include intron sequences which are either derived from a chromosomal MEKK gene or from an unrelated chromosomal gene. Exemplary recombinant genes encoding the subject MEKK polypeptides are represented in the appended Sequence Listing.

An isolated nucleic acid molecule of the present invention can be obtained from its natural source either as an entire (i.e., complete) gene or a portion thereof capable of forming a stable hybrid with that gene. As used herein, the phrase "at least a portion of" an entity refers to an amount of the entity that is at least sufficient to have the functional aspects of that entity. For example, at least a portion of a nucleic acid sequence, as used herein, is an amount of a nucleic acid sequence capable of forming a stable hybrid with a particular desired gene (e.g., MEKK genes) under stringent hybridization conditions. An isolated nucleic acid molecule of the present invention can also be produced using recombinant DNA technology (e.g., polymerase chain reaction (PCR) amplification, cloning) or chemical synthesis. Isolated MEKK protein nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode a MEKK protein of the present invention or to form stable hybrids under stringent conditions with natural nucleic acid molecule isolates of MEKK.

Preferred modifications to a MEKK protein nucleic acid molecule of the present invention include truncating a full-length MEKK protein nucleic acid molecule by, for example: deleting at least a portion of a MEKK protein nucleic acid molecule encoding a regulatory domain to produce a constitutively active MEKK protein; deleting at least a portion of a MEKK protein nucleic acid molecule encoding a catalytic domain to produce an inactive MEKK protein; and modifying the MEKK protein to achieve desired inactivation and/or stimulation of the protein, for example, substituting a codon encoding a lysine residue in the catalytic domain (i.e., phosphotransferase domain) with a methionine residue to inactivate the catalytic domain.

A preferred truncated MEKK nucleic acid molecule encodes a form of a MEKK protein containing a catalytic domain but that lacks a regulatory domain. Preferred catalytic domain truncated MEKK nucleic acid molecules encode amino acid residues from about 409 to about 672 of MEKK 1.1; amino acids 1331 to about 1594 of MEKK 1.2; from about 361 to about 620 of MEKK 2.1 or 2.2; from about 366 to about 626 of MEKK 3; from about 631 to about 890 of MEKK 4.1; or from about 1338 to about 1597 for MEKK 4.2.

Another preferred truncated MEKK nucleic acid molecule encodes a form of a MEKK protein comprising an $N14_2$-terminal regulatory domain a catalytic domain but lacking a catalytic domain. Preferred regulatory domain truncated MEKK nucleic acid molecules encode amino acid residues from about 1 to about 408 of MEKK 1.1; amino acids 1 to about 1328 of MEKK 1.2; from about 1 to about 360 of MEKK 2.1 or 2.2; from about 1 to about 365 of MEKK 3; from about 1 to about 630 of MEKK 4.1; or from about 1 to about 1337 for MEKK4.2.

An isolated nucleic acid molecule of the present invention can include a nucleic acid sequence that encodes at least one MEKK protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides that comprise the nucleic acid molecule, the two phrases can be used interchangeably. As heretofore disclosed, MEKK proteins of the present invention include, but are not limited to, proteins having full-length MEKK protein coding regions, portions thereof, and other MEKK protein homologues.

As used herein, a MEKK protein gene includes all nucleic acid sequences related to a natural MEKK protein gene such as regulatory regions that control production of a MEKK protein encoded by that gene (including, but not limited to, transcription, translation or post-translation control regions) as well as the coding region itself. A nucleic acid molecule of the present invention can be an isolated natural MEKK protein nucleic acid molecule or a homologue thereof. A nucleic acid molecule of the present invention can include one or more regulatory regions, full-length or partial coding regions, or combinations thereof. The minimal size of a MEKK protein nucleic acid molecule of the present invention is the minimal size capable of forming a stable hybrid under stringent hybridization conditions with a corresponding natural gene.

A MEKK protein nucleic acid molecule homologue can be produced using a number of methods known to those skilled in the art (see, e.g., Sambrook et al., ibid.). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid (e.g., the ability of a homologue to phosphorylate MEK protein or JNKK protein) and/or by hybridization with isolated MEKK protein nucleic acids under stringent conditions.

One embodiment of the present invention is a MEKK protein nucleic acid molecule capable of encoding at least a portion of a MEKK protein, or a homologue thereof, as described herein. A preferred nucleic acid molecule of the present invention includes, but is not limited to, a nucleic acid molecule that encodes a protein having at least a portion of an amino acid sequence represented by SEQ ID NO:2, SEQ ID NO:4, SEQ ID NO:6, SEQ ID NO:8, SEQ ID NO:10, SEQ ID NO:12, and SEQ ID NO:14, or homologues thereof. Proteins at least 50%, preferably at least about 75%, more preferably at least about 85%, and most preferably at least about 95% homologous to these sequences are contemplated.

A preferred nucleic acid molecule of the present invention is capable of hybridizing under stringent conditions to a nucleic acid that encodes at least a portion of a MEKK protein, or a homologue thereof. Also preferred is a MEKK protein nucleic acid molecule that includes a nucleic acid sequence having at least about 50% homology, preferably 75% homology, preferably 85% homology, or even more preferably 95% homology with one of SEQ ID NO:1, 3, 5, 7, 9,11, or 13. In other embodiments nucleic acids have 50%, preferably at least about 75%, and more preferably at least about 85%, and most preferably at least about 95% homology with the corresponding region(s) of the nucleic acid sequence encoding the catalytic domain of a MEKK protein, or a homologue thereof. Also preferred is a MEKK protein nucleic acid molecule that includes a nucleic acid sequence having at least about 50%, preferably at least about 75%, more preferably at least about 85%, and even more preferably at least about 95% homology with the corresponding region(s) of the nucleic acid sequence encoding the $NH_2$-terminal regulatory domain of a MEKK protein, or a homologue thereof. A particularly preferred nucleic acid sequence is a nucleic acid sequence having at least about 50%, preferably at least about 75%, and more preferably at least about 85%, and most preferably at least about 95% homology with a nucleic acid sequence encoding the catalytic domain amino acid residues from about 409 to about 672 of SEQ ID NO:2; amino acids 1331 to about 1594 of SEQ ID NO:4; from about 361 to about 620 of SEQ ID NO:6 or 8; from about 366 to about 626 of SEQ ID NO:10; from about 631 to about 890 of SEQ ID NO:12; or from about 1338 to about 1597 for SEQ ID NO:14. Another preferred MEKK homologue has at least about 50%, more preferably at least about 75%, more preferably at least about 85% and even more preferably about 95% amino acid homology with the $NH_2$-terminal regulatory domain of a MEKK protein having an amino acid sequence represented by amino acid residues from about 1 to about 408 of SEQ ID NO:2; amino acids 1 to about 1328 of SEQ ID NO:4; from about 1 to about 360 of SEQ ID NO:6 or 8; from about 1 to about 365 of SEQ ID NO:10; from about 1 to about 630 of SEQ ID NO:12; or from about 1 to about 1337 for SEQ ID NO:14.

Such nucleic acid molecules can be a full-length gene and/or a nucleic acid molecule encoding a full-length protein, a hybrid protein, a fusion protein, a multivalent protein or a truncation fragment. More preferred nucleic acid molecules of the present invention comprise isolated nucleic acid molecules having a nucleic acid sequence as represented by one of SEQ ID NOS: 1, 3, 5, 7, 9, 11, or 13, or nucleic acid molecules capable of hybridizing to said sequences under stringent conditions.

Knowing a nucleic acid molecule of a MEKK protein of the present invention allows one skilled in the art to make copies of that nucleic acid molecule as well as to obtain additional portions of MEKK protein-encoding genes (e.g., nucleic acid molecules that include the translation start site and/or transcription and/or translation control regions), and/or MEKK protein nucleic acid molecule homologues. Knowing a portion of an amino acid sequence of a MEKK protein of the present invention allows one skilled in the art to clone nucleic acid sequences encoding such a MEKK protein.

The present invention also includes nucleic acid molecules that are oligonucleotides capable of hybridizing, under stringent conditions, with complementary regions of other, preferably longer, nucleic acid molecules of the present invention that encode at least a portion of a MEKK protein, or a homologue thereof. A preferred oligonucleotide is capable of hybridizing, under stringent conditions, with a nucleic acid molecule that is capable of encoding at least a portion of an amino acid sequence represented by SEQ ID NO:2, SEQ ID NO:4, SEQ ID NO:6, SEQ ID NO:8, SEQ ID NO:10, SEQ ID NO:12, SEQ ID NO:14, or homologues thereof. A more preferred oligonucleotide is capable of hybridizing to a nucleic acid molecule having a nucleic acid sequence as represented by SEQ ID NO:1, SEQ ID NO:3, SEQ ID NO:5, SEQ ID NO:7, SEQ ID NO:9, SEQ ID NO:11, SEQ ID NO:13 or complements thereof.

Oligonucleotides of the present invention can be RNA, DNA, or derivatives of either. The minimal size of such oligonucleotides is the size required to form a stable hybrid between a given oligonucleotide and the complementary sequence on another nucleic acid molecule of the present invention. Minimal size characteristics of preferred oligonucleotides are at least about 10 nuclotides, preferably at least about 20 nucleotides, more preferably at least about 50 nucleotides and most preferably at least about 60 nucleotides. Larger fragments are also contemplated. The size of the oligonucleotide must also be sufficient for the use of the oligonucleotide in accordance with the present invention. Oligonucleotides of the present invention can be used in a variety of applications including, but not limited to, as probes to identify additional nucleic acid molecules, as primers to amplify or extend nucleic acid molecules or in therapeutic applications to inhibit, for example, expression of MEKK proteins by cells. Such therapeutic applications include the use of such oligonucleotides in, for example, antisense-, triplex formation-, ribozyme- and/or RNA drug-based technologies. The present invention, therefore, includes use of such oligonucleotides and methods to interfere with the production of MEKK proteins. In addition oligonucleotides encoding portions of MEKK proteins which bind to MEKK binding proteins can be used a therapeutics. In other embodiments, the peptides encoded by these nucleic acids are used.

To further illustrate, another aspect of the invention relates to the use of the isolated nucleic acid in "antisense" therapy. As used herein, "antisense" therapy refers to administration or in situ generation of oligonucleotide probes or their derivatives which specifically hybridize (e.g. bind) under cellular conditions, with the cellular mRNA and/or genomic DNA encoding one or more of the subject MEKK proteins so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a vertebrate MEKK protein. Alternatively, the antisense construct is an oligonucleotide probe which is generated ex vivo and which, when introduced into the cell causes inhibition of expression by hybridizing with the mRNA and/or genomic sequences of a vertebrate MEKK gene. Such oligonucleotide probes are preferably modified oligonucleotides which are resistant to endogenous nucleases, e.g. exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) *Biotechniques* 6:958–976; and Stein et al. (1988) *Cancer Res* 48:2659–2668.

Accordingly, the modified oligomers of the invention are useful in therapeutic, diagnostic, and research contexts. In therapeutic applications, the oligomers are utilized in a manner appropriate for antisense therapy in general. For such therapy, the oligomers of the invention can be formulated for a variety of loads of administration, including systemic and topical or localized administration. Techniques and formulations generally may be found in *Remmington's Pharmaceutical Sciences*, Meade Publishing Co., Easton, Pa. For systemic administration, injection is preferred, including intramuscular, intravenous, intraperitoneal, and subcutaneous. For injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For oral administration, the oligomers are formulated into conventional oral administration forms such as capsules, tablets, and tonics. For topical administration, the oligomers of the invention are formulated into ointments, salves, gels, or creams as generally known in the art.

In addition to use in therapy, the oligomers of the invention may be used as diagnostic reagents to detect the presence or absence of the target DNA or RNA sequences to which they specifically bind. Such diagnostic tests are described in further detail below.

Likewise, the antisense constructs of the present invention, by antagonizing the normal biological activity of one of the MEKK proteins, can be used in the manipulation of tissue, e.g. tissue differentiation, both in vivo and for ex vivo tissue cultures.

Furthermore, the anti-sense techniques (e.g. microinjection of antisense molecules, or transfection with plasmids whose transcripts are anti-sense with regard to a MEKK mRNA or gene sequence) can be used to investigate role of MEKK in disease states, as well as the normal cellular function of MEKK in healthy tissue. Such techniques can be utilized in cell culture, but can also be used in the creation of transgenic animals. The present invention also includes a recombinant vector which includes at least one MEKK protein nucleic acid molecule of the present invention inserted into any vector capable of delivering the nucleic acid molecule into a host cell. Such a vector contains heterologous nucleic acid sequences, for example nucleic acid sequences that are not naturally found adjacent to MEKK protein nucleic acid molecules of the present invention. The vector can be either RNA or DNA, and either prokaryotic or eukaryotic, and is typically a virus or a plasmid. Recombinant vectors can be used in the cloning, sequencing, and/or otherwise manipulating of MEKK protein nucleic acid molecules of the present invention. One type of recombinant vector, herein referred to as a recombinant molecule and described in more detail below, can be used in the expression of nucleic acid molecules of the present invention. Preferred recombinant vectors are capable of replicating in the transformed cell.

Preferred nucleic acid molecules to insert into a recombinant vector includes a nucleic acid molecule that encodes at least a portion of a MEKK protein, or a homologue thereof. A more preferred nucleic acid molecule to insert into a recombinant vector includes a nucleic acid molecule encoding at least a portion of an amino acid sequence represented by SEQ ID NO:2, SEQ ID NO:4, SEQ ID NO:6, SEQ ID NO:8, SEQ ID NO:10, SEQ ID NO:12, and/or SEQ ID NO:14, or homologues thereof. An even more preferred nucleic acid molecule to insert into a recombinant vector includes a nucleic acid molecule represented by SEQ ID NO:1, SEQ ID NO:3, SEQ ID NO:5, SEQ ID NO:7, SEQ ID NO:9, SEQ ID NO:11, and/or SEQ ID NO: 13 or complements thereof. In particularly preferred embodiments portions of a MEKK nucleic acid which encodes a MEKK catalytic domain is used. In another particularly preferred embodiment, at least a portion of a nucleic acid which encodes the portion of a MEKK protein which binds to a MEKK substrate or a MEKK regulatory protein is used.

Suitable host cells for transforming a cell can include any cell capable of producing MEKK proteins of the present invention after being transformed with at least one nucleic acid molecule of the present invention. Host cells can be either untransformed cells or cells that are already transformed with at least one nucleic acid molecule. Suitable host cells of the present invention can include bacterial, fungal (including yeast), insect, animal and plant cells. Preferred host cells include bacterial, yeast, insect and mammalian cells, with mammalian cells being particularly preferred.

A recombinant cell is preferably produced by transforming a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, insect, animal, and/or plant cells. As such, nucleic acid molecules of the present invention can be operatively linked to expression vectors containing regulatory sequences such as promoters, operators, repressors, enhancers, termination sequences, origins of replication, and other regulatory sequences that are compatible with the recombinant cell and that control the expression of nucleic acid molecules of the present invention. As used herein, a transcription control sequence includes a sequence which is capable of controlling the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, and mammalian cells, such as, but not limited to, tac, lac, trp, trc, oxy-pro, omp/lpp, rrnB, bacteriophage lambda (X) (such as $\lambda_{PL}$ and $\lambda_{PR}$ and fusions that include such promoters), bacteriophage T7, T7lac, bacteriophage T3, bacteriophage SP6, bacteriophage SP01, metallothionein, alpha mating factor, baculovirus, vaccinia virus, herpesvirus, poxvirus, adenovirus, simian virus 40, retrovirus actin, retroviral long terminal repeat, Rous sarcoma virus, heat shock, phosphate and nitrate transcription control sequences, as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with a DNA sequence encoding a MEKK protein.

Preferred nucleic acid molecules for insertion into an expression vector include nucleic acid molecules that encode at least a portion of a MEKK protein, or a homologue thereof. A more preferred nucleic acid molecule for insertion into an expression vector includes a nucleic acid molecule encoding at least a portion of an amino acid sequence represented by SEQ ID NO:2, SEQ ID NO:4, SEQ ID NO:6, SEQ ID NO:8, SEQ ID NO:10, SEQ ID NO:12, and/or SEQ ID NO:14 or homologues thereof. An even more preferred nucleic acid molecule for insertion into an expression vector includes a nucleic acid molecule represented by SEQ ID NO:1, SEQ ID NO:3, SEQ ID NO:5, SEQ ID NO:7, SEQ ID NO:9, SEQ ID NO: 11 and/or SEQ ID NO: 13, or complements thereof.

Expression vectors of the present invention may also contain fusion sequences which lead to the expression of inserted nucleic acid molecules of the present invention as fusion proteins. Inclusion of a fusion sequence as part of a MEKK nucleic acid molecule of the present invention can enhance the stability during production, storage and/or use of the protein encoded by the nucleic acid molecule. Furthermore, a fusion segment can function as a tool to simplify purification of a MEKK protein, such as to enable purification of the resultant fusion protein using affinity chromatography. A suitable fusion segment can be a domain of any size that has the desired function (e.g., increased stability and/or purification tool). It is within the scope of the present invention to use one or more fusion segments. Fusion segments can be joined to amino and/or carboxyl termini of a MEKK protein. Linkages between fusion segments and MEKK proteins can be constructed to be susceptible to cleavage to enable straight-forward recovery of the MEKK proteins. Fusion proteins are preferably produced by culturing a recombinant cell transformed with a fusion nucleic acid sequence that encodes a protein including the fusion segment attached to either the carboxyl and/or amino terminal end of a MEKK protein.

Moreover, the gene constructs of the present invention can also be used as a part of a gene therapy protocol to deliver nucleic acids encoding either an agonistic or antagonistic form of one of the subject MEKK proteins. Thus, another aspect of the invention features expression vectors for in vivo or in vitro transfection and expression of a MEKK polypeptide in particular cell types so as to reconstitute the function of, constituitively activate, or alternatively, abrogate the function of a signal pathway dependent on a MEKK activity. Such therapies may useful where the naturally-occurring form of the protein is misexpressed or inappropriately activated; or to deliver a form of the protein which alters differentiation of tissue; or which inhibits neoplastic transformation.

Expression constructs of the subject MEKK polypeptide, and mutants thereof, may be administered in any biologically effective carrier, e.g. any formulation or composition capable of effectively delivering the recombinant gene to cells in vivo. Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically. Furthermore, it will be recognized that the particular gene construct provided for in vivo transduction of MEKK expression are also useful for in vitro transduction of cells, such as for use in the ex vivo tissue culture systems described below.

A preferred approach for in vivo introduction of nucleic acid into a cell is by use of a viral vector containing nucleic acid, e.g. a cDNA, encoding the particular MEKK polypeptide desired. Infect ion of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) *Blood* 76:271). Thus, recombinant retrovirus can be constructed in which part of the retroviral coding sequence (gag, pot, env) has been replaced by nucleic acid encoding one of the subject proteins rendering the retrovirus replication defective. The replication defective retrovirus is then packaged into virions which can be used to infect a target cell through the use of a helper virus by standard techniques.

Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pW[]E and pEM which are well known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including neuronal cells, in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc. Nail. Acad. Sci. USA* 85:3014–3018; Armentano et al. (1990) *Proc. Natl. Acad. Sci. USA* 87:6141–6145; huber et al. (1991) *Proc. Natl. Acad. Sci. USA* 88:8039–8043; Ferry et al. (1991) *Proc. Natl. Acad. Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci. USA* 89:10892–10895; hwu et al. (1993) *J. Immunol* 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein (Roux et al. (1989) *PNAS* 86:9079–9083; Julan et al. (1992) *J Gen Virol* 73:3251–3255; and Goud et al. (1983) *Virology* 163:251–254); or coupling cell surface receptor ligands to the viral env proteins (Neda et al. (1991) *J Biol Chem* 266:14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, can also be used to convert an ecotropic vector in to an amphotropic vector.

Moreover, use of retroviral gene delivery can be further enhanced by the use of tissue- or cell-specific transcriptional regulatory sequences which control expression of the MEKK gene of the retroviral vector.

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See for example Berkner et al. (1988) *Biotechniques* 6:616; Rosenfeld et al. (1991) *Science* 252:431–434; and Rosenfeld et al. (1992) *Cell* 68:143–155.

Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they can be used to infect a wide variety of cell types, including airway epithelium (Rosenfeld et al. (1992) cited supra), endothelial cells (Lemarchand et al. (1992) *Proc. Natl. Acad. Sci. USA* 89:6482–6486), hepatocytes (Herz and Gerard (1993) *Proc. Natl. Acad. Sci. USA* 90:2812–2816) and muscle cells (Quantin et al. (1992) *Proc. Natl. Acad. Sci. USA* 89:2581–2584). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) *Cell* 16:683; Berkner et al., supra; and Graham et al. in *Methods in Molecular Biology*, E. J. Murray, Ed. (Humana, Clifton, N.J., 1991) vol. 7. pp. 109–127). Expression of the inserted MEKK gene can be under control of, for example, the E1A promoter, the major late promoter (MLP) and associated leader sequences, the E3 promoter, or exogenously added promoter sequences.

Yet another viral vector system useful for delivery of one of the subject MEKK genes is the adeno-associated virus (AMINO ACIDSV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J Respir. Cell. Mol. Biol.* 7:349–356; Samulski et al. (1989) *J Virol.* 63:3822–3828; and McLaughlin et al. (1989) *J. Virol.* 62:1963–1973). Vectors containing as little as 300 base pairs of AMINO ACIDSV can be packaged and can integrate. Space for exogenous DNA is limited to about 4.5 kb. An AMINO ACIDSV vector such as that described in Tratschin et al. (1985) Mol. Cell. Biol. 5:3251–3260 can be used to introduce DNA into cells. A variety of nucleic acids have been introduced into different cell types using AMINO ACIDSV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol.* 51:611–619; and Flotte et al. (1993) *J Biol. Chem.* 268:3781–3790).

In addition to viral transfer methods, such as those illustrated above, non-viral methods can also be employed to cause expression of a subject MEKK polypeptide in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject MEKK polypeptide gene by the targeted cell. Exemplary gene delivery systems of this type include liposomal derived systems, polylysine conjugates, and artificial viral envelopes.

In clinical settings, the gene delivery systems for the therapeutic MEKK gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) *PNAS* 91: 3054–3057). A MEKK gene, such as any one of the clones represented in the appended Sequence Listing, can be delivered in a gene therapy construct by electroporation using techniques described, for example, by Dev et al. ((1994) *Cancer Treat Rev* 20:105–115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

Still another aspect of the present invention pertains to recombinant cells, e.g., cells which are transformed with at least one of any nucleic acid molecule of the present invention. A preferred recombinant cell is a cell transformed with at least one nucleic acid molecule that encodes at least a portion of a MEKK protein, or a homologue thereof. A more preferred recombinant cell is transformed with at least one nucleic acid molecule that is capable of encoding at least a portion of an amino acid sequence represented by SEQ ID NO:2, SEQ ID NO:4, SEQ ID NO:6, SEQ ID NO:8, SEQ ID NO:10, SEQ ID NO:12 and/or SEQ ID NO:14, or homologues thereof. An even more preferred recombinant cell is transformed with at least one nucleic acid molecule represented by SEQ ID NO:1, SEQ ID NO:3, SEQ ID NO:5, SEQ ID NO:7, SEQ ID NO:9, SEQ ID NO:11, and/or SEQ ID NO:13, or complements thereof. Particularly preferred recombinant cells include mammalian cells involved in a disease transformed with at least one of the aforementioned nucleic acid molecules.

It may be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids. integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgamo sequences), modification of nucleic acid molecules of the present invention to correspond to the codon usage of the host cell, deletion of sequences that destabilize transcripts, and use of control signals that temporally separate recombinant cell growth from recombinant protein production during fermentation. The activity of an expressed recombinant protein of the present invention may be improved by fragmenting, modifying, or derivatizing the resultant protein.

As used herein, amplifying the copy number of a nucleic acid sequence in a cell can be accomplished either by increasing the copy number of the nucleic acid sequence in the cell's genome or by introducing additional copies of the nucleic acid sequence into the cell by transformation. Copy number amplification is conducted in a manner such that greater amounts of enzyme are produced, leading to enhanced conversion of substrate to product. For example, recombinant molecules containing nucleic acids of the present invention can be transformed into cells to enhance enzyme synthesis. Transformation can be accomplished using any process by which nucleic acid sequences are inserted into a cell. Prior to transformation, the nucleic acid sequence on the recombinant molecule can be manipulated to encode an enzyme having a higher specific activity.

In accordance with the present invention, recombinant cells can be used to produce a MEKK protein of the present invention by culturing such cells under conditions effective to produce such a protein, and recovering the protein. Effective conditions to produce a protein include, but are not limited to, appropriate media, bioreactor, temperature, pH and oxygen conditions that permit protein production. An appropriate, or effective, medium refers to any medium in which a cell of the present invention, when cultured, is capable of producing a MEKK protein. Such a medium is typically an aqueous medium comprising assimilable carbohydrate, nitrogen and phosphate sources, as well as appropriate salts, minerals, metals and other nutrients, such as vitamins. The medium may comprise complex nutrients or may be a defined minimal medium.

A preferred cell to culture is a recombinant cell that is capable of expressing the MEKK protein, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained.

With respect to methods for producing the subject MEKK polypeptide, a host cell transfected with a nucleic acid vector directing expression of a nucleotide sequence encoding the subject polypeptides can be cultured under appropriate conditions to allow expression of the peptide to occur. The cells may be harvested, lysed and the protein isolated. A cell culture includes host cells, media and other byproducts. Suitable media for cell culture are well known in the art. The recombinant MEKK polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant MEKK polypeptide is a fusion protein containing a domain which facilitates its purification, such as GST fusion protein or poly(His) fusion protein.

Cells of the present invention can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art.

Depending on the vector and host system used for production, resultant MEKK proteins may either remain within the recombinant cell or be secreted into the fermentation medium. The phrase "recovering the protein" refers simply to collecting the whole fermentation medium containing the protein and need not imply additional steps of separation or purification. MEKK proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, chromatofocusing and differential solubilization.

Alternatively, a MEKK protein of the present invention can be produced by isolating the MEKK protein from cells or tissues recovered from an animal that normally express the MEKK protein. For example, a cell type, such as T cells, can be isolated from the thymus of an animal. MEKK protein can then be isolated from the isolated primary T cells using standard techniques described herein.

The availability of purified and recombinant MEKK polypeptides as described in the present invention facilitates the development of assays which can be used to screen for drugs, including MEKK homologs, which are either agonists or antagonists of the normal cellular function of the subject MEKK polypeptides, or of their role in the pathogenesis of cellular differentiation and/or proliferation, and disorders related thereto. In one embodiment, the assay evaluates the ability of a compound to modulate binding between a MEKK polypeptide and a molecule that interacts either upstream or downstream of the MEKK polypeptide in the a cellular signaling pathway. A variety of assay formats will suffice and, in light of the present inventions, will be comprehended by a skilled artisan.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with upstream or downstream elements. Accordingly, in an exemplary screening assay of the present invention, the compound of interest is contacted with proteins which may function upstream (including both activators and repressors of its activity such as, Ras, Rac, Cdc 42 or Rho or other Ras superfamily members) or to proteins or nucleic acids which may function downstream of the MEKK polypeptide, whether they are positively or negatively regulated by it. For convenience, such polypeptides of a signal transduction pathway which interact directly with MEKK will be referred to below as MEKK-binding proteins (MEKK-bp). These proteins include the downstream targets of MEKKs, namely, members of the MAP kinase kinase family (MEKs or MKKs), as MEK1, MEK2, MKK1, MKK2, the stress-activated kinases (SEKs), also known as the Jun kinase kinases (JNKKs), MEKK3 and MEKK4 or the like. Other downstream targets of the MEKK family can include proteins from the mammalian MAP kinase family which includes, for example, the extracellular signal-regulated protein kinases (ERKs), c-Jun $NH_2$-terminal kinases (JNKs, or SAPKs), and the so-called "p38 subgroup" kinases (p38 kinases).

To the mixture of the compound and the MEKK-bp is then added a composition containing a MEKK polypeptide. Detection and quantification of complexes including MEKK and the MEKK-bp provide a means for determining a compound's efficacy at inhibiting (or potentiating) complex formation between MEKK and the MEKK-binding protein. The efficacy of the compound can be assessed by generating dose response curves from data obtained using various concentrations of the test compound. Moreover, a control assay can also be performed to provide a baseline for comparison. In the control assay, isolated and purified MEKK polypeptide is added to a composition containing the MEKK-binding protein, and the formation of a complex is quantitated in the absence of the test compound.

In an exemplary embodiment the Ras effector domain or MEKK4 or MEKK4.2 sequence IIGQVCDTPKSYDNVM-HVGLR is used to inhibit the interaction of a MEKK protein with a MEKK binding protein.

Complex formation between the MEKK polypeptide and a MEKK-binding protein may be detected by a variety of techniques. Modulation of the formation of complexes can be quantitated using, for example, detectably labeled proteins such as radiolabeled, fluorescently labeled, or enzymatically labeled MEKK polypeptides, by immunoassay, or by chromatographic detection.

Typically, it will be desirable to immobilize either MEKK or its binding protein to facilitate separation of complexes from uncomplexed forms of one or both of the proteins, as well as to accommodate automation of the assay. Binding of the two proteins, in the presence and absence of a candidate agent, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/MEKK (GST/MEKK) fusion proteins can be adsorbed onto glutathione sepharose beads (Sigma Chemical, St. Louis, Mo.) or glutathione derivatized microtitre plates? which are then combined with the MEKK-bp, e.g. an $^{35}$S-labeled, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintilant), or in the supernatant after the complexes are subsequently dissociated. Alternatively, the complexes can be dissociated from the matrix, separated by SDS-PAGE, and the level of MEKK-binding protein found in the bead fraction quantitated from the gel using standard electrophoretic techniques such as described in the appended examples.

Other techniques for immobilizing proteins on matrices are also available for use in the subject assay. For instance, either MEKK or its cognate binding protein can be immobilized utilizing conjugation of biotin and streptavidin. For instance, biotinylated MEKK molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with MEKK but which do not interfere with binding of upstream or downstream elements can be derivatized to the wells of the plate, and MEKK trapped in the wells by antibody conjugation. As above, preparations of a MEKK-binding protein and a test compound are incubated in the MEKK-presenting wells of the plate, and the amount of complex trapped in the well can be quantitated. Exemplary methods for detecting such complexes, in addition to those described above for the GST-immobilized complexes, include immunodetection of complexes using antibodies reactive with the MEKK binding protein, or which are reactive with the MEKK protein and compete with the binding protein; as well as enzyme-linked assays which rely on detecting an enzymatic activity associated with the binding protein, either intrinsic or extrinsic activity. In the instance of the latter, the enzyme can be chemically conjugated or provided as a fusion protein with the MEKK-bp. To illustrate, the MEKK-bp can be chemically cross-linked or genetically fused with horseradish peroxidase, and the amount of polypeptide trapped in the complex can be assessed with a chromogenic substrate of the enzyme, e.g. 3,3'-diamino-benzadine terahydrochloride or 4-chloro-1-napthol. Likewise, a fusion protein comprising the polypeptide and glutathione-S-transferase can be provided, and complex formation quantitated by detecting the GST activity using 1-chloro-2,4-dinitrobenzene (Habig et al (1974) J Biol Chem 249:7130).

For processes which rely on immunodetection for quantitating one of the proteins trapped in the complex, antibodies against the protein, such as anti-MEKK antibodies, can be used. Alternatively, the protein to be detected in the complex can be "epitope tagged" in the form of a fusion protein which includes, in addition to the MEKK sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) J Biol Chem 266:21150–21157) which includes a 10-residue sequence from c-myc, as well as the pFLAG system (International Biotechnologies, Inc.) or the pEZZ-protein A system (Pharamacia, N.J.).

In addition to cell-free assays, such as described above, the readily available source of vertebrate MEKK proteins provided by the present invention also facilitates the generation of cell-based assays for identifying small molecule agonists/antagonists and the like. Cells which are sensitive to MEKK-mediated signal transduction events can be caused to overexpress a recombinant MEKK protein in the presence and absence of a test agent of interest, with the assay scoring for modulation in MEKK-dependent responses by the target cell mediated by the test agent. As with the cell-free assays, agents which produce a statistically significant change in MEKK-dependent signal transduction (either inhibition or potentiation) can be identified.

For example, as described in the appended examples, overexpression of MEKK1 and MEKK3 (and possibly MEKK2 and MEKK4) in certain cells can cause constitutive induction of apoptotic pathways and result in cell death. Accordingly, such recombinant cells can be used to identify inhibitors of MEKK protein signaling by the compound's ability to inhibit signal transduction events downstream of the MEKK proteins and thereby rescue the cell from apoptosis. To illustrate, the recombinant MEKK1 cells of Example 18 or 19 can be contacted with a panel of test compounds, and inhibitors scored by the ability to rescue the cells from an apoptotic fate (such as may be detected by use of dyes such as Hoechst 33258). Compounds which cause a statistically significant decrease in apoptosis of the MEKK1-overexpressing cells can be selected for further testing.

In another embodiment of a drug screening, a two hybrid assay can be generated with a MEKK and MEKK-binding protein. This assay permits the detection of protein-protein interactions in yeast such that drug dependent inhibition or potentiation of the interaction can be scored. As an illustrative example, GAL4 protein is a potent activator of transcription in yeast grown on galactose. The ability of GAL4 to activate transcription depends on the presence of an N-terminal sequence capable of binding to a specific DNA sequence (UASG) and a C-teminal domain containing a transcriptional activator. A sequence encoding a MEKK protein, "A", may be fused to that encoding the DNA binding domain of the GAL4 protein. A second hybrid protein may be created by fusing sequence encoding the GAL4 transactivation domain to sequence encoding a MEKK-bp, "B". If protein "A" and protein "B" interact, that interaction serves to bring together the two domains of GAL4 necessary to activate transcription of a UASG-containing gene. In addition to co-expressing plasmids encoding both hybrid proteins, yeast strains appropriate for the detection of protein-protein interactions would contain, for example, a GAL1-lacZ fusion gene to permit detection of transcription from a UASG sequence. Other examples of two-hybrid assays or interaction trap assays are known in the art.

In an illustrative embodiment, a portion of MEKK4 providing a Rac/Cdc42 binding site is provided in one fusion protein, along with a second fusion protein including a Rac/Cdc42 polypeptide. This embodiment of the subject assay permits the screening of compounds which inhibit or potentiate the binding of MEKK4 and Cdc42.

Phosphorylation assays may also be used. MEKK binding proteins can be tested for their ability to phosphorylate substrates in addition, compounds that inhibit or activate MEKK regulated pathways and phenotypic responses can be tested.

Furthermore, each of the assay systems set out above can be generated in a "differential" format. That is, the assay format can provide information regarding specificity as well as potency. For instance, side-by-side comparison of a test compound's effect on different MEKKs can provide information on selectivity, and permit the identification of compounds which selectively modulate the bioactivity of only a subset of the MEKK family.

The present invention also includes a method to identify compounds capable of regulating signals initiated from a receptor on the surface of a cell, such signal regulation involving in some respect, MEKK protein. Such a method comprises the steps of: (a) contacting a cell containing a MEKK protein with a putative regulatory compound; (b) contacting the cell with a ligand capable of binding to a receptor on the surface of the cell; and (c) assessing the ability of the putative regulatory compound to regulate cellular signals by determining activation of a member of a MEKK-dependent pathway of the present invention. A preferred method to perform step (c) comprises measuring the phosphorylation of a member of a MEKK-dependent pathway. Such measurements can be performed using immunoassays having antibodies specific for phosphotyrosines, phosphoserines and/or phosphothreonines. Another preferred method to perform step (c) comprises measuring the ability of the MEKK protein to phosphorylate a substrate molecule comprising a protein including MKK1, MKK2, MKK3, or MKK4, Raf-1, Ras-GAP and neurofibromin using methods described herein. Preferred substrates include MEK1, MEK2, JNKK1 and JNKK2. Yet another preferred method to perform step (c) comprises determining the ability of MEKK protein to bind to Ras, rac or Cdc 42 protein. In particular, determining the ability of MEKK protein to bind to GST-Ras$^{V12}$(GTP$\gamma$S) or GST-Rac$^{v14}$(GTP$\gamma$S).

Putative compounds as referred to herein include, for example, compounds that are products of rational drug design, natural products and compounds having partially defined signal transduction regulatory properties. A putative compound can be a protein-based compound, a carbohydrate-based compound, a lipid-based compound, a nucleic acid-based compound, a natural organic compound, a synthetically derived organic compound, an anti-idiotypic antibody and/or catalytic antibody, or fragments thereof. A putative regulatory compound can be obtained, for example, from libraries of natural or synthetic compounds, in particular from chemical or combinatorial libraries (i.e., libraries of compounds that differ in sequence or size but that have the same building blocks; see for example, U.S. Pat. Nos. 5,010,175 and 5,266,684 of Rutter and Santi) or by rational drug design.

In another embodiment, a method to identify compounds capable of regulating signal transduction in a cell can comprise the steps of: (a) contacting a putative inhibitory compound with a MEKK protein to form a reaction mixture; (b) contacting the reaction mixture with MEK protein; and (c) assessing the ability of the putative inhibitory compound to inhibit phosphorylation of the MEK protein by the MEKK protein. The results obtained from step (c) can be compared with the ability of a putative inhibitory compound to inhibit the ability of Raf protein to phosphorylate MEK protein, to determine if the compound can selectively regulate signal transduction involving MEKK protein independent of Raf protein. MEKK, MEK and Raf proteins used in the foregoing methods can be recombinant proteins or naturally-derived proteins.

In another embodiment, a method to identify compounds capable of regulating signal transduction in a cell can comprise the steps of: (a) contacting a putative inhibitory compound with either a MEKK protein or a Ras superfamily protein, or functional equivalents thereof, to formn a first reaction mixture; (b) combining the first reaction mixture with either Ras protein (or a functional equivalent thereof) if MEKK protein was used in the first reaction mixture, or MEKK protein (or a functional equivalent thereof) if Raf protein was added to the first reaction mixture; and (c) assessing the ability of the putative inhibitory compound to inhibit the binding of the Ras protein to the MEKK protein. The lack of binding of the MEKK protein to the Ras protein indicates that the putative inhibitory compound is effective at inhibiting binding between MEKK and Ras. MEKK and Ras proteins used in the foregoing method can be recombinant proteins or naturally-derived proteins. Preferred Ras superfamily proteins for use with the foregoing method includes, but is not limited to, GST-Ras$^{v12}$(GTPγS) or GST-Rac$^{v14}$(GTPγS).

The portion of MEKK1, for example, which binds to Ras has been identified. The binding of MEKK1 and Ras occurs via the COOH kinase catalytic domain of MEKK1 and residues 17–42 of Ras as determined by the ability of a Ras effector peptide to block the interaction. In addition, the binding of MEKK4. 1 and MEKK4.2 to Rac has been localized to the amino acid sequence IIGQVCDTPKSYD-NVMHVGLR as described in the appended Examples. Interestingly this sequence has some homology to the Cdc42/Rac interactive binding (CRIB) region. The consensus CRIB sequence, ISXPXXFXIIXXIIVG, even with slight variation within this core sequence, confers binding to Cdc42 and/or Rac GTPases (Burbelo et al. (1995) J. Biol Chem 270:29071–29074). Others have posutlated that Rac1 is an intermediate between Ha-Ras and MEKK in the signaling cascade leading from growth factor receptors and v-Src to JNK activation based on experiments with dominant interfering alleles (Minden et al. (1995) Cell. 81:1147–1157).

Preferred MEKK protein for use with the method includes recombinant MEKK protein. More preferred MEKK protein includes at least a portion of a MEKK protein having the kinase domain of MEKK. Even more preferred MEKK protein includes a protein encoded by p-MEKK1, MEKKCOOH, and/or MEKKCOOH-His (see appended Examples). MEKK proteins comprising the aas 409–672 of SEQ ID NO:2, 1329–1594 of SEQ ID NO:4, 361–620 of SEQ ID NOS: 6 or 8, amino acids 366–626 of SEQ ID NO: 10, 631–890 of SEQ ID NO: 12, or amino acids 1338–1597 of SEQ ID NO: 14 are also preferred.

The inhibition of binding of MEKK protein to Ras superfamily protein can be determined using a variety of methods known in the art. For example, immunoprecipitation assays can be performed to determine if MEKK and Ras co-precipitate. In addition, immunoblot assays can be performed to determine if MEKK and Ras co-migrate when resolved by gel electrophoresis. Another method to determine binding of MEKK to Ras comprises combining a substrate capable of being phosphorylated by MEKK protein with the Ras protein of the reaction mixture of step (b). In this method, Ras protein is separated from the reaction mixture of step (b) following incubation with MEKK protein. If MEKK protein is able to bind to the Ras, then the bound MEKK will be co-isolated with the Ras protein. The substrate is then added to the isolated Ras protein. Any co-isolated MEKK protein will phosphorylate the substrate. Thus, inhibition of binding between MEKK and Ras can be measured by determining the extent of phosphorylation of the substrate upon combination with the isolated Ras protein. The extent of phosphorylation can be determined using a variety of methods known in the art, including kinase assays using [γ$^{32}$P]ATP. Similar assays can be performed with MEKK proteins and their binding to other GTP-binding proteins in the Ras superfamily (i.e. Rac, Cdc 42, or Rho).

Moreover, one can determine whether the site of inhibitory action along a particular signal transduction pathway involves both Raf and MEKK proteins by carrying out experiments set forth above (i.e., see discussion on MEKK-dependent pathways).

Another aspect of the present invention includes a kit to identify compounds capable of regulating signals initiated from a receptor on the surface of a cell, such signals involving in some respect, MEKK protein. Such kits include: (a) at least one cell containing MEKK protein; (b) a ligand capable of binding to a receptor on the surface of the cell; and (c) a means for assessing the ability of a putative regulatory compound to alter phosphorylation of the MEKK protein. Such a means for detecting phosphorylation include methods and reagents known to those of skill in the art, for example, phosphorylation can be detected using antibodies specific for phosphorylated amino acid residues, such as tyrosine, serine and threonine. Using such a kit, one is capable of determining, with a fair degree of specificity, the location along a signal transduction pathway of particular pathway constituents, as well as the identity of the constituents involved in such pathway, at or near the site of regulation.

In another embodiment, a kit of the present invention can include: (a) MEKK protein; (b) MEKK substrate, such as MEK; and (c) a means for assessing the ability of a putative inhibitory compound to inhibit phosphorylation of the MEKK substrate by the MEKK protein. A kit of the present invention can further comprise Raf protein and a means for detecting the ability of a putative inhibitory compound to inhibit the ability of Raf protein to phosphorylate the MEK protein.

In yet another embodiment, a mammalian MEKK gene can be used to rescue a yeast cell having a defective ste11 (or byr2) gene, such as a temperature sensitive mutant ste11 mutant (cf., Francois et al. (1991) J Biol Chem 266:6174–80; and Jenness et al. (1983) Cell 35:521–9). For example, a humanized yeast can be generated by amplifying the coding sequence of the human MEKK clone, and subcloning this sequence into a vector which contains a yeast promoter and termination sequences flanking the MEKK coding sequences. This plasmid can then be used to transform an ste11$^{TS}$ mutant. To assay growth rates, cultures of the transformed cells can be grown at an permissive temperature for the TS mutant. Turbidity measurements, for example, can be used to easily determine the growth rate. At the non-permissive temperature, pheromone responsivenes of the yeast cells becomes dependent upon expression of the human MEKK protein. Accordingly, the humanized yeast cells can be utilized to identify compounds which inhibit the action of the human MEKK protein. It is also deemed to be within the scope of this invention that the humanized yeast cells of the present assay can be generated so as to comprise other human cell-cycle proteins. For example, human MEK and human MAPK can also be expressed in the yeast cell in place of ste7 and Fus3/Kss 1. In this manner, the reagent cells of the present assay can be generated to more closely approximate the natural interactions which the mammalian MEKK protein might experience.

Furthermore, certain formats of the subject assays can be used to identify drugs which inhibit proliferation of yeast cells or other lower eukaryotes, but which have a substantially reduced effect on mammalian cells, thereby improving therapeutic index of the drug as an anti-mycotic agent. For instance, in one embodiment, the identification of such compounds is made possible by the use of differential screening assays which detect and compare drug-mediated disruption of binding between two or more different types of MEKK/MEKK-bp complexes, or which differentially inhibit the kinase activity of, for example, ste11 relative to a mammalian MEKK. Differential screening assays can be used to exploit the difference in drug-mediated disruption of human MEKK complexes and yeast ste11/byr2 complexes in order to identify agents which display a statistically significant increase in specificity for disrupting the yeast complexes (or kinase activity) relative to the human complexes. Thus, lead compounds which act specifically to inhibit proliferation of pathogens, such as fungus involved in mycotic infections, can be developed. By way of illustration, the present assays can be used to screen for agents which may ultimately be useful for inhibiting at least one fungus implicated in such mycosis as candidiasis, aspergillosis, mucormycosis, blastomycosis, geotrichosis, cryptococcosis, chromoblastomycosis, coccidioidomycosis, conidiosporosis, histoplasmosis, maduromycosis, rhinosporidosis, nocaidiosis, para-actinomycosis, penicilliosis, monoliasis, or sporotrichosis. For example, if the mycotic infection to which treatment is desired is candidiasis, the present assay can comprise comparing the relative effectiveness of a test compound on mediating disruption of a human MEKK with its effectiveness towards disrupting the equivalent ste1/byr2 kinase from genes cloned from yeast selected from the group consisting of *Candida albicans, Candida stellatoidea, Candida tropicalis, Candida parapsilosis, Candida krusei, Candida pseudotropicalis, Candida quillermondii,* or *Candida rugosa.* Likewise, the present assay can be used to identify anti-fungal agents which may have therapeutic value in the treatment of aspergillosis by making use of genes cloned from yeast such as *Aspergillus fumigatus, Aspergillus flavus, Aspergillus niger, Aspergillus nidulans,* or *Aspergillus terreus.* Where the mycotic infection is mucormycosis, the complexes can be derived from yeast such as *Rhizopus arrhizus, Rhizopus oryzae, Absidia corymbifera, Absidia ramosa,* or *Mucor pusillus.* Sources of other ste1/byr2 homologs for comparison with a human MEKK includes the pathogen *Pneumocystis carinii.*

Another aspect of the present invention relates to the treatment of an animal having a medical disorder that is subject to regulation or cure by manipulating a signal transduction pathway in a cell involved in the disorder. Such medical disorders include disorders which result from abnormal cellular growth or abnormal production of secreted cellular products. In particular, such medical disorders include, but are not limited to, cancer, autoimmune disease, inflammatory responses, allergic responses and neuronal disorders, such as Parkinson's disease and Alzheimer's disease. Preferred cancers subject to treatment using a method of the present invention include, but are not limited to, small cell carcinomas, non-small cell lung carcinomas with overexpressed EGF receptors, breast cancers with overexpressed EGF or Neu receptors, tumors having overexpressed growth factor receptors of established autocrine loops and tumors having overexpressed growth factor receptors of established paracrine loops. According to the present invention, the term treatment can refer to the regulation of the progression of a medical disorder or the complete removal of a medical disorder (e.g., cure). Treatment of a medical disorder can comprise regulating the signal transduction activity of a cell in such a manner that a cell involved in the medical disorder no longer responds to extracellular stimuli (e.g., growth factors or cytokines), or the killing of a cell involved in the medical disorder through cellular apoptosis.

According to this aspect of the present invention relates to a method of inducing and/or maintaining a differentiated state, enhancing survival, and/or promoting (or alternatively inhibiting) proliferation of a cell responsive to a growth factor, morphogen or other environmental cue which effects the cell through at least one signal transduction pathway which includes a MEKK protein. In general, the method comprises contacting the cells with an amount of an agent which significantly (statistical) modulates MEKK-dependent signaling by the factor. For instance, it is contemplated by the invention that, in light of the present finding of an apparently broad involvement of members of the MEKK protein family in signal pathways implicated in the formation of ordered spatial arrangements of differentiated tissues in vertebrates, the subject method could be used to generate and/or maintain an array of different vertebrate tissue both in vitro and in vivo. A "MEKK therapeutic," whether inductive or anti-inductive with respect to signaling by a MEKK-dependent pathway, can be, as appropriate, any of the preparations described above, including isolated polypeptides, gene therapy constructs, antisense molecules, peptidomimetics or agents identified in the drug assays provided herein.

There are a wide variety of pathological cell proliferative conditions for which MEKK therapeutics of the present invention can be used in treatment. For instance, such agents can provide therapeutic benefits where the general strategy being the inhibition of an anomalous cell proliferation. Diseases that might benefit from this methodology include, but are not limited to various cancers and leukemias, psoriasis, bone diseases, fibroproliferative disorders such as involving connective tissues, atherosclerosis and other smooth muscle proliferative disorders, as well as chronic inflammation.

In addition to proliferative disorders, the present invention contemplates the use of MEKK therapeutics for the treatment of differentiative disorders which result from. for example, de-differentiation of tissue which may (optionally) be accompanied by abortive reentry into mitosis, e.g. apoptosis. Such degenerative disorders include chronic neurodegenerative diseases of the nervous system, including Alzheimer's disease, Parkinson's disease, Huntington's chorea, amylotrophic lateral sclerosis and the like, as well as spinocerebellar degenerations. Other differentiative disorders include, for example, disorders associated with connective tissue, such as may occur due to de-differentiation of chondrocytes or osteocytes, as well as vascular disorders which involve de-differentiation of endothelial tissue and smooth muscle cells, gastric ulcers characterized by degenerative changes in glandular cells, and renal conditions marked by failure to differentiate, e.g. Wilm's tumors.

It will also be apparent that, by transient use of modulators of MEKK pathways, in vivo reformation of tissue can be accomplished, e.g. in the development and maintenance of organs. By controlling the proliferative and differentiative potential for different cells, the subject MEKK therapeutics can be used to reform injured tissue, or to improve grafting and morphology of transplanted tissue. For instance, MEKK agonists and antagonists can be employed in a differential manner to regulate different stages of organ repair after physical, chemical or pathological insult. For example, such regimens can be utilized in repair of cartilage, increasing bone density, liver repair subsequent to a partial hepatectomy, or to promote regeneration of lung tissue in the treatment of emphysema.

To further illustrate, the present method is applicable to cell culture techniques. In vitro neuronal culture systems have proved to be fundamental and indispensable tools for the study of neural development, as well as the identification of trophic and growth factors such as nerve growth factor (NGF), ciliary trophic factors (CNTF), and brain derived neurotrophic factor (BDNF). Once a neuronal cell has become terminally-differentiated it typically will not change to another terminally differentiated cell-type. However, neuronal cells can nevertheless readily lose their differentiated state. This is commonly observed when they are grown in culture from adult tissue, and when they form a blastema during regeneration. The present method provides a means for ensuring an adequately restrictive environment in order to maintain neuronal cells at various stages of differentiation, and can be employed, for instance, in cell cultures designed to test the specific activities of other trophic factors. In such embodiments of the subject method, the cultured cells can be contacted with a MEKK therapeutic in order to induce neuronal differentiation (e.g. of a stem cell), or to maintain the integrity of a culture of terminally-differentiated neuronal cells by preventing loss of differentiation. As described in PCT publication PCT/US94/11745, the default fate of ectodermal tissue is neuronal rather than mesodermal and/or epidermal. In particular, it has been reported that preventing or antagonizing signaling by activin can result in differentiation along a neuronal-fated pathway. The potential role of MEKK signaling in mesoderm induction by activin, and consequently neuronal patterning and development, is further supported by, for example, LaBonne et al. (1994) *Development* 120: 463–72, and LaBonne et al. (1995) *Development* 121: 1475–86. Accordingly, the manipulating the activities of such MAP kinases as the ERKs, p38 kinases and JNKs, the subject method can be used advantagously to maintain a differentiated state, or at least to potentiate the activity of a maintenance factor such as CNTF, NGF or the like.

In an exemplary embodiment, the role of the MEKK therapeutic in the present method to culture, for example, stem cells, can be to potentiate differentiation of uncommitted progenitor cells and thereby give rise to a committed progenitor cell, or to cause further restriction of the developmental fate of a committed progenitor cell towards becoming a terminally-differentiated neuronal cell. For example, the present method can be used in vitro as part of a regimen for inducution and/or maintenance of the differentiation of neural crest cells into glial cells, schwann cells, chromaffin cells, cholinergic sympathetic or parasympathetic neurons, as well as peptidergic and serotonergic neurons. The MEKK therapeutic can be used alone, or can be used in combination with other neurotrophic factors which act to more particularly enhance a particular differentiation fate of the neuronal progenitor cell. In the later instance, a MEKK therapeutic might be viewed as ensuring that the treated cell has achieved a particular phenotypic state such that the cell is poised along a certain developmental pathway so as to be properly induced upon contact with a secondary neurotrophic factor. In similar fashion, even relatively undifferentiated stem cells or primitive neuroblasts can be maintained in culture and caused to differentiate by treatment with MEKK therapeutics. Exemplary primitive cell cultures comprise cells harvested from the neural plate or neural tube of an embryo even before much overt differentiation has occurred.

Yet another aspect of the present invention concerns the application of MEKK therapeutics to modulating morphogenic signals involved in other vertebrate organogenic pathways in addition to neuronal differentiation. Thus, it is contemplated by the invention that compositions comprising MEKK therapeutics can also be utilized for both cell culture and therapeutic methods involving generation and maintenance of non-neuronal tissue.

In one embodiment, the present invention makes use of the notion that MEKK proteins are likely to be involved in controlling the development and formation of the digestive tract, liver, pancreas, lungs, and other organs which derive from the primitive gut. As described in the Examples below, MEKK proteins are presumptively involved in cellular activity in response to inductive signals. Additionally, it has been demonstrated that the activity of a JNK enzyme is markedly stimulated during regeneration after partial hepatectomy, with a concomitant increase in phosphorylated c-Jun. Accordingly, MEKK agonists and/or antagonists can be employed in the development and maintenance of an artificial liver which can have multiple metabolic functions of a normal liver. In an exemplary embodiment, MEKK therapeutics can be used to induce and/or maintain differentiation of digestive tube stem cells to form hepatocyte cultures which can be used to populate extracellular matrices, or which can be encapsulated in biocompatible polymers, to form both implantable and extracorporeal artificial livers.

In another embodiment, compositions of MEKK therapeutics can be utilized in conjunction with transplantation of such artificial livers, as well as embryonic liver structures, to promote intraperitoneal implantation, vascularization, and in vivo differentiation and maintenance of the engrafted liver tissue.

Similar utilization of MEKK therapeutics are contemplated in the generation and maintenance of pancreatic cultures and artificial pancreatic tissues and organs.

In another embodiment, in vitro cell cultures can be used for the identification, isolation, and study of genes and gene products that are expressed in response to disruption of MEKK-mediated signal transduction, and therefore likely involved in development and/or maintenance of tissues. These genes would be "downstream" of the MEKK gene products. For example, if new transcription is required for a MEKK-mediated induction, a subtractive cDNA library prepared with control cells and cells overexpressing a MEKK gene can be used to isolate genes that are turned on or turned off by this process. The powerful subtractive library methodology incorporating PCR technology described by Wang and Brown is an example of a methodology useful in conjunction with the present invention to isolate such genes (Wang et al. (1991) *PNAS* 88:11505–11509). Utilizing control and treated cells, the induced pool can be subtracted from the uninduced pool to isolate genes that are turned on, and then the uninduced pool from the induced pool for genes that are turned off. From this screen, it is expected that two classes of mRNAs can be identified. Class I RNAs would include those RNAs expressed in untreated cells and reduced or eliminated in induced cells, that is the down-regulated population of RNAs. Class II RNAs include RNAs that are upregulated in response to induction and thus more abundant in treated than in untreated cells. RNA extracted from treated vs untreated cells can be used as a primary test for the classification of the clones isolated from the libraries.

In still another embodiment of the present invention, compositions comprising MEKK therapeutics can be used for the in vitro generation of skeletal tissue, such as from skeletogenic stem cells, as well as for the in vivo treatment of skeletal tissue deficiencies. The present invention contemplates the use of MEKK therapeutics which upregulate or mimic the inductive activity of a bone morphogenetic protein (BMP) or TGF-β, such as may be useful to control chondrogenesis and/or osteogenesis. By "skeletal tissue deficiency", it is meant a deficiency in bone or other skeletal connective tissue at any site where it is desired to restore the bone or connective tissue, no matter how the deficiency originated, e.g. whether as a result of surgical intervention, removal of tumor, ulceration, implant, fracture, or other traumatic or degenerative conditions, so long as modulation of a TGF-β inductive response is appropriate.

For instance, the present invention makes available effective therapeutic methods and MEKK therapeutic compositions for restoring cartilage function to a connective tissue. Such methods are useful in, for example, the repair of defects or lesions in cartilage tissue which is the result of degenerative wear such as that which results in arthritis, as well as other mechanical derangements which may be caused by trauma to the tissue, such as a displacement of torn meniscus tissue, meniscectomy, a Taxation of a joint by a torn ligament, malignment of joints, bone fracture, or by hereditary disease. The present reparative method is also useful for remodeling cartilage matrix, such as in plastic or reconstructive surgery, as well as periodontal surgery. The present method may also be applied to improving a previous reparative procedure, for example, following surgical repair of a meniscus, ligament, or cartilage. Furthermore, it may prevent the onset or exacerbation of degenerative disease if applied early enough after trauma.

The present invention further contemplates the use of the subject method in the field of cartilage transplantation and prosthetic device therapies. To date, the growth of new cartilage from either transplantation of autologous or allogenic cartilage has been largely unsuccessful. Problems arise, for instance, because the characteristics of cartilage and fibrocartilage varies between different tissue: such as between articular, meniscal cartilage, ligaments, and tendons, between the two ends of the same ligament or tendon, and between the superficial and deep parts of the tissue. The zonal arrangement of these tissues may reflect a gradual change in mechanical properties, and failure occurs when implanted tissue, which has not differentiated under those conditions, lacks the ability to appropriately respond. For instance, when meniscal cartilage is used to repair anterior cruciate ligaments, the tissue undergoes a metaplasia to pure fibrous tissue. By helping to control chondrogenesis, the subject method can be used to particularly addresses this problem, by causing the implanted cells to become more adaptive to the new environment and effectively resemble hypertrophic chondrocytes of an earlier developmental stage of the tissue. Thus, the action of chondrogensis in the implanted tissue, as provided by the subject method, and the mechanical forces on the actively remodeling tissue can synergize to produce an improved implant more suitable for the new function to which it is to be put.

In similar fashion, the subject method can be applied to enhancing both the generation of prosthetic cartilage devices and to their implantation. In one embodiment of the subject method, the implants are contacted with a MEKK therapeutic during the culturing process so as to induce and/or maintain differentiated chondrocytes in the culture in order to further stimulate cartilage matrix production within the implant. In such a manner, the cultured cells can be caused to maintain a phenotype typical of a chondrogenic cell (i.e. hypertrophic), and hence continue the population of the matrix and production of cartilage tissue.

In another embodiment, the implanted device is treated with a MEKK therapeutic in order to actively remodel the implanted matrix and to make it more suitable for its intended function. As set out above with respect to tissue transplants, the artificial transplants suffer from the same deficiency of not being derived in a setting which is comparable to the actual mechanical environment in which the matrix is implanted. The activation of the chondrocytes in the matrix by the subject method can allow the implant to acquire characteristics similar to the tissue for which it is intended to replace.

In yet another embodiment, the subject method is used to enhance attachment of prosthetic devices. To illustrate, the subject method can be used in the implantation of a periodontal prosthesis, wherein the treatment of the surrounding connective tissue stimulates formation of periodontal ligament about the prosthesis, as well as inhibits formation of fibrotic tissue proximate the prosthetic device.

In still further embodiments, the subject method can be employed for the generation of bone (osteogenesis) at a site in the animal where such skeletal tissue is deficient. A variety of factors which may signal through MEKK proteins are associated with the hypertrophic chondrocytes that are ultimately replaced by osteoblasts as well as the production of bone matrix by osteocytes. Consequently, administration of a MEKK therapeutic can be employed as part of a method for treating bone loss in a subject, e.g. to prevent and/or reverse osteoporosis and other osteopenic disorders, as well as to regulate bone growth and maturation. For example, preparations comprising MEKK therapeutics can be employed, for example, to induce endochondral ossification by mimicking or potentiating the activity of a BMP, at least so far as to facilitate the formation of cartilaginous tissue precursors to form the "model" for ossification. Therapeutic compositions of such MEKK therapeutics can be supplemented, if required, with other osteoinductive factors, such as bone growth factors (e.g. TGF-β factors, such as the bone morphogenetic factors BMP-2 and BMP-4, as well as activin), and may also include, or be administered in combination with, an inhibitor of bone resorption such as estrogen, bisphosphonate, sodium fluoride, calcitonin, or tamoxifen, or related compounds.

In yet another embodiment, treatment with a MEKK therapeutic may permit disruption of autocrine loops, such as PDGF autostimulatory loops, believed to be involved in the neoplastic transformation of several neuronal tumors. Modulation of certain of the MEKK proteins may, therefore, be of use to either prevent de-differentiation into mitotic phenotype, or even to induce apoptosis in such cells. Accordingly, the subject MEKK therapeutics may be useful in the treatment of, for example, malignant gliomas, medulloblastomas, neuroectodermal tumors, and ependymonas.

For certain cell-types, particularly in epithelial and hemopoietic cells, normal cell proliferation is marked by responsiveness to negative autocrine or paracrine growth regulators. This is generally accompanied by differentiation of the cell to a post-mitotic phenotype. However, it has been observed that a significant percentage of human cancers derived from these cells types display a reduced responsiveness to growth regulators such as TGFβ. For instance, some tumors of colorectal, liver epithelial, and epidermal origin show reduced sensitivity and resistance to the growth-inhibitory effects of TGFβ as compared to their normal counterparts. Treatment of such tumors with MEKK therapeutics provides an opportunity to mimic the effective function of TGFβ-mediated inhibition by constitutive activation of that pathway, and/or offset other competing pathways which become dominant upon lose of TGFβ responsiveness.

To further illustrate the use of the subject method, the therapeutic application of a MEKK therapeutic can be used in the treatment of a neuroglioma. Gliomas account for 40–50% of intracranial tumors at all ages of life. Despite the increasing use of radiotherapy, chemotherapy, and sometimes immunotherapy after surgery for malignant glioma, the mortality and morbidity rates have not substantially improved. However, there is increasing experimental and clinical evidence that for a significant number of gliomas, loss of TGFβ responsiveness is an important event in the loss of growth control. Where the cause of decreased responsivenessis due to loss of receptor or loss of other TGFβ signal transduction downstream of the receptor, treatment with a MEKK therapeutic can be used to constitutively activate the TGFβ pathway and restore growth inhibition. Alternatively, by manipulation of the level activation of the ERKs, apoptosis may be induced.

The subject MEKK therapeutics can also be used in the treatment of hyperproliferative vascular disorders, e.g. smooth muscle hyperplasia (such as atherosclerosis) or restinosis, as well as other disorders characterized by fibrosis, e.g. rheumatoid arthritis, insulin dependent diabetes mellitus, glomerulonephritis, cirrhosis, and scleroderma, particularly proliferative disorders in which aberrant autocrine or paracrine signaling is implicated.

For example, restinosis continues to limit the efficacy of coronary angioplasty despite various mechanical and pharmaceutical interventions that have been employed. An important mechanism involved in normal control of intimal proliferation of smooth muscle cells appears to be the induction of autocrine and paracrine TGFβ inhibitory loops in the smooth muscle cells (Scott-Burden et al. (1994) *Tex Heart Inst J* 21:91–97; Graiger et al. (1993) *Cardiovasc Res* 27:2238–2247; and Grainger et al. (1993) *Biochem J* 294:109–112). Loss of sensitivity to TGFβ, or alternatively, the overriding of this inhibitory stimulus such as by PDGF autostimulation, can be a contributory factor to abnormal smooth muscle proliferation in restinosis. It may therefore be possible to treat or prevent restinosis by the use of MEKK therapapeutics which mimic or restore induction by TGFβ or which inhibit PDGF stimulation.

Aberrant signaling by both positive and negative growth regulators also play a significant role in local glomerular and interstitial sites in human kidney development and disease. Consequently, the subject method provides a method of treating or inhibiting glomerulopathies and other renal proliferative disorders comprising the in vivo delivery of a subject MEKK therapeutic.

Yet another aspect of the present invention concerns the therapeutic application of a MEKK therapeutic to enhance survival of neurons and other neuronal cells in both the central nervous system and the peripheral nervous system. The ability of signals transduced through MEKK proteins to regulate neuronal differentiation and survival indicates that certain of the MEKK proteins can be reasonably expected to participate in control of adult neurons with regard to maintenance, functional performance, and aging of normal cells; repair and regeneration processes in chemically or mechanically lesioned cells; and prevention of degeneration and premature death which result from loss of differentiation in certain pathological conditions. In light of this understanding, the present invention specifically contemplates applications of the subject method to the treatment of (prevention and/or reduction of the severity of) neurological conditions deriving from: (i) acute, subacute, or chronic injury to the nervous system, including traumatic injury, chemical injury, vasal injury and deficits (such as the ischemia resulting from stroke), together with infectious/inflammatory and tumor-induced injury; (ii) aging of the nervous system including Alzheimer's disease; (iii) chronic neurodegenerative diseases of the nervous system, including Parkinson's disease, Huntington's chorea, amylotrophic lateral sclerosis and the like, as well as spinocerebellar degenerations; and (iv) chronic immunological diseases of the nervous system or affecting the nervous system, including multiple sclerosis.

Many neurological disorders are associated with degeneration of discrete populations of neuronal elements and may be treatable with a therapeutic regimen which includes a MEKK therapeutic. For example, Alzheimer's disease is associated with deficits in several neurotransmitter systems, both those that project to the neocortex and those that reside with the cortex. For instance, the nucleus basalis in patients with Alzheimer's disease have been observed to have a profound (75%) loss of neurons compared to age-matched controls. Although Alzheimer's disease is by far the most common form of dementia, several other disorders can produce dementia. Several of these are degenerative diseases characterized by the death of neurons in various parts of the central nervous system, especially the cerebral cortex. However, some forms of dementia are associated with degeneration of the thalmus or the white matter underlying the cerebral cortex. Here, the cognitive dysfunction results from the isolation of cortical areas by the degeneration of efferents and afferents. Huntington's disease involves the degeneration of intrastraital and cortical cholinergic neurons and GABAergic neurons. Pick's disease is a severe neuronal degeneration in the neocortex of the frontal and anterior temporal lobes, sometimes accompanied by death of neurons in the striatum. Treatment of patients suffering from such degenerative conditions can include the application of MEKK therapeutics, in order to control, for example, differentiation and apoptotic events which give rise to loss of neurons (e.g. to enhance survival of existing neurons) as well as promote differentiation and repopulation by progenitor cells in the area affected.

In addition to degenerative-induced dementias, a pharmaceutical preparation of one or more of the subject MEKK therapeutics can be applied opportunely in the treatment of neurodegenerative disorders which have manifestations of tremors and involuntary movements. Parkinson's disease, for example, primarily affects subcortical structures and is characterized by degeneration of the nigrostriatal pathway, raphe nuclei, locus cereleus, and the motor nucleus of vagus. Ballism is typically associated with damage to the subthalmic nucleus, often due to acute vascular accident.

Also included are neurogenic and myopathic diseases which ultimately affect the somatic division of the peripheral nervous system and are manifest as neuromuscular disorders. In an illustrative embodiment, the subject method is used to treat amyotrophic lateral sclerosis. ALS is a name given to a complex of disorders that comprise upper and lower motor neurons. Patients may present with progressive spinal muscular atrophy, progressive bulbar palsy, primary lateral sclerosis, or a combination of these conditions. The major pathological abnormality is characterized by a selective and progressive degeneration of the lower motor neurons in the spinal cord and the upper motor neurons in the cerebral cortex. The therapeutic application of a MEKK therapeutic, can be used alone, or in conjunction with neurotrophic factors such as CNTF, BDNF or NGF to prevent and/or reverse motor neuron degeneration in ALS patients.

MEKK therapeutics can also be used in the treatment of autonomic disorders of the peripheral nervous system, which include disorders affecting the innervation of smooth muscle and endocrine tissue (such as glandular tissue). For instance, the subject method can be used to treat tachycardia or atrial cardiac arrythmias which may arise from a degenerative condition of the nerves innervating the striated muscle of the heart.

In yet another embodiment, modulation of a MEKK-dependent pathway can be used to inhibit spermatogenesis. Spermatogenesis is a process involving mitotic replication of a pool of diploid stem cells, followed by meiosis and terminal differentiation of haploid cells into morphologically and functionally polarized spermatoza. This process exhibits both temporal and spatial regulation, as well as coordinated interaction between the germ and somatic cells. It has been previously shown that the signals coupling extracellular stimulus to regulation of mitotic, meiotic events which occur during spermatogenesis include pathways which rely on, for example, MAP kinases, for propagation. Accordingly, certain of these pathways may include MEKK proteins and be alterable by the subject MEKK therapeutics.

Likewise, members of the MAPK proteins are important in the regulation of female reproductive organs (Wu. T. C. et al. (1994) *Mol. Reprod Dev.* 38:9–15). Accordingly, certain of the MEKK therapeutics may be useful to prevent oocyte maturation as part of a contraceptive formulation. In other aspects, regulation of induction of meiotic maturation with MEKK therapeutics can be used to synchronize oocyte populations for in vitro fertilization. Such a protocol can be used to provide a more homogeneous population of oocytes which are healthier and more viable and more prone to cleavage, fertilization and development to blastocyst stage. In addition the MEKK therapeutics could be used to treat other disorders of the female reproductive system which lead to infertility including polycysitic ovarian syndrome.

Another aspect of the invention features transgenic non-human animals which express a heterologous MEKK gene of the present invention, or which have had one or more genomic MEKK genes disrupted in at least one of the tissue or cell-types of the animal. Accordingly, the invention features an animal model for developmental diseases, which animal has MEKK allele which is mis-expressed. For example, a mouse can be bred which has one or more MEKK alleles deleted or otherwise rendered inactive. Such a mouse model can then be used to study disorders arising from mis-expressed MEKK genes, as well as for evaluating potential therapies for similar disorders.

Another aspect of the present invention concerns transgenic animals which are comprised of cells (of that animal) which contain a transgene of the present invention and which preferably (though optionally) express an exogenous MEKK protein in one or more cells in the animal. A MEKK transgene can encode the wild-type form of the protein, or can encode homologs thereof, including both agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosaic expression of a MEKK protein can be essential for many forms of lineage analysis and can additionally provide a means to assess the effects of, for example, lack of MEKK expression which might grossly alter development in small patches of tissue within an otherwise normal embryo. Toward this and, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques which allow for the expression of transgenes can be regulated via site-specific genetic manipulation in vivo are known to those skilled in the art. For instance, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of one of the subject MEKK proteins. For example, excision of a target sequence which interferes with the expression of a recombinant MEKK gene, such as one which encodes an antagonistic homolog or an antisense transcript, can be designed to activate expression of that gene. This interference with expression of the protein can result from a variety of mechanisms, such as spatial separation of the MEKK gene from the promoter element or an internal stop codon. Moreover, the transgene can be made wherein the coding sequence of the gene is flanked by recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

In an illustrative embodiment, either the crelloxp recombinase system of bacteriophage P1 (Lakso et al. (1992) *PNAS* 89:6232–6236; Orban et al. (1992) PNAS 89:6861–6865) or the FLP recombinase system of *Saccharomyces cerevisiae* (O'Gorman et al. (1991) *Science* 251:1351–1355; PCT publication WO 92/15694) can be used to generate in vivo site-specific genetic recombination systems. Cre recombinase catalyzes the site-specific recombination of an intervening target sequence located between loxp sequences. loxP sequences are 34 base pair nucleotide repeat sequences to which the Cre recombinase binds and are required for Cre recombinase mediated genetic recombination. The orientation of loxp sequences determines whether the intervening target sequence is excised or inverted when Cre recombinase is present (Abremski et al. (1984) *J. Biol. Chem.* 259:1509–1514); catalyzing the excision of the target sequence when the loxp sequences are oriented as direct repeats and catalyzes inversion of the target sequence when loxp sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of a recombinant MEKK protein can be regulated via control of recombinase expression.

Use of the crelloxp recombinase system to regulate expression of a recombinant MEKK protein requires the construction of a transgenic animal containing transgenes encoding both the Cre recombinase and the subject protein. Animals containing both the Cre recombinase and a recombinant MEKK gene can be provided through the construction of "double" transgenic animals. A convenient method for providing such animals is to mate two transgenic animals each containing a transgene, e.g., a MEKK gene and recombinase gene.

One advantage derived from initially constructing transgenic animals containing a MEKK transgene in a recombinase-mediated expressible format derives from the likelihood that the subject protein, whether agonistic or antagonistic, can be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues and/or a desired temporal pattern. Thus, the creation of a founder population in which, for example, an antagonistic MEKK transgene is silent will allow the study of progeny from that founder in which disruption of MEKK mediated induction in a particular tissue or at certain developmental stages would result in, for example, a lethal phenotype.

Similar conditional transgenes can be provided using prokaryotic promoter sequences which require prokaryotic proteins to be simultaneous expressed in order to facilitate expression of the MEKK transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, a MEKK transgene could remain silent into adulthood until "turned on" by the introduction of the trans-activator.

In an exemplary embodiment, the "transgenic non-human animals" of the invention are produced by introducing transgenes into the germline of the non-human animal. Embryonic target cells at various developmental stages can be used to introduce transgenes. Different methods are used depending on the stage of development of the embryonic target cell. The zygote is the best target for micro-injection. In the mouse, the male pronucleus reaches the size of approximately 20 micrometers in diameter which allows reproducible injection of 1–2 µl of DNA solution. The use of zygotes as a target for gene transfer has a major advantage in that in most cases the injected DNA will be incorporated into the host gene before the first cleavage (Brinster et al. (1985) PNAS 82:4438–4442). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

Retroviral infection can also be used to introduce MEKK transgenes into a non-human animal. The developing non-human embryo can be cultured in vitro to the blastocyst stage. During this time, the blastomeres can be targets for retroviral infection (Jaenich, R. (1976) *PNAS* 73:1260–1264). Efficient infection of the blastomeres is obtained by enzymatic treatment to remove the zona pellucida (*Manipulating the Mouse Embryo*, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927–6931; Van der Putten et al. (1985) *PNAS* 82:6148–6152). Transfection is easily and efficiently obtained by culturing the blastomeres on a monolayer of virus-producing cells (Van der Putten, supra; Stewart et al. (1987) *EMBO J.* 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1 982) supra).

A third type of target cell for transgene introduction is the embryonic stem cell (ES). ES cells are obtained from pre-implantation embryos cultured in vitro and fused with embryos (Evans et al. (1981) *Nature* 292:154–156; Bradley et al. (1984) *Nature* 309:255–258; Gossler et al. (1 986) *PNAS* 83: 9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

Methods of making MEKK knock-out or disruption transgenic animals are also generally known. See, for example, *Manipulating the Mouse Embryo*, (Cold Spring Harbor Laboratory Press, Cold Spring Harbor, N.Y., 1986). Recombinase dependent knockouts can also be generated, e.g. by homologous recombination to insert recombinase target sequences flanking portions of an endogenous MEKK gene, such that tissue specific and/or temporal control of inactivation of a MEKK allele can be controlled as above.

One aspect of the present invention involves the recognition that a MEKK protein of the present invention is capable of regulating the homeostasis of a cell by regulating cellular activity such as cell growth cell death, and cell function (e.g., secretion of cellular products). Such regulation, in most cases, is independent of Raf, however, as discussed above (and as shown in FIG. 2), some pathways capable of regulation by MEKK protein may be subject to upstream regulation by Raf protein. Therefore, it is within the scope of the present invention to either stimulate or inhibit the activity of Raf protein and/or MEKK protein to achieve desired regulatory results. Without being bound by theory, it is believed that the regulation of Raf protein and MEKK protein activity at the divergence point from Ras protein (see FIG. 2) can be controlled by a "2-hit" mechanism. For example, a first "hit" can comprise any means of stimulating Ras protein, thereby stimulating a Ras-dependent pathway, including, for example, contacting a cell with a growth factor which is capable of binding to a cell surface receptor in such a manner that Ras protein is activated. Following activation of Ras protein, a second "hit" can be delivered that is capable of increasing the activity of JNK activity compared with MAPK activity, or vice versa. A second "hit" can include, but is not limited to, regulation of JNK or MAPK activity by compounds capable of stimulating or inhibiting the activity of MEKK, JNKK (MKK3 or MKK4), Raf and/or MEK. For example, compounds such as protein kinase C or phospholipase C kinase, can provide the second "hit" needed to drive the divergent Ras-dependent pathway down the MEKK-dependent pathway in such a manner that JNK is preferentially activated over MAPK.

One embodiment of the present invention comprises a method for regulating the homeostasis of a cell comprising regulating the activity of a MEKK-dependent pathway relative to the activity of a Raf-dependent pathway in the cell. As used herein, the term "homeostasis" refers to the tendency of a cell to maintain a normal state using intracellular systems such as signal transduction pathways. Regulation of the activity of a MEKK-dependent pathway includes increasing the activity of a MEKK-dependent pathway relative to the activity of a Raf-dependent pathway by regulating the activity of a member of a MEKK-dependent pathway, a member of a Raf-dependent pathway, and combinations thereof, to achieve desired regulation of phosphorylation along a given pathway, and thus effect apoptosis. Preferred regulated members of a MEKK-dependent pathway or a Raf-dependent pathway to regulate include, but are not limited to, proteins including MEKK, Ras, Rac, Cdc 42, Raf, MKK, JNKK, MEK, MAPK, JNK, TCF, ATF-2, Jun and Myc, and combinations thereof.

In one embodiment, the activity of a member of a MEKK-dependent pathway, a member of a Raf-dependent pathway, and combinations thereof, are regulated by altering the concentration of such members in a cell. One preferred regulation scheme involves altering the concentration of proteins including MEKK, Ras, Rac, Cdc 42, Raf, JNKK, MEK, MAPK, JNK, TCF, Jun, ATF-2, and Myc, and combinations thereof. A more preferred regulation scheme involves increasing the concentration of proteins including MEKK, Ras, Rac, Cdc 42, JNKK, JNK, Jun, ATF-2, and Myc, and combinations thereof. Another more preferred regulation scheme involves decreasing the concentration of proteins including Raf, MEK, MAPK, and TCF, and combinations thereof. It is also within the scope of the present invention that the regulation of protein concentrations in two or more of the foregoing regulation schemes can be combined to achieve an optimal apoptotic effect in a cell.

A preferred method for increasing the concentration of a protein in a regulation scheme of the present invention includes, but is not limited to, increasing the copy number of a nucleic acid sequence encoding such protein within a cell, improving the efficiency with which the nucleic acid sequence encoding such protein is transcribed within a cell, improving the efficiency with which a transcript is translated into such a protein, improving the efficiency of post-translational modification of such protein, contacting cells capable of producing such protein with anti-sense nucleic acid sequences, and combinations thereof.

In a preferred embodiment of the present invention, the homeostasis of a cell is controlled by regulating the apoptosis of a cell. A suitable method for regulating the apoptosis of a cell is to regulate the activity of a MEKK-dependent pathway in which the MEKK protein regulates the pathway substantially independent of Raf. A particularly preferred method for regulating the apoptosis of a cell comprises increasing the concentration of MEKK protein by contacting a cell with a nucleic acid molecule encoding a MEKK protein that possesses unregulated kinase activity. A preferred nucleic acid molecule with which to contact a cell includes a nucleic acid molecule encoding a MEKK protein represented by SEQ ID NO:2, SEQ ID NO:4, SEQ ID NO:6, SEQ ID NO:8, SEQ ID NO: 10, SEQ ID NO:12, SEQ ID NO:14, and combinations thereof. A more preferred nucleic acid molecule with which to contact a cell includes a nucleic acid molecule encoding a truncated MEKK protein having only the kinase catalytic domain (i.e., no regulatory domain) of a MEKK protein represented by SEQ ID NO:2, SEQ ID NO:4, SEQ ID NO:6, SEQ ID NO:8, SEQ ID NO:10, SEQ ID NO:12 and/or SEQ ID NO:14. An even more preferred nucleic acid molecule with which to contact a cell includes a nucleic acid molecule including the kinase catalytic domain of a MEKK protein, for example, MEKK1.1$_{409-672}$ MEKK1.1$_{1329-1594}$, MEKK2.1$_{361-620}$, MEKK2.2$_{361-620}$ MEKK3$_{366-626}$, MEKK4.1$_{631-890}$, MEKK4.2$_{1338-1597}$. Again, suitable variations of MEKK proteins described herein comprise those proteins encoded by a nucleic acid molecule that are able to hybridize to any of the above sequences under stringent conditions.

It is within the scope of the invention that the foregoing method can further comprise the step of decreasing the activity of MEK protein in the cell by contacting the cell with a compound capable of inhibiting MEK activity. Such compounds can include: peptides capable of binding to the kinase domain of MEK in such a manner that phosphorylation of MAPK protein by the MEK protein is inhibited; and/or peptides capable of binding to a portion of a MAPK protein in such a manner that phosphorylation of the MAPK protein is inhibited.

In another embodiment, the activity of a member of a MEKK-dependent pathway, a member of a Raf-dependent pathway, and combinations thereof, can be regulated by directly altering the activity of such members in a cell. A preferred method for altering the activity of a member of a MEKK-dependent pathway, includes, but is not limited to, contacting a cell with a compound capable of directly interacting with a protein including MEKK, Ras, Rac, Cdc 42, JNKK, JNK, Jun, ATF-2, and Myc, and combinations thereof, in such a manner that the proteins are activated; and/or contacting a cell with a compound capable of directly interacting with a protein including Raf, MEK, MAPK, TCF protein, and combinations thereof in such a manner that the activity of the proteins are inhibited. A preferred compound with which to contact a cell that is capable of regulating a member of a MEKK-dependent pathway includes a peptide capable of binding to the regulatory domain of proteins including MEKK, Ras, Rac, Cdc 42, JNKK, JNK, Jun, ATF-2, and Myc, in which the peptide inhibits the ability of the regulatory domain to regulate the activity of the kinase domains of such proteins. Another preferred compound with which to contact a cell includes TNFα, growth factors regulating tyrosine kinases, hormones regulating G protein-coupled receptors and FAS ligand.

A preferred compound with which to contact a cell that is capable of regulating a member of a Raf-dependent pathway includes a peptide capable of binding to the kinase catalytic domain of a protein selected from the group consisting of Raf, MEK-1, MEK-2, MAPK, and TCF, in which the peptide inhibits the ability of the protein to be phosphorylated or to phosphorylate a substrate.

In accordance with the present invention, a compound can regulate the activity of a member of a MEKK-dependent pathway by affecting the ability of one member of the pathway to bind to another member of the pathway. Inhibition of binding can be achieved by directly interfering at the binding site of either member, or altering the conformational structure, thereby precluding the binding between one member and another member.

Another preferred compound with which to contact a cell that is capable of regulating a member of a MEKK-dependent pathway includes an isolated compound that is capable of regulating the binding of MEKK protein to a protein of the Ras superfamnily, such as Ras, Rac, Cdc 42, or Rho (referred to herein as a Ras:MEKK binding compound). In one embodiment, a Ras:MEKK binding compound of the present invention comprises an isolated peptide (or mimetope thereof) comprising an amino acid sequence derived from a Ras superfamily protein. In another embodiment, a Ras:MEKK binding compound of the present invention comprises an isolated peptide (or mimetope thereof) comprising an amino acid sequence derived from a MEKK protein.

According to the present invention, an isolated, or biologically pure, peptide, is a peptide that has been removed from its natural milieu. As such, "isolated" and "biologically pure" do not necessarily reflect the extent to which the protein has been purified. An isolated compound of the present invention can be obtained from a natural source or produced using recombinant DNA technology or chemical synthesis. As used herein, an isolated peptide can be a full-length protein or any homolog of such a protein in which amino acids have been deleted (e.g., a truncated version of the protein), inserted, inverted, substituted and/or derivatized (e.g., by glycosylation, phosphorylation, acetylation, myristylation, prenylation, palmitilation, and/or amidation) such that the peptide is capable of regulating the binding of Ras superfamily protein to MEKK protein.

In accordance with the present invention, a "mimetope" refers to any compound that is able to mimic the ability of an isolated compound of the present invention. A mimetope can be a peptide that has been modified to decrease its susceptibility to degradation but that still retain regulatory activity. Other examples of mimetopes include, but are not limited to, protein-based compounds, carbohydrate-based compounds, lipid-based compounds, nucleic acid-based compounds, natural organic compounds, synthetically derived organic compounds, anti-idiotypic antibodies and/or catalytic antibodies, or fragments thereof. A mimetope can be obtained by, for example, screening libraries of natural and synthetic compounds as disclosed herein that are capable of inhibiting the binding of Ras superfamily protein to MEKK. A mimetope can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes by, for example, computer modelling. The predicted mimetope structures can then be produced by, for example, chemical synthesis, recombinant DNA technology, or by isolating a mimetope from a natural source (e.g., plants, animals, bacteria and fungi).

In one embodiment, a Ras:MEKK binding compound of the present invention comprises an isolated peptide having a domain of a Ras superfamily protein that is capable of binding to a MEKK protein (i.e., that has an amino acid sequence which enables the peptide to be bound by a MEKK protein). A Ras peptide of the present invention is of a size that enables the peptide to be bound by a MEKK protein, preferably, at least about 4 amino acid residues, more preferably at least about 12 amino acid residues, and even more preferably at least about 25 amino acid residues. In particular, a Ras peptide of the present invention is capable of being bound by the COOH-terminal region of MEKK, in certain embodiments the region of MEKK containing the MEKK kinase domain. Preferably, a Ras peptide of the present invention comprises the effector domain of Ras and more preferably amino acid residues 17–42 of H-Ras. In addition, similar domains of Rac are important for the binding of Rac, Cdc 42 or Rho to certain MEKK proteins.

In another embodiment, a Ras:MEKK binding compound of the present invention comprises an isolated MEKK peptide that has a domain of a MEKK protein that is capable of binding to a Ras protein (i.e., that has an amino acid sequence which enables the peptide to be bound by a Ras protein). A MEKK peptide of the present invention is of a size that enables the peptide to be bound by a Ras protein, in particular by the effector domain of a Ras protein. Preferably, a MEKK peptide of the present invention at least about 320 amino acids in length. Preferably, a MEKK peptide of the present invention comprises the COOH-terminal region of a MEKK protein and more preferably MEKKCOOH (as described in detail in the appended examples).

As an illustrative example, the sequence of a MEKK protein which binds to Cdc42 and Rac, such as IIGQVCDTPKSYDNVMHVGLR, occurring around residue 1306–1326 of MEKK4.2 or 599–619 of MEKK4 or mimetics thereof could be used therapeutically. In one embodiment the Rac-binding portion of a MEKK protein or a fragment thereof is used to block the binding of the MEKK catalytic domain with Cdc42 and Rac, thus inhibiting MEKK activity. Preferred fragment lengths are at least about 4 amino acids, preferably about 8 amino acids, more preferably about 12 amino acids, although longer framents are also contemplated. Similarly the consensus PAK sequence or fragments thereof could be used to block the binding of MEKK and Cdc42 or Rac. In another embodiment peptidomimetics or mimetopes of these fragments are used. In another embodiment a Ras effector domain peptide is used to blocks the binding of the MEKK catalytic domain with the GTP-bound form of Ras. Alternatively, the portion of the MEKK catalytic domain which binds to Ras, or the Ras effector domain can be used to competitively inhibit binding of Ras and a MEKK protein.

Ras is a critical component of tyrosine kinase growth factor receptor and G-protein coupled receptor regulation of signal transduction pathways controlling mitogenesis and differentiation. According to the present invention, the protein serine-threonine kinases Raf-1 and MEKK1 are Ras effectors and selectively bind to Ras in a GTP dependent manner. The p110 catalytic subunit of the lipid kinase has also been shown to directly interact with Ras in a GTP dependent manner. Ras-GAP and neurofibromin also regulate Ras GTPase activity. Raf-1, MEKK1 and P13-kinase are capable of increasing the activity in cells expressing GTPase-deficient Ras consistent with their interaction with Ras-GTP being involved in their regulation.

Different functional domains of Ras effectors bind to Ras in a GTP dependent manner. The Ras binding domain for Raf-1 is encoded in the extreme $NH_2$-terminal regulatory domain of Raf-1. The Ras binding domain is encoded within the catalytic domain of MEKK1. Both Raf-1 and MEKK1 binding to Ras is blocked by a Ras effector domain peptide. Thus, Raf-1, MEKK1 and other Ras effectors can compete for interaction with Ras-GTP presumably at the Ras effector domain. The relative abundance and affinity of each Ras effector in different cells may influence the magnitude, onset and duration of each effector response. Secondary inputs, such as phosphorylation of the different Ras effectors, can also influence their interaction with Ras-GTP. The kinetic properties of Ras effector activation in cells relative to effector affinity for Ras-GTP are predictable based on the foregoing information. For example, MEKK1 can preferentially regulate the SEK/Jun kinase pathways relative to MAPK. Activation of the SEK/Jun kinase pathway is generally slower in onset and maintained as maximal activity longer than the activation of MAPK.

As additional MEKKs are characterized it will be important to characterize their regulation and interaction with other members of the Ras superfamily. For example, MEKK4.1 and 4.2 have been found to bind to Rac/Cdc42 as described herein. Rho, Rac, and Cdc42 are small GTPases that have been implicated in the formation of a variety of actin structures and the assembly of associated integrin complexes (Burbelo, et al. (1995) J. Biol Chem. 270:29071–29074). One of the targets of the Cdc42 and Rae GTPases is the PAK family of protein kinases (Bagrodia et al (1995) J. Biol. Chem 270:27995–27998). Rae and Cdc42 have been shown to regulate the activity of the JNK/SAPK signaling pathway in ways different from Ras. While activated Ras stimulates MAPK, but poorly induces JNK activity, mutationally activated Rac1 and Cdc42 GTPases potently activate JNK without affecting MAPK (Coso et al. (1995) Cell 81:1137–1146). Undoubtedly additional Ras effectors which interact with and regulate MEKK proteins, perhaps resulting in the selective activation of certain substrates, will be identified in the near future. The present invention also includes a method to administer isolated compounds of the present invention to a cell to regulate signal transduction activity in the cell. In particular, the present invention includes a method to administer an isolated compound of the present invention to a cell to regulate apoptosis of the cell.

Compounds of the present invention may influence cellular mitogenesis, DNA synthesis, cell division and differentiation. MAPK is also recognized as being involved in the activation of oncogenes, such as c-jun and c-myc. While not bound by theory, the present inventor believes that MAPK is also intimately involved in various abnormalities having a genetic origin. MAPK is known to cross the nuclear membrane and is believed to be at least partially responsible for regulating the expression of various genes. As such, MAPK is believed to play a significant role in the instigation or progression of cancer, neuronal diseases, autoimmune diseases, allergic reactions, wound healing and inflammatory responses. The present inventor, by being first to identify nucleic acid sequences encoding MEKK, recognized that it is now possible to regulate the expression of MEKK, and thus regulate the activation of MAPK.

The present invention also includes a method for regulating the homeostasis of a cell comprising injecting an area of a subject's body with an effective amount of a naked plasmid DNA compound (such as is taught, for example in Wolff et al., 1990, Science 247, 1465–1468). A naked plasmid DNA compound comprises a nucleic acid molecule encoding a MEKK protein of the present invention, operatively linked to a naked plasmid DNA vector capable of being taken up by and expressed in a recipient cell located in the body area. A preferred naked plasmid DNA compound of the present invention comprises a nucleic acid molecule encoding a truncated MEKK protein having deregulated kinase activity. Preferred naked plasmid DNA vectors of the present invention include those known in the art. When administered to a subject, a naked plasmid DNA compound of the present invention transforms cells within the subject and directs the production of at least a portion of a MEKK protein or RNA nucleic acid molecule that is capable of regulating the apoptosis of the cell.

A naked plasmid DNA compound of the present invention is capable of treating a subject suffering from a medical disorder including cancer, autoimmune disease, inflammatory responses, allergic responses and neuronal disorders, such as Parkinson's disease and Alzheimer's disease. For example, a naked plasmid DNA compound can be administered as an anti-tumor therapy by injecting an effective amount of the plasmid directly into a tumor so that the plasmid is taken up and expressed by a tumor cell, thereby killing the tumor cell. As used herein, an effective amount of a naked plasmid DNA to administer to a subject comprises an amount needed to regulate or cure a medical disorder the naked plasmid DNA is intended to treat, such mode of administration, number of doses and frequency of dose capable of being decided upon, in any given situation, by one of skill in the art without resorting to undue experimentation.

One aspect of the present invention relates to the recognition that a MEKK protein is capable of activating MAPK and that MAPK can regulate various cellular functions as disclosed in U.S. Pat. No. 5,405,941, which is incorporated herein by this reference.

One example of a therapeutic compound of the present invention is the nucleic acid encoding the amino acid residues 1306–1326 of MEKK4.2 or 599–619 of MEKK 4. In other embodiments the peptide or fragments thereof can be used. The Cdc42/Rac binding region of a MEKK peptide (IIGQVCDTPKSYDNVMHVGLR) or the nucleic acid which encodes it can be used to inhibit the binding of MEKK and a member of the Ras superfamily. Alternatively, the domain of Rac or Cdc42 to which it binds could be used. In another embodiment the region of the Ras effector domain which blocks the binding of the MEKK catalytic domain with the GTP-bound form of Ras could be used. Alternatively, the portion of the MEKK catalytic domain which binds to Ras could be used to block MEKK-Ras interaction.

An isolated compound of the present invention can be used to formulate a therapeutic composition. In one embodiment, a therapeutic composition of the present invention includes at least one isolated peptide of the present invention. A therapeutic composition for use with a treatment method of the present invention can further comprise suitable excipients. A therapeutic compound for use with a treatment method of the present invention can be formulated in an excipient that the subject to be treated can tolerate. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful excipients include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In another embodiment, a therapeutic compound for use with a treatment method of the present invention can also comprise a carrier. Carriers are typically compounds that increase the half-life of a therapeutic compound in the treated animal. Suitable carriers include, but are not limited to, liposomes, micelles, cells, polymeric controlled release formulations, biodegradable implants, bacteria, viruses, oils, esters, and glycols. Preferred carriers include liposomes and micelles.

A therapeutic compound for use with a treatment method of the present invention can be administered to any subject having a medical disorder as herein described. Acceptable protocols by which to administer therapeutic compounds of the present invention in an effective manner can vary according to individual dose size, number of doses, frequency of dose administration, and mode of administration. Determination of such protocols can be accomplished by those skilled in the art without resorting to undue experimentation. An effective dose refers to a dose capable of treating a subject for a medical disorder as described herein. Effective doses can vary depending upon, for example, the therapeutic compound used, the medical disorder being treated, and the size and type of the recipient animal. Effective doses to treat a subject include doses administered over time that are capable of regulating the activity, including growth, of cells involved in a medical disorder. For example, a first dose of a naked plasmid DNA compound of the present invention can comprise an amount that causes a tumor to decrease in size by about 10% over 7 days when administered to a subject having a tumor. A second dose can comprise at least the same the same therapeutic compound than the first dose.

Another aspect of the present invention includes a method for prescribing treatment for subjects having a medical disorder as described herein. A preferred method for prescribing treatment comprises: (a) measuring the MEKK protein activity in a cell involved in the medical disorder to determine if the cell is susceptible to treatment using a method of the present invention; and (b) prescribing treatment comprising regulating the activity of a MEKK-dependent pathway relative to the activity of a Raf-dependent pathway in the cell to induce the apoptosis of the cell. The step of measuring MEKK protein activity can comprise: (1) removing a sample of cells from a subject; (2) stimulating the cells with a TNFα; and (3) detecting the state of phosphorylation of MKK3, MKK4 or JNKK protein using an immunoassay using antibodies specific for phosphothreonine and/or phosphoserine.

The present invention also includes antibodies capable of selectively binding to a MEKK protein of the present invention. Such an antibody is herein referred to as an anti-MEKK antibody. Polyclonal populations of anti-MEKK antibodies can be contained in a MEKK antiserum. MEKK antiserum can refer to affinity purified polyclonal antibodies, ammonium sulfate cut antiserum or whole antiserum. As used herein, the term "selectively binds to" refers to the ability of such an antibody to preferentially bind to MEKK proteins. Binding can be measured using a variety of methods known to those skilled in the art including immunoblot assays, immunoprecipitation assays, enzyme immunoassays (e.g., ELISA), radioimmunoassays, immunofluorescent antibody assays and immunoelectron microscopy; see, for example, Sambrook et al., *Molecular Cloning: A Laboratory Manual*, Cold Spring Harbor Labs Press, 1989.

Antibodies of the present invention can be either polyclonal or monoclonal antibodies and can be prepared using techniques standard in the art. Antibodies of the present invention include functional equivalents such as antibody fragments and genetically-engineered antibodies, including single chain antibodies, that are capable of selectively binding to at least one of the epitopes of the protein used to obtain the antibodies. Preferably, antibodies are raised in response to proteins that are encoded, at least in part, by a MEKK nucleic acid molecule. More preferably antibodies are raised in response to at least a portion of a MEKK protein, and even more preferably antibodies are raised in response to either the amino terminus or the carboxyl terminus of a MEKK protein. Preferably, an antibody of the present invention has a single site binding affinity of from about $10^3 M^{-1}$ to about $10^{12} M^{-1}$ for a MEKK protein of the present invention.

A preferred method to produce antibodies of the present invention includes administering to an animal an effective amount of a MEKK protein to produce the antibody and recovering the antibodies. Antibodies of the present invention have a variety of potential uses that are within the scope of the present invention. For example, such antibodies can be used to identify unique MEKK proteins and recover MEKK proteins.

Another aspect of the present invention comprises a therapeutic compound capable of regulating the activity of a MEKK-dependent pathway in a cell identified by a process, comprising: (a) contacting a cell with a putative regulatory molecule; and (b) determining the ability of the putative regulatory compound to regulate the activity of a MEKK-dependent pathway in the cell by measuring the activation of at least one member of said MEKK-dependent pathway. Preferred methods to measure the activation of a member of a MEKK-dependent pathway include measuring the transcription regulation activity of c-Myc protein, measuring the phosphorylation of a protein selected from the group consisting of MEKK, JNKK, JNK, Jun, ATF-2, Myc, and combinations thereof.

Mitogen-activated protein kinase kinase (MEKK1) is a serine/threonine protein kinase that functions parallel to Raf-1 in the regulation of sequential protein kinase pathways that involve both mitogen-activated and stress-activated protein kinases. In this study, we examined the interaction of MEKK1 with 14-3-3 proteins. The T cell 14-3-3 isoform, but not the β and stratifin isoforms, interacted with MEKK1 in the two-hybrid system. GST fusion proteins of the T cell, β, and stratifin 14–3–3 isoforms were prepared to further characterize the domains of MEKK1 and Raf-1 that interact with these proteins. It was demonstrated that the T cell and β14–3–3 isoform, but not stratifin, interact with COS cell-expressed MEKK1. Furthermore, the amino-terminal moiety, but not the carboxyl-terminal moiety, of expressed MEKK1 interacts with the GST•14–3–3 although the interaction is best when holoMEKK1 is expressed. In contrast, GST•14–3–3 proteins interact with both the amino- and carboxyl-regions of COS cell-expressed Raf-1 protein. Thus, although MEKK1 and Raf-1 function at a parallel point in the sequential protein kinase pathways, the interaction of 14–3–3 proteins with these kinases is not identical, suggesting a differential regulation between Raf-1 and MEKK1-stimulated pathways.

The foregoing description of the invention has been presented for purposes of illustration and description. Further, the description is not intended to limit the invention to the form disclosed herein. Consequently, variations and modifications commensurate with the above teachings, and the skill or knowledge in the relevant art are within the scope of the present invention. The preferred embodiment described herein above is further intended to explain the best mode known of practicing the invention and to enable others skilled in the art to utilize the invention in various embodiments and with various modifications required by their particular applications or uses of the invention. It is intended that the appended claims be construed to include alternate embodiments to the extent permitted by the prior art.

The following examples are provided for the purposes of illustration and are not intended to limit the scope of the present invention.

EXAMPLES

Example 1

This Example Describes the Structural Characterization of MEKK1 Protein

A. MEKK1 Nucleotide Sequence

MEKK1.1 and 1.2 protein was cloned by the following method. Unique degenerate inosine oligodeoxynucleotides were designed to correspond to regions of sequence identity between the yeast Ste11 and Byr2 genes. With primers and cDNA templates derived from polyadenylated RNA from NIH 3T3 cells, a polymerase chain reaction (PCR) amplification product of 320 base pairs (bp) was isolated. This 320 bp cDNA was used as a probe to identify a MEKK1.2 cDNA of 3260 bp from a mouse brain cDNA library using standard methods in the art. The MEKK1.2 nucleotide sequence was determined by dideoxynucleotide sequencing of double-stranded DNA using standard methods in the art.

Referring to SEQ ID NO:3, based on the Kozak consensus sequence for initiation codons, the starting methionine can be predicted to occur at nucleotide 486. With this methionine at the start, the cDNA encodes a protein of 672 amino acids, corresponding to a molecular size of 73 kD. When run on a gel, the protein has an apparent molecular size of 69 kD. There is another in-frame methionine at position 441, which does not follow the Kozak rule, but would yield a protein of 687 amino acid residues (74.6 kD). Also referring to SEQ ID NO:2, 20% of the NH2-terminal 400 amino acids are serine or threonine and there are only two tyrosines. Several potential sites of phosphorylation by protein kinase C are apparent in the $NH_2$-terminal region. The kinase catalytic domain is located in the COOH-terminal half of the MEKK 1.

B. Southern Blot Analysis of MEKK1 Transcript

Equal amounts (20 μg) of total RNA were loaded onto the gel as indicated by ethidium bromide staining. Blots were probed with either a 320-bp cDNA fragment encoding a portion of the MEKK kinase domain or an 858-bp fragment encoding a portion of the $NH_2$ terminal region of MEKK using standard methods in the art. A 7.8 kb mRNA was identified with probes derived from both the 5' and 3' ends of the MEKK cDNA in several cell lines and mouse tissues. The MEKK mRNA was highly expressed in mouse heart and spleen, an in lower amounts in liver.

C. Southern Blot Analysis

Mouse genomic DNA (10 μg) was digested with either Bam HI, Hind III or Eco RI and applied to gels using standard methods in the art. Blots were probed with a 320-bp fragment of the MEKK gene. The appearance of one band was detected in the Bam HI and Hind III digests which indicates that MEKK is encoded by one gene. The appearance of two bands in the Eco RI digest indicates the likely presence of an Eco RI site within an intron sequence spanned by the probe.

D. Immunoblots Using Anti-MEKK Antibodies

Three polyclonal antisera were prepared using three different antigens. A first polyclonal antiserum was prepared using an antigen comprising a 15 amino acid peptide DRPPSRELLKHPVER (corresponding to amino acids 655 to 669 of SEQ ID NO:2 derived from the COOH-terminus of MEKK. NZW rabbits were immunized with the peptide and antisera was recovered using standard methods known in the art. This first polyclonal antiserum is hereinafter referred to as the DRPP antiserum.

A second polyclonal antiserum was produced using a DNA clone comprising a MEKK cDNA digested with EcoR1 and PstI, thereby creating a 1270 bp fragment that encodes the amino terminus of MEKK. This fragment was cloned into pRSETC to form the recombinant molecule pMEKK1–369 comprising amino acid residues 1 to 369 of MEKK1. The pMEKK11–369 recombinant molecule was expressed in *E. coli* and protein encoded by the recombinant molecule was recovered and purified using standard methods known in the art. NZW rabbits were immunized with the purified recombinant MEKK11–369 protein and antisera was recovered using standard methods known in the art. This second polyclonal antiserum is hereinafter referred to as the MEKK11–369 antiserum.

A third polyclonal antiserum was produced using a DNA clone comprising a MEKK cDNA digested with Pst I and Kpn 1, thereby creating a 1670 bp fragment that encodes the catalytic domain of MEKK. This fragment was cloned into pRSETC to form the recombinant molecule pMEKK370–738 comprising amino acid residues 370 to 738 of MEKK1 (encoded by base pairs 1592–3260). The pMEKK1370–738 recombinant molecule was expressed in *E. coli* and protein encoded by the recombinant molecule was recovered and purified using standard methods known in the art. NZW rabbits were immunized with the purified recombinant MEKK1370–738 protein and antisera was recovered using standard methods known in the art. This second polyclonal antiserum is hereinafter referred to as the MEKK1 370–738 antiserum.

The DRPP antiserum was used to probe Western Blots of soluble cellular protein derived from several rodent cell lines. Soluble cellular protein (100 μg) or recombinant MEKK COOH-terminal fusion protein (30 ng) was loaded onto a 10% Tris Glycine SDS-PAGE gel and the protein transferred to a nylon filter using methods standard in the art. The nylon filter was immunoblotted with affinity purified DRPP antiserum (1:300 dilution). A 78 kD immunoreactive protein was identified in the samples comprising protein from Pheochromocytoma (PC12), Rat 1a, and NIH 3T3 cells. A prominent 50 kD immunoreactive band was also commonly present but varied in intensity from preparation to preparation indicating the band is a proteolytic fragment. Visualization of both the 78 kD and 50 kD immunoreactive bands on immunoblots was inhibited by pre-incubation of the 15 amino acid peptide antigen with the affinity purified DRPP antiserum. The MEKK protein detected by immuno-blotting is similar to the molecular size predicted from the open reading frame of the MEKK cDNA.

In a second immunoblot experiment, PC12 cells stimulated or not stimulated with EGF were lysed and resolved on 10% Tris Glycine SDS-PAGE gel as described above. MEKK proteins contained in the cell lysates were identified by immunoblot using affinity purified MEKK11–369 antiserum (1:300) using methods standard in the art. MEKK1 and two higher molecular weight proteins having MEKK activity, MEKK α and MEKK β, were identified using the affinity purified MEKK11–369 antiserum. MEKK1, and not MEKK cc and MEKK β, were identified using the affinity purified MEKK11–369 antiserum.

Using the same procedure described above, two MEKK immunoreactive species of approximately 98 kD and 82 kD present in PC12, Rat1a, NIH3T3, and Swiss3T3 cell lysates were recognized by affinity purified MEKK11–369 antiserum. It should be noted that the 98 kD MEKK protein described herein was originally identified as a 95 kD MEKK protein in the related PCT application (International application no. PCT/US94/04178). Subsequent Tris Glycine SDS-PAGE gel analysis has led to the determnination that the modification in molecular weight. Visualization of both of these proteins was inhibited by incubation of the affinity purified MEKK11–369 antiserum with purified recombinant MEKK11–369 fusion protein antigen. A single 98 kD MEKK protein was present in MEKK immunoprecipitates, but not in immunoprecipitates using preimmune serum. More of the 98 kD MEKK was expressed in PC12 cells relative to fibroblast cell lines. Immunoblotting with antibodies that specifically recognize Raf-1 or Raf-B indicated that neither of these enzymes were present as contaminants of MEKK immunoprecipitates. 98 kD MEKK in MEKK immunoprecipitates did not comigrate with Raf-1 or Raf-B in PC12 cell lysates and no cross-reactivity between MEKK and Raf antibodies was observed.

Example 2

This Example Describes the Isolation of Nucleic Acid Sequences Encoding MEKK 2, MEKK 3 Proteins and Their Activities Cloning of MEKK 2 and 3. The degenerate primers GA(A/G)(C/T)TIATGGCIGTIAA(A/G)CA (SEQ ID NO:

13) (sense) and TTIGCICC(T/C)TTIAT(A/G)TCIC(G/T)(A/G)TG (SEQ ID NO: 14) (antisense) were used in a PCR using first strand cDNA generated from polyadenylated RNA prepared from NIH 3T3 cells. The PCR reaction involved 30 cycles (1 min, 94° C.; 2 min, 52° C.; 3 min 72° C.). A band of approximately 300 base pairs was recovered from the PCR mixture, and the products were cloned into pGEM-T (Promega). The PCR cDNA products were sequenced and compared to the MEKK1 sequence. A unique cDNA sequence of 322 base pairs having significant homology to MEKK1 cDNA was identified and used to screen an oligo (dT)-primed mouse brain cDNA library (Stratagene). The k phage library was plated and DNA from plaques was transferred to Hybond N filters (Amersham) followed by UV-cross-linking of DNA to the filters. Filters were prehybridized for 2 h and then hybridized overnight in 0.5M $Na_2$ $h_2PO_4$ (pH 7.2), 10% bovine serum albumin, 1 mM EDTA, 7% SDS at 68° C. Filters were washed twice at 42° C. with 2× SSC, once with 1× SSC, and once with 0.5× SSC containing 0.1% SDS. Positive hybridizing clones were purified and sequenced.

To resolve GC-rich regions, cDNAs were subcloned into Ml 3 vectors (New England Biolabs), and single strand DNA was sequenced. In all cases, both strands of DNA were sequenced. MEKK 2 encodes a 619-amino aid protein having a mass of 69.7 kDa. MEKK 3 encodes a 626-amino acid protein having a mass of 71 kDa. The two proteins share a common structure with the kinase catalytic domain encoded in the COOH-terminal moiety. The amino-terminal moiety does not encode any definable domain such as a SH2 or SH3 domain sequence.

The 5' ends of both MEKK 2 and 3 are highly G/C-rich making DNA sequencing difficult. To verify the presence of stop codons in all three possible reading frames 5' to the predicted start site methionine, the MEKK 2 and 3 cDNAs were inserted in pRSET A, B, and C (Invitrogen) and expressed in *Escherichia coli*. Each construct gave a truncated RSET fragment confirming that the MEKK 2 and 3 cDNAs encoded 5' stop sites and that the isolated cDNAs encode full-length proteins.

Alignment of the deduced amino acid sequences demonstrated significant homology between the two proteins. Overall, the two proteins are approximately 77% homologous. The catalytic domain is encoded in the COOH-terminal moiety of both MEKK 2 and 3. The first consensus kinase domain comprising the catalytic site of MEKK 2 and 3 begins at residues 361 and 367, respectively. The COOH-terminal catalytic domains of MEKK 2 and 3 are approximately 94% conserved, whereas the $NH_2$-terminal moieties are only 65% conserved in amino acid sequence. These findings indicate that the primary sequences of MEKK 2 and 3 diverge significantly in the $NH_2$-terminal half of the proteins. The conservation in sequence of the catalytic domains suggests they may recognize an overlapping set of substrates. The divergent $NH_2$ termini would be consistent with this region encoding sequences for the differential regulation of the two proteins.

The COOH terminus of MEKK1 encoding the catalytic domain is only 50% homologous to the corresponding regions of MEKK 2 and 3. Thus, the catalytic domains of MEKK 2 and 3 are very similar to each other but significantly divergent from MEKK 1. As shown below, MEKK 1, 2, and 3 can all stimulate JNK and $p42/44^{MAPK}$ activities in transfected cells. The significance of the sequence differences in the catalytic domains of MEKK 1, 2, and 3 is presently unclear.

Plasmid Expression of MEKK2 and 3. The proteins for MEKK2 and 3 were epitope-tagged at their $NH_2$ terminus with the hemagglutinin (HA) tag sequence GYPYDVPD-YAS (SEQ ID NO: 15) using a PCR strategy. For inserting the NH2-terminal epitope tag in MEKK2 and 3, sense oligonucleotides were synthesized having a methionine codon (ATG), 33 bases coding for the GYPYDVPDYAS (SEQ ID NO: 15) epitope tag sequences, and 20 bases of MEKK 2 or 3 sequence starting at codon 2. For MEKK2, the sense oligonucleotide was ATGGGGTACCCGTAC-GACGTGCCGGACTACGCTTCCGATGAT-CAGCAAGCTTTGA A (SEQ ID NO: 16). the sense oligonucleotide for MEKK3 was ATGGGGTACCCGTACGAC GTGCCGGACTACGCTTCCGATGAACAA-GAGGCATTAGA (SEQ ID NO: 17). The antisense oligonucleotides for MEKK2 and 3 were AGACTTAGATCT-CAGGTCTTC (SEQ ID NO: 18) encoding a BglII site for MEKK2 and GATTCTGACGTCACTCTGCCT (SEQ ID NO: 19) encoding an ActII site for MEKK3. The PCR reactions were performed for 30 cycles using MEKK2 or MEKK3 cDNAs as template. The PCR products were purified, and a second PCR reaction was performed using the first PCR product as template, the MEKK2 or 3 antisense oligonucleotide described above and the common sense oligonucleotide encoding a XbaI restriction site, a consensus Kozak initiation site and 17 bases overlapping with the initiation methionine and HA tag sequence (TCACGTTCTAGAGCCACCATGGGGTACCCGTACGA) (SEQ ID NO: 20). The resulting PCR products were digested with XbaI and BglII for MEKK2 and XbaI and AatII for MEKK3 and ligated in frame into the appropriate MEKK2 or 3 cDNA. The sequences were confirmed by DNA sequencing and the cDNAs were inserted into the expression plasmid pCMV5. hEK 293 cells were transfected with pCMV5 expression plasmids using Lipofect AMINE (Life Technologies, Inc.) and assayed 48 h later. The 12CA5 monoclonal antibody (Berkely Antibody Co.) was used for recognition of the HA epitope tag encoded in expressed MEKK2 and 3.

Antibody Production. Peptides corresponding to COOH-terminal sequences of MEKK3 (CEARQRPSAEELLTHHFAQ) (SEQ ID NO: 21) and p38 (CFVFPPLDQEEMES) (SEQ ID NO: 22) were conjugated to keyhole limpet hemocyanin and used to immunize rabbits. Antisera were characterized for specificity by immunoblotting of lysates prepared from appropriately transfected HEK923 cells.

MEKK 2 and 3 Activate c-Jun Kinase and p42/44, tAPK Activity—Transient expression of MEKK 2 and 3 resulted in the stimulation of c-Jun kinase (JNK) activity. JNK activity was measured using GSTc-Jun 1–79) coupled to glutathione Sepharose 4B. Cells transfected with MEKK2 or 3 and control transfected cells were lysed in 0.5% Nonidet P-40, 20 mM Tris HCl, pH 7.6, 0.25 M NaCl, 3 mM EDTA, 3 mM EGTA, 1 mM dithiothreitol, 1 mM PMSFm 2 mM sodium vanadate, 20 ug/ml aprotinin, and 5 ug/ml leupeptin. Nuclei were removed by centrifugation at 15,000× g for 10 min and the supematrats (25 ug of protein) were mixed with 10 ul of a slurry of GST c-Jun (1–79) Sepharos (3–5 ug of GST $cJun_{(1-79)}$). The mixture was rotated at 4° C. for 1 h, washed twice in lysis buffer and once in kinase buffer (20 mM Hepes, pH 7.5, 10 mM $MgCl_2$, 20 mM β-glycerophosphate, 10 mM p-nitrophenyl phosphate, 1 mM dithiothreitol, 50 uM sodium vanadate). Beads were suspended in 40 ul of kinase assay buffer containing 10 $\mu$Ci of [$\gamma^{32}$P]ATP and incubated at 30° C. for 20 min. Reaction mistures were added to Laemmli sample buffer, boiled, and phosphorylated proteins were resolved on SDS-10% polyacrylamide gels. The JNK activity also eluted early from a Mono Q column using a linear sodium chloride elution gradient. Immunoblotting demonstrated that this activity corresponded to the JNK/stress-activated protein kinase. When JNK activity was assayed following fractionation by Mono Q ion exchange chromatography, 50 ul of each fraction was incubated with the GST cJun ($_{1-79}$) beads.

Transient expression of MEKK 2 and 3 also stimulated p42/44$^{MAPK}$ activity. Immunoblotting of hemagglutinin (HA) epitope-tagged MEKK 2 and 3 indicated that MEKK 2 and 3 were expressed at similar levels in HEK293 cells when 2 $\mu$g of plasmid DNA was used per transfection. MAPK activity following Mono Q FPLC fractionation was measured using the epidermal growth factor receptor 662–631 peptide as a selective p42/44 MAPK substrate. Alternatively, for cells transfected with varying amounts of MEKK plasmids, MAPK activity was assayed after elution from DEAE Sephacel columns. To determine whether MEKK 2 and 3 demonstrated selectivity in activating the JNK and p42/44$^{MAPK}$ relative to JNK, plasmid DNAs were titrated over a range of concentrations in the transfections. MEKK 2 was found to have a greater selectivity for stimulation of the JNK pathway. In contrast, MEKK3 had a greater selectivity for activating p42/44 MAPK relative to JNK. Thus, even though the kinase domains are approximately 94% conserved, MEKK 2 and 3 differ in their selectivity for regulation of the JNK and p42/44MAPK pathways. This was particularly evident for MEKK 3 at low plasmid concentrations where the p42/44MAPK pathway was preferentially activated.

MEKK 2 Phosphorylates Both MEK1 and JNK Kinase in Vitro. HEK293 cells expressing MEKK 2 and 3 were lysed in !% Triton x-100, 0.5% Nonidet P-40, 20 mM Tris HCL, pH 7.5, 150 mM NaCl, 20 mM NaF, 0.2 mM sodium vanadate, 1 mM EDTA, 1 mM EDTA, 1 mM EGTA, 5 mM PMSF. Nuclei were removed by centrifugation at 15,000× g for 5 min. HA epitope-tagged MEKK2 and 3 were immunoprecipitated with the 12CA5 antibody recognizing the HA epitope-tag. The immunoprecipitates were washed twice in lysis buffer, twice in PAN (10 mM Pipes, pH 7.0, 100 mM NaCl, 20 ug/ml aprotinin), suspended in 20 mM Pipes, 10 mM MnCl$_2$, 20 ug/ml aprotinin, and used in an in vitro kinase assay with 20–50 ng of recombinant MEK1 or JNKK as substrates and 20 uCi of [$\gamma^{32}$P]ATP. Reactions were terminaed by the addition of Laemmli sample buffer, boiled, and proteins were resolved by SDS-10% PAGE.

To demonstrate MEKK activation of JNKK activity, the in vitro kinase reactions were performed with different combinations of recombinant, wild type or kinase inactive JNKK (lysine 116 mutated to methionine) and wild type or kinase-inactive JNK. Kinase-inactive JNK was made by mutating the active site lysine 55 to methionine (provided by Dr. Matt Jarpe). Incubations were for 30 min at 30° C. in the presence of 50 uM ATP. GST-cJun ($^{1-79}$) Sepharose beads were then added, and the mixture was rotated at 4° C. for 30 min. The beads were washed, suspended in 40 ul of c-Jun kinase assay buffer containing 20 uCi of [$\gamma$32P]ATP, and incubated for 15 min at 30° C. Reaction mixtures were added to Laemmli sample buffer, boiled, and phosphorylated proteins were resolved on SDS 10% PAGE.

MEKK 2 clearly phosphorylates both MEK1 and JNKK consistent with its ability to activate JNK and p42/44$^{MAPK}$ in HEK298 cells. MEKK 2-catalyzed phosphorylation of recombinant JNKK resulted in the enhancement of JNKK activity. Thus, JNKK is a MEKK 2 substrate whose activity is stimulated both in vitro and in vivo by MEKK 2. We were unable to demonstrate the ability of MEKK 3 to phosphorylate MEK 1, MEK 2, or JNKK in vitro using a variety of immunoprecipitation procedures. Although MEKK 3 was efficiently immunoprecipitated, as determined by Western blot analysis, it did not show measurable kinase activity toward MEK 1 or JNKK or show detectable autophosphorylation. This contrasted dramatically with the ability of MEKK 3 to activate both JNK and p42/44$^{MAPK}$ in cells. MEKK 3 protein was clearly immunoprecipitated using the 12CA5 antibody in these experiments, and a rabbit antisera raised against a keyhole limpet hemocyanin-conjugated peptide encoding the last 15 amino acids of MEKK 3 recognized the intact immunoprecipitated protein indicating that it was not degraded. The failure of immunoprecipitated MEKK 3 to phosphorylate recombinant MEK1 or JNKK suggests one of three possibilities: (i) MEKK 3 is denatured but not degraded during immunoprecipitation, (ii) MEKK 3 requires an additional protein or co-factor for its activity in vitro that is lost during immunoprecipitation, (iii) the relevant substrate for MEKK 3 in cells is neither MEK1 or 2 nor JNKK. At present, it is not clear which of these possibilities is responsible for the failure to detect MEKK 3 activity in vitro. We demonstrated that a mutant MEKK 3 having lysine 391 mutated to methionine, rendering it kinase-inactive, did not stimulate JNK or p42/44$^{MAPK}$ activity when expressed in HEK293 cells. This finding indicated that the functional kinase activity of MEKK 3 was required for the in vivo regulation of JNK and p42/44$^{MAPK}$.

MEKK 2 and 3 Do Not Regulate p38 Activity in HEK293 Cells. The p38 kinase is activated by hypersmotic conditions and recognizes the transcription factor ATF 2 as an in vitro substrate. Sorbitol treated (0.4M, 20 min) or control HEK293 cells were lysed in the same buffer as that used for immunoprecipitation of p38 using rabbit antiserum raised against the COOH terminal peptide sequence of p38. Immunoprecipitates were washed once in lysis buffer, once in assay buffer (25 mM Hepes, pH1 7.4, 25 mM $\beta$-glycerophosphate, 25 mM NaCl$_2$, 2 mM dithiothreitol, 0.1 mM sodium vanadate) resuspended, and used in an invitro kinase assay with a recombianant NH$_2$-terminal fragment of ATF 2 (20–50 ng). For analysis of p38 kinase activity from Mono Q FPLC fractions, 20 ul aliquots were mixed with kinase buffer containing 20–50 ng of recombinant ATF 2 and 10 uCi of [$\beta$32P]PATP. Reactions were quenched in Laemmli sample buffer, boiled, and proteins were resolved using SDS 10% PAGE. Immunoprecipitation and in vitro kinase assay of p38 from MEKK 2 and 3 transfected HEK293 cells indicated that neither MEKK 2 nor MEKK 3 stimulated p38 kinase activity. Mono Q FPLC fractionation of lysates from MEKK 2 or 3 transfected HEK293 cells confirmed that p38 kinase activity was similar to that from control transfected cells.

ATF 2 is also a substrate for JNK. Fractions 2–8 from cells transfected with MEKK 2 or 3, that contain immunoreactive JNK, have increased kinase activity toward ATF 2. This is a predicted result based on the ability of both MEKK 2 and 3 to stimulate JNK activity in HEK293 cells. Expression of MEKK 2 and 3 also activated additional ATF 2 phosphorylating activities resolved by Mono Q fractionation. These activities are seen to elute in fractions 9–12 and 13–18 for lysates from both MEKK 2 and 3 expressing cells.

These activities do not correspond by immunoblotting to JNK, p42/44$^{MAPK}$, p88, or MEKK 2 or 3 and represent novel kinase activities capable of phosphorylating recombinant ATF 2 that are regulated by both MEKK 2 and 3.

Example 3

This Example Describes the Expression of MEKK 1 Protein in COS-1 Cells to Define its Function in Regulating the Signaling System that includes MAPK COS cells in 100-mm culture dishes were transfected with either the pCVMV5 expression vector alone (1 $\mu$g: control)

or the pCVMV5 MEKK construct (1 µg: MEKK). After 48 hours, the cells were placed in serum-free medium containing bovine serum albumin (0.1 percent) for 16 to 18 hours to induce quiescence. Cells were then treated with human EGF (30 ng/ml)(+EGF) or buffer (control) for 10 minutes, washed twice in cold phosphate buffered saline (PBS), and lysed in cell lysis buffer containing 50 mM B-glycerophosphate (pH 7.2), 100 µM sodium vanadate, 2 mM MgCl$_2$, 1 mM EGTA Triton X-100 (0.5 percent), leupeptin (2 µg/ml), aprotinin (2µg/ml), and 1 mM dithiothreitol (600 µl). After centrifugation for 10 minutes at maximum speed in a microfuge, COS cell lysates containing 0.5 to 1 mg of soluble protein were subjected to FPLC on a MONO Q column, and eluted fractions were assayed for MAPK activity according to the method described in Heasley et al., p. 545, 1992, *Mol. Biol. Cell, Vol. 3*.

Figure 3:
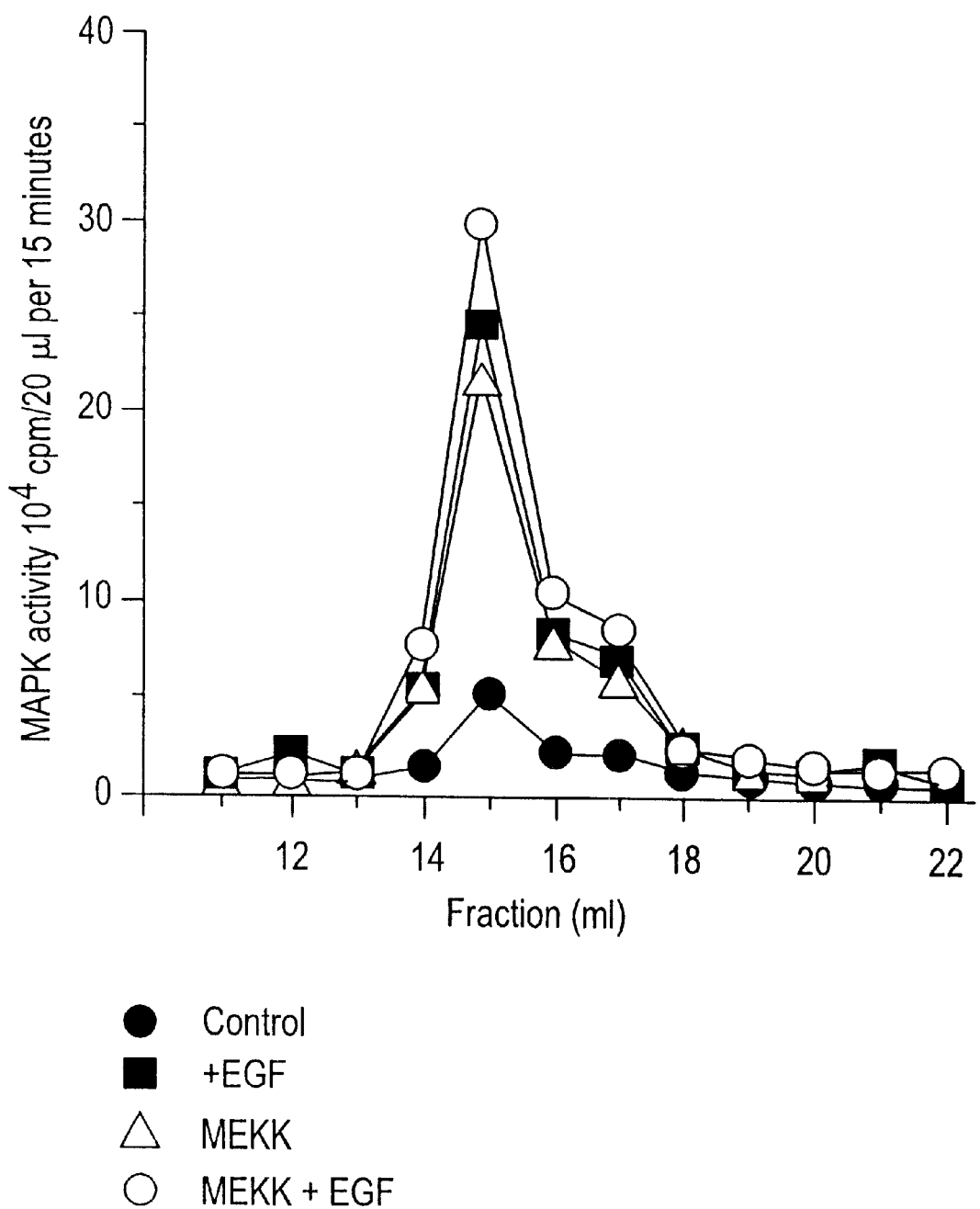
FIG. 3 shows the activation of MAPK in COS cells transfected with MEKK.

Referring to FIG. 3, when MEKK 1 was overexpressed in COS 1 cells, MAPK activity was four to five times greater than that in control cells transfected with plasmid lacking a MEKK1 cDNA insert. The activation of MAPK occurred in COS cells deprived of serum and in the absence of any added growth factor. The activity of MAPK was similar to that observed after stimulation of control cells with EGF. Stimulation of COS cells transiently overexpressing MEKK with EGF resulted in only a slight increase in MAPK activity compared to that observed with MEKK expression alone.

To ensure that MEKK protein was present in the samples tested for MAPK activity, protein from cell lysates of the transfected COS 1 cells were immunoblotted with MEKK specific antiserum. Equal amounts (100 µg) of soluble protein lysate from COS cells were placed on the gel for immunoblotting using the methods described in Example 1. The filters were immunoblotted using the affinity purified DRPP antiserum (1:300) and affinity purified MEKK1–369 antiserum (1:300). The results indicate that expression of MEKK in cells transfected with vector encoding MEKK that were treated with or without EGF. Only the 50 kD MEKK immunoreactive fragment was detected in lysates from control COS cells using the DRPP antiserum. Transient expression of MEKK in COS cells yielded a predominant 82 kD band that was slightly larger than that observed in PC12, Rat 1a, or NIH 3T3 cells. Addition of the 15 amino acid DRPP peptide antigen to the antiserum during immunoblotting prevented detection of all of the immunoreactive bands, these bands were not detected in extracts of control COS cells, an indication that they were derived from the expressed MEKK protein.

Example 4

This Example Describes the Expression of MEKK1 in COS Cells to Test the Ability of MEKK Protein to Activate MEK Protein Recombinant MAPK was used to assay MEK activity in COS cell lysates that had been fractionated by fast protein liquid chromatography (FPLC) on a Mono S column. A cDNA encoding p42 MAPK from *Xenopus laevis* was cloned into the pRSETB expression vector. This construct was used for expression in the LysS strain of *Escherichia coli* BL21(DE3) of a p42 MAPK fusion protein containing a polyhistidine sequence at the NH$_2$-terminus. Cultures containing the expression plasmid were grown at 37° C. to an optical density of 0.7 to 0.9 at 600 nM. Isopropyl-p-thiogalactopyranoside (0.5 mM) was added to induce fusion protein synthesis and the cultures were incubated for 3 hours. The cells were then collected and lysed by freezing, thawing, and sonication. The lysate was centrifuged at 10,000 g for 15 minutes at 4° C. The supernatant was then passed over a Ni$^{2+-}$ charged Sepharose resin and the soluble recombinant MAPK was eluted in sodium phosphate buffer (pH 4.5). The purified recombinant MAPK was more than 80 percent pure. The purified recombinant MAPK served as a substrate for MEK and catalyzed the phosphorylation of a peptide consisting of residues 662 to 681 of the EGF receptor (EGFR$^{662-681}$).

Soluble cell lysates from COS cells transiently transfected with MEKK, mock-transfected (control), or mock-transfected and treated with EGF (30 ng/ml) (+EGF), were fractionated by FPLC on a Mono S column and endogenous MEK activity was measured. Endogenous MAPK eluted in fractions 2 to 4, whereas MEK was contained in fractions 9 to 13. For assaying endogenous MEK activity, cells were washed twice in cold PBS and lysed in 650 µl of a solution containing 50 mM β-glycerophosphate, 10 mM 2-N-morpholinoethane-sulfonic acid (pH 6.0), 100 µM sodium vanadate, 2 mM MgCl$_2$, 1 mM EGTA, Triton X-100 (0.5 percent), leupeptin (5 µg/ml), aprotinin (2 µg/ml), and 1 mM dithiothreitol. After centrifugation at maximum speed for 10 minutes in a microfuge, soluble cell lysates (1 to 2 mg of protein) were applied to a Mono S column equilibrated in elution buffer (50 mM β-glycerophosphate, 10 mM MES (pH 6.0), 100 µM sodium vanadate, 2 mM MgCl$_2$, 1 mM EGTA, and 1 mM dithiothreitol. The column was washed with buffer (2 ml) and bound proteins were eluted with a 30 ml linear gradient of 0 to 350 mM NaCl in elution buffer. A portion (30 µl) of each fraction was assayed for MEK activity by mixing with buffer (25 mM β-glycerophosphate, 40 mM N-(2-hydroxyethyl)piperazine-N'-(2-ethanolsulfonic acid)(pH 7.2) 50 mM sodium vanadate, 10 mM MgCl$_2$, 100 µM γ-$^{32}$P-ATP (3000 to 4000 cpm/pmol), inhibitor protein-20 (IP-20; TTYADFIASGRTGRRNAIHD (SEQ ID NO:23); 25 µg/ml), 0.5 mM EGTA, recombinant MAP kinase (7.5 µg/ml), and 200 µM EGFR$^{662-681}$) in a final volume of 40 µl. After incubation at 30° C. for 20 minutes, the incorporation of γ-$^{32}$P-ATP into EGFR$^{662-681}$ was measured. In this assay, the ability of each column fraction to activate added recombinant MAPK was measured by the incorporation of γ-$^{32}$P-ATP into the MAPK substrate, a peptide derived from the EGF receptor (EGFR).

Figure 4:
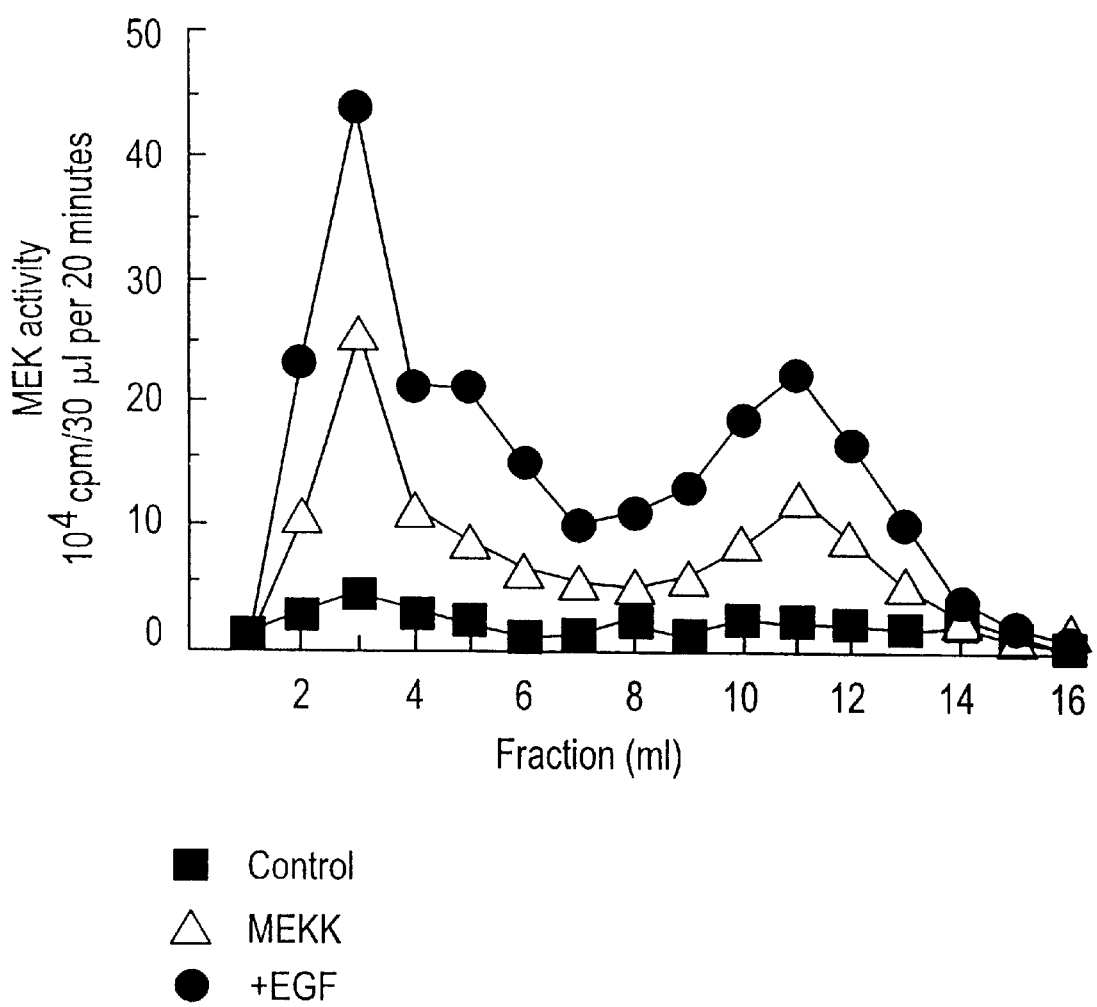
FIG. 4 shows the activation and phosphorylation of MEK in COS cells transfected with MEKK.

Referring to FIG. 4, the first peak of activity eluted represents endogenous activated MAPK, which directly phosphorylates the EGFR peptide substrate. The second peak of activity represents the endogenous MEK in COS cells.

The activity of endogenous MEK activity was characterized by fractionation of Mono S FPLC. COS cell lysates were fractionated by FPLC on a Mono Q column to partially purify the expressed MEKK. Purified recombinant MEK-1 was then used as a substrate for MEKK in the presence of γ-$^{32}$P-ATP to determine whether MEKK directly phosphorylates MEK-1.

A cDNA encoding MEK-1 was obtained from mouse B cell cDNA templates with the polymerase chain reaction and oligodeoxynucleotide primers corresponding to portions of the 5' coding region and 3' untranslated region of MEK-1. The catalytically inactive MEK-1 was generated by site-directed mutagenesis of Lys343 to Met. The wild-type MEK-1 and catalytically inactive MEK-1 proteins were expressed in pRSETA as recombinant fusion proteins containing a polyhistidine sequence at their NH$_2$-termini.

Lysates from COS cells transfected with MEKK or mock-transfected (control) were subjected to FPLC on a Mono Q column as described above. Portions (20 pl) of fractions containing MEKK were mixed with buffer containing 50 mM 13-glycerophosphate (pH 7.2), 100 μM sodium vanadate, 2 mM MgCl$_2$, 1 mM EGTA, 50 μM ATP, IP-20 (50 μg/ml), and 10 μl γ-$^{32}$P-ATP in a reaction volume of 40 –1 and incubated for 40 minutes in the presence (+) or absence (–) of recombinant, catalytically inactive MEK-1 (150 ng) (kinase-MEK-1). Reactions were stopped by the addition of 5× SDS sample buffer (10 μl), 1× SDS buffer contains 2 percent SDS, 5 percent glycerol, 62.5 mM tris-HCl (pH 6.8), 5 percent β-mercaptoethanol, and 0.001 percent bromophenol blue. The samples were boiled for 3 minutes and subjected to SDS-PAGE and autoradiography.

Autophosphorylated recombinant wild-type MEK-1 (WT MEK-1) comigrated with phosphorylated catalytically inactive MEK-1. Thus, MEKK was capable of phosphorylating MEK-1. Corresponding fractions of lysates from control cells, however, were not able to phosphorylate MEK-1.

Example 5

This Example Describes Studies Showing that the Modified Form of MEK-1 that Was Used in the Phosphorylation Assay of Example 4 Did Not Autophosphorylate as Does Wild-type MEK-1

Phosphorylation of catalytically inactive MEK-1 by MEKK was time dependent; MEKK was also phosphorylated. Fraction 22 from FPLC on a Mono Q column (20 μl) was incubated with or without recombinant catalytically inactive MEK-1 (0.15 μg) for the indicated times. Phosphorylation of kinase MEK-1 and MEKK was visable after 5 minutes and maximal after about 20 minutes. The time-dependent increase in MEKK phosphorylation correlated with a decreased mobility of the MEKK protein during SDS-PAGE. Immunoblotting demonstrated that the MEKK protein co-eluted (after FPLC on a Mono Q column) with the peak of activity (fraction 22) that phosphorylated MEK. The slowly migrating species of MEKK were also detected by immunoblotting. Thus, expression of MEKK appears to activate MAPK by activating MEK.

Example 6

This Example Describes That the Phosphorylation of MEK By Overexpressed MEKK Resulted in Activation of MEK, Recombinant Wild-type MEK-1 and a Modified Form of MAPK That is Catalytically Inactive COS cell lysates were separated by Mono Q-FPLC and fractions containing MEKK were assayed for their ability to activate added wild-type MEK-1 such that it would phosphorylate catalytically inactive recombinant MAPK in the presence of γ-$^{32}$P-ATP.

Lysates from COS cells transfected with MEKK or mock-transfected (control) were fractionated by FPLC on a Mono Q column and portions (20 μl) of fractions containing MEKK were mixed with buffer. Each fraction was incubated in the presence (+) or absence (–) of purified recombinant wild-type MEK-1 (150 ng) and in the presence of purified recombinant, catalytically inactive (kinase-) MAPK (300 ng). Fractions 20 to 24 from lysates of COS cells transfected with MEKK activated MEK-1. Thus, MEKK phosphorylated and activated MEK-1, leading to MAPK phosphorylation.

Example 7

This Example Describes Studies Demonstrating That MEKK Activated MEK Directly, and Not Through the Activation of One or More Other Kinases Contained in the Column Fractions Overexpressed MEKK was immunoprecipitated from COS cell lysates with affintiy purified MEKK1–369 antiserum. Immunoprecipitated MEKK was resuspended in 10 to 15 μl of PAN (10 mM piperazine-N,N'-bis-2-ethanesulfonic acid (Pipes) (pH 7.0), 100 mM NaCl, and aprotinin (20 μg/ml) and incubated with (+) or without (–) catalytically inactive MEK-1 (150 ng) and 25 μCi of γ-$^{32}$P-ATP in 20 mM pipes (pH 7.0), 10 mM MnCl$_2$, and aprotinin (20 μg/ml) in a final voume of 20 μl for 15 minutes 30° C. Reactions were stopped by the addition of 5× SDS sample buffer (5 μl). The samples were boiled for 3 minutes and subjected to SDS-PAGE and autoradiography.

MEKK phosphorylated catalytically inactive MEK-1, which comigrated with wild-type MEK-1 on SDS-PAGE. Several phosphorylated bands of overexpressed MEKK were detected in the immunoprecipitates. These bands probably resulted from autophosphorylation of MEKK and corresponded to the forms of MEKK identified by immunoblotting of lysates from COS cells transfected with MEKK. Immunoprecipitates obtained with pre-immune serum contained no MEKK and did not phosphorylate MEK-1. Thus, MEKK appears to directly phosphorylate MEK.

Taken together, the results from Examples 4 through 7 show that MEKK can phosphorylate and activate MEK, which in turn phosphorylates and activates MAPK.

Example 8

This Example Demonstrates That Raf Can Also Phosphorylate and Activate MEK

COS cells deprived of serum were stimulated with EGF, and Raf was immunoprecipitated with an antibody to the COOH-terminus of Raf-1. Cos cells were transiently transfected with vector alone (control) or with the PCV/M5-MEKK construct (MEKK). Quiescent control cells were treated with or without human EGF (30 ng/ml) for 10 minutes and Raf was immunoprecipitated from cell lysates with an antibody to a COOH-terminal peptide from Raf. Immunoprecipitated Raf was incubated with catalytically inactive MEK-1 (150 ng) and 25 μl of γ-$^{32}$P-ATP. The immunoprecipitated Raf phosphorylated MEK-1 in the presence of γ-$^{32}$P-ATP. Little or no phosphorylation of MEK-1 by Raf was observed in immunoprecipitates of Raf from COS cells overexpressing MEKK. Treatment of COS cells overexpressing) MEKK with EGF resulted in a similar degree of phosphorylation of MEK-1 by immunoprecipitated Raf. Cells transfected with MEKK and deprived of serum were treated with EGF, and Raf was immunoprecipitated and incubated with catalytically inactive MEK-1. Equal amounts of Raf were immunoprecipitated in each sample as demonstrated by immunoblotting with antibodies to Raf. The slowest migrating band represents an immunoprecipitated phosphoprotein that is unrelated to Raf or MEK-1. The amount of Raf in the immunoprecipitates from control cells and cells transfected with MEKK was similar as shown by subsequent SDS-PAGE and immunoblotting with the antibody to Raf. Thus, both MEKK and Raf can independently activate MEK.

Example 9

This Example Describes the Activation of a 98 kD MEKK Protein Isolated From PC12 Cells in Response to Stimulation of Cells Containing MEKK Protein By Growth Factors PC12 cells were deprived of serum by incubation in starvation media (DMEM, 0.1% BSA) for 18–20 hours and MEKK was immunoprecipitated from lysates containing equal amounts of protein from untreated controls or cells treated with EGF (30 ng/ml) or NGF (100 ng/ml) for 5 minutes with the above-described anti-MEKK antibodies speicific for the $NH_4$-terminal portion of MEKK. Immunoprecipitated MEKK was resuspended in 8 µl of PAN (10 mM piperazine-N,N'-bis-2-ethanesulfonic acid (Pipes) (pH 7.0), 100 mM NaCl, and aprotinin (20 µg/ml)) and incubated with catalytically inactive MEK-1 (150 ng) and 40 µCi of($\gamma$-$^{32}$P)ATP in universal kinase buffer (20 mM piperazine-N, N'-bis-2-ethanesulfonic acid (Pipes) (pH 7.0), 10 mM $MnCl_2$, and aprotinin (20 µg/ml)) in a final volume of 20 µl for 25 minutes at 30° C. Reactions were stopped by the addition of 2× SDS sample buffer (20 µl). The samples were boiled for 3 minutes and subjected to SDS-PAGE and autoradiography. Raf-B was immunoprecipitated from the same untreated and treated PC12 cell lysates as above with an antiserum to a COOH-terminal peptide of Raf-B (Santa Cruz Biotechnology, Inc.) and assayed similarly. Raf-1 was immunoprecipitated with an antiserum to the 12 COOH-terminal amino acids of Raf-1(Santa Cruz Biotechnology, Inc.). Epidermal growth factor (EGF) treatment of serum starved PC12 cells resulted in increased MEKK activity.

Figure 5:
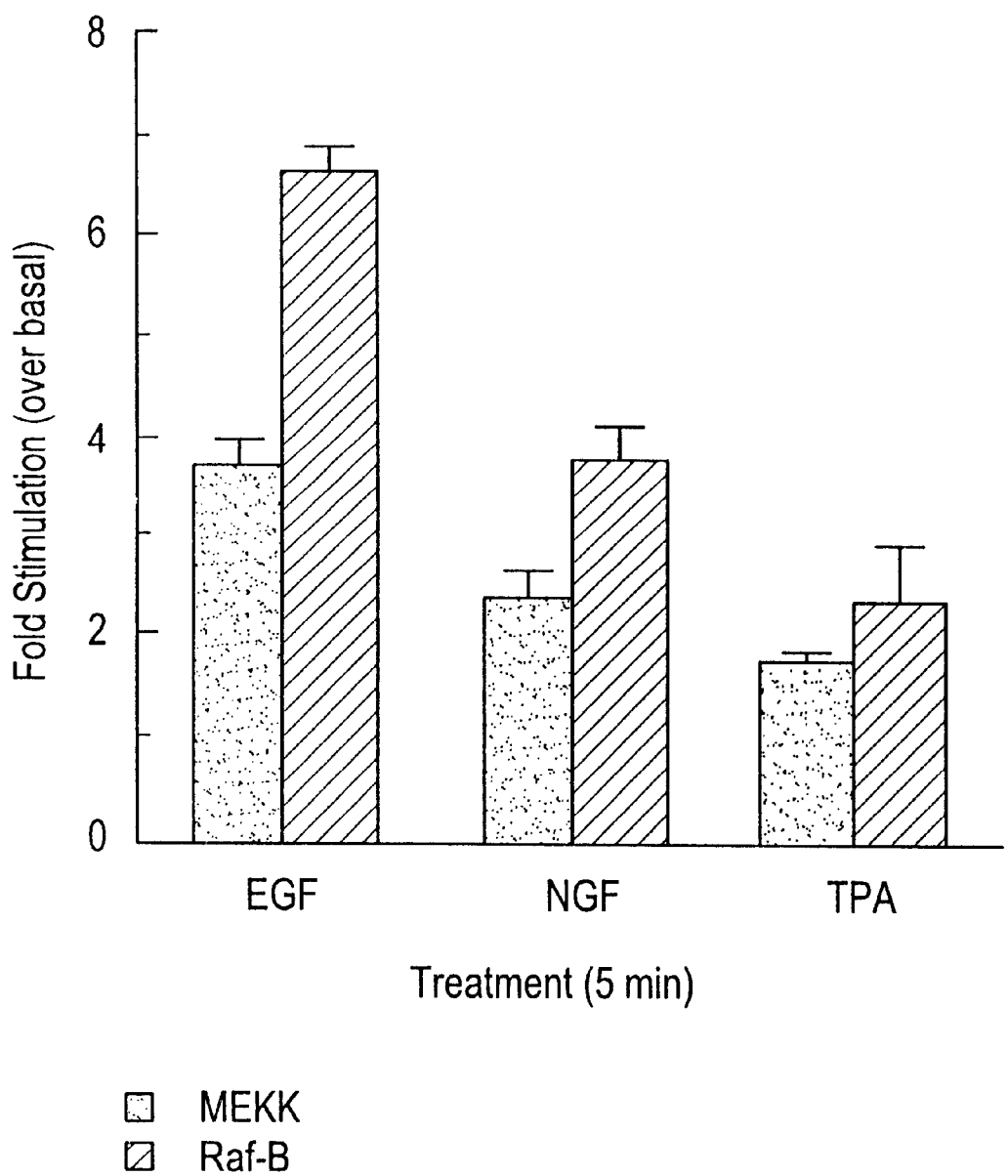
FIG. 5 shows the relative ability of immunoprecipitated MEKK and Raf-B to phosphorylate kinase inactive MEK-1.

Referring to FIG. 5, the results were obtained by measuring the phosphorylation of purified MEK-1 (a kinase inactive form) by immunoprecipitates of MEKK in in vitro kinase assays. NGF stimulated a slight increase in MEKK activity compared to control immunoprecipitates from untreated cells. Stimulation of MEKK activity by NGF and EGF was similar to Raf-B activation by these agents, although Raf-B exhibited a high basal activity. Activation of c-Raf-1 by NGF and EGF was almost negligible in comparison to that of MEKK or Raf-B.

Figure 6:
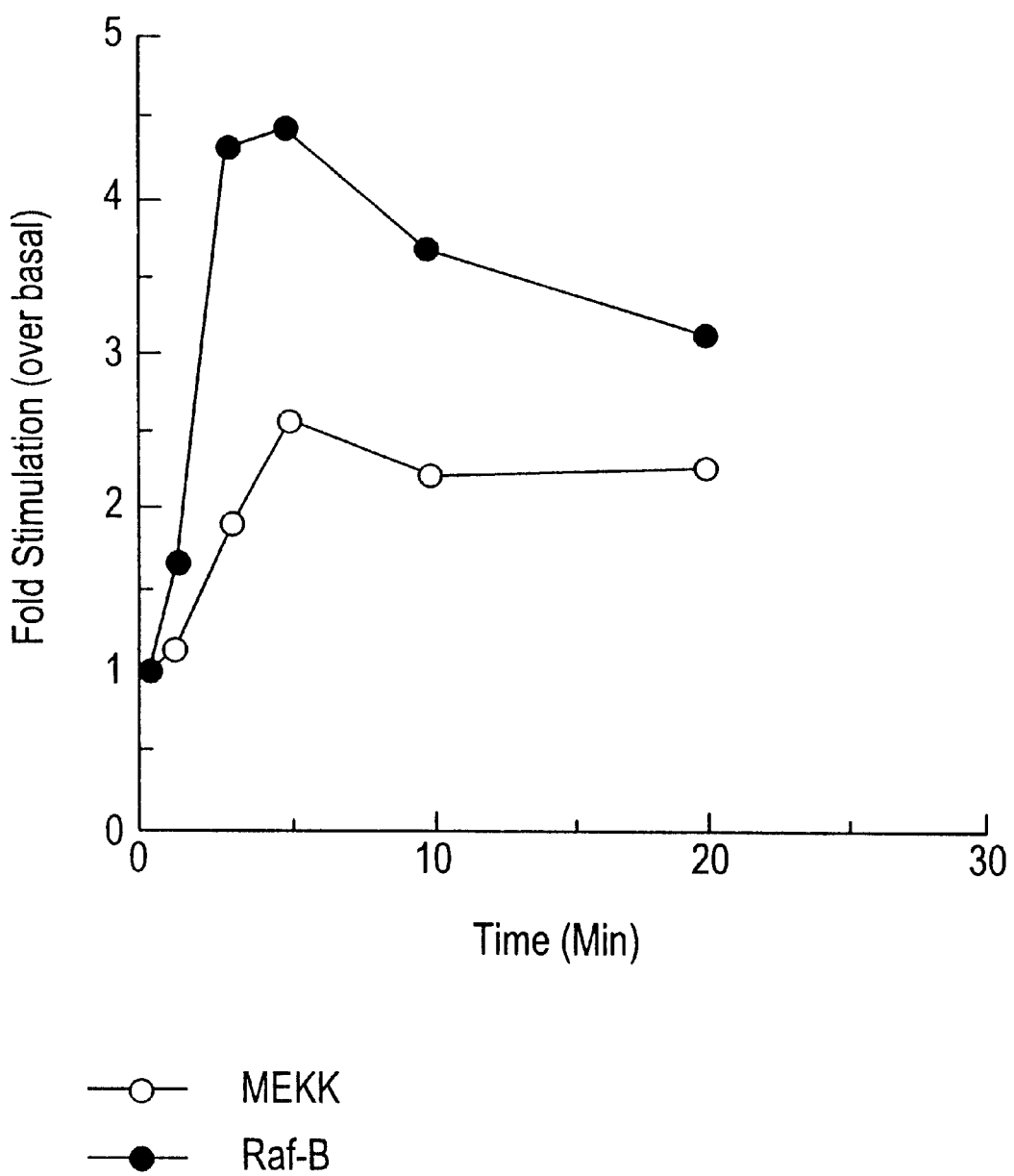
FIG. 6 shows a time course of EGF-stimulated MEKK and Raf-B activation.

A timecourse of MEKK stimulation by EGF was established by immunoprecipitating MEKK or Raf-B protein from lysates of PC12 cells treated with EGF (30 ng/ml) for 0, 1, 3, 5, 10, or 20 minutes and incubating the protein with catalytically inactive MEK-1 (1 50 ng) and ( $\gamma$-$^{32}$P)ATP as described above. Data represent the relative magnitude of the response for each timepoint as quantitated by phosphorimager analysis of radioactive gels from a typical experiment. As shown in FIG. 6 a timecourse of EGF treatment indicated that MEKK activation reached maximal levels following 5 minutes and persisted for at least 30 minutes. Raf-B exhibited a similar timecourse; peak activity occurred within 3–5 minutes following EGF treatment and was persistent for up to 20 minutes.

Figure 7:
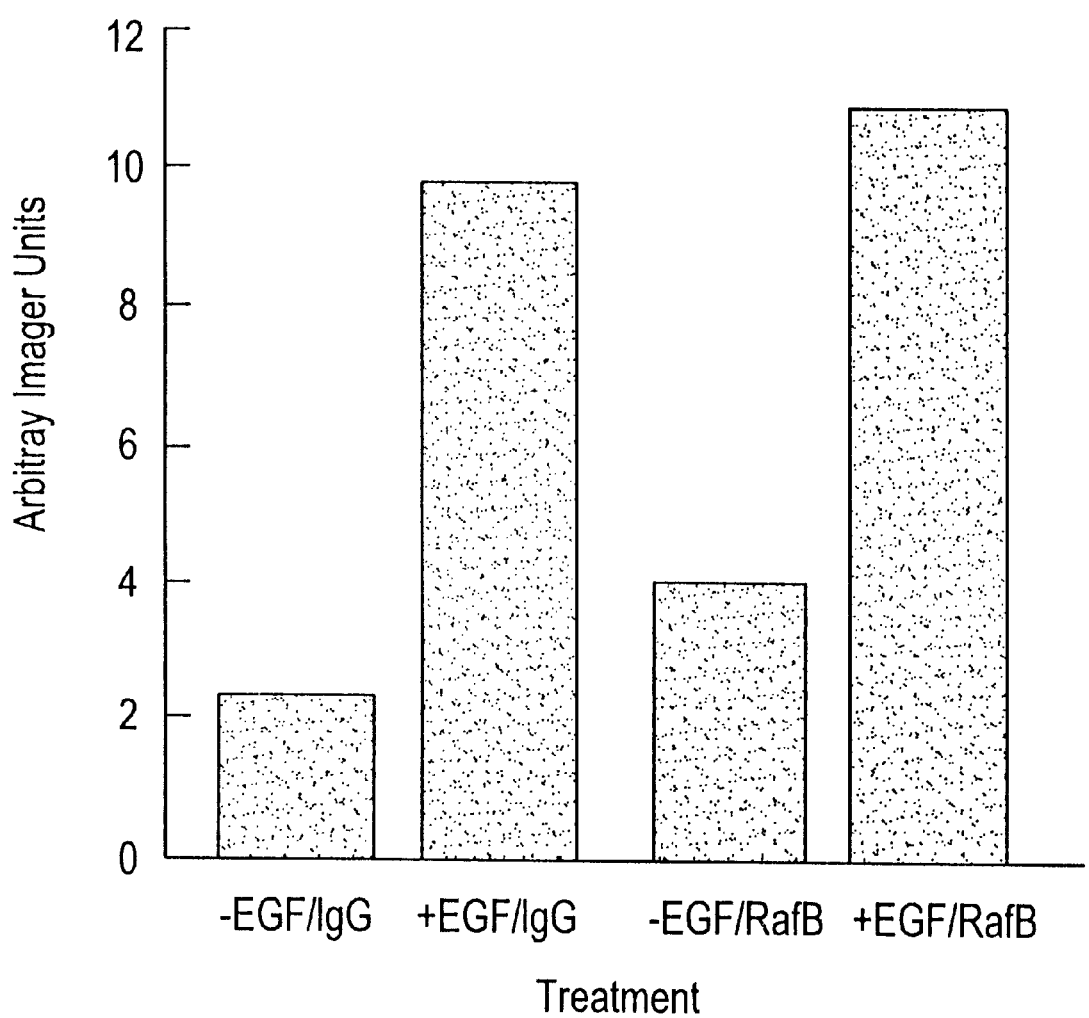
FIG. 7 shows that the immunodepletion of Raf-B from MEKK immunoprecipitates has no effect on MEKK activity.

To further dissociate EGF-stimulated MEKK activity from that of Raf-B, Raf-B was immunodepleted from cell lysates prior to MEKK immunoprecipitation. Raf-B was precleared from lysates of serum-starved PC12 cells which had been either treated or not treated with EGF (30 ng/ml) for 5 minutes. Raf-B was pre-cleared two times using antisera to Raf-B or using preimmune IgG antisera as a control. The pre-cleared supernatant was then immunoprecipitated with either MEKK or Raf-B antisera and incubated with catalytically inactive MEK-1 and ($\gamma$-$^{32}$P)ATP as described in detail above. EGF-stimulated and unstimulated PC12 cell lysates were precleared with either IgG or Raf-B antisera and then subjected to immunoprecipitation with MEKK antiserum or Raf-B antibodies. The results shown in FIG. 7 indicate that pre-clearing with Raf-B resulted in a 60% diminution of Raf-B activity as measured by phosphorimager analysis of Raf-B in vitro kinase assays. EGF-stimulated MEKK activity was unaffected by Raf-B depletion, suggesting that Raf-B is not a component of MEKK immunoprecipitates. At least 40% of the Raf-B activity is resistant to preclearing with Raf-B antibodies.

Recombinant wild type MEKK over-expressed in COS cells readily autophosphorylates on serine and threonine residues and the amino-terminus of MEKK is highly serine and threonine rich. MEKK contained in immunoprecipitates of PC12 cells were tested for selective phosphorylation of purified recombinant MEKK amino-terminal fusion protein in in vitro kinase assays.

Figure 8:
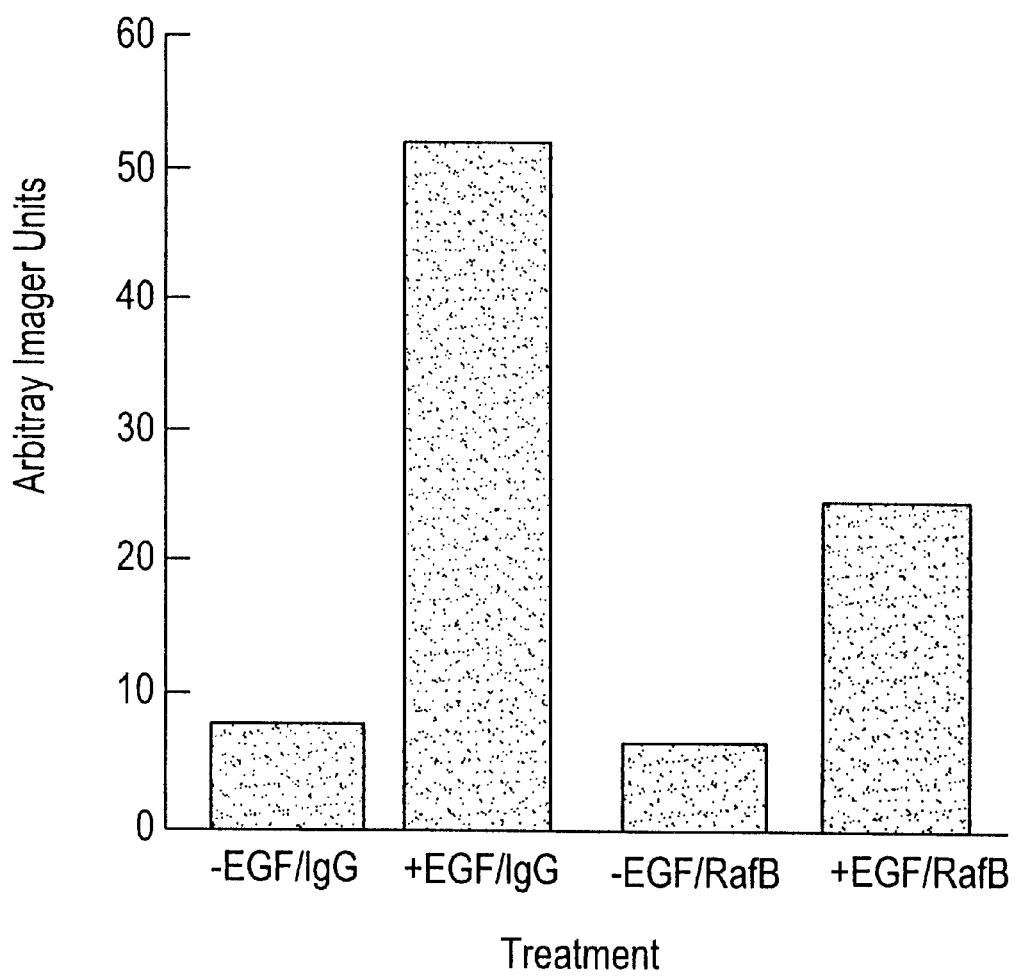
FIG. 8 shows that the immunodepletion of Raf-B from MEKK immunoprecipitates decreases Raf-B activity.

Serum-starved PC12 cells were treated with EGF (30 ng/ml) for 5 minutes and equal amounts of protein from the same cell lysates were immunoprecipitated with either MEKK, Raf-B, or preimmune antiserum as a control. Immunoprecipitates were incubated with purified recombinant MEKK $NH_2$-terminal fusion protein (400 ng) and ($\gamma$-$^{32}$P) ATP as described above. The results shown in FIG. 8 indicate that MEKK immunoprecipitated from lysates of EGF-stimulated and unstimulated PC12 cells robustly phosphorylated the inert 50 kD MEKK $NH_2$-fusion protein, while Raf-B or preimmune immunoprecipitates from EGF-stimulated or unstimulated cells did not use the MEKK $NH_2$-fusion protein as a substrate. Thus, the EGF-stimulated MEKK activity contained in MEKK immunoprecipites is not due to contaminating Raf kinases.

Example 10

This Example Describes MEKK Activity in FPLC Mono Q Ino-exchnage Column Fractions of PC12 Cell Lysates Cell lysates were prepared from EGF-stimulated PC12 cells. Portions (900 µl) of 1 ml column fractions (1 to 525 mM NaCl gradient) were concentrated by precipitation with trichloroacetic acid and loaded on gels as described above. The gels were blotted and then immunoblotted with MEKK specific antibody. The 98 kD MEKK immunoreactivity eluted in fractions 10 to 12. The peak of B-Raf immunoreactivity eluted in fraction 14, whereas Raf-1 was not detected in the eulates from the column. Portions (30 Pl) of each fraction from the PC12 lysates of unstimulated control cells or EGF-treated cells were assayed as described above in buffer containing purified recombinant MEK-1 (150 ng) as a substrate. These results indicate that the peak of MEKK activity eluted in fractions 10 to 12 from EGF-stimulated PC12 cells phosphorylated MEK, whereas little MEK phosphorylation occurred in fractions from unstimulated cells.

Example 11

This Example Describes Studies Demonstrating That the Phosphorylation of Both

MEK-1 and the MEKK $NH_2$-terminal fusion protein were due to the activity of the 98 kD PC12 cell MEKK.

Cell lysates prepared from EGF-stimulated and unstimulated cells were fractionated by FPLC on a Mono-Q column to partially purify the endogenous MEKK. Lysates from unstimulated control PC12 cells or cells treated with EGF (30 ng/ml) for 5 minutes were fractionated by FPLC on a Mono Q column using a linear gradient of 0 to 525 mM NaCl. A portion (30 µl) of each even numbered fraction was mixed with buffer (20 mM piperazine-N,N'-bis-2-ethanesulfonic acid (Pipes) (pH 7.0), 10 mM $MnCl_2$, aprotinin (201 g/ml), 50 mM P -glycerophosphate (pH 7.2), 1 mM EGTA, IP-20 (50 µg/ml), 50 mM NaF, and 30° Ci ($\gamma$-$^{32}$P)ATP) containing purified recombinant MEK-1 (150 ng) as a substrate in a final volume of 40 µl and incubated at 30° C. for 25 minutes. Reactions were stopped by the addition of 2× SDS sample buffer (40 µl), boiled and subjected to SDS-PAGE and autoradiography. The peak of MEKK activity eluted in fractions 10–12. Portions (30 μl) of each even numbered fraction from lysates of EGF-treated PC12 cells were mixed with buffer as described above except containing purified recombinant MEKK $NH_2$-terminal fusion protein (400 ng) as a substrate instead of MEK-1. Purified recombinant kinase inactive MEK-1 or the MEKK $NH_2$-terminal fusion protein were then used as substrates in the presence of ($\gamma$-$^{32}$P)ATP to determine whether 98 kD MEKK directly phosphorylates either substrate. Fractions 10–14 of lysate from PC12 cells treated with EGF phosphorylated MEK-1 while little MEK-1 phosphorylation occurred in untreated control fractions. The MEKK $NH_2$-terminal fusion protein was also phosphorylated in the same fractions as was MEK-1, although the peak of activity was slightly broader (fractions 8–16).

Immunoblotting of column fractions demonstrated that the 98 kD MEKK protein co-eluted with the peak of activity that phosphorylated either exogenously added kinase inactive MEK-1 or the 50 kD MEKK $NH_2$-terminal fusion protein. Portions (900 μl) of even numbered column fractions were concentrated by precipitation with trichloroacetic acid and immunoblotted with MEKK antibody. The peak of immunoreactivity eluted in fractions 10–12.

Example 12

This Example Describes the Activation of MEK By a 98 kD MEKK 98 kD MEKK was immunoprecipitated using the $MEKK_{1-369}$ antiserum described in Example 1 from untreated (−) or EGF-treated (+) PC12 cell lysates. The immunoprecipitates were incubated in the presence (+) or absence (−) of purified recombinant wild-type MEK (150 ng) and in the presence of purified recombinant catalytically inactive MAPK (300 ng) and ($\gamma$-$^{32}$P)ATP. The results indicate that immunoprecipitated MEKK from EGF-stimulated cells phosphorylated and activated MEK, leading to MAPK phosphorylation. No phosphorylation of MAPK occurred in the absence of added recombinant MEK. Immunoblotting demonstrated that there was no contaminating MAPK or contaminating MEK in the MEKK immunoprecipitates from the EGF-stimulated PC12 cells. Thus, phosphorylation and activation of MEK is due to EGF stimulation of MEKK activity measured in the immunoprecipitates.

Example 13

Figure 9:
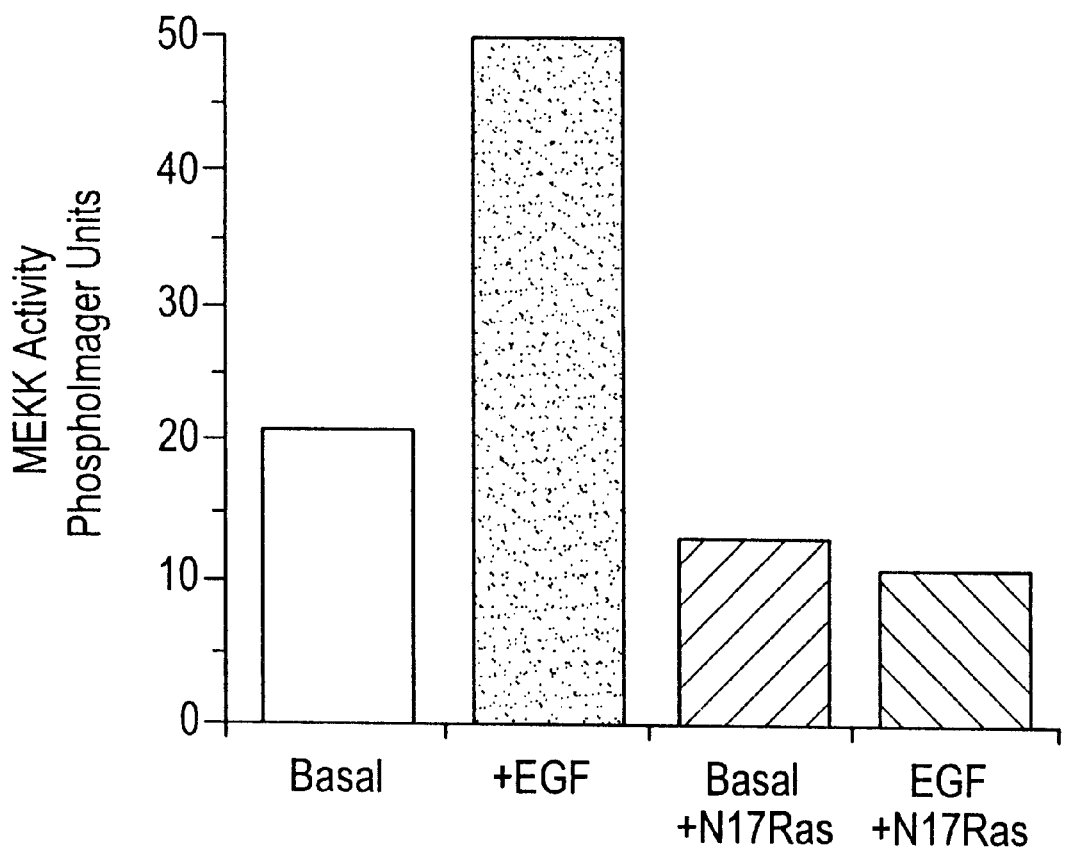
FIG. 9 shows inhibition of MEKK and Raf-B activation by dominant negative $N^{17}$ RAS expression.
Figure 10:
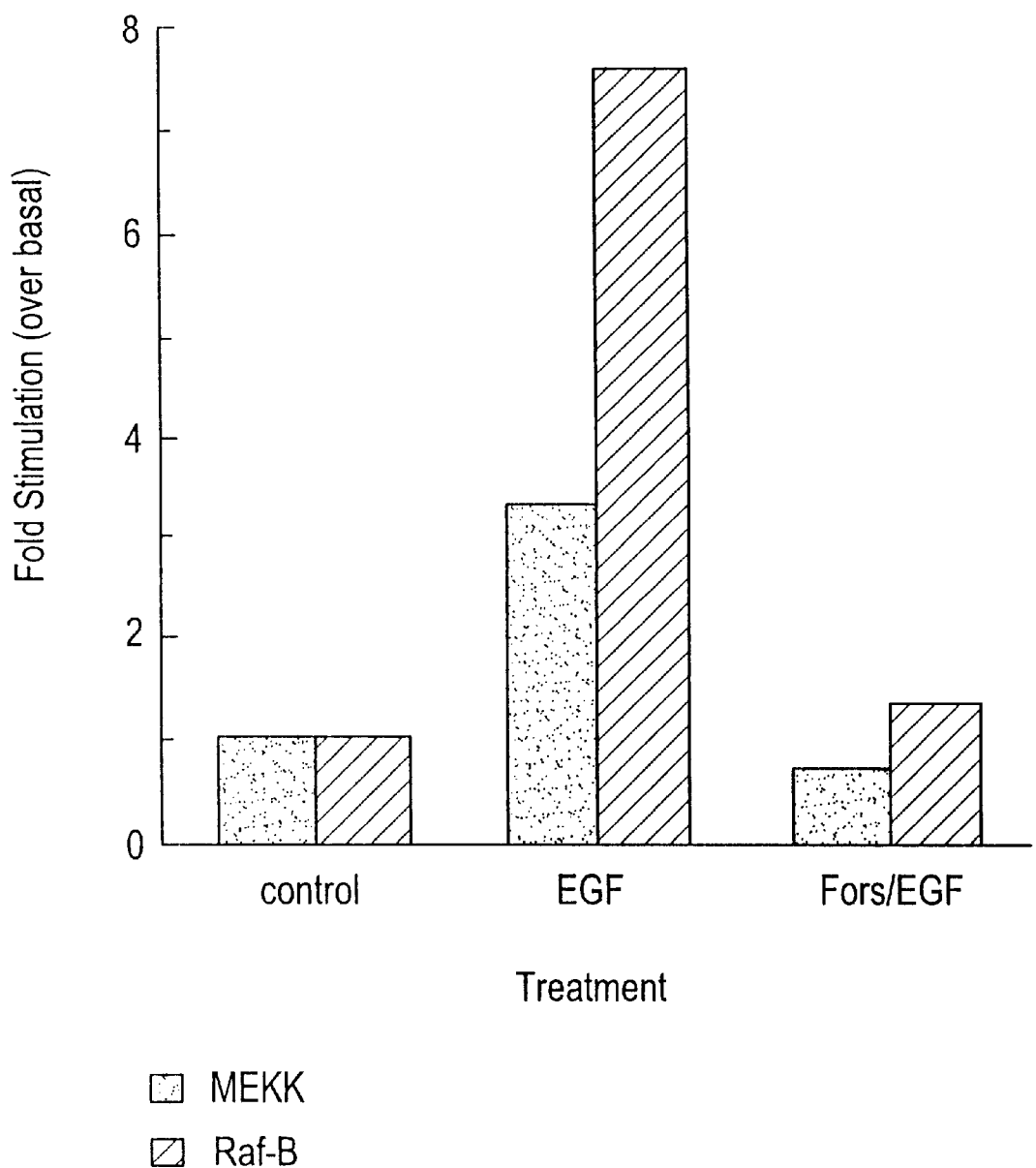
FIG. 10 shows inhibition of EGF activation of MEKK by forskolin.

This Example Describes Whether 98 kD PC12 Cell MEKK and Raf-B Require Functional Ras Proteins For Growth Factor Mediated Signaling Dominant negative Ha-ras(Asn 17) ($N^{17}$Ras) was expressed in PC12 cells and EGF-stimulated MEKK or Raf-B activation was assayed in immunoprecipitates using kinase inactive MEK-1 as a substrate. PC12 cells stably expressing dexamethasone inducible $N^{17}$Ras were serum starved for 18–20 hours in media containing 0.1% BSA with or without 1 μM dexamethasone and then untreated or treated with EGF (30 ng/ml) for 5 minutes. Equal amounts of soluble protein from cell lysates was immunoprecipitated with either MEKK or Raf-B antisera and incubated with purified recombinant catalytically inactive MEK-1 and ($\gamma$-$^{32}$P)ATP as described above. Expression of $N^{17}$Ras was induced in PC12 clones stabley transfected with the $N^{17}$Ras gene by the addition of dexamethasone to the starvation media. As shown in FIG. 9, $N^{17}$Ras expression inhibited the activation of MEKK by EGF as measured by its ability to phosphorylate kinase inactive MEK. EGF-mediated activation of Raf-B was also greatly reduced in $N^{17}$Ras expressing PC12 cells compared to uninduced $N^{17}$Ras transfectants. Addition of dexamethasone to wild type PC12 cells had no effect on the magnitude of MEKK or Raf-B activation elicited by EGF. PC12 cell clones stably transfected with the $N^{17}$Ras gene are less responsive to EGF-mediated activation of MEKK activity than are wild type PC12 cells. These results indicate that functional Ras is required for growth factor stimulated activation of both Raf-B and MEKK in PC12 cells, suggesting that Ras may mediate its effects on cell growth and differentiation through the activation of multiple protein kinase effectors from both the Raf and MEKK families. Thus, EGF stimulated a peak of MEKK activity within 5 minutes which persisted for at least 30 minutes following treatment, and was similar to the time-course of Raf-B activation. Nerve growth factor (NGF) and the phorbol ester TPA also activated MEKK, although to a lesser degree than EGF. MEKK activity in immunoprecipitates or column fractions was dissociable from that of EGF-stimulated c-Raf-1 and Raf-B activities. Forskolin pretreatment abolished both MEKK and Raf-B activation by EGF, NGF, and TPA (FIG. 10). Both MEKK and Raf-B activation in response to EGF was inhibited by stable expression of dominant negative $N^{17}$ Ras. These findings represent the first demonstration of Ras-dependent MEKK regulation by growth factors and suggest the emergence of a complex intracellular kinase network in which Ras may alternately couple between members of the Raf and MEKK families.

To determine whether the growth factor-mediated activation of 98 kD PC12 cell MEKK was inhibited by PKA, forskolin was used to elevate intracellular cAMP and activate PKA. Serum-starved PC12 cells were pretreated with or without forskolin (50μM) for 3 minutes to activate protein kinase A and then with EGF (30 ng/ml), NGF (10 ng/ml), or TPA (200 nM) for 5 minutes and MEKK was immunoprecipitated from equal amounts of soluble protein from cell lysates and incubated with purified recombinant catalytically inactive MEK-1 and ($\gamma$-$^{32}$P)ATP as described above. Raf-B activity was also assayed from the same cell lysates to test whether its regulation differed from that of MEKK. Raf-B was immunoprecipitated from the same cell lysates as described above and assayed for its ability to phosphoryl ate MEK-1 as described above. Forskolin pretreatment abolished the activation of both MEKK and Raf-B by EGF, NGF, and TPA, as measured by their ability to phosphorylate kinase-inactive MEK-1 (FIG. 10). Forskolin treatment alone had no appreciable effect on either kinase. These results demonstrate that in addition to Raf-1 and Raf-B, PKA activation inhibits growth factor stimulation of 98 kD PC12 cell MEKK, suggesting the existence of a common regulatory control point for PKA action which lies between or downstream of Ras and upstream or at the level of each of these three kinases.

Example 14

This Example Describes the Determination of Whether a Similar or Distinct MEK Activity is Involved in Activation of MAPK Though $G_i$ Protein Coupled Receptors By Measuring MEK activity in cell lysates from thrombin stimulated Rat 1a cells Thrombin stimulated cells exhibited a MEK activity which co-fractionated with the major MEK peak detected in EGF stimulated cells. The magnitude of MEK activity from thrombin challenged cells was generally two to three-fold less than that observed with EGF stimulation, which correlates with the smaller MAPK response the present inventors have observed in thrombin challenged cells.

Differential regulation of MEK in Rat 1a and NIH3T3 cells expressing gip2, v-src, V-ras, or v-raf led the present inventor to investigate the protein kinases that are putative regulators of MEK-1. Recently, it was shown that Raf-1 can phosphorylate and activate MEK. Raf activation was assayed in the following manner. Cells were serum starved and challenged in the presence or absence of the appropriate growth factors, as described above. Serum starved Rat 1a cells were challenged with buffer alone or with EGF and Raf was immunoprecipitated using an antibody recognizing the C terminus of Raf. Cells were lysed by scraping in ice cold RIPA buffer (50 mM Tris, pH 7.2, 150 mM NaCl, 0.1% SDS, 0.5% sodium deoxycholate, 1.0% Triton X 100, 10 mM sodium pyrophosphate, 25 mM sodium glycerophosphate, 2 mM sodium vanadate, 2.1 µg/ml aprotinin) and were micro fuged for 10 min to remove nuclei. The supernatants were normalized for protein content and precleared with protein A Sepharose prior to immunoprecipitation with rabbit antiserum to the C terminus of Raf-1 and protein A Sepharose for 2–3 h at 4° C. The beads were washed twice with ice cold RIPA and twice with PAN (10 mM Pipes, pH 7.0, 100 mM NaCl, 21 µg/ml aprotinin). A portion of the immunoprecipitate was diluted with SDS sample buffer and used for immunoblot analysis. The remainder was resuspended in kinase buffer (20 mM Pipes pH 7.0, 10 mM $MnCl_2$, 150 ng kinase-inactive MEK-1, 30 µCi $\gamma$-$^{32}$P-ATP and 20 µg/ml aprotinin) in a final volume of 50 µl for 30 min at 30° C. Wild type recombinant MEK-1 was autophosphorylated in parallel as a marker. Reactions were terminated by the addition of 12.5 µl 5× SDS sample buffer, boiled for 5 minutes and subjected to SDS-PAGE and autoradiography.

The immunoprecipitated Raf, in the presence of $\gamma$-$^{32}$P-ATP, was able to phosphorylate MEK-1. The recombinant MEK-1 used in this assay was kinase inactive to ensure it did not autophosphorylate as is observed with wild type MEK-1. Little or no phosphorylation of MEK-1 by Raf was observed in immunoprecipitates from control cells. EGF challenge clearly stimulated Raf catalyzed phosphorylation of MEK-1; in contrast, thrombin challenge of Rat 1a cells did not measurably activate Raf even though endogenous MEK was clearly activated. EGF stimulated Raf phosphorylation of recombinant MEK-1 by approximately 2.6-fold over basal. Little phosphorylation of MEK by Raf was observed in Raf immunoprecipitates from Gip2 or v-Src expressing Rat 1a cells. EGF stimulation was still capable of activating Raf catalyzed phosphorylation of MEK-1 in these cell lines by 1.8 and 1.4-fold, respectively. The blunting of the EFG response in Gip2 and v-Src expressing cells is likely a result of desensitization of the EFG receptor upon constitutive activation of MAPK. The amount of Raf in the immunoprecipitates was shown to be similar by subsequent SDS-PAGE and immunoblotting using Raf antibody. Since thrombin stimulation of MEK is two to three-fold over basal, at least a 1.5-fold stimulation of MEK phosphorylation is expected if Raf significantly contributed to MEK activation by this growth factor. This level of activation was detectable in the EGF stimulated Gip2 and v-Src expressing cells lines. Thus, it is unlikely that the failure to detect thrombin activation of Raf is due to the sensitivity of the assay. Thrombin stimulation of MAPK is maximal at 3 minutes. Stimulation of Rat 1a cells for 1 or 5 minutes with thrombin did not increase Raf activity.

In NIH3T3 cells, as in Rat 1a cells, EGF activates Raf approximately 2.7-fold, while thrombin does not. V-Raf expressing NIH3T3 cells showed no increase in MEK-1 phosphorylation. This result was unexpected since MEK was clearly activated in v-Raf expressing NIH3T3 cells. Both the p90 and p75 gag-raf fusion proteins in addition to c-Raf-1 were immunoprecipitated from v-Raf NIH3T3 cells by the antisera. P75 gag-raf has been shown to exhibit protein kinase activity, but it is possible that the $NH_2$ terminal gag fusion protein sterically hinders Raf phosphorylation of recombinant MEK-1 in the in vitro assay system. Further studies will have to be done to measure v-Raf kinase activity. The results argue that activation of MEK cannot be accounted for exclusively by the activation of Raf. Additional regulatory kinases for MEK must exist which contribute to MEK activation in thrombin stimulated, Gi protein coupled pathways and in gip2 and v-src transfected cells.

Example 15

Figure 11:
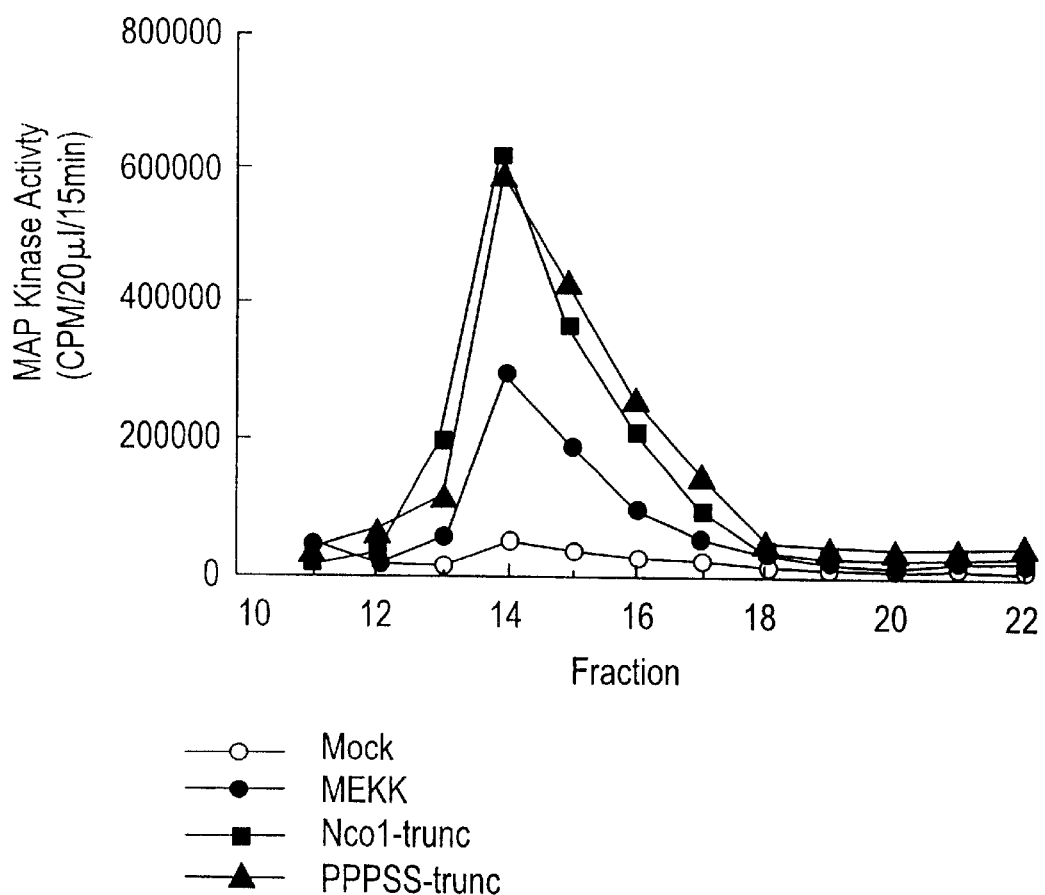
FIG. 11 shows improved MEKK activity by truncated MEKK molecules (e.g., PPPSS-trunc MEKK, PPPSS corresponding to amino acids 211 to 215 of SEQ ID NO:2).

This Example Demonstrates the Ability of a PPPSS-trunc PPPSS corresponds to amino acids 211 to 215 of SEQ ID NO:2 and Ncol-trunc of MEKK Protein to Activate MAPK Activity Compared With Full-length MEKK Protein and a Negative Control Protein The results shown in FIG. 11 indicate that the truncated MEKK molecules were more active than the full-length MEKK. Indeed, the truncated MEKK molecules were at least about 1.5 times more active than full-length MEKK protein. Thus, removal of the regulatory domain of MEKK deregulates the activity of the catalytic domain resulting in improved enzyme activity.

Example 16

Figure 12:
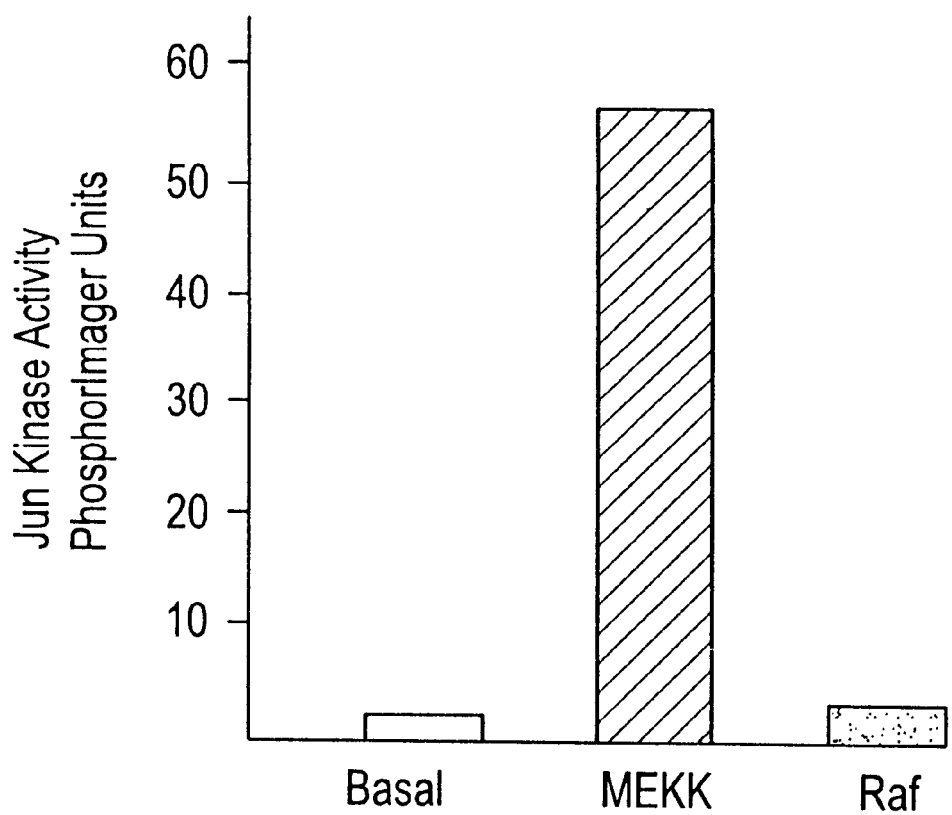
FIG. 12 shows JNK activation by MEKK protein.

This Example Describes the Preferential Activation of JNK By MEKK Compared With Raf HeLa cells were transiently transfected with truncated MEKK370–738 under control of an inducible mammary tumor virus promoter, together with epitope tagged JNK1 (described in detail in Derijard et al., p. 1028, 1994, Cell, Vol. 76). Other HeLa cells were also transiently transfected with truncated BXB-Raf under control of an inducible mammary tumor virus promoter, together with epitope tagged JNK1(Derijard et al., ibid). The following day, MEKK370–738 expression and BXB-Raf expression were induced by administration of dexamethasone (10 µM) for 17 hours. Cell extracts were then prepared and assayed for JNK activity using an immune complex kinase assay (detailed in Derijard et al., ibid.). Phosphorylation was quantitated by phosphorimager analysis. The results shown in FIG. 12 indicate that MEKK stimulated about 30-fold to about 50-fold activation more JNK activity over unstimulated cells (basal) and about 15-fold to about 25-fold JNK activity over Raf stimulated cells.

Example 17

This Example Describes That the Phosphorylation of c-Myc Transactivation Domain in Response to MEKK Expression Activates MYC-GAL 4 Transcriptional Activity Two separate expression plasmids were constructed as follows. The expression plasmid pLNCX was ligated to a cDNA clone comprising c-myc (1–103) ligated to GAL4

(1–147) (Seth et al., pp. 23521–23524, 1993, *J Biol. Chem.*, Vol. 266) to form the recombinant molecule pMYC-GAL 4. The expression plasmid $UAS_G$-TK Luciferase (Sadowski et al., pp. 563–564, 1988, *Nature*, Vol. 335) was transfected with either pMYC-GAL 4 or pLU-GAL into Swiss 3T3 cells using standard methods in the art to form recombinant cells herein referred to as LU/GAL cells. Recombinant control cells were also produced by transfecting in pGAL4-Control plasmids containing GAL4 (1–147) alone in the absence of c-myc (1–103).

LU/Gal cells were transfected with either pMEKK370–738, pMEKK (encoding full-length MEKK1-738), BXB-Raf, pMyc-Gal4, pCREB-Gal4 (encoding $CREB_{1-261}$ fused to Gal $4_{1-147}$; Hoeffler et al., pp. 868–880, 1989, *Mol. Endocrinol.*, Vol. 3), pGal4, or CREB fusion protein referred to as GAL4.

Figure 13:
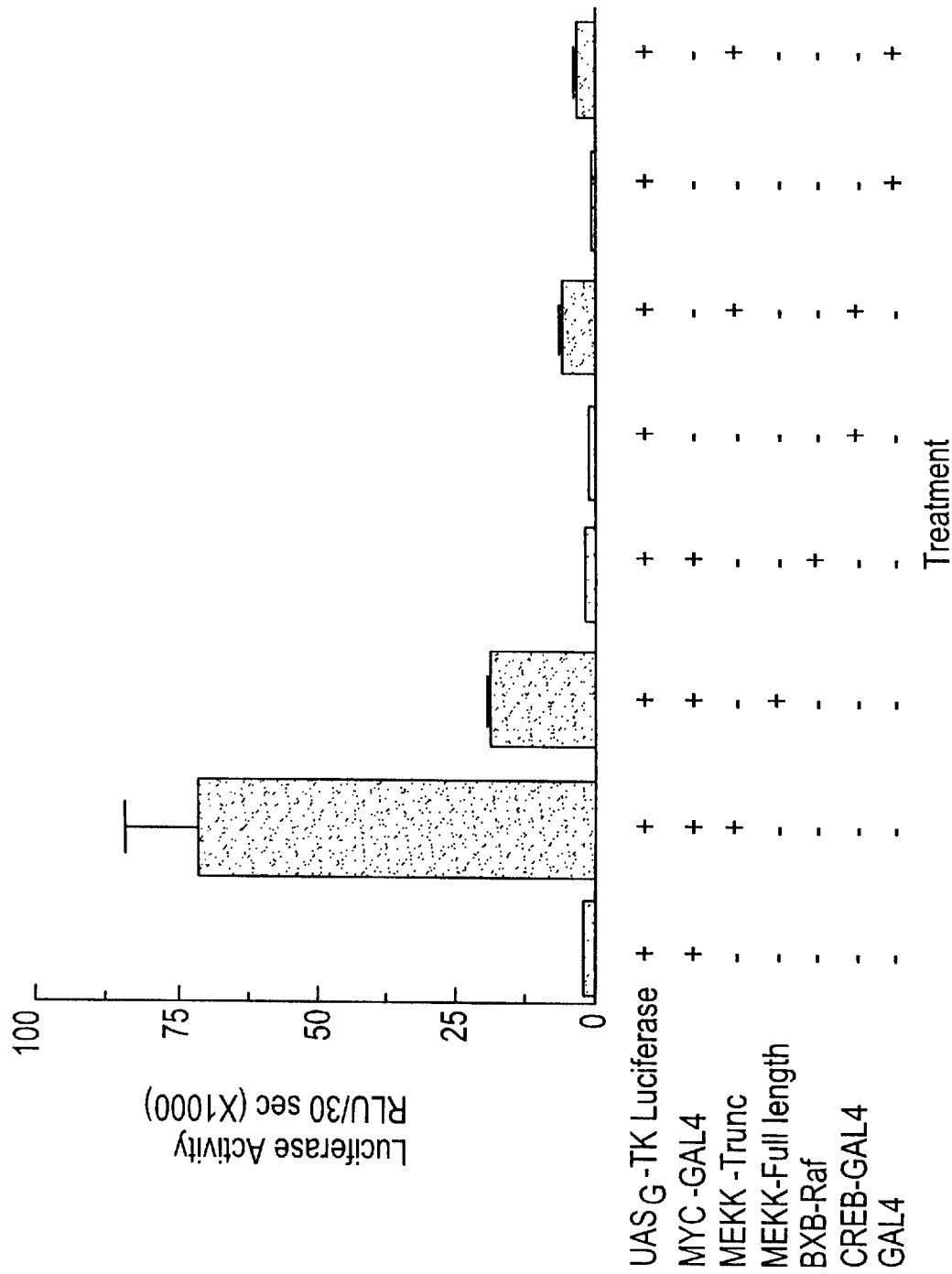
FIG. 13 shows regulation of c-Myc controlled transcription and not CREB controlled transcription by MEKK protein.
Figure 14A:
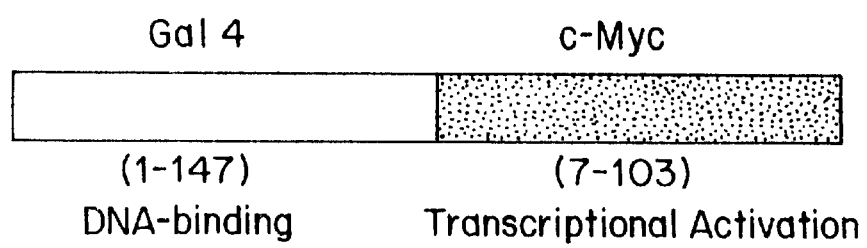
FIG. 14 is a schematic representation of MEKK regulation of c-Myc controlled transcription.
Figure 14B:
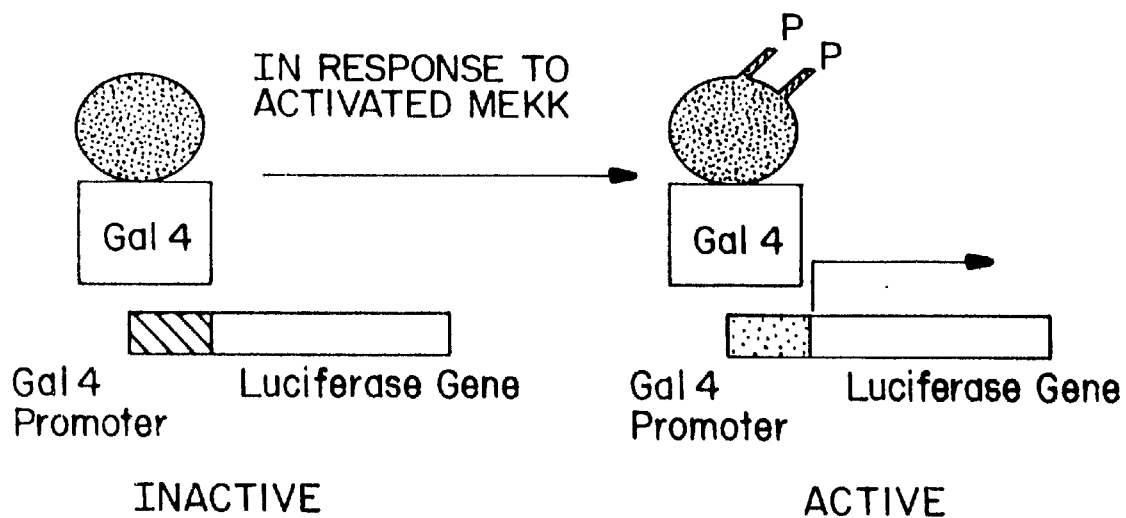

The transfected cells were incubated overnight and then lysed using methods standard in the art. The luciferase activity of each cell lysate was measure on a luminometer. The results shown in FIG. 13 indicate that MEKK is selectively capable of stimulating the phosphorylation of c-Myc transactivation domain in such a manner that the c-Myc domain is activated and induces transcription of the transfected luciferase gene. In addition, the results indicate that MEKK does not stimulate CREB activation. Also, activated Raf is unable to stimulate Myc activation. A schematic representation of the activation mechanism of c-Myc protein by MEKK is shown in FIG. 14.

Example 18

This Example Describes the Phosphorylation of p38 MAPK Protein in Response to the Expression of MEKK3 Protein and Not MEKK1 Protein COS cells were transfected with the expression plasmid pCVM5 ligated to cDNA clones encoding either MEKK1 or MEKK 3 protein, or a control pCVM5 plasmid lacking MEKK cDNA inserts. Forty-eight hours after transfection, the COS cells were lysed and the lysate fractionated on a Mono Q FPLC column using conditions described in Example 4. The fractions were analyzed for tyrosine phosphorylation of MAP kinase-like enzymes using the kinase assay described in Example 4. Expression of MEKK 3 induces tyrosine phosphorylation of p38 MAPK and the p42 and p44 forms of MAPK. MEKK 1, however, only induces weak phosphorylation of p38 MAPK but does induce phosphorylation of p42 and p44 MAPK.

Example 19
This Example Describes MEKK-induced Apoptosis

Cells were prepared for the apoptosis studies as follows. Swiss 3T3 cells and REF52 cells were transfected with an expression plasmid encoding β-Galactoctosidase (β-Gal) detection of injected cells. One set of β-Gal transfected cells were then microinjected with an expression vector encoding MEKK370–738 protein. Another set of β-Gal transfected cells were then microinjected with an expression vector encoding truncated BXB-Raf protein.
A. Beauvericin-induced apoptosis A first group of transfected Swiss 3T3 cells and REF52 cells were treated with 50 μM beauvericin for 6 hours at 37° C. Beauvericin is a compound known to induce apoptosis in mammalian cells. A second group of cells were treated with a control buffer lacking beauvericin. The treated cells were then fixed in paraformaldehyde and permeabilized with saponin using protocols standard in the art. The permeabilized cells were then labelled by incubating the cells with a fluorescein-labelled anti-tubulin antibody (1:500; obtained from GIBCO, Gaithersburg, Md.) to detect cytoplasmic shrinkage or 10 μM propidium iodide (obtained from Sigma, St. Louis, Mo.) to stain DNA to detect nuclear condensation. The labelled cells were then viewed by differential fluorescent imaging using a Nikon Diaphot fluorescent microscope. The cells treated with beauvericin demonstrated cytoplasmic shrinkage (monitored by the anti-tubulin antibodies) and nuclear condensation (monitored by the propidium iodide) characteristic of apoptosis.
B. MEKK-induced apoptosis Swiss 3T3 cells and REF52 cells microinjected with a β-galatoctosidase expression plasmid, and an MEKK encoding plasmid or a BXB-Raf encoding plasmid, were treated and viewed using the method described above in Section A. An anti-β-Gal antibody (1:500, obtained from GIBCO, Gaithersburg Md.) was used to detect injected cells. Microscopic analysis of REF52 cells indicated that the cells expressing MEKK protein underwent cytoplasmic shrinkage and nuclear condensation leading to apoptotic death. In contrast, cells expressing BXB-Raf protein displayed normal morphology and did not undergo apoptosis. Similarly, microscopic analysis of Swiss 3T3 cells indicated that the cells expressing MEKK protein underwent cytoplasmic shrinkage and nuclear condensation leading to apoptotic death. In contrast, cells expressing BXB-Raf protein displayed normal morphology and did not undergo apoptosis. Thus, MEKK and not Raf protein can induce apoptotic programmed cell death.

Example 20

This Example Describes MEKK-induced Apoptosis, Which is Independent of JNK/SAPK Activation
Methods
Microinjection Swiss 3T3 and REF52 cells were plated on acid-washed glass cover slips in Dulbecco's Modified Eagle's Medium (DMEM) and 10% bovine calf serum (BCS) or newborn calf serum (NCS). Cells were placed in DMEM/0.1% calf serum for overnight incubation prior to microinjection and used for injection at 50–70% confluence. Injections were performed with an Eppendorf automated microinjection system with needles pulled from glass capillaries on a vertical pipette puller (Kopf, Tujunga, Calif.). Cells were injected with pCMVβ-gal in the presence or absence of $pCMV5MEKK_{COOH}$ or pCMV5BxBRaf at 20–100 ng/μl for each expression plasmid in 100 mM KCl, 5 mM $NaPO_4$, pH 7.3. Following injection cells were placed in 1% NCS for 12–18 hr (Swiss 3T3) or 42 hr (REF52) prior to fixation with paraformaldehyde and staining. Similar results were obtained when cells were placed in 10% NCS after microinjection. Propidium iodide (5 μg/ml) was used to stain DNA. X-Gal reactions were performed for six hr.

Swiss 3T3 cells were microinjected with 100 ng/μl pCMVP-gal and 20 ng/μl $pCMV5MEKK_{COOH}$. To label free DNA ends fixed and rehydrated cells were incubated with terminal deoxytransferase (TDT) and 10 nM biotin-dUTP following the manufacturer's instructions (Boehringer-Mannheim). Cells were stained with FITC-streptavidin to label DNA fragments. β-gal was detected using rabbit anti-β-gal antibody (Cappel Labs) and a rhodamine-labeled goat anti-rabbit antibody (Cappel Labs).
Transactivation analysis Swiss 3T3 cells were transfected using calcium phosphate or lipofectamine with the reporter plasmid Gal4-TK-luciferase, which contains four Gal4 binding sites (Sadowski, I., et al. (1988). *Nature* 335, 563–564). adjacent to a minimal thymidine kinase (TK) promoter that controls expression of luciferase, in the presence or absence of activator plasmids encoding Gal4$_{(1-147)}$/Myc$_{(7-101)}$ (Gupta et al. (1993) *Proc. Natl. Acad. Sci. USA* 90:3216–3220), Gal4$_{(1-147)}$/Elk-1$_{(83-428)}$ (Marais, et al. (1993) *Cell* 73:381–393)or Gal4$_{(1-147)}$/c-Jun$_{(1-233)}$ hibi et al. (1993) *Genes & Development* 7:2135–2148). Transfections included pCMV5 without a cDNA insert (basal control), pCMV5MEKK$_{COOH}$ and in some experiments pCMV5BxBRaf. Cells were incubated for 24–48 hr after transfection, lysed and assayed for luciferase activity. Values were normalized to equivalent μg protein for all experiments.

Protein kinase assays

JNK/SAPK: Activity was measured using GST (glutathione S-transferase)-c-Jun (1–79) BOUND to glutathione-Sepharose-4B (Hibi et al. supra). Cells expressing MEKK$_{COOH}$ or control cells were lysed in 0.5% Nonidet P40 (NP40), 20 mM Tris-HCl, pH 7.6, 0.25 NaCl, 3 mM EDTA, 3 mM EGTA, 1 mM dithiothreitol, 1 mM phenylmethylsulfonyl fluoride, 2 mM sodium vanadate, 20 μg/ml aprotinin and 5 μg/ml leupeptin. Lysates were centirfuged at 15,000× g for 10 min to remove nuclei and supernatants (25 μg protein) mixed with 10 μl of GST-c-JUN$_{(1-79)}$-Sepharose (3–5 μg of GST-c-Jun$_{(1-79)}$). The mixture was rotated at 4° C. for 1 hr, washed 2× in lysis buffer and 1× in kinase buffer (20 mM Hepes, pH 7.5, 10 mM MgCl$_2$, 20 mM β-glycerophosphate, 10 mM p-nitrophenyl phosphate, 1 mM dithiothreitol, 50 μM sodium vanadate). Beads were suspended in 40 μl of kinase buffer with 10 μCi Of [γ$^{32}$P]ATP and incubated at 30° C. for 20 min. Samples were boiled in Laemmli buffer and phosphorylated proteins resolved on SDS/10% polyacrylamide gels. To verify the selectivity of the JNK/SAPK assay cell lysates were fractionated by Mono Q ion exchange chromatography and each fraction assayed as described above. Fractions were also immunoblotted with a rabbit antisera recognizing JNK/SAPK. Only fractions containing immunoreactive JNK/SAPK phosphorylated the GST-c-Jun$_{(1-79)}$ protein.

p42/44 ERK MAPK: ERK activity was assayed after fractionation of cell lysates on DEAE-Sephacel (Heasley, L. E. et al. (1994) *Am J. Physiol.* 267:F366–F373). Alternatively, ERK activity was assayed following Mono Q ion exchange chromatography as previously described and characterized (Heasley, et al. (1992) *Mol. Biol. Cell.* 3:545–553). The EGF receptor 662–681 peptide was used as a selective substrate for measuring ERK activity (Russell, M. et al. (1995) *Biochemistry.* 34:6611–6615.

p38/hog-1: Cells were lysed in 1% Triton X-100, 0.5% NP40, 20 mM Tris-HCl, pH 7.5, 150 mM NaCl, 20 mM NaF, 0.2 mM sodium vanadate, 1 mM EDTA, 1 mM EGTA, 5 mM phenylmethylsulfonyl fluoride. Nuclei were removed by centrifugation at 15,000× g for 5 min. Supernatants (200 μg protein) were used for immunoprecipitation of p38/hog-1 using rabbit antiserum raised against the COOH-terminal peptide sequence of p38/hog-1 (CFVPPPLDQEEMES) (Han, J. et al. (1992) *Mol. Endocrinol.* 6:2079–2089) and protein A Sepharose. Immunoprecipitates were washed 1× in lysis buffer, lx in assay buffer (25 mM Hepes, pH 7.4, 25 mM β-glycerophosphate, 25 mM NaCl$_2$, 2 mM dithiothreitol, 0.1 mM sodium vanadate), resuspended in kinase assay buffer with 20–50 ng of a recombinant NH$_2$-terminal fragment of ATF-2 as substrate and 20 μCi [γ$^{32}$P] ATP (Abdel-Hafig, et al. (1992) *Mol. Endocrinol* 6:2079–2089). For verification of the immunoprecipitation assay lysates were fractionated by Mono Q ion exchange chromatography and each fraction assayed for ATF-2 kinase activity and immunoblotted with anti-p38 antibody. The results demonstrated that p38/hog-1 containing fractions selectively phosphorylated the recombinant ATF-2 protein.

Competitive Inhibitory Mutant JNK/SAPK and JNKK/SEK-1: The competitive inhibitory JNK/SAPK mutant referred to JNK/SAPK(APF) had the amino acids threonine 183 and tyrosine 185 mutated to alanine and phenylalanine, respectively (Lin et al. (1995) *Science* 268:286–290). These are the sites phosphorylated by JNKK/SEK-1 and required for activation of the JNK/SAPK kinase activity (Lin et al. supra; Sanchez, I. (1994) *Nature* 372:794–800). Competitive inhibitory JNKK/SEK-1 was made by mutation of the active site lysine at residue 116 mutated to an arginine (K116R) rendering the protein kinase inactive (Lin et al. supra).

A. Expression of activated MEKK induces cell death

Attempts to isolate stable transfectants expressing MEKK$_{COOH}$ in several fibroblast lines failed despite repeated attempts. The findings suggested that expression of activated MEKK inhibited clonal expansion of transfected cells. For this reason, we characterized the functional consequence of expressing activated MEKK in Swiss 3T3 and REF52 cells using nuclear microinjection of an expression plasmid encoding an activated form of MEKK1. Cells were microinjected with an expression plasmid encoding β-galactosidase (β-gal) in the presence or the absence of the expression plasmid encoding MEKK$_{COOH}$, a truncated activated form of MEKK1 (Yan, M. et al. (1994) *Nature* 372:798–800; Lange-Carter, C. A., et al. (1993) *Science* 260:315–319). When Swiss 3T3 cells microinjected with expression plasmids for β-gal alone (control) or β-gal plus MEKK$_{COOH}$ it was readily apparent that expression of the activated MEKK1 induced a strong morphological change of the cells. In contrast, cells microinjected with the β-gal plasmid alone were similar in morphology to uninjected cells. Injected cells became highly condensed with a very dark staining of the cytoplasm that has dramatically shrunken relative to the flattened morphology of the cells injected with β-gal alone. The results indicated MEKK$_{COOH}$ expression resulted in death of the cells.

For further analysis and comparison cells were microinjected with BxBRaf, a truncated activated form of Raf-1 (Rapp, U. R. (1991) *Oncogene* 6:495–500) that selectively activates the ERK pathway (Kyriakis, J. M. et al. (1992) *Nature* 358:417–421). In microinjected cells, expression of β-gal, MEKK$_{COOH}$ or BxBRaf was demonstrated by indirect immunofluorescence using specific antibodies recognizing each protein. Swiss 313 cells and REF 52 cells microinjected with the indicated expression plasmid were fixed and stained only eight hours postinjection to demonstrate that each protein was being expressed in the cytoplasm of the cells. It was apparent with the REF 52 cells expressing MEKK began to undergo a morphological changes relative to β-gal expressing cells.

TABLE 1

Quantitation of MEKK$_{COOH}$-induced cell death.

| DNA Injected | Cells Injected | Condensed Cells |
|---|---|---|
| β-gal | 336 | 4 (1%) |
| β-gal + BxBRaf | 175 | 5 (3%) |
| β-gal + MEKK$_{COOH}$ | 200 | 167 (84%) |
| β-gal + Kin~MEKK$_{COOH}$ | 50 | 0 (0%) |

Swiss 3T3 cells were injected with solutions containing 100 ng/μl CMV-βgal in the presence or absence of 100 ng/μl of pCMV5-BxEBRaf, pCMV5-MEKKCooH or pCMV5-Kin~MEKK$_{COOH}$ (kinase inactive mutant; 13). Seventeen hours after injection cells were fixed and stained for, β-galactosidase activity with X-Gal. Injected cells attached to the coverslip were scored as positive for cell death when they were highly condensed, small round cells.

The results of this experiment demonstrated that expression of MEKK$_{COOH}$ resulted in significant cell death characterized by the dramatic morphological condensation. In contrast, BxBRaf expression did not affect cell viability relative to control cells expressing only β-gal. Approximately 84% of all MEKK$_{COOH}$ injected cells had a highly condensed cellular morphology seventeen hours after injection. This count actually underestimates the number of condensed cells because Swiss 3T3 cells in advanced stages of the cell death response were often nonadherent to coverslips. Some of the nonadherent highly condensed cells could be found to be released from the coverslip into the culture medium, but were not scored in the quantitation. In contrast, fewer than 3% of BxBRaf and 1% of control β-gal injected cells had an altered morphology even after 48–72 hours post-injection.

These data also show that cell death resulting from MEKK$_{COOH}$ expression required the kinase activity of the enzyme; the kinase inactive mutant of MEKK$_{COOH}$ was without effect. The apoptotic-like cell death was also dependent on the MEKK$_{COOH}$ concentration as measured by serial dilution (0–100 ng/μl) of the expression plasmid used for microinjection. Maintenance of the MEKK$_{COOH}$ expressing cells in 10% serum slightly prolonged the time required for induction of cytoplasmic shrinkage, nuclear condensation and cell death suggesting that growth factors and cytokines had some influence on the onset of the response induced by MEKK$_{COOH}$ but high serum could not prevent MEKK$_{COOH}$ induced cell death. Greater than 80% of MEKK$_{COOH}$ expressing cells had a cytoplasmic and nuclear morphology characteristic of apoptosis 18 hrs postinjection.

More dramatic morphological changes in Swiss 3T3 cells also resulted from expression of MEKK$_{COOH}$. Cytoplasmic shrinkage is evident from the β-gal staining and nuclear condensation is evident in MEKK1 expressing cells stained with propidium iodide. In contrast, cells expressing BxBRaf do not demonstrate any detectable morphological difference from control cells expressing only β-gal. Similar dramatic cytoplasmic shrinkage and nuclear condensation was observed with MEKK$_{COOH}$ expression in REF52 cells, where BxBRaf again had no effect on cytoplasmic and nuclear integrity. To assess if DNA fragmentation was induced by MEKK$_{COOH}$ expression, terminal deoxytransferase (TDT) was used to covalently transfer biotin-dUTP to the ends of DNA breaks in situ. Streptavidin-FITC was then used for detection of dUTP incorporated into cellular DNA. Even though Swiss 3T3 cells do not undergo significant DNA degradation and laddering at the nucleosomal level they do generate larger DNA fragments when stimulated to undergo apoptosis (Obeid, L. M. et al. (1993). *Science* 259:1769–1771). The condensed nuclei of MEKK$^{COOH}$ injected cells were highly fluorescent indicating significant DNA fragmentation. It is also apparent that the cytoplasm has become highly condensed and the condensed chromatin is distinct from the cytoplasm. Microinjected cells not yet undergoing cytoplasmic and nuclear condensation in response to MEKK$_{COOH}$ did not incorporate dUTP into their DNA. Thus, expression of MEKK$_{COOH}$ induced all the hallmarks of apoptosis including cytoplasmic shrinkage, nuclear condensation and DNA fragmentation.

Figure 15:
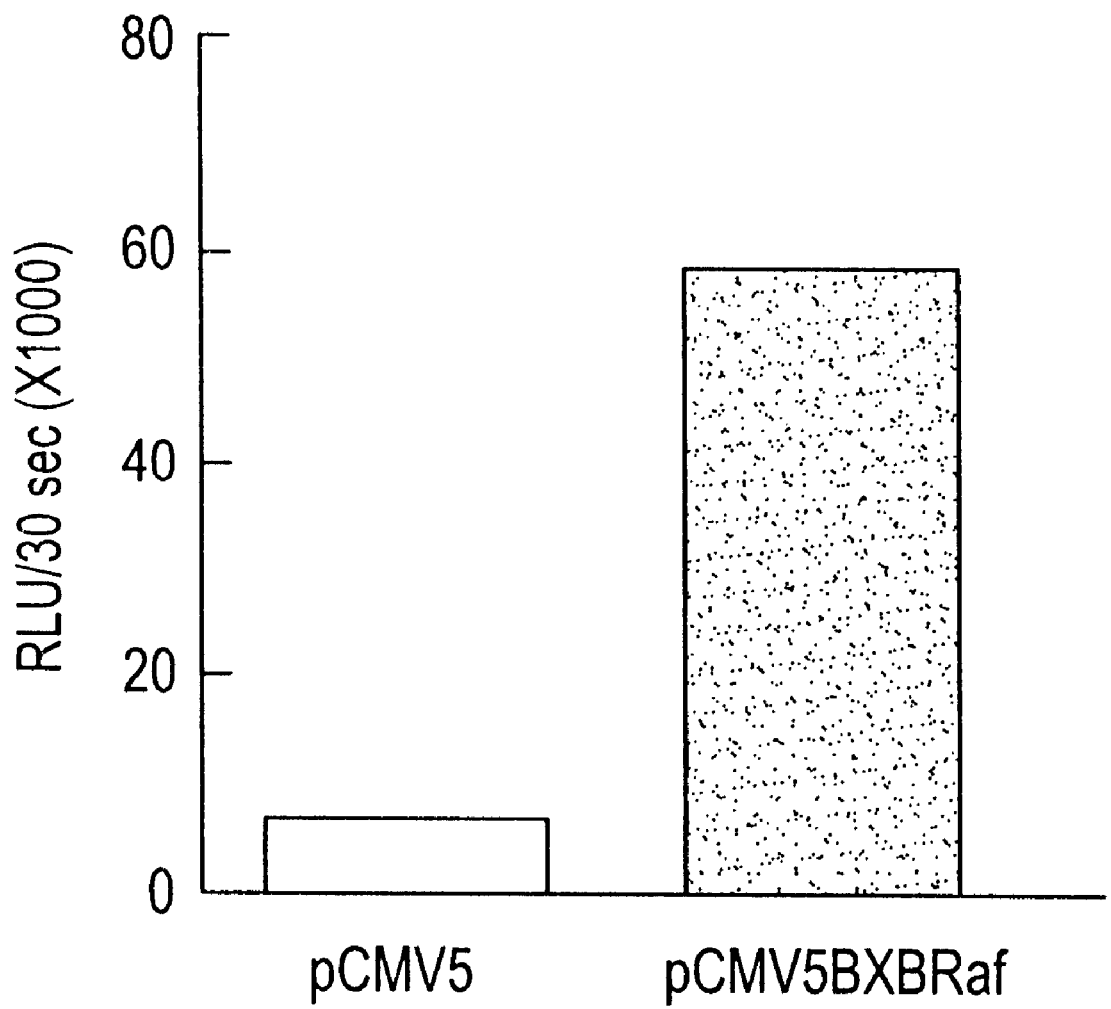
FIG. 15 shows wild type Swiss 3T3 cells transfected with pCMV5BXBRaf or pCMV5 without a cDNA insert in the presence of expression plasmids encoding GA14/Elk-1 and Gal4-TK-luciferase. Cells were lysed and assayed for luciferase activity 48 hours post-transfection.

Expression of BxBRaf did not induce a response measured by any of the criteria mentioned above. BxBRaf expressing cells displayed a normal flattened morphology similar to β-gal expressing cells or to uninjected cells. Transient BxBRaf expression in Swiss 3T3 cells stimulated ERK activity (not shown) and the transactivation function of the Gal4/Elk-1 chimeric transcription factor, shown in FIG. 15, whose activation is dependent on phoshorylation by Erk members of the MAPK family (Marais, R., Cell 73:381–393; Gille, et al. (1995) EMBO J. 14:951–962; Price, M. A., et al. (1995) EMBO J. 14:2589–2601). Cumulatively, the results indicate that activation of the Raf/ERK pathway does not induce the cytoplasmic and nuclear changes observed with MEKK.

B. Induction of activated MEKK sensitizes Swiss 3T3 cells to UV-induced apoptosis Because stable expression of MEKK$_{COOH}$ appeared to inhibit clonal expansion of Swiss 3T3 cells under G418 drug selection, clones were isolated having inducible expression of the kinase. The Lac Switch expression system (Stratagene) was used to control the expression of MEKK$_{COOH}$. Several independent clones were isolated and their properties analyzed in the presence or absence of IPTG-induced expression of MEKK$_{COOH}$. The parental LacR+clone expressing only the Lac repressor was used as the control. Clones expressing inducible MEKK$_{COOH}$, as determined using an antibody recognizing the extreme COOH-terminus of MEKK, showed a small increase in the number of cells having a condensed cytoplasmic and nuclear morphology relative to control cells even in the absence of IPTG-induced MEKK$_{COOH}$. This is probably due to a basal level of MEKK$_{COOH}$ expression in uninduced cells. The addition of IPTG to the culture media induced the expression of MEKK$_{COOH}$ and resulted in an increase in cells having the condensed morphology relative to the control IPTG-treated LacR+clone. However, MEKK$_{COOH}$ expressing cells did not growth arrest and only a fraction of the cells assumed a condensed morphology as dramatic as what was observed with microinjection of the MEKK$_{COOH}$ expression plasmid. This maybe related to selection of cells during the cloning procedure that adapted to a low, constitutive level of MEKK$_{COOH}$ expression. Interestingly, no clones were isolated from a total of one hundred fifty that were analyzed that had a significant constitutive MEKK$_{COOH}$ expression measured by immunoblotting. In addition, the level of MEKK$_{COOH}$ expression following IPTG induction is certainly less than that achieved with nuclear microinjection.

It was found that IPTG-induced MEKK$_{COOH}$ expression stimulated signal transduction pathways that made the cells significantly more sensitive to stresses that induce cell death. For example, cells expressing MEKK$_{COOH}$ were highly sensitive to ultraviolet irradiation. Two hours after exposure to ultraviolet irradiation greater than 30% of the MEKK$_{COOH}$ expressing cells became morphologically highly condensed and appeared apoptotic. In contrast, the population of uninduced cells showed no increase in condensed apoptotic-like cells at this time point (FIG. 16). Thus, overnight induction of MEKK$_{COOH}$ expression modestly increased the basal index of morphologically condensed cells and primed the cells for apoptosis in response to UV irradiation. The results indicate that MEKK-regulated signal transduction pathways enhance apoptotic responses to external stimuli.

C. Expression of MEKK$_{COOH}$ stimulates JNK/SAPK and the transactivation of c-Myc and Elk-1. The ability of MEKK$_{COOH}$ but not BxBRaf expression to induce cell death indicates that each kinase regulates different sequential protein kinase pathways. Cells were incubated for 17 hours in the absence or presence of IPTG and assayed for JNK/

Figure 17A:
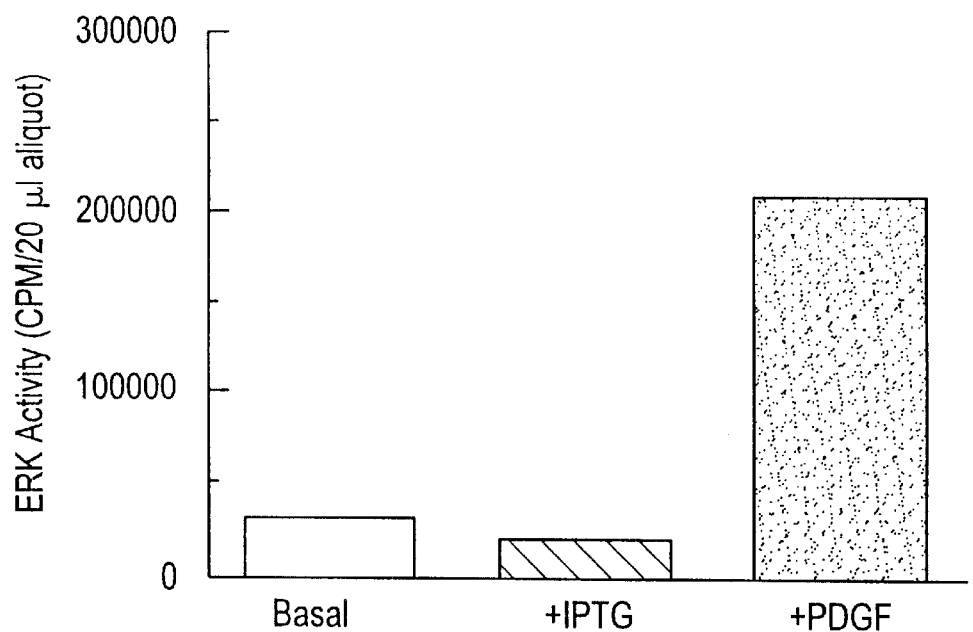
FIGS. 17A and B show that MEKKCOOH stimulates JNK/SAPKm but did not activate ERK (p42/44 MAPK) or p58 hog1. As shown in panel A, induction of MEKKCOOH does not activate ERK, whereas PDGF does activate ERK. As shown in panel B, induction of MEKKCOOH does not activate p38, whereas orbitol does activate p38.
Figure 17B:
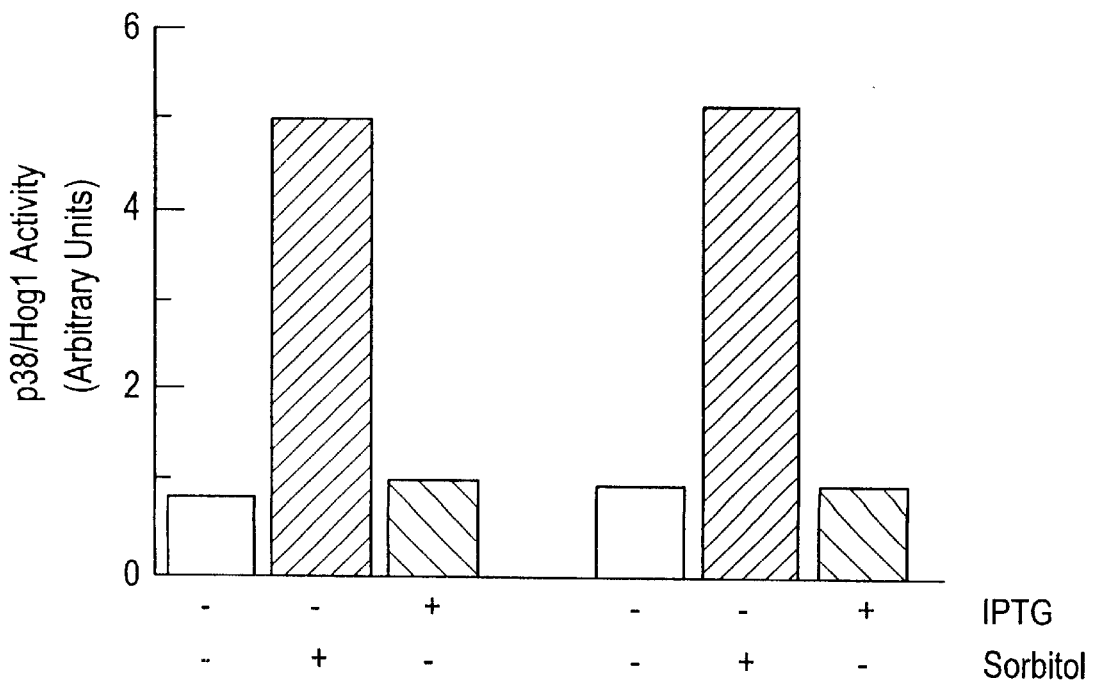
Figure 18B:
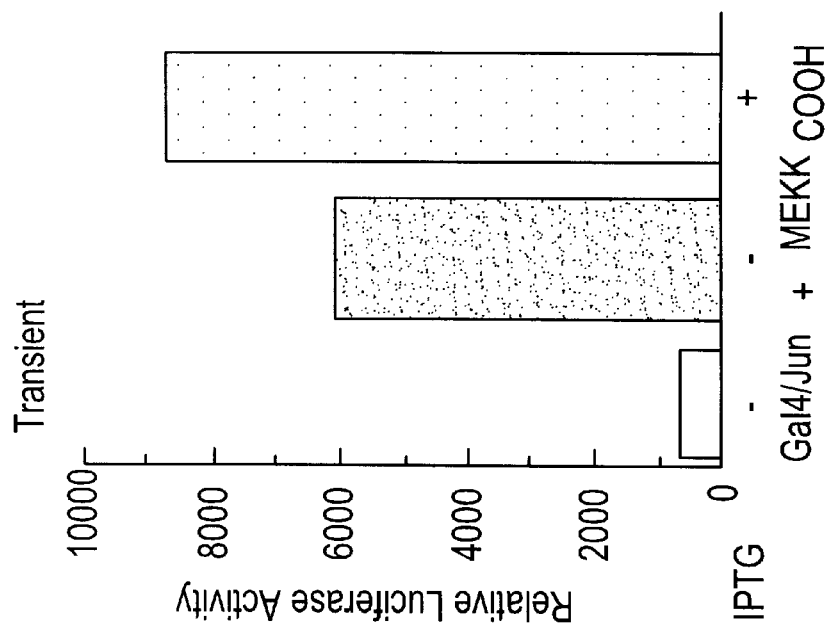
FIGS. 18A and B show that induction of MEKKCOOH expression did not significantly increase Gal4/Jun transactivation (panel A). Transient transfection of MEKKCOOH resulted in increased Gal4/Jun transactivation in the MEKK2 Swiss 3T3 clone (panel B).
Figure 18A:
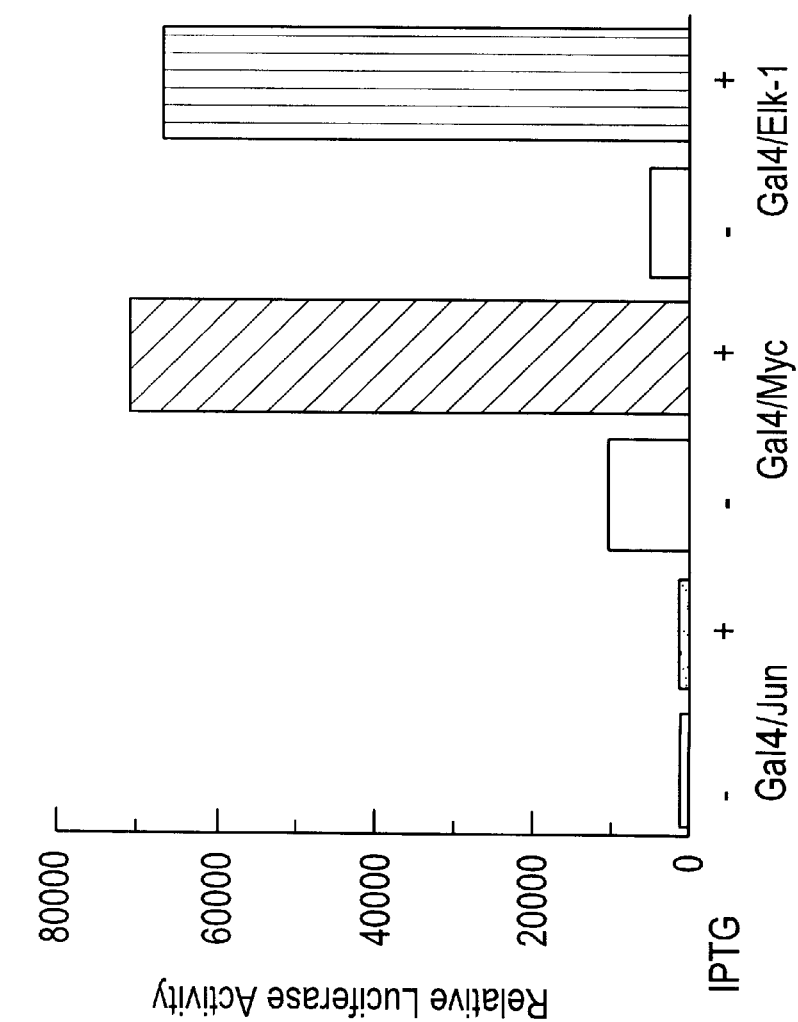

SAPK activity. The induction of MEKK$_{COOH}$ expression in Swiss 3T3 cells, as predicted, stimulated JNK/SAPK activity but did not activate either ERK or p38/hog1 activity as shown in FIGS. 17 and 18. The results indicate that induction of MEKKCOOH results in the activation of JNK/SAPK which phosphorylates GST-c-Jun. Because known substrates for JNK/SAPK are transcription factors, we assayed MEKK$_{COOH}$ inducible clones for transactivation of specific gene transcription. Chimeric transcription factors having the Gal4 DNA binding domain and the transactivation domain of c-Myc, Elk-1 or c-Jun were used for assay of MEKK$_{COOH}$ signaling using a Gal4 promoter-luciferase reporter gene (Hibi et al. supra; Sadowski, I et al. (1988) *Nature* 335:563–564; Gupta et al. supra; Marais et al. supra.). Surprisingly, IPTG-induced stable expression of MEKK$_{COOH}$ markedly activated the transactivation function of c-Myc and Elk-1 but had little effect on Gal4/Jun activity as illustrated in FIG. 18. This result was unexpected since MEKK$_{COOH}$ transient expression stimulated Gal4/Jun activity, indicating that transient expression of MEKK$_{COOH}$ was capable of transactivating c-Jun function in Swiss 3T3 cells. In addition, the JNK/SAPK activity stimulated by IPTG-induction of MEKK$_{COOH}$ correlated with the characterized JNK/SAPK enzyme by fractionation on Mono Q FPLC. Thus, MEKK$_{COOH}$ expression in stable clones achieved with IPTG-induction selectively regulated Gal4/Myc and Gal4/Elk-1 but not Gal4/Jun even though JNK/SAPK was activated.

The failure of IPTG-induced MEKK$_{COOH}$ expression to activate Gal4/Jun may be related to the multiple c-Jun NH2-terminal phosphorylation sites involved in regulating c-Jun transactivation. Serines 63 and 73 and threonines 91 and 93 are apparent regulatory phosphorylation sites in c-Jun (Kyriakis et al. (1994) *Nature* 369:156–160; Derijard, B et al. (1994) *Cell* 76:1025–1037; Pulverer et al. (1991) *Nature* 353:670–674; Papavassiliou, et al. (1995) *EMBO J.* 14:2014–2019). Both clusters are proposed to be sites of phosphorylation for ERKs and JNK/SAPKs (Papavassiliou et al. supra). Transient transfection of MEKK$_{COOH}$ activates JNK/SAPK but also activates ERKs (Lange-Carter et al. supra). In contrast IPTG-induction of MEKK$_{COOH}$ results in the activation of JNK/SAPK but not Erks. The difference in regulation of c-Jun transactivation may be related to the differential phosphorylation of these sites by JNK/SAPK and ERKs.

Expression of activated Raf in Swiss 3T3 cells stimulated Elk-1 transactivation, but not c-Myc or c-Jun transactivation. This result indicates that Elk-1 transactivation alone does not mediate the cell death response in fibroblasts observed with MEKK$_{COOH}$. Cumulatively, the findings demonstrate that induction of MEKK$_{COOH}$ expression enhances cell death independent of ERK, p38/hog-1 or c-Jun transactivation in Swiss 3T3 cells and may involve c-Myc transactivation.

Figure 19A:
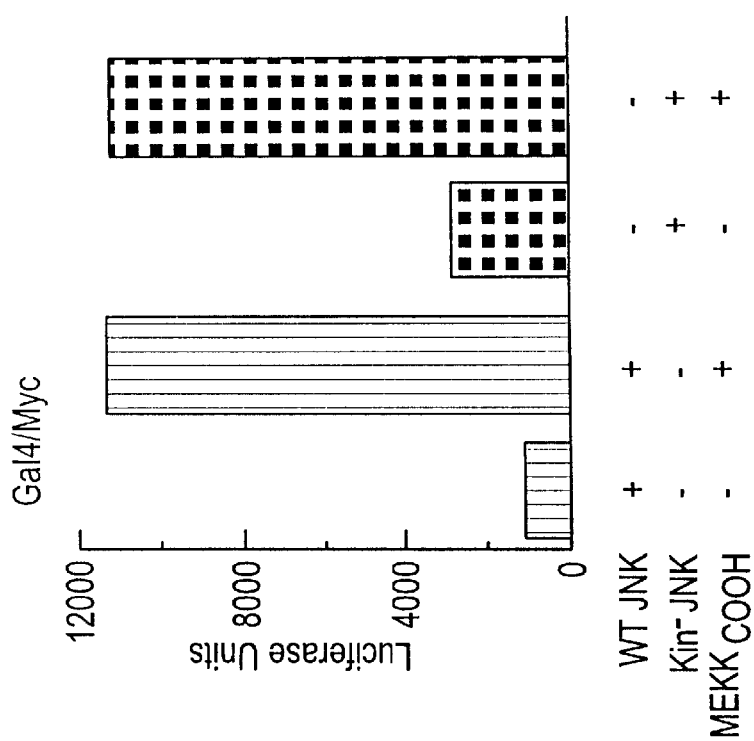
FIGS. 19A and B show that competitive inhibitory JNK/SAPK(APF) attenuates GA14/Jun but not Gal4/myc activation. The results are representative of three independent experiments where a three-fold excess of JNK/SAPK(APF) inhibited approximately 65% of Gal4/Jun activation (panel A) with no effect on Gal4/myc activation (panel B).
Figure 19B:
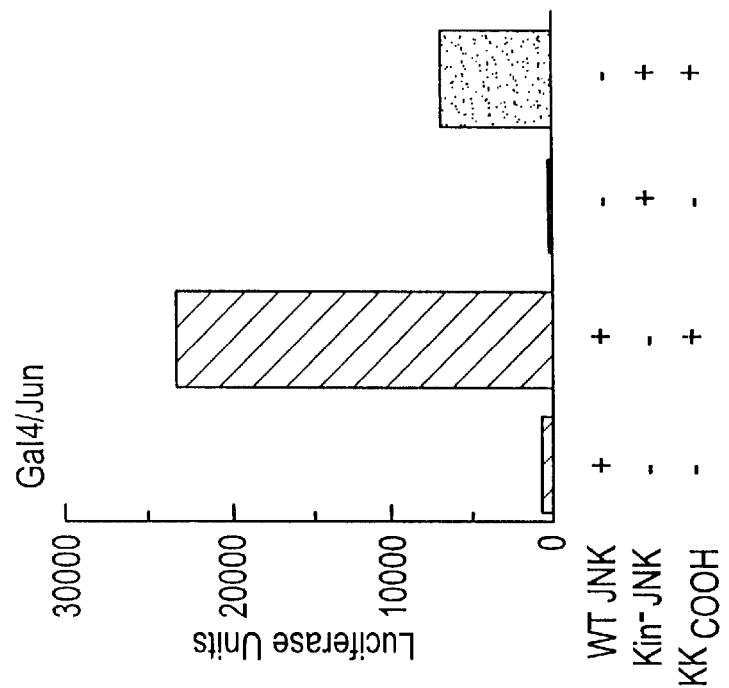

D. Inhibitory JNK/SAPK does not attenuate MEKK stimulated c-Myc transactivation or cell condensation To determine if JNK/SAPK activation was required for c-Myc transactivation in response to MEKK$_{COOH}$, Gal4/Myc activation was assayed in the presence or absence of JNK/SAPK(APF). The results are shown in FIG. 19. The JNK/SAPK(APF) was used as a competitive inhibitor of JNK/SAPK for activation by the immediate upstream JNK kinase/SEK-1 enzyme (Kyriakis et al. supra; Sluss, et al (1994). *Mol. Cell. Biol.* 14:8376–8384; Lin et al (1994) *Science* 268:286–290; Sanchez et al. (1994) *Nature* 372:794–800). In transient transfection assays, expression of JNK/SAPK(APF) inhibited approximately 65% of the Gal4/Jun activation in response to MEKK$_{COOH}$. In contrast, expression of JNK/SAPK(APF) had no effect on MEKK$_{COOH}$ activation of Gal4/Myc induction of luciferase activity. Thus, c-Jun transactivation appears to be independent of the MEKK$_{COOH}$ stimulated pathway leading to c-Myc transactivation. Similarly, JNK/SAPK activation can be significantly inhibited with no effect on c-Myc transactivation.

The cell death response to MEKK$_{COOH}$ also appeared to be largely independent of JNK/SAPK. In several experiments, expression of JNK/SAPK(APF) alone had no demonstrative effect on Swiss 3T3 cells. The expressed JNK/SAPK(APF) was localized in both the cytoplasm and nucleus while β-gal expression was restricted to the cytoplasm. Co-expression of JNK/SAPK(APF) with MEKK$_{COOH}$ did not block MEKK$_{COOH}$-induced cytoplasmic shrinkage and cellular condensation. A 20-fold lower concentration of MEKK$_{COOH}$ still induced the cytoplasmic shrinkage characteristic of apoptosis in microinjected Swiss 3T3 cells. Co-microinjection of a 30-fold greater concentration of JNK/SAPK(APF) plasmid relative to the MEKK$_{COOH}$ plasmid did not affect the MEKK$_{COOH}$-mediated cell death response. Cells undergoing a dramatic cytoplasmic shrinkage. Because of the low amount of MEKK$_{COOH}$ expression plasmid used, the cell condensation response was slower in onset. The percentage of MEKK$_{COOH}$ microinjected cells committed to cytoplasmic shrinkage and cellular condensation and the timing of this response was the same in the presence or absence of JNK/SAPK(APF). In addition, the competitive inhibitory mutant K 116RJNKK/SEK-1, the kinase immediately upstream of JNK/SAPK which phosphorylates and activates JNK/SAPK (Lin et al supra; Sanchez, 1 (1994) *Nature* 372:794–800) also unable to attenuate MEKK$_{COOH}$ induced cell death. Expression of JNK/SAPK(APF) or K116RJNKK/SEK-1 alone had no measurable effect on the morphology of Swiss 3T3 cells (not shown). Thus, MEKK$_{COOH}$ induces cell death via the regulation of signal pathways that appear largely independent of JNK/SAPK regulation and c-Jun transactivation. Finally, BxBRaf neither induced cell death nor activated c-Myc (not shown) indicating that MEKK$_{COOH}$-regulated responses were not mediated by the Erk1 and 2 proteins (p42/p44 MAP kinases), consistent with the lack of ERK activation in the inducible MEKK$_{COOH}$ Swiss 3T3 cells.

These results demonstrate, for the first time, a role for MEKK in mediating a cell death response characteristic of apoptosis. Receptors such as the cytotoxic TNFα receptor and Fas must be capable of regulating signal transduction pathways controlling cytoplasmic and nuclear events involved in apoptosis. The enhanced apoptosis to ultraviolet irradiation observed with MEKK$_{COOH}$ expression in Swiss 3T3 cells indicates that MEKK-regulated signal transduction pathways integrate with the apoptotic response system. MEKK$_{COOH}$ expressing cells have a higher basal apoptotic index and are primed to undergo apoptosis in response to a stress stimulation. The short time required to observe the enhance apoptosis (2 hr) suggests that cell cycle traverse, DNA synthesis, or significant transcription/translation is not required for the enhanced cell death in response to ultraviolet irradiation in cells expressing MEKK$_{COOH}$. This finding is striking and suggests that genetic or pharmacological manipulation of MEKK activity could be used to sensitize cells to irradiation-induced death.

The ability to dissociate c-Jun transactivation from MEKK$_{COOH}$-stimulated cell death argues that the JNK/SAPK activity achieved in the inducible Swiss 3T3 cell clones is insufficient alone to activate c-Jun transactivation or induce cell death. It is more likely that the JNK/SAPK activity we have measured is involved in stimulating a protective program in response to potentially lethal stimuli as previously proposed (Devary,Y et al. (1992) Cell 71:1081–1091). Protective responses could involve changes in metabolism or alterations in the activity of proteins such as Bc 1–2 (Gottschalk, A. R., et al. (1994) Proc. Natl. Acad. Sci. USA 91:7350–7354; Korsmeyer, S. J. (1992) Immunol. Today 13:285–290). This prediction is consistent with the activation of JNK/SAPK mediated by CD40 ligation in B cells which protects against rather than stimulates apoptosis (Sumimoto, S. I., et al. (1994) J. Immunol. 163:2488–2496; Tsubata, T. et al. (1993) Nature 364:645–648).

Recently, it was shown that dominant negative c-Jun could protect neurons from serum deprivation-induced apoptosis (Ham, J. et al. (1995) Neuron 14:927–939). It was proposed that the dominant negative cJun inactivated c-Jun and prevented an attempt by the post mitotic neurons to enter an abortive cell cycle progression that triggered a cell death program. Thus, dominant negative c-Jun was believed to maintain the neurons in stringent growth arrest. At first glance, the protective effect of dominant negative c-Jun seems contradictory to our results that JNK/SAPK and c-Jun transactivation are not involved in MEKK-induced cell death. Our results demonstrate that the dramatic cytoplasmic shrinkage, nuclear condensation and onset of cell death induced by MEKK$_{COOH}$ are largely independent of JNK or c-Jun transactivation. Importantly, MEKK$_{COOH}$-induced cell death occurs in high serum where growth factor and cytokine stimulation of the cells is normal. We have also determined that expression of MEKK$_{COOH}$ in Swiss 3T3 cells does not significantly inhibit or alter cell cycle progression. Thus, an abnormal cell cycle event that may occur with serum deprivation does not appear to account for MEKK-induced cell death.

Expression of MEKK$_{COOH}$ increased the transactivation of c-Myc and Elk-1 in Swiss 3T3 cells. c-Myc has been shown to be required for apoptosis in lymphocytes (Fanidi, A et al. (1994) Nature 359:554–556; Janicke, R. U. et al (1994) Mol. Cell. Biol. 14, 5661–5670; Shi et al. (1992) Science 257:212–214), to induce apoptosis when overexpressed in growth factor-deprived fibroblasts (Harrington, E. A. et al. (1994) EMBO J. 13:3286–3295); Askew, D. W., et al. (1991) Oncogene 6:1915–1922; Evan, G. I. et al. (1992) Cell 69:119–128), and to enhance TNF-mediated apoptosis (Klefstrom, J., et al. (1994) EMBO J. 13:5442–5450). The requirement of c-Myc for apoptosis is not understood mechanistically, but c-Myc is proposed to transcriptionally activate an apoptotic pathway (Harrington, E. A.et al. (1994) EMBO J. 13:3286–3295); Askew et al. supra; Evan et al. supra, Janicke et al. supra; Shi et al. supra). The activation of Elk-1 by MEKK$_{COOH}$ induction in Swiss 3T3 cells correlates best with the stimulation of JNK/SAPK. Recently, it was found that JNK/SAPK in addition to Erks phosphorylated and activated Elk-1 consistent with our findings (Whitmarsh, A. J. et al. (1995) Science 269:403–407). In contrast, we demonstrate that c-Jun is not significantly activated in MEKK$_{COOH}$ expressing cells. These findings are provocative because they indicate that MEKK-stimulated JNK/SAPK activation preferentially regulated Elk-1 and not c-Jun. A second signal in addition to JNK/SAPK may be required for c-Jun transactivation in cells (Papavassiliou, A. G., et al. (1995) EMBO J. 14:2014–2019). There does not seem to be a proposed role for Elk-1 in inducing an apoptotic response, but serum deprivation-induced apoptosis of Swiss 3T3 cells results in the increased expression of early cell cycle genes consistent with an increased SRF/SRE activity associated with elevated Elk-1 activity (Pandey, S. and Wang, E. (1995) J. Cell. Biochem. 58:135–150). The induction of apoptosis in several cell types does not appear to require transcription, but the use of inducible cell lines and plasmid microinjection experiments do not facilitate testing whether MEKK$_{COOH}$ can induce cell death in the absence of transcription. In cells where transcription is not necessary for the induction of apoptosis it is likely that proteins required for apoptosis are already expressed and may be post translationally regulated by sequential protein kinase pathways involving MEKK. For example, the phosphorylation of nuclear proteins could alter their activity independent of transcription and contribute to a cell death response.

In Jurkat cells, a human T cell line, Fas-induced apoptosis has been proposed to involve a ceramide stimulated, Ras-dependent signaling pathway (Gulbins, E., ct al. (1995) Immunity 2:34351). We recently demonstrated that MEKK activity can be stimulated by Ras and that MEKK1 physically binds to Ras in a GTP-dependent manner (Russell, M. et al. (1995) J. Biol. Chem. 270:11757–11760; Winston, B. W., et al. (1995) Proc. Natl. Acad. Sci. USA (1995) 92:1614–1618). The ability of MEKK to regulate an apoptotic-like cell death response suggests it is a candidate component for the ceramide regulated apoptotic pathway.

The importance of our observations describing the involvement of MEKK regulated sequential protein kinase pathways in physiologically relevant signaling leading to cell death is supported by several findings. First, MEKK$_{COOH}$ induces or enhances a cell death response in the presence of 10% calf serum, indicating that growth factor deprivation is not a prerequisite for MEKK-induced cell death. This is similar to TNFα, Fas and ceramide-mediated apoptosis which proceeds in high serum. Thus, the involvement of MEKK in cell death responses is not simply to activate a subset of growth factor stimulated signaling events causing an aborted cell cycle-induced apoptosis that would normally be prevented by serum factors. Second, the enhanced cell death to ultraviolet irradiation indicates that expression of MEKK$_{COOH}$ may activate signals that potentiate stresses to the cell. This finding indicates that MEKK-regulated signal transduction pathways integrate with cellular responses involved in mediating apoptosis, that ultraviolet irradiation likely activates additional pathways and that MEKK$_{COOH}$-mediated signaling synergizes with the ultraviolet response to accelerate apoptosis. Third, MEKK stimulated sequential protein kinase pathways independent of ERK, JNK/SAPK, p38/hog 1 and c-Jun transactivation that can stimulate c-Myc transactivation. These results indicate that MEKK-regulated pathways traverse the cytoplasm to regulate as yet undefined protein kinases that activate cMyc in the nucleus. The regulation of c-Myc activity is a unique function of MEKK signaling and one that we postulate is likely to contribute to the cell death response. Serum deprivation significantly induces JNK/SAPK activation in several cell types including Swiss 3T3 cells. Similarly, TNF a stimulates a JNK/SAPK pathway (Minden et al. (1994) Science 266:1719–1723) and we have recently demonstrated TNFα stimulation of MEKK activity in mouse macrophages (Winston et al. supra). c-Myc overexpression has been shown to enhance TNFα receptor stimulation of apoptosis (White et al. (1992) Mol. Cell. Biol. 12:2570–2580). These findings are consistent with a linkage between TNFα. receptor signaling, MEKK and c-Myc. Cumulatively, the findings define MEKK as a potentially important component in the regulation of signal transduction pathways involved in apoptosis.

Example 21

Figure 20:
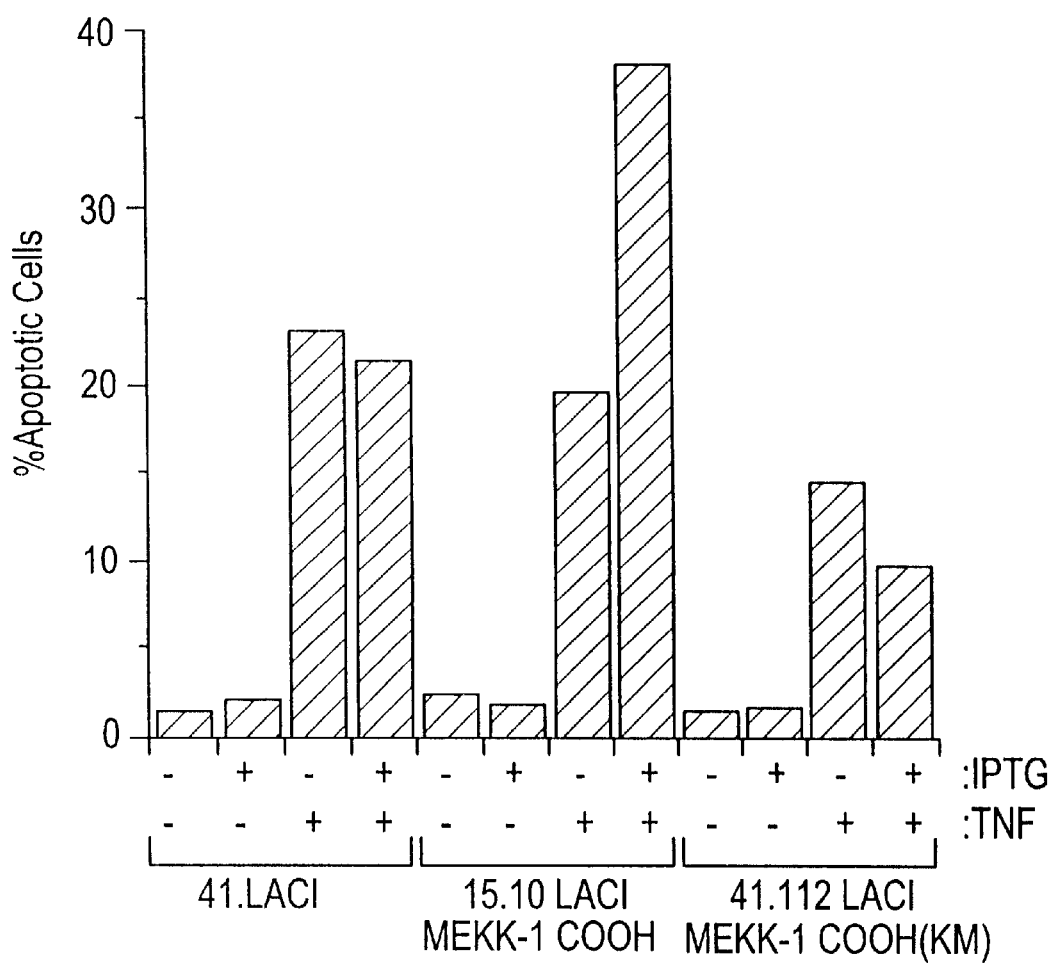
FIG. 20 shows the induction of apoptosis in L929 cells expressing MEKKCOOH domain by TNF.

This Example Illustrates that TNF and Expression of MEKK$_{COOH}$ Synergize to Induce Apoptosis in Cells Control L929 fibroblasts (4.1 LAC1), fibroblasts expressing MEKK$_{COOH}$ domain (15.10 LAC1), or fibroblasts expressing the kinase inactive mutant of MEKK1 cool, (41.112 LAC1) using the Lac Switch expression system described in Example 19, were treated with TNF in the presence or absence of IPTG and the percentage of apoptotic cells was calculated. As shown in FIG. 20, approximately 20% of control L929 cells became apoptotic upon TNF exposure either in the presence and absence of IPTG. In L929 cells expressing the MEKK1$_{COOH}$ domain, exposure to TNF and IPTG increased the percentage of apoptotic cells to 40%, approximately a 2-fold increase. In L929 cells expressing the MEK kinase inactive mutant, exposure to TNF did not increase the level of apoptotic cells above levels seen in controls, in fact the percentage of apoptotic cells was slightly decreased in cells exposed to both TNF and IPTG.

Example 22

This Example Describes Regulation of MAPK Activity by Both MEKK and Raf Protein COS cells were prepared using the method described in Example 3. In addition, COS cells were transfected with the pCVMV5 Raf construct (1 μg: Raf). FPLC MONO Q ion-exchange column fractions were prepared as described in Example 3 and assayed for MAPK activity according to the method described in Heasley et al., ibid.

Figure 21:
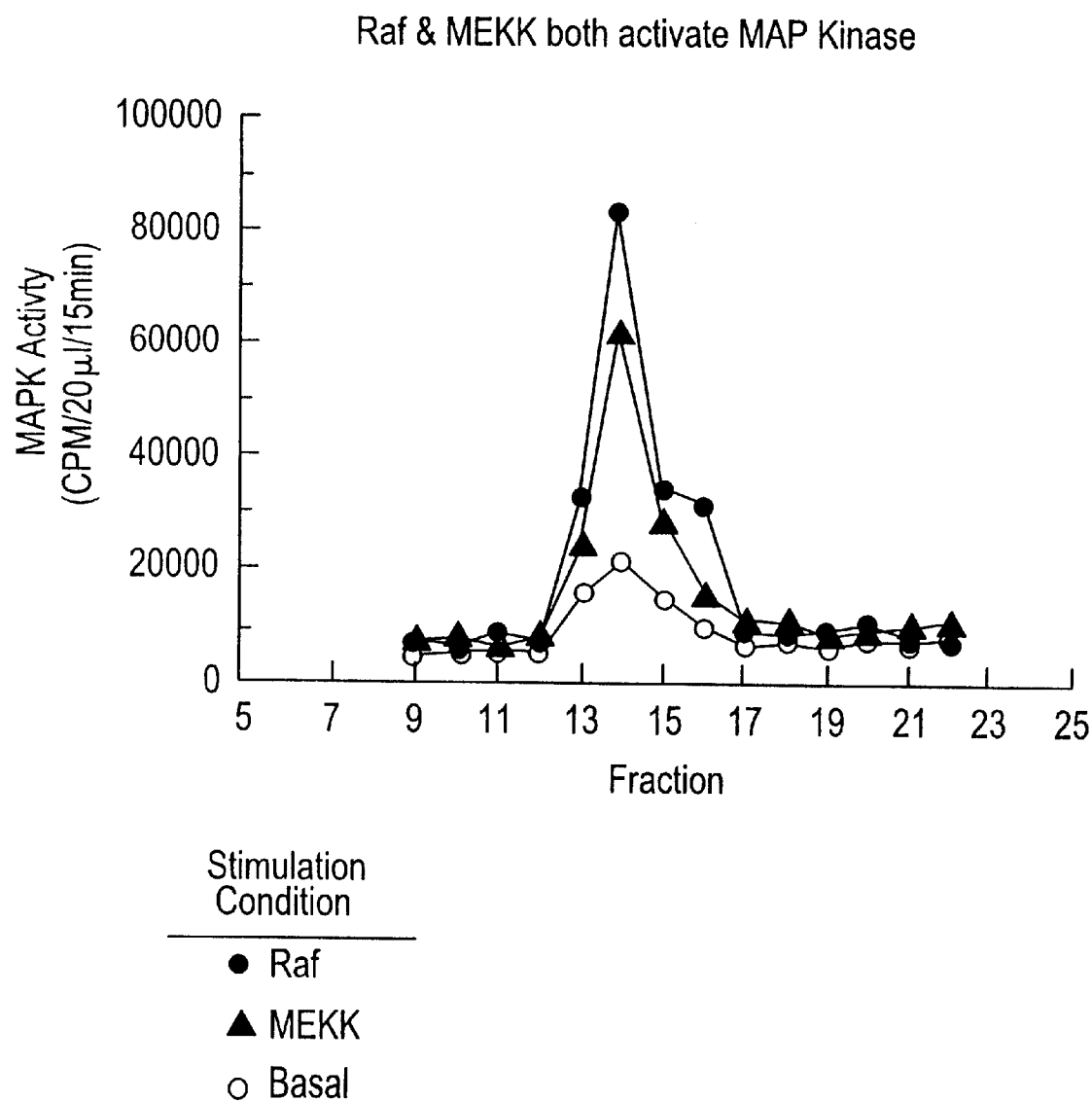
FIG. 21 shows similar stimulation of MAPK activity by MEKK protein and Raf protein.

Referring to FIG. 21, both MEKK and Raf overexpression in COS 1 cells resulted in similar levels of stimulation of MAPK activity over basal levels.

Example 23

This Example Demonstrates the Ability of COS Cell-expressed MEKK1 Proteins to Bind to GST-Ras$^{V12}$ COS cells were transiently transfected by the DEAE-dextran protocol as generally described in Example 3. Cos cells were transfected with: (1) p-MEKK1 containing a nucleic acid molecule encoding MEKK1 as described in Lange-Carter et al. (Science 260:315–319, 1994); (2) p-MEKK$_{NH2}$ containing a nucleic acid molecule that encodes a 858 base pair Pvull(682)-Ncol(1541) restriction digest fragment of the amino terminus of MEKK1 ligated into pCMV5; (3) p-MEKK$_{COOH}$ containing a nucleic acid molecule that encodes a 1435 base pair Ncol(1541)-Sspl (2976) restriction digest fragment that includes the entire kinase domain of MEKK1 ligated into pCMV5; (4) pCMV5 without insert; or (5) p-C4 Raf containing a nucleic acid molecule that encodes the amino terminus of Raf-1 ligated into pCMV5. COS cells expressing the various MEKK1 proteins were selected by the method described in COS cells expressing the various MEKK1 proteins were lysed in EB (1% Triton X—100, 10 mM Tris HCl [pH 7.4], 5 mM EDTA, 50 mM NaCl, 50 mM NaF, 0.1% bovine serum albumin, 0.2 U/ml aprotinin, 1 mM phenylmethyl-sulfonyl fluoride and 2 mM Na$_3$ VO$_4$). The lysates were separated into two equal parts for separate binding reactions. Half of the lysate was incubated with GST agarose (1.5 μg) while half of the lysate was incubated with GST-Ras$^{V12}$ agarose (1.5 μg) (purchased from UBI) for 1 hr at 4° C. The GST-Ras$^{V12}$ was preincubated at 30° C. for 30 min with 1 mM nucleotide (GDP or GTPγS). The nucleotide binding reaction was stopped by adding MgCl$_2$ to a final concentration of 20 mM. After the 1 hr binding reaction the agarose beads were pelleted at 2000 rpm for 2 min and washed 3 times with PBS+1.0% Triton X-100. The washed agarose beads were boiled in Laemmli SDS sample buffer and the proteins resolved by SDS polyacrylamide gel electrophoresis. Proteins were transferred onto nitrocellulose for immunoblotting with antibodies specific for an NH$_2$ terminal fusion protein (described in Example 1) or a COOH terminal peptide (described in Example 1). C4 Raf binding was detected using an antibody specific for Raf described in Example 8.

Initial immunoblotting results using anti-Raf antibodies demonstrated that C4 Raf bound to GST-Ras$^{V12}$(GTPγS) agarose but not to the GST agarose control. Additionally, no Raf immunoreactive proteins were detected bound to Ras from COS cells transfected with pCMV5. These results indicated that the Ras binding assay was functional.

Immunoblotting results using anti-MEKK antibodies indicate that protein encoded by p-MEKK1 (MEKK1) transiently expressed in COS cells was capable of binding GST-Ras$^{V12}$ in a GTP dependent manner. MEKK1 from COS cell lysates bound to GST-Ras$^{V12}$(GTPγS), while little binding to GST-Ras$^{V12}$(GDP) was detectable. With the conditions used, MEKK1 binding to GST-Ras$^{V12}$(GTPγS) was at least 5-fold greater than the binding to GST-Ras$^{V12}$(GDP). No detectable MEKK1 was bound to GST.

The domain critical for the binding of MEKK1 to Ras was then identified. The protein encoded by p-MEKK$_{COOH}$ (MEKK$_{COOH}$) bound to GST-Ras$^{V12}$ in a GTP dependent manner. Little MEKK$_{COOH}$ bound to GST-Ras$^{V12}$(GDP). No detectable MEKK$_{COOH}$ was bound to GST. In addition, when protein encoded by p-MEKK$_{NH2}$ (MEKK$_{NH2}$) was expressed in COS cells, no binding to Ras was detected. In contrast to the ability of Raf-1 to bind to Ras through its amino terminus, MEKK$^{NH2}$ failed to bind GST-Ras$^{V12}$(GTPγS) even though the protein was expressed to similar levels as MEKK1 in the same experiment. Thus, GST-Ras$^{V12}$ binds to MEKK1 at a site located within the COOH-terminal catalytic domain of MEKK1.

Example 24

This Example Demonstrates the Ability of Purified Recombinant MEKK1Proteins to Bind Directly to GST-Ras$^{V12}$ A construct encoding the kinase domain of a Rat MEKK1 cDNA (95% identical to mouse MEKK1) with a N-terminal hexahistidine tag (referred to herein as MEKK$_{COOH}$-His; provided by Dr. Melanie Cobb, Department of Pharmacology, University of Texas Southwestern Medical School, Dallas, Tex.) was expressed in bacteria and soluble active enzyme was purified on Ni$_2$+-NTA agarose according to the method generally described in Gardner et al. (*Methods of Enzymology* 238:258–270, 1994) Purified recombinant MEKK$_{COOH}$-His was incubated with either GST or GST-Ras$^{V12}$ in PAN buffer(10 mM PIPES [pH 7.0], 100 mM NaCl, 0.2 U/ml aprotinin) for 1 hr at 4° C. The agarose beads were pelleted and washed 3 times in PAN buffer. The washed agarose beads were then incubated in kinase buffer (20 mM PIPES [pH 7.0], 10 mM MnCl$_2$, 40μCi[γ$^{32}$P]ATP, 20 μg/ml aprotinin) containing 100 ng recombinant kinase inactive MEK1 as substrate in a final volume of 150 μl, at 30° C. for 20 min. To test the direct interaction of MEKK1 with the effector domain of Ras, samples were prepared by pre-incubating the agarose beads with either 100 μM of Ras peptide consisting of residues 17–42 of H-Ras or 100 μM of Ras control peptide ([D-Arg$^1$,D-Phe$^5$,DTrp$^{7,9}$,Leu$^{11}$] substance P peptide for 1 hr at 4° C. prior to addition of the MEK1 substrate. A control reaction containing wild-type MEKK1 which autophosphorylates, served as a marker for the MEKK1 substrate. Reactions were terminated by addition of 5× Laemmlei SDS sample buffer, boiled and resolved by SDS-PAGE.

The results indicate that there was direct binding of Ras-GTPγS to purified MEKK$_{COOH}$-His as measured by the increased phosphorylation of KM MEK1 using GST-Ras$^{V12}$ (GTPγS) beads incubated with recombinant MEKK$_{COOH}$-His. The interaction between Ras and MEKK$_{COOH}$-His was GTP dependent because essentially no KM MEK1phosphorylation could be detected with GST-Ras$^{V12}$ (GDP) beads incubated with recombinant MEKK$_{COOH}$.

The results indicate that the presence of Ras effector peptide prevented the binding of GST-Ras$^{V12}$(GTPγS) agarose to MEKK$_{COOH}$-His, thereby preventing the phosphorylation of KM MEK1 substrate present in the sample. MEKK$_{COOH}$-His was able to bind to GST-Ras$^{V12}$(GTPγS) in the presence of buffer alone or in the presence of a control peptide ([D-Arg$^1$,D-Phe$^5$,D-Trp$^{7,9}$,Leu$^{11}$] substance P peptide), resulting in the phosphorylation of KM MEK1 substrate.

Taken together, the results described in Examples 22 and 23 demonstrate that MEKK1 is a Ras effector and selectively binds to Ras in a GTP dependent manner. In addition, the binding of MEKK1 to Ras in vitro is direct and occurs via the COOH terminal region of MEKK1 that encodes the catalytic kinase domain.

Example 25

This Example Demonstrates the Cloning of MEKK4.1 and MEKK4.2, a Splicing Variant of MEKK4

The degenerate primers GA(A or G)(C or T)TIATGGCIGTIAA(A or G)CA SEQ ID NO: 13 (sense) and TTIGCICC(TorC)TTIAT(A or G)TCIC(G or T_)(A or G)TG SEQ ID NO: 14 (antisense) were used in a polymerase chain reaction (PCR) using first strand cDNA generated from polyadenylated RNA prepared from NIH 3T3 cells. The PCR reaction involved 30 cycles (1 minute, 94° C./2 minutes, 52° C./3 minutes, 72° C.) followed by a 10 minute cycle at 72° C. A band of approximately 300 bp was recovered from the PCR mixture and the products cloned into pGEM-T (Promega). The PCR cDNA products were sequenced and compared to the MEKK1 sequence. A unique cDNA sequence having signnificant homology to MEKK1 cDNA was identified and used to screen an oligo dT primed mouse brain cDNA library (Stratagene). The λ phage library was plated and DNA from plaques transferred to hybond-N filters (Amersham) followed by UV-crosslinking of DNA to the filters. Filters were pre-hybridized for 2 hours and then hybridized overnight in 0.5 M Na$_2$ H$_2$PO$_4$ (pH 7.2), 10% bovine serum albumin, 1 mM EDTA, 7% SDS at 68° C. Filters were washed 2× at 42° C. with 2× SSC, 1× with 1× SSC and 1× with 0.5× SSC containing 0.1% SDS (1× SSC is 0.15 M NaCl, 0.015M sodium citrate, pH 7.0). Positive hybridizing clones were purified and sequenced. To resolve GC-rich regions cDNAs were subcloned into M13 vectors (New England Biolabs) and single strand DNA sequenced. In all cases both strands of DNA were sequemced. Clones were truncated at the 5'-region and were therefore not full length in the coding region. To obtain the 5' region of MEKK4 poly RNA was isolated and primers from the partial cDNA used for reverse transcription. cDNAs were generated using the RACE procedure and sequenced. The 5' region of MEKK4 with upstream in frame stop codons was obtained and ligated to the partial MEKK4 cDNA to give a full length MEKK4 cDNA having an open reading frame of 1597 codons.

Example 26

This Example Demonstrates the Differential Expression of MEKK4.2

RNA was isolated from the indicated tissues of a Balb/c mouse tissues. RNA was isolated from the indicated tissues of a Balb/c mouse, resolved on an agarose gel, transferred to nitrocellulose paper and hybridized with $^{32}$P-labeled MEKK4.2 cDNA probe. A single mRNA band approximately 5.8 kb is hybridized with the labeled MEKK4.2 probe.

Example 27

Figure 22:
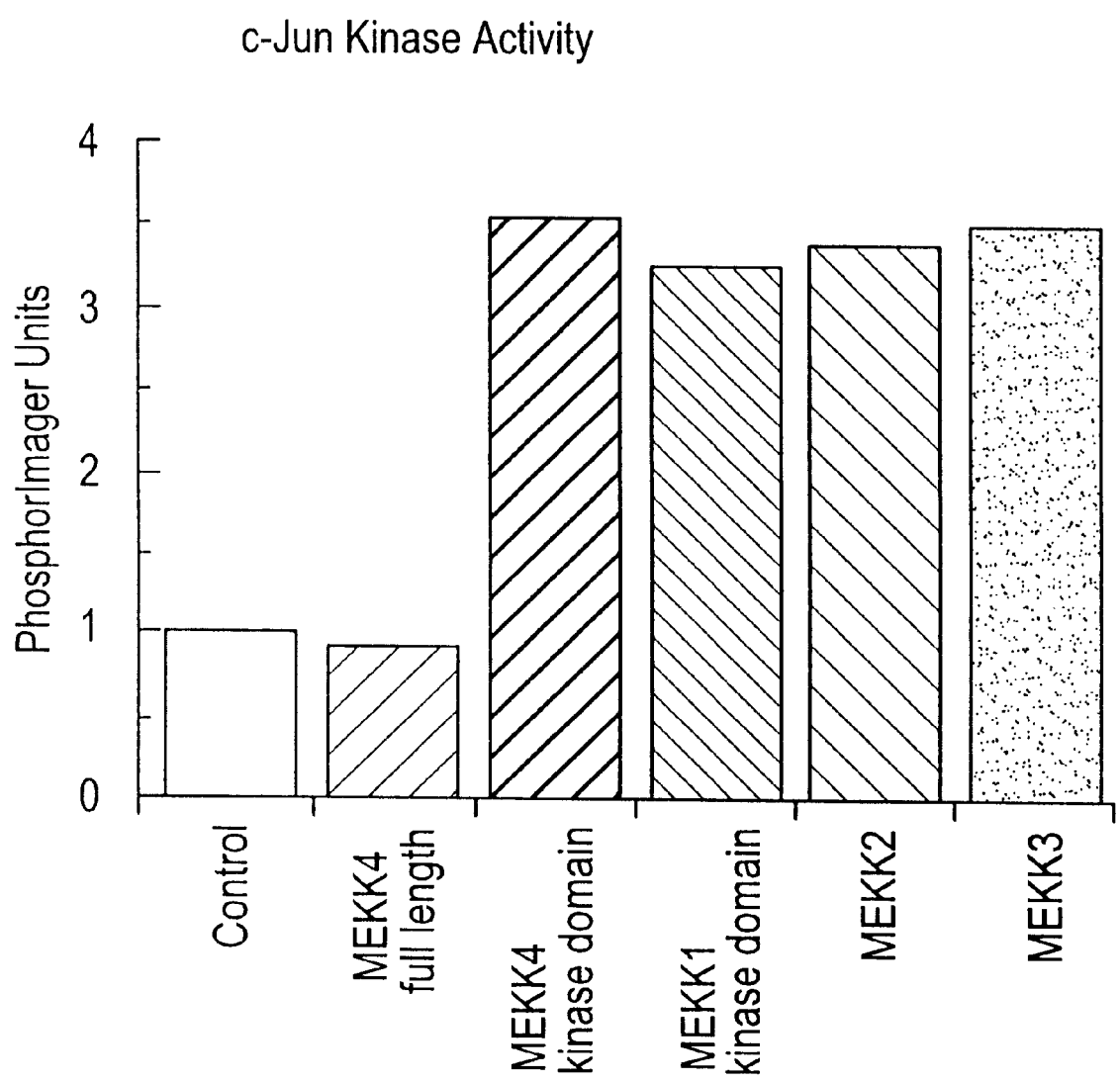
FIG. 22 is a graph illustrating the ability of various MEKK proteins, and fragments thereof, to activate a JNK activity.

This Example Demonstrates That the MEKK4 Kinase Domain Activates c-Jun Kinases Activity COS cells were transfected with pCMV5 expression plasmid encoding no cDNA insert (control), full length MEKK4 or the truncated MEKK4 encoding only the catalytic kinase domain. The truncated MEKK4 kinase domain is consitutitively active when expressed in COS cells. The MEKK1 kinase catalytic domain, and MEKK2 and -3 also activate the c-Jun kinase pathway (see FIG. 22).

Example 28

Figure 23:
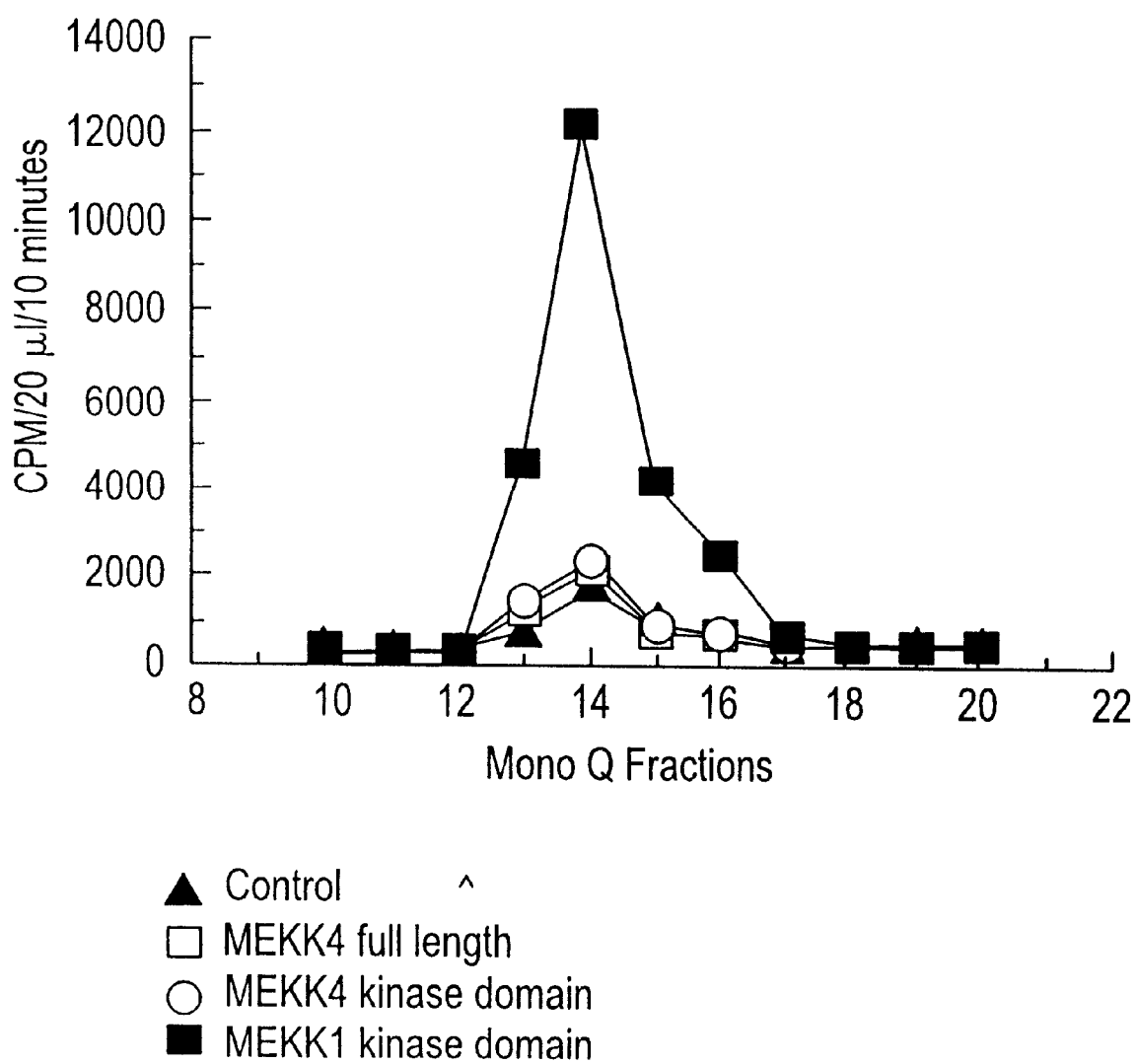
FIG. 23 is a graph illustrating the ability of various MEKK proteins, and fragments thereof, to activate ERK1 and ERK2.

This Example Demonstrates That MEKK4 Does Not Activate p42/p44 MAP Kinases (ERK1 and ERK2) Activity COS cells were transfected with pCMV5 expression plasmid encoding no cDNA insert (control), full length MEKK4, the truncated MEKK4 encoding only the catalytic kinase domain or the MEKK1 catalytic domain. The MEKK1 catalytic domain but not the MEKK4 catalytic domain is capable of activating ERK1 and ERK2 (see FIG. 23).

Example 29

This Example Demonstrates That MEKK4 Interacts With Cdc42/Rac

GST fusion proteins encoding Cdc42 or Rac loaded with either GTPγs or GDP were incubated with MEKK4 using previously described methods (Russell, M. et al. (1995) J. Biol. Chem. 270:11757–11760). The source of MEKK4 was either from a Cos cell transient transfection or a recombinant MEKK4 protein expressed in *E. coli*. The recombinant MEKK4 protein was truncated to express residues from 1261–1597 of the full length protein. A GST fusion protein of Ha-Ras was used as a control. The MEKK4 protein was incubated for 1 hr at 4° C. with either GST-Cdc42, GST-Rac or GST-Ras bound to glutathione-Sepharose beads. Each GSTfusion protein had GTPγs or GDP bound to the Cdc42, Rac or Ras moiety of the fusion protein. Following the incubation the beads were washed extensively and the bound proteins removed in SDS-Laemmli buffer and resolved by SDS-PAGE using 10% acrylamide gels. The proteins were transferred to nitrocellulose and immunoblotted using a MEKK4 specific antibody recognizing the extreme COOH-terminus of MEKK4. MEKK4 specifically bound to GST-Cdc42 and GST-Rac in the GTPγS form. The GDP bound forms of GST-Cdc42 and GST-Rac bound less than 10% of the MEKK4 bound in the presence of GTPγS. MEKK4 did not bind significantly to GST-Ras in either the GTPγS or GDP bound form.

The sequence HGQVCDTPKSYDNVHVGLRKV (residues 599–621) of the MEKK4 sequence set forth as SEQ ID NO: 12)) was synthesized as a GST-fusion protein by standard PCR techniques. The GST-fusion peptide bound Cdc42 and Rac in the GTPγS bound form. This fusion protein did not bind Ras using the procedures described above.

Example 30

Tumor necrosis factor a (TNFα) is a multifunctional cytokine secreted primarily by activated monocytes (Tracy, K. J., and Cerami, A. (1993) *Annu. Rev. Cell Biol.* 9:317–343). It has a wide range of biological activities depending upon cell type, stage of differentiation and transformation state. TNFα acts as a growth factor for fibroblasts (Vilcek, J.,et al.(1986) *J. Exp. Med.* 163:632–643; Victor, I., et al.(1993) *J. Biol. Chem.* 268:18994–18999), is cytotoxic towards certain cells and tumors (Larrick, J. W., and Wright, S. C. (1990) *FASEB J.* 4:3215–3216), induces monocyte differentiation of the human HL-60 myeloid leukemia cell line (Trinchieri, G., et al. (1986) *J. Exp. Med.* 164:1206–1225; Kim, M., et al. (1991) *J. Biol. Chem.* 266:484–489), represses adipocyte (Torti, F. M., et al. (1985) *Science* 229:867–869) and myoblast differentiation (Miller, S. C., et al. (1988) *Mol. Cell. Biol.* 8:2295–2301), and mediates endotoxic shock (Tracey, K. J., et al. (1986) *Science* 234:470–474). The peiotropic effects of this cytokine make it an important mediator in processes as diverse as proliferation, differentiation and cytotoxicity.

TNFα exerts these responses by binding to two cell surface receptore, the 55 kD TNFR (p55 TNFR) and the 75 kD TNFR (p75 TNFR) (Loetscher, H., et al. (1990) *Cell* 61:351–359; Schall, T. J., et al.(1990) *Cell* 61:361–370; Smith, C. A., et al. (1990) *Science* 248:1019–1023; heller, R. A., et al. (1990) *Proc. Natl. Acad. Sci. (USA)* 87:6151–6155). The receptors are single transmembrane spanning glycoproteins present on almost all cells analyzed (Kull, Jr., et al. (1985) *Proc. Natl. Acad. Sci (USA)* 82:5756–5760; Lewis, M., et al. (1991) *Proc. Natl. Acad. Sci. (USA)* 88:2830–2834 ). The extracellular domain of the p55 TNFR is homologous to the extracellular domains of the low affinity nerve growth factor receptor, the Fas/APO1 receptor, CD40, OX40, and CD27. The p55 TNFR and Fas share a 65 residue homology region in the cytplasmic domains (Tartaglia, L. A., and Goeddel, D. V. (1992) *Immunol. Today* 13:151–153; Smith, C. A., et al.(1994) *Cell* 76:959–962) which deletion studies have implicated in the TNFα signaling cascade leading to apoptosis (Itoh, N., and Nagata, S. (1993) *J. Biol. Chem.* 268:10932–10937; Tartaglia, L. A., et al. (1993) *Cell* 74:845–853). Most of the known TNFα responses occur by activation of the p55 TNFR. However, thymocyte proliferation is associated with p75 TNFR and eytotoxicity may be a function of p75 TNFR acting alone or in concert with the p55 TNFR (Heller, R. A., et al. (1992) *Cell* 70:47–56).

Apoptosis involves the activation of a specific suicide program within a cell. It occurs when a cell initiates a series of biochemical and morphological events which result in nuclear disintegration and eventual fragmentation of the dying cell into a cluster of membrane-bound apoptotic bodies (Kerr, J., Wyllie, A., and Currie, A. (1972) *Br. J. Cancer* 26:239–257). Apoptosis is responsible for such diverse activities as the elimination of cells during normal embryological development and determination of the immune receptor repertoire (Raff, M. C. (1992) *Nature* 356:297–300; Krammer, P. H., et al. (1994) *Curr. Opin. in Immunol* 6:279–289; Green, D. R., and Scott, D. W. (1994) *Curr. Opin. in Immunol.* 6:476–487) ). Apoptosis can be triggered in multiple ways, but it is not yet known whether different inducers of apoptosis have a common pathway or whether there are multiple pathwyas with perhaps some common components.

In many peptide-hormone receptor systems signal transduction to the nucleus involves the sequential activation of protein kinases. The extracellular response kinase (ERK) group of mitogen-activated protein kinases (p42 and p44 MAPK) are activated by growth factors via a Ras/Raf dependent signal transduction pathway (Davis, R. J. (1993) *J. Biol. Chem.* 268:14553–14556; Cano, E. and Mahadevan, L. (1995) *Trends Biochem. Sci.* 20:117–122). In contrast, the JNK/SAPK (Jun kinase/stress-activated protein kinase) members of MAPKs are activated by proinflammatory cytokines and environmental stresses (Devary, et. al. (1992) *Cell* 71:1081–1091; hibi, M., et al.(1993) *Genes & Development* 7:2135–2148; Sluss, H., et al. (1994) *Mol. Cell. Biol.* 14:8376–8384; Kyriakas, J. M., et al. (1994) *Nature* 369:156–160; Minden, A., et al. (1994) *Mol. Cell. Biol.* 14:6683–6688).

TNFα has been shown to initiate apoptotic cell death and DNA fragmentation in several mammalian cell lines, including the murine fibrosarcoma cell line L929 (Kyprianou, N., et al. (1991) *J. Natl. Cancer Inst.* 83:346–350; Feshel, K., et al.(1991) *Am. J Pathol.* 139:251–254). RNFa also has been shown to activate p42/p44 MAPK in this cell line (Van Lint, J., et al. (1992) *J. Biol. Chem.* 267:25916–25921). Recently JNKs were shown to be activated by TNFα (Westwick, J., et al. (1994) *J. Biol. Chem.* 269:26396–6401) and activation of the JNK pathway correlated with enhanced apoptosis of PC12 cells in response to trophic factor deprivation (Xia, Z., et al. (1995) *Science* 270:1326–1331). We have characterized the regulation of MAPKs and JNKs in L929 cells challenged with TNFα and basic fibroblast growth factor (bFGF). We show that TNFα preferentially activates JNK in L929 cells; but that JNK activation is not sufficient to induce apoptosis, since bFGF mediates a protective effect against TNFα mediated apoptosis without affecting JNK activation. Furthermore, our data indicate that p42/p44 MAPK activation is required for bFGF supression of TNFα mediated apoptosis.

Materials and Methods

Cell lines and culture. L929 cells (ATCC CCL1 were maintained in Dulbecco's modified Eagle's medium with 5% newborn claf serum and 5% bovine calf serum (BCS) supplemented with 100 ug/ml streptomycin and 100U/ml penicillin. The cells were grown in 10 cm dishes at 37° C. in 7.5% CO2. Cells were made quiescent where indicated by incubation in Dulbecco's modified Eagle's medium and 0.1% bovine serum albumin for 24 h. Recombinant murine TNFα and recombinant humanbFGF (147aa) were from R&D Systems, Minneapolis, Minn. Cells were pretreated where indicated with the MEK-1 inhibitor PD#098059 (Parke-Davis Pharmaceutical Corp. Ann Arbor, Mich.) for 1 h at 37° C. Cells were stimulated by incubation with the indicated cytokine or growth factor for various times at 37°

C. Cells were stimulated by incubation wit the indicated cytokine or growth factor for various times at 37° C. Stimulation was stopped by rinsing the plates twice with ice cold phosphate buffered saline (PBS) and lysing the cells in the appropriate lysis buffer. Cells were scraped from the plates and nuclei were pelleted for 10 min at 14,000 RPM in a microcentrifuge.

JNK assay. JNK activity was measured using a solid state kinase assay in which glutathione S-transferase-c-Jun$_{(1-79)}$ (GST-JUN) cound to glutathione-Sepharose 4B beads was used to affinity pruify JNK and then JNK activity was measured in an in vitro kinase assay using the sepharose bound GST-Jun as a substrate (Hibi, M., et al. (1993) *Genes & Development* 7:2135–2148). Stimulated or unstimulated cells were lysed in 0.5% Nonidet P-40, 20 mM HEPES pH 7.2, 100 mM NaCl, 2 mM dithiothreitol, 1 mM EDTA, 1.0 mM phenylmethylsulfonylfluoride, 1 µg/ml aprotinin and the nuclei pelleted. Lysates were normalized for protein content. JNK was affinity purified from 50–100 µg of cell lysate by the addition of 10 ul of GST-Jun sepharose slurry (2 µg GST-Jun). Binding to GST-Jun efficiently isolates the two major forms of JNK (p45 and p55) and under the conditions used JNK isolation was linear for 10–250 µg of cell lysate. The lysates were rotated at 4° C. for 1–3 h. Beads were washed twice in lysis buffer and then twice in PAN (10 mM PIPES, pH 7.0, 100 mM NaCl, 21 1 g/ml aprotinin). Kinase reactions were carried out at 30° C. for 15 min in 20 mM Hepes pH 7.2, 20 mM β-glycerophosphate, 10 mM p-nitrophenyl phosphate, 10 mM MgCl$_2$, 1 mM dithiothreitol, 50 µm sodium vanadate, 10 µCi γ$^{32}$P-ATP 4300 Ci/mmole. The kinase reaction was linear from 0–30 min.

MAPK Assay MAPK activity was measured exactly as described previously (Gardner, A. M., et al. (1994) *Meth. Enzymol.* 238:258–270) with the exception that MonoQ FPLC fractionation was replaced by step elution from a DEAE-Sephacel column using 0.5 M NaCl in loading buffer. The eluate was assayed in triplicate using the epidermal growth factor receptor 662–681 peptide (EGFR$_{662-681}$) as a selective substrate for MAPK activity (Heasley, L. E., et al. (1994) *American Journal of Physiology* (*Renal Fluid Electrolyte Physiol.* 36) 267:F366–F373).

Raf Activation Assay Cells were serum starved and challenged in the presence or absence of the appropriate cytokine or growth factors, as described above. Cells were lysed by scraping in ice cold RIPA buffer (50 mM Tris-HCl, pH 7.2, 150 mM NaCl, 0.1% SDS, 0.5% sodium deoxycholate, 1.0% Triton X-1 00, 10 mM sodium pyrophosphate, 25 mM γ-glycerophosphate, 2 mM sodium vanadate, 2.1 µg/ml aprotinin) and the nuclei were pelletted. The supernatants were normalized for protein content and precleared with protein A Sepharose prior to immunoprecipitation with rabbit antiserum to the C terminus of C-Raf, rabbit antiserum to A-Raf or rabbit antiserum to B-Raf (Santa Cruz Biotech., Santa Cruz, Calif.) and protein A Sepharose for 2–3 hr at 4° C. The beads were washed twice with ice cold RIPA and twice with PAN. A third of the immunoprecipitate was diluted with SDS sample buffer and used for immunoblot analysis. The remainder was resuspended in kinase buffer (20 mM Pipes pH 7.0, 10 mM MnCl$_2$, 150 ng kinase-inactive MEK-1, 30 µCi γ$^{32}$P-ATP and 20 µg/ml aprotinin) in a final volume of 40 li for 30 min at 30° C. Wild-type recombinant MEK-1 was autophosphorylated in parallel as a marker. Reactions were terminated by the addition of 12.5 µl 5× SDS sample buffer, boiled, and subjected to SDS-PAGE and autoradiography.

Neutral Red Assay Uptake of the dye neutral red was used as one measure of cell viability following cytokine or growth factor treatment (Finter, N. B. (1969) *J Gen Virol.* 5:419–427). 1.5×104–2.5×10$^5$ L929 cells/well were plated in 12 well tissue culture dishes in 1.25 ml of media. Cells were treated for 15–20 hr with various concentrations of TNFα and/or bFGF. 2.5 µl of 1% neutral red was added to the wells and incubated for 2 hr at 37° C. PBS. The neutral red was extracted with 1.0 ml of 50% ethanol, 50 mM Na-citrate pH 4.2 and absorbency was measured at 540 mM.

Propidium iodide staining Cells were plated on glass chamber slides (Nunc, Naperville, Ill.) at a concentration of 0.2–0.6×10$^5$ cells/ml. Ras expression was induced with 5 mM IPTG in Dulbecco's modified Eagle's medium with 0.1% BCS for 8–12 hr. Cells were exposed to TNFα (5 ng/ml) and/or bFGF (500 µg/ml) in Dulbecco's modified Eagle's medium with 0.1% BCS for 16 hr. The parental LACI expressing cell line (see below) was used as a control. Cells were washed twice in PBS, fixed in acetone:methanol (1:1)-20° C. for 5 min, air dried, washed twice in PBS, stained with 1 µg/ml propidium iodide (PI) in PBS for 20 min, washed in PBS, washed in H$_2$O and mounted in 25% glycerol/PBS. PI fluorescence was observed using a Nikon inverted microscope equipped with epifluorescence and a 580 mm filter. Images were analyzed using IP lab.

Cell transfections L929 cells were transfected by CaPO$_4$ (Ausubel, F. (1994) *Current Protocols in Molecular Biology* Vol. 1, pp. 9.1.1–9.1.4, John Wiley & Sons, Inc., New York) with the vector 3'SS (Stratagene, La Jolla, Calif.) expressing the LACI repressor. Stable clones were selected in 200 µg/ml hygromycin (Calbiochem, La Jolla, Calif.) and screened for LACI expression by indirect immunofluorescence using rabbit anti-sera to LACI (Stratagene, La Jolla, Calif.) and FITC-donkey anti-rabbit. One clone expressing a high level of nuclear LACI was then transfected with hemaglutinin (HA)-tagged inhibitory N 17 (Feig, L. A. and Cooper, G. M. (1988) Mol Cell. Biol. 8:3235–3243) Ras or activated V12 Ras (Tobin, C.,et al.(1982) Nature 300:143–148; Reddy, E. P., et al.(1982) Nature 300:149–152); Taparowsky, E., Suard, Y., Fassano, D., Simiger, K., Goldfarb, M., and Wigler, M. (1982) *Nature* 300:149–152) cloned into the LACI repressible pOPRSVI vector. Stable clones were selected in 500 µg/ml G418 and screened for inducible expression of HA-Ras by immunoblotting. Incubation in 5 mM isopropyl-1-thio-β-D-galactopyranoside (IPTG) for 8–24 hr was used to induce Ras expression. Several independent, inducible N17 Ras or V12 Ras clones were isolated and two each were chosen for further analysis.

Immunoblotting 100 µg of cell lysate was fractionated by SDS PAGE (12.5% acrylamide) and blotted to nitrocellulose in 10 mM CAPS, pH 11, 20% MeOH using a Transphor apparatus (Hoeffer, San Diego, Calif.) for 1 hr at 1 amp. Blots were blocked in 5% powdered milk in Tris-HCl, pH 7.5 buffered saline. Ras was detected with Y-13259 anti-Ras monoclonal antibody (Fruth, M. E., Davis, L. J., Fleurdelys, B., and Skolnick, E. M. (1982) J Virol. 43:294–304) followed by enhanced chemiluminescence (Amersham, Chicago, Ill.) using HRP-anti-mouse IgG (BioRad, Richmond, Calif.).

Quantitation of data PhosphorImager analysis of phosphorylated proteins provided a quantitative measure of kinase activation in arbitrary phosphorimaging units. Statistical analysis was performed using the JMP program and the method of Tukey & Kramer was used to determine statistical differences.

Figure 24A:
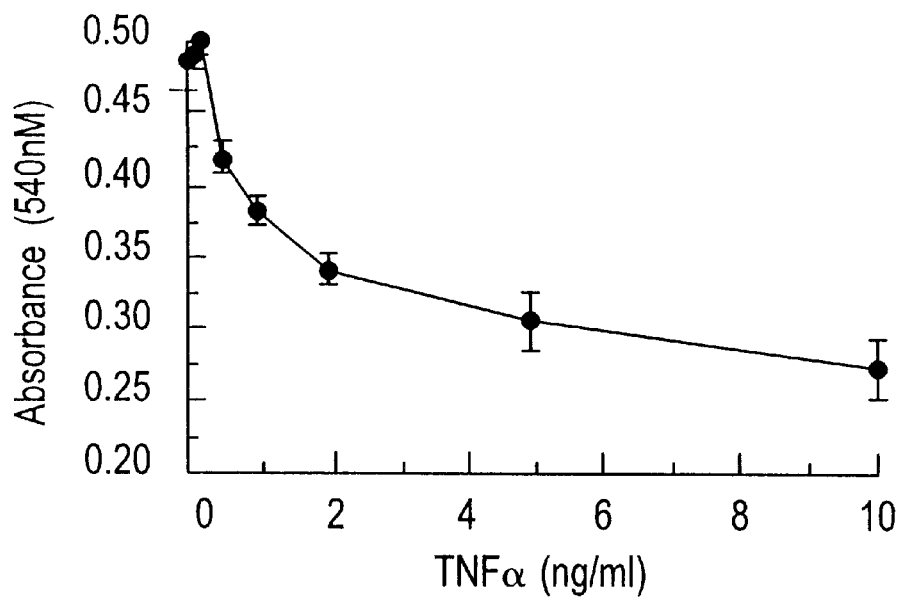
FIGS. 24A and B show that TNF induces apoptosis in L929 cells and that this effect is blocked by bFGF. In panel A cells were treated with the indicated concentrations of TNFα for 15 hours and were assayed for uptake of neutral red. In panel B cells were untreated (solid bars), treated with 0.5 ng/ml bFGF (dotted bars) or 5.0 ng/ml bFGF (hatched bars) and the indicated concentrations of TNFα for 18 hours. Cell viability was assessed by neutral red assay.
Figure 24B:
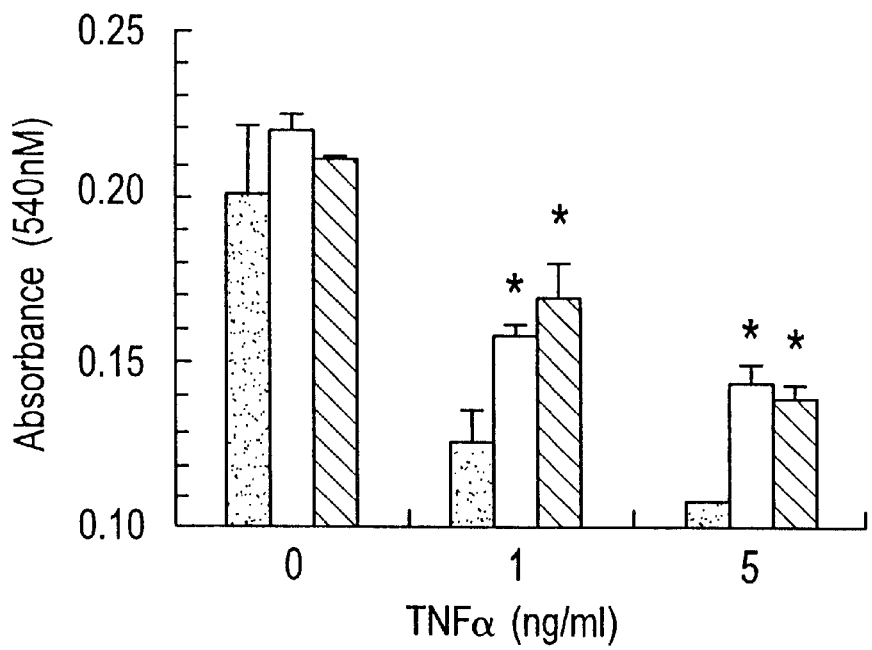
Figure 25A:
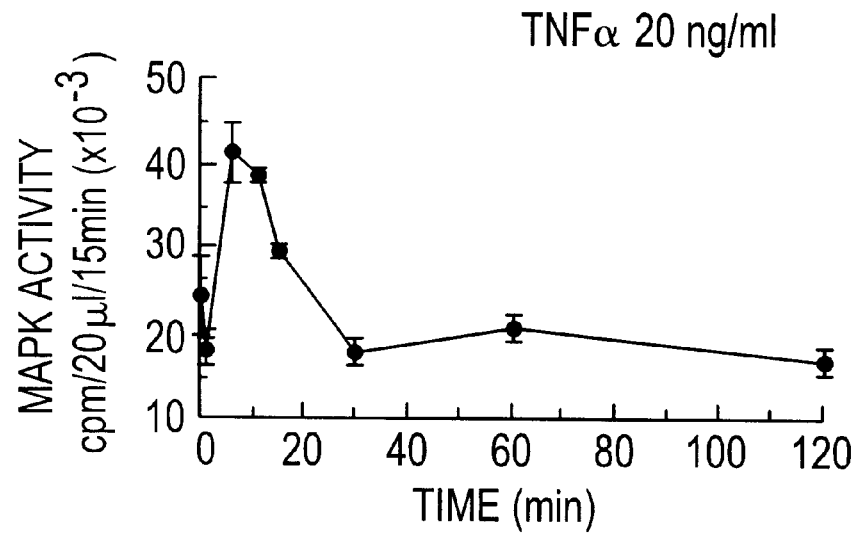
FIGS. 25A and B show the activation of JNK and MAPK in L929 cells. In panel A cells were treated for 10 minutes with the indicated concentration of TNFα. JNK activation was measured using a solid phase kinase assay resulting in phosphorylation of GST-Jun. In panel A the time course of MAPK activation is shown. MAPK was isolated from cell lysates on DEAE sephacel columns and MAPK activation was measured by phosphorylation of the EGFR peptide substrate. Panel B depicts the concentration curve of MAPK activation by TNFα. Cells were treated with the indicated concentration of TNFα and MAPK was assayed.
Figure 25B:
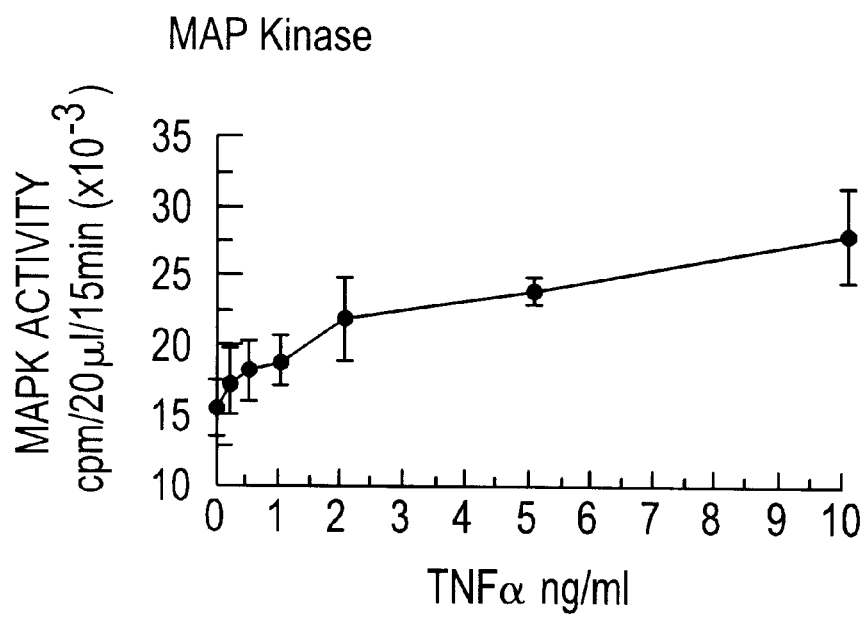

Results bFGF protects L929 from TNF α-mediated apoptosis TNFα activates a cell death program resulting in the apoptosis of L929 cells (Feshel, K., Kolb-Bachofen, V., and Kolb, H. (1991) *Am. J Pathol.* 139:251–254). FIG. 24A shows that treatment of L929 cells overnight with TNFα resulted in substantial cell death using the neutral red assay as a measure of viable cells (see Methods). The time course of cell death was dependent on the concentration of TNFα. Treatment with 10 ng/ml TNFα resulted in greater than 40% of the L929 cells being apoptotic in 15 hr; 1 ng/ml TNFα required 24–48 hr to induce a similar level of L929 cell death (not shown). Serum and growth factor withdrawal induces apoptosis in several cell systems (Oppenheim, R. W. (1991) *Annu. Rev. Neurosci.* 14:453–501; Kinoshita, T., et al.(1995) *EMBO J.* 14:266–275), indicating that growth factors have a protective effect against apoptosis. Consistent with this observation was our finding that bFGF affected TNFα mediated apoptosis (FIG. 24B). Incubation of L929 cells with TNFα in the presence of bFGF was effective at blocking TNFα-mediated cell death. The protective effect of bFGF was not simply due to an increased proliferative response of L929 cells, because bFGF in the absence of TNFα did not measurably increase cell number (FIG. 24B). Regulation of JNK and MAPK by TNFα and bFGF TNFα has been previously shown to activate p24/p44 MAPK in L929 cells (Van Lint, J., Agostinis, P., Vandevoorde, V., Haegeman, G., Fiers, W., Merlevede, W., and Vandenheede, J. (1992) *J. Biol. Chem.* 267:25916–25921) but recent studies have indicated that TNFα is a potent activator of the Jun kinase (JNK) members of the MAPK family (Sluss, H., et al. (1994) *Mol. Cell. Biol.* 14:8376–8384; Kyriakas, J. M., et al. (1994) *Nature* 369:156–160; Westwick, J., Weitzel, C., Minden, A., Karin, M., and Brenner, D. (1994) *J. Biol. Chem.* 269:26396–6401). Analysis of the time course and dose response of TNFα on L929 cells demonstrated significant differences in the activation of JNK and p42/p44 MAPK activity. Extracts from TNFα-treated versus control L929 cells were assayed for JNK activity using GST-c-Jun$_{(1-79)}$ as substrate. TNFα induced a transient increase in JNK activity that peaked at 10–15 min and returned to two-fold above basal JNK activity 1–2 hr post-stimulation. Maximal JNK activation was achieved at 1 ng/ml TNFα and 0.1 ng/ml TNFα activated JNK greater than four-fold. TNFα. stimulation of p42/p44 MAPK activity was slightly more rapid than JNK activation, reaching maximal stimulation in 5–10 min that returned to near basal levels by 30 min (FIG. 25A). The dose-response curve for p42/p44 MAPK activation is dramatically shifted to higher TNFα concentrations than that for JNK (FIG. 25B). Greater than 10 ng/ml TNFα was required to stimulate p42/p44 MAPK 2–3 fold; at 1 ng/ml TNFα the MAPK activity was stimulated only 20% above basal, a concentration of TNFα that gave maximal JNK activation. Thus, TNFα preferentially regulates the JNK pathway relative to p42/p44 MAPK in L929 cells. These findings indicate that the localized concentration of cytokines such as TNFα will determine the selectivity and magnitude of cellular JNK and p42/p44 MAPK responses.

Figure 26:
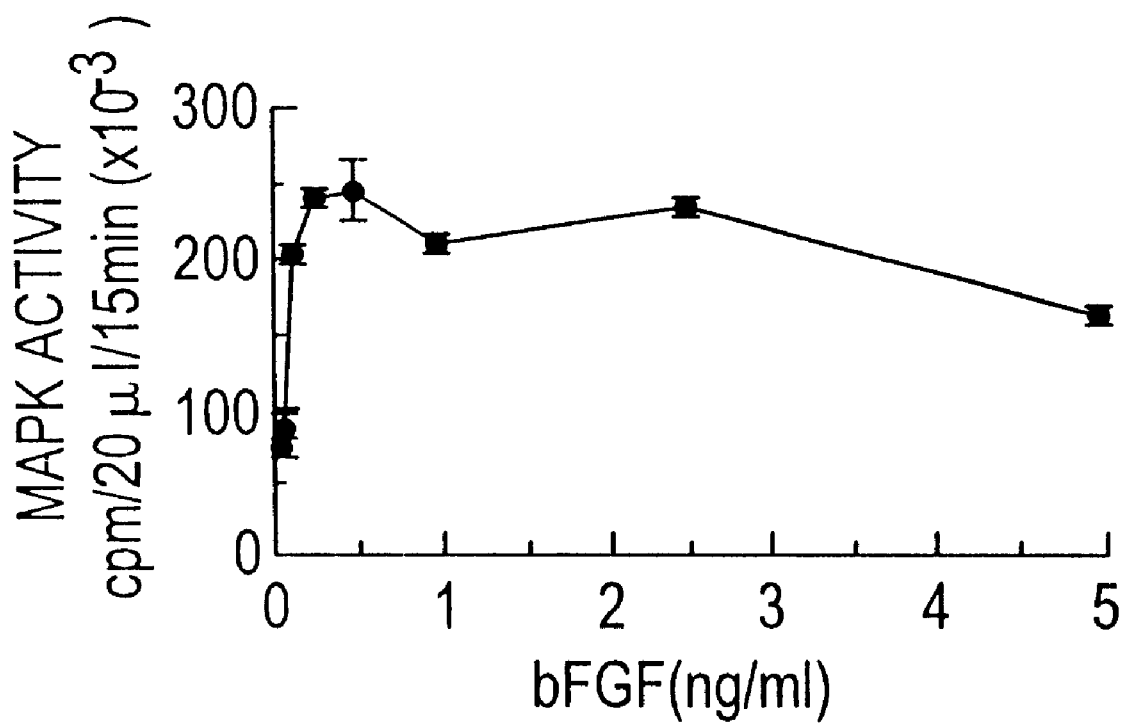
FIG. 26 depicts the activation of MAPK by bFGF in L929 cells. Serum starved L929 cells were stimulated for 10 min with the indicated concentration of bFGF.
Figure 27A:
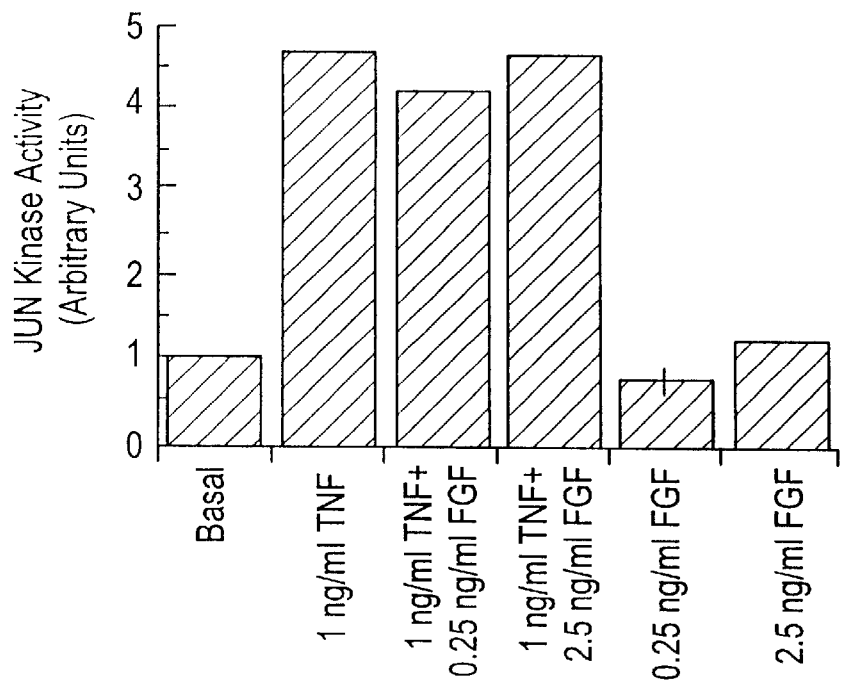
FIGS. 27A and B show that bFGF does not inhibit TNFα stimulation of JNK activity. In panel A serum starved L929 cells were treated as indicated. Radiolabel incorporated into GST-Jun is expressed in arbitrary phosphorimaging units. In panel B cells were stimulated as indicated and assayed for MAPK activity.
Figure 27B:
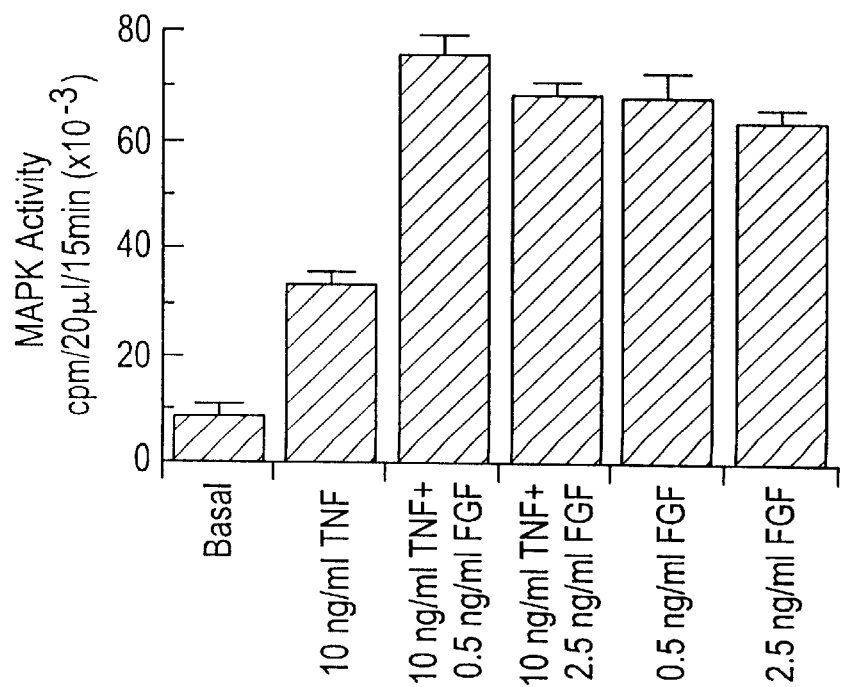

In contrast to proinflammatory cytokines such as TNFα, growth factor receptor tyrosine kinases are generally mitogenic in fibroblasts and stimulate the p42/p44 MAPK pathway. The bFGF receptor possesses intrinsic tyrosine kinase activity and is present on L929 cells. FIG. 26 demonstrates that bFGF stimulates a robust activation of MAPK in L929 cells. Concentrations of 0.25–0.5 ng/ml of bFGF gave maximal stimulation of MAPK activity. Fractionation of stimulated cell lysates by MonoQ fast pressure liquid chromatography indicated that both p42 and p44 MAPK were activated by bFGF (not shown). Activation of the MAPK pathway by tyrosine kinases involves Ras and the Raf serine-threonine protein kinases. Immunoblotting demonstrated that B-Raf and C-Raf are expressed in L929 cells (not shown). Treatment of L929 cells with bFGF resulted in the activation of both B-Raf and C-Raf as measured by their ability to phosphorylate a recombinant kinase-inactive MEK-1 protein (Gardner, A. M., Lange-Carter, C. A., Vaillancourt, R. R., and Johnson, G. L. (1994) *Meth. Enzymol.* 238:258–270). MEK-1 is the protein kinase phosphorylated and activated by Raf, which in turn phosphorylates MAPK on both a tyrosine and threonine resulting in MAPK activation (Crews, C. M., Allesandrini, A., and Erikson, R. L. (1992) *Science* 258:478–480; Crews, C. M., and Erikson, R. L. (1992) *Proc. Natl. Acad. Sci. (USA)* 89:8205–8209; Nakielny, S., et al. (1992) *EMBO J.* 11:2123–2129; Seger, R., et al.(1992) *J. Biol. Chem.* 267:14373–14381). In contrast, TNFα does not significantly activate either isoform of Raf in L929 cells.

bFGF and TNFα independently regulate cytoplasmic protein kinase cascades FIG. 27 demonstrates that 1 ng/ml TNFα has only modest stimulatory effects on MAPK activity (panel B) and 2.5 ng/ml bFGF has little or no effect on JNK activity (Panel A). These concentrations of bFGF and TNFα give maximal activation of MAPK and JNK, respectively. Co-stimulation of L929 cells with bFGF, at concentrations that show partial protection against TNFα-mediated killing, did not alter the magnitude of JNK activation in response to TNFα. Similarly, co-stimulation of L929 cells with TNFα, at concentrations capable of causing cell death, had little or no effect on bFGF stimulation of MAPK activity (Panel B). Thus, in relation to JNK and MAPK, TNFα and bFGF receptors independently regulate the activity of these two sequential protein kinase pathways in L929 cells.

Figure 28B:
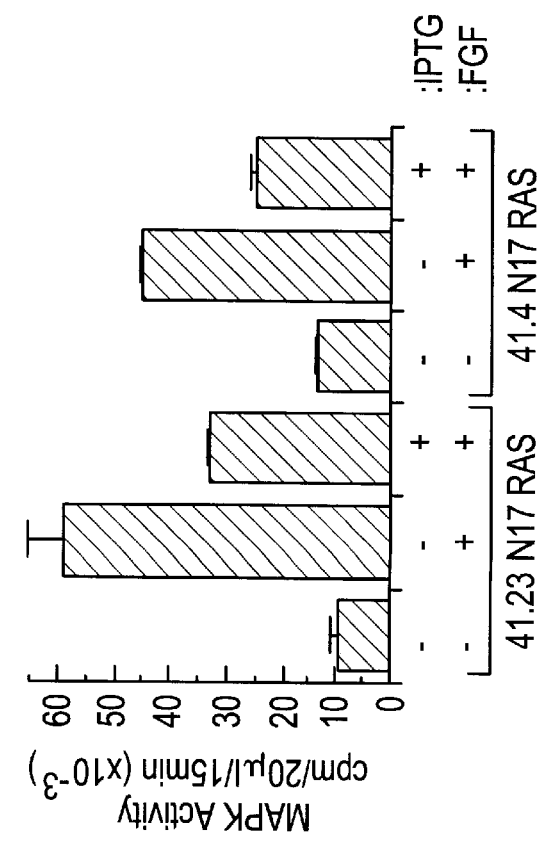
FIGS. 28A and B show the effect of dominant negative N 17 Ras or constitutively active V 12 Ras on MAPK and JNK activities. In panel A cells were uninduced (−) or induced (+) to express Ni 7 Ras by overnight treatment with 5 mM IPTG. The cells were unstimulated (−) or stimulated (+) for 10 min with 0.5 ng/ml bFGF. MAPK activity was assayed. In panel B 41 .LAC1 or V12 Ras cells were induced with IPTG, stimulated as indicated and analyzed for MAPK activation.
Figure 28A:
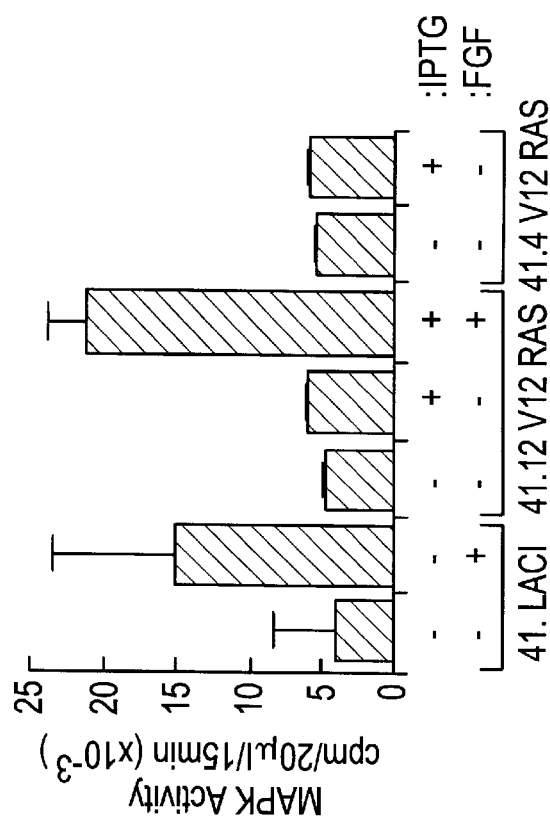

Inducible expression of inhibitory and activated Ras influences apoptosis Ras activation is required for many of the phenotypic responses resulting from the activation of tyrosine kinases. Signaling by the bFGF receptor involves several different effector pathways including Ras activation. To test the involvement of Ras in the bFGF protective response, the Lac Switch inducible expression system (see Methods) was used to control the expression of inhibitory N17 Ras and constitutively activated V12 Ras in L929 cells. FIG. 28 shows the functional consequence of expressing inhibitory N 17 Ras or activated V 12 Ras on MAPK and JNK activation in response to bFGF and TNFα, respectively. IPTG-regulated expression of the HA epitope-tagged Ras mutants (N17 and V12 Ras) is shown in Panel D. Expression of N 17 Ras significantly blunted bFGF stimulation of MAPK (Panel A), but had no effect on TNF stimulation of JNK (Panel C). With two independent clones, expression of VI 2 Ras did not constitutively activate the MAPK pathway, but did appear to enhance bFGF stimulation of MAPK (Panel B). V12 Ras expression also had no effect on TNFα stimulation of JNK activity (Panel C). Similar results were found with independent L929 cell clones indicating the responses were the result of specific mutant Ras expression.

Figure 29:
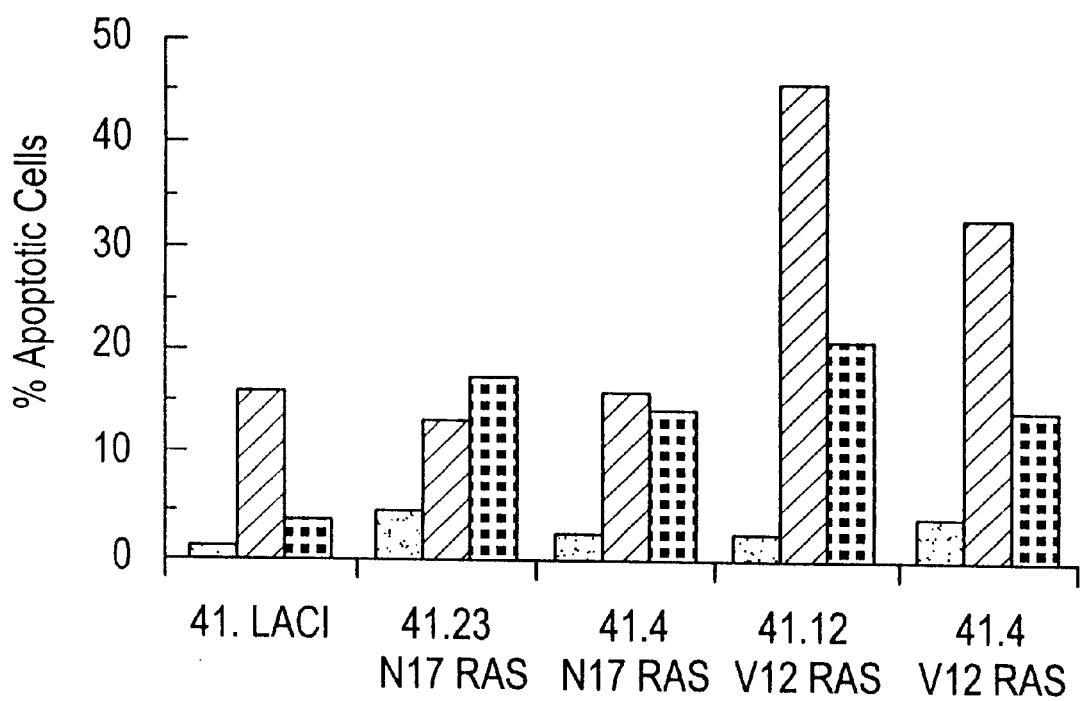
FIG. 29 shows the effect of N17 Ras on TNFα killing and bFGF protection. Ras expression was induced with 5 mM IPTG for 10 hours and cells were subsequently treated with 5 ng/ml TNFα. in the presence or absence of 0.5 ng/ml bFGF for 16 hours. Cells were fixed and stained with propidium iodide. The percentage of apoptotic cells was calculated. Solid bars represent cells induced with IPTG; hatched bars, induced with IPTG and treated with TNFα; checked bars, induced with IPTG and treated with TNFα and bFGF.

Expression of N 17 Ras did not affect TNFα induced apoptosis of L929 cells; N 17 Ras did, however, markedly inhibit the ability of bFGF to protect cells against TNFα-mediated cell death. These findings indicated that functional Ras signaling is not required for the TNF cc-induced apoptotic response, but is required for the protective action of bFGF. Strikingly, constitutively activated V12 Ras has markedly enhanced TNFα-stimulated apoptosis, but had little or no effect on the apoptotic index of L929 cells in the absence of TNFα. This observation indicates that VI 2 Ras is functional in L929 cells, despite the fact MAPK is not constitutively activated in this cell line and implies that activated Ras likely regulates pathways in addition to MAPK that are involved in apoptosis. Co-stimulation with bFGF and TNFα resulted in a diminished apoptotic response relative to TNFα alone in V12 Ras expressing cells, indicating that bFGF pathways required for protection against TNFα stimulated cell death were functional in these cells (FIG. 29). Thus, inhibitory Ras expression prevented bFGF protective responses and activated Ras enhanced TNFα killing. The results suggest multiple Ras-dependent events are involved in controlling apoptosis and the role of Ras signaling can be either positive or negative in regulating the phenotypic response to cytokines such as TNFα.

Figure 30A:
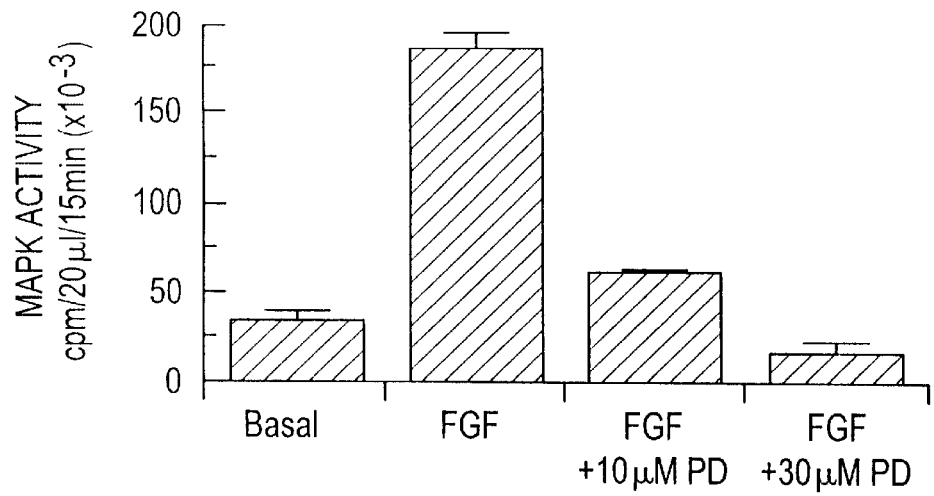
FIGS. 30A and B show the inhibition of MAPK activity and elimination of the bFGF protective effect of treatment with the MEK-1 inhibitor PD #098059. In panel A serum starved L929 cells were untreated or treated for 1 hour at 37° C. with the MEK-1 inhibitor (PD) and then unstimulated or stimulated with bFGF. MAPK activity was measured. In panel B L929 cells were untreated or treated for 1 hour at 37° C. with PD and then were untreated or treated with TNFα alone or in combination with bFGF for 18 hours. Cell viability was assessed by neutral red assay.
Figure 30B:
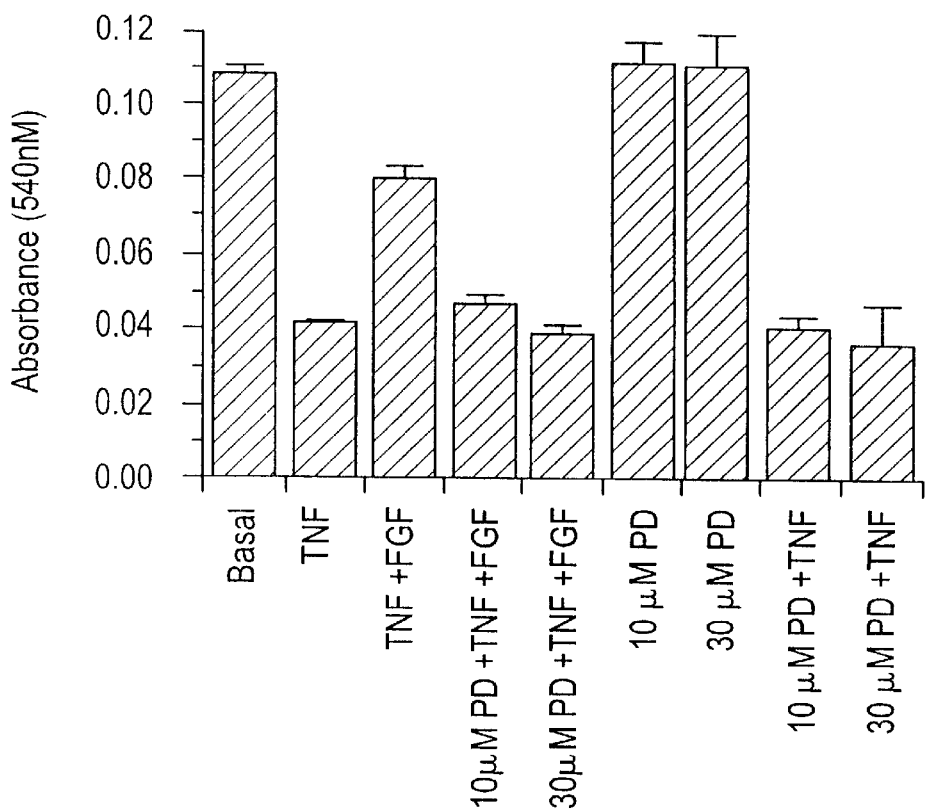

Inhibition of MEK and MAPK stimulation prevents bFGF protection from apoptosis The Parke-Davis compound, PD #098059 inhibits the dual specificity protein kinase, MEK-1, which specifically activates p42/p44 MAPK (Alesssi, D. R., Cuenda, A., Cohen, P., Dudley, D. T., and Saltiel, A. R. (1995) *J. Biol. Chem.* 270:27489–27494). PD #098059 did not inhibit JNK kinase or the activation of JNK (not shown). Pretreatment of L929 cells with PD #098059 inhibited bFGF stimulation of MAPK activity (FIG. 30A). The PD #098059 compound had no effect on TNFα-mediated apoptosis but inhibited the protective action of bFGF (FIG. 30B). Thus, MEK activation of MAPK is required for bFGF protection against TNFα-mediated apoptosis. Interestingly, the phosphatidylinositol 3-kinase inhibitor, wortmannin, did not influence the cell death response to TNFα nor did it inhibit the protective response to bFGF (not shown ). Treatment of L929 cells with wortmannin had no effect on the ability of bFGF to stimulate MAPK activity. Apparently, phosphatidylinositol 3-kinase activity is not required for the action of either TNFα or bFGF on the control of the cell death program L929 cells.

TNFα induces apoptosis of L929 cells and bFGF is protective against this cell death response. Our results indicate that the activation of JNK in response to TNFα stimulation of L929 cells is not sufficient for the induction of cell death. TNFα maximally stimulates JNK activity in the presence of bFGF concentrations that are capable of protecting against cell death. Signals in addition to JNK activation must be involved in the TNFα-mediated death response. The bFGF protective response was only partial in that not all the cells were prevented from dying in response to TNFα treatment. This may, in part, be related to cell cycle dependent signaling by TNFα and bFGF; the L929 cells used in these studies were asynchronous so that we can not rule out this possibility. Our findings also demonstrate that Ras is involved in integrating responses that control apoptosis. Expression of activated or inhibitory Ras influences TNFα killing of L929 cells. The mechanism for enhanced TNFα killing of L929 cells resulting from V12 Ras expression is unclear, although it has been observed in C3 h mouse fibroblasts as well (Fernandez, A., et al. (1994) *Oncogene* 9:2009–2017). It may involve an alteration in the expression of specific genes such as c-Jun, c-Fos and c-Myc which appear to be involved in both growth and apoptotic responses (Westwick, J., et al. (1994) *J. Biol. Chem.* 269:26396–6401; Pulverer, B. J., et al. (1991) *Nature* 353:670–674; Seth, A., et al. (1991) *J. Biol. Chem.* 266:23521–23524; Evan, G. I., et al. (1992) *Cell* 69:119–128; Gupta, S., Seth, A., and Davis, R. J. (1993) *Proc. Natl. Acad. Sci. (USA)* 90:3216–3220; Klefstrom, J., et al. (1994) *EMBO J.* 13:5442–5450; Shi, Y., et al (1992) *Science* 257:212–214; Janicke, R. U., Lee, F. H. H., and Porter, A. G. (1994) *Mol. Cell. Biol.* 14:5661–5670; (Harrington, E. A., et al. (1994) *EMBO J.* 13:3286–3295). In contrast, the effect of inhibitory N17 Ras appears to primarily be the inhibition of MAPK activation in response to bFGF. This finding is substantiated by the loss of bFGF protection against TNFα-mediated apoptosis by the MEK inhibitor PD #098059. Studies using the fungal metabolite, wortmannin, demonstrated that hosphatidylinositol 3-kinase was not involved in bFGF protection against apoptosis in L929 cells.

Recently, it was demonstrated using PC12 cells that the JNK pathway was involved in mediating apoptosis in response to serum deprivation and that activation of the MAPK pathway was protective against serum deprivation (Xia, Z., et al.(1995) *Science* 270:1326–1331). Phosphatidylinositol 3-kinase activity has also been reported to be necessary to protect PC12 cells from serum deprivation induced apoptosis (Yao, R., and Gooper, G. M. (1995) *Science* 267:2003–2006). Interestingly, the expression of N17 Ras protected PC12 cells from nerve growth factor withdrawal induced apoptosis (Ferrari, G., and Greene, L. A. (1994) *EMBO J.* 13:5922–5928). The findings indicated that N17 Ras maintained PC12 cells in a quiescent state that allowed them to survive in the absence of trophic factors. Removal of trophic factors from PC12 cells appeared to induce an aberrant proliferative response that resulted in apoptosis. Our findings using N17 Ras expression in L929 cells contrast with those in PC12 cells. TNF induced apoptosis in growing L929 cells, N17 Ras expression did not affect the apoptotic response, while V12 Ras expression significantly enhanced apoptosis. Thus, the involvement of Ras dependent signaling on apoptotic responses of cycling versus quiescent cells may be quite different.

In human B cells, crosslinking of surface IgM stimulated a host of signaling pathways including MAPK but not JNK and resulted in apoptosis (Sakata, N., Patel, H., Aruffo, A., Johnson, G. L., and Gelfand, E. W. (1995) *J Biol. Chem.* 270:30823–30828). CD40, a member of the TNF receptor family, activated JNK while rescuing B cells from anti-IgM mediated apoptosis (Sakata, N., Patel, H., Aruffo, A., Johnson, G. L., and Gelfand, E. W. (1995) *J. Biol. Chem.* 270:30823–30828). Thus, in human B cells MAPK activation is insufficient to protect against apoptosis and signals including the stimulation of JNK are generated during a protective response. Clearly, the integration of multiple signals appears to be required for apoptosis.

The overlap of signals involved in committing cells to growth or apoptosis is also evident in many transformed cell types. Tumors frequently have a high growth rate, but also a high apoptotic index (Evan, G. I., et al. (1992) *Cell* 69:119–128; Fanidi, A., Harrington, E. A., and Evan, G. I. (1992) *Nature* 359:554–556). The growth rate is simply greater than the apoptotic rate so that the net result is tumor expansion. In addition, transformed cells frequently have selected mutations and growth factor autocrine loops to inhibit apoptosis. For example, Ras function has been shown to be involved in both transformation and protection against apoptosis in Bcr-Abl transformed cells (Cortey, D., Kadlec, L., and Pendergast, A. M. (1995) *Mol. Cell. Biol.* 15:5531–5541; Goga, A., et al. (1995) *Cell* 82:981–988).

Cumulatively, the results in different cell types indicate that it is the integration of multiple signals from cytokines and growth factors that determines the commitment to apoptosis. Similarly, integration of multiple signals and not a single dominant signaling pathway is likely involved in the commitment to growth or differentiation. The requirement for signal integration may allow for specific checkpoints so that cells do not die or grow inappropriately. In this regard, cell systems where specific cytokines or growth factors are added or removed are most relevant in defining the integration of signals controlling growth versus death.

The implication of our findings is that it should be possible to define signal pathways and their integration that controls apoptosis in specific cell types. As these findings are further defined it will be possible to develop strategies to selectively induce a cell type-specific apoptotic response. Development of gene therapy, cytokine and drug treatments may be possible to selectively promote the death of undesirable cell populations in animals.

Example 31

This Example Illustrated the Translocation of MEKK 1 and MEKK2 in Response to EGF and TNFα

Swiss 3T3 cells were serum starved overnight and then treated for 10 minutes with either EGF or TNFα. Cells were fixed and stained with an antibody specifically recognizing either MEKK1 or MEKK2. Secondary FITC-conjugated anti-rabbit IgG antibody was used for staining.

The results indicated that MEKK1 was localized primarily in the cytoplasm. A weak plasma membrane staining was also evident. MEKK2 was primarily cytoplasmic with little or no plasma membrane staining.

Stimulation with EGF induced a dramatic translocation of MEKK1 to the plasma membrane. treatment of the cells with EGF did not effect the cellular localization of MEKK2. Stimulation of the cells with TNFα induced a translocatin of MEKK2 to the plasma membrane. TNFα had no effect on the cellular localization of MEKK1. Both EGF and TNFα stimulate the Jun kinase (JNK) pathway but regulate different MEKKS. EGF selectively regulates MEKK1 and TNFα selectively regulates MEKK2. The significance of this finding is the demonstration that growth factor receptor tyrosine kinases and cytokine receptors of the TNF family selectively and differentially regulate specific MEKK enzymes.

The foregoing description of the invention has been presented for purposes of illustration and description. Further, the description is not intended to limit the invention to the form disclosed herein. Consequently, variations and modifications commensurate with the above teachings, and the skill or knowledge in the relevant art are within the scope of the present invention. The preferred embodiment described herein above is further intended to explain the best mode known of practicing the invention and to enable others skilled in the art to utilize the invention in various embodiments and with various modifications required by their particular applications or uses of the invention. It is intended that the appended claims be construed to include alternate embodiments to the extent permitted by the prior art.

What is claimed is:

1. An isolated nucleic acid molecule comprising the nucleotide sequence of SEQ ID NO: 1.

2. An isolated nucleic acid molecule comprising the nucleotide sequence of SEQ ID NO:3.

3. An isolated nucleic acid molecule which encodes a mitogen ERK kinase kinase (MEKK) protein comprising the amino acid sequence of SEQ ID NO:2.

4. An isolated nucleic acid molecule which encodes a mitogen ERK kinase kinase (MEKK) protein comprising the amino acid sequence of SEQ ID NO:4.

5. An isolated nucleic acid molecule comprising the nucleotide sequence of SEQ ID NO:5.

6. An isolated nucleic acid molecule comprising the nucleotide sequence of SEQ ID NO:7.

7. An isolated nucleic acid molecule which encodes a mitogen ERK kinase kinase (MEKK) protein comprising the amino acid sequence of SEQ ID NO:6.

8. An isolated nucleic acid molecule which encodes a mitogen ERK kinase kinase (MEKK) protein comprising the amino acid sequence of SEQ ID NO:8.

9. An isolated nucleic acid molecule comprising the nucleotide sequence of SEQ ID NO:9.

10. An isolated nucleic acid molecule which encodes a mitogen ERK kinase kinase (MEKK) protein comprising the amino acid sequence of SEQ ID NO: 10.

11. An isolated nucleic acid molecule comprising the nucleotide sequence of SEQ ID NO: 11.

12. An isolated nucleic acid molecule comprising the nucleotide sequence of SEQ ID NO: 13.

13. An isolated nucleic acid molecule which encodes a mitogen ERK kinase kinase (MEKK) protein comprising the amino acid sequence of SEQ ID NO:12.

14. An isolated nucleic acid molecule which encodes a mitogen ERK kinase kinase (MEKK) protein comprising the amino acid sequence of SEQ ID NO: 14.

15. An isolated nucleic acid molecule comprising a nucleotide sequence encoding a mitogen ERK kinase kinase (MEKK) catalytic domain selected from the group consisting of amino acids 409–672 of SEQ ID NO:2, 1329–1593 of SEQ ID NO: 4, 361–619 of SEQ ID NO:6, 361–619 of SEQ ID NO:8, 366–626 of SEQ ID NO:10, 631–890 of SEQ ID NO:12 and 1338–1597 of SEQ ID NO:14.

16. An isolated nucleic acid molecule comprising a nucleotide sequence encoding a mitogen ERK kinase kinase (MEKK) NH$_2$-terminal regulatory domain selected from the group consisting of amino acids 1–408 of SEQ ID NO:2, 1–1328 of SEQ ID NO:4, 1–360 of SEQ ID NO:6, 1–360 of SEQ ID NO:8, 1–365 of SEQ ID NO: 10, 1–630 of SEQ ID NO:12 and 1–1337 of SEQ ID NO:14.

* * * * *

SEQUENCE LISTING

<160> NUMBER OF SEQ ID NOS: 25

<210> SEQ ID NO 1
<211> LENGTH: 3260
<212> TYPE: DNA
<213> ORGANISM: Mus musculus
<220> FEATURE:
<221> NAME/KEY: CDS
<222> LOCATION: (486)..(2501)

<400> SEQUENCE: 1

```
tacactcctt gccacagtct ggcagaaaga atcaaacttc agagactcct ccggccagtt      60
gtagacacta tccttgtcaa gtgtgcagat ccaacagccg cacgagtcag ctgtccatat     120
ctacagtgct ggaactctgc aagggccaag caggagagct ggcggttggg agagaaatac     180
ttaaagctgg gtccatcggg gttggtggtg tcgattacgt cttaagttgt atccttggaa     240
accaagctga atcaaacaac tggcaagaac tgctgggtcg cctctgtctt atagacaggt     300
tgctgttgga atttcctgct gaattctatc ctcatattgt cagtactgat gtctcacaag     360
ctgagcctgt tgaaatcagg tacaagaagc tgctctccct cttaaccttt gccttgcaat     420
ccattgacaa ttcccactcg atggttggca agctctctcg gaggatatat ctgagctctg     480 ccagg atg gtg acc gca gtg ccc gct gtg ttt tcc aag ctg gta acc atg     530
      Met Val Thr Ala Val Pro Ala Val Phe Ser Lys Leu Val Thr Met
        1               5                  10                  15 ctt aat gct tct ggc tcc acc cac ttc acc agg atg cgc cgg cgt ctg     578
Leu Asn Ala Ser Gly Ser Thr His Phe Thr Arg Met Arg Arg Arg Leu
                20                  25                  30 atg gct atc gcg gat gag gta gaa att gcc gag gtc atc cag ctg ggt     626
Met Ala Ile Ala Asp Glu Val Glu Ile Ala Glu Val Ile Gln Leu Gly
            35                  40                  45 gtg gag gac act gtg gat ggg cat cag gac agc tta cag gcc gtg gcc     674
Val Glu Asp Thr Val Asp Gly His Gln Asp Ser Leu Gln Ala Val Ala
        50                  55                  60
```

```
ccc acc agc tgt cta gaa aac agc tcc ctt gag cac aca gtc cat aga      722
Pro Thr Ser Cys Leu Glu Asn Ser Ser Leu Glu His Thr Val His Arg
    65                  70                  75 gag aaa act gga aaa gga cta agt gct acg aga ctg agt gcc agc tcg      770
Glu Lys Thr Gly Lys Gly Leu Ser Ala Thr Arg Leu Ser Ala Ser Ser
80                  85                  90                  95 gag gac att tct gac aga ctg gcc ggc gtc tct gta gga ctt ccc agc      818
Glu Asp Ile Ser Asp Arg Leu Ala Gly Val Ser Val Gly Leu Pro Ser
                100                 105                 110 tca aca aca aca gaa caa cca aag cca gcg gtt caa aca aaa ggc aga      866
Ser Thr Thr Thr Glu Gln Pro Lys Pro Ala Val Gln Thr Lys Gly Arg
            115                 120                 125 ccc cac agt cag tgt ttg aac tcc tcc cct ttg tct cat gct caa tta      914
Pro His Ser Gln Cys Leu Asn Ser Ser Pro Leu Ser His Ala Gln Leu
        130                 135                 140 atg ttc cca gca cca tca gcc cct tgt tcc tct gcc ccg tct gtc cca      962
Met Phe Pro Ala Pro Ser Ala Pro Cys Ser Ser Ala Pro Ser Val Pro
    145                 150                 155 gat att tct aag cac aga ccc cag gca ttt gtt ccc tgc aaa ata cct     1010
Asp Ile Ser Lys His Arg Pro Gln Ala Phe Val Pro Cys Lys Ile Pro
160                 165                 170                 175 tcc gca tct cct cag aca cag cgc aag ttc tct cta caa ttc cag agg     1058
Ser Ala Ser Pro Gln Thr Gln Arg Lys Phe Ser Leu Gln Phe Gln Arg
                180                 185                 190 aac tgc tct gaa cac cga gac tca gac cag ctc tcc cca gtc ttc act     1106
Asn Cys Ser Glu His Arg Asp Ser Asp Gln Leu Ser Pro Val Phe Thr
            195                 200                 205 cag tca aga ccc cca ccc tcc agt aac ata cac agg cca aag cca tcc     1154
Gln Ser Arg Pro Pro Pro Ser Ser Asn Ile His Arg Pro Lys Pro Ser
        210                 215                 220 cga ccc gtt ccg ggc agt aca agc aaa cta ggg gac gcc aca aaa agt     1202
Arg Pro Val Pro Gly Ser Thr Ser Lys Leu Gly Asp Ala Thr Lys Ser
    225                 230                 235 agc atg aca ctt gat ctg ggc agt gct tcc agg tgt gac gac agc ttt     1250
Ser Met Thr Leu Asp Leu Gly Ser Ala Ser Arg Cys Asp Asp Ser Phe
240                 245                 250                 255 ggc ggc ggc ggc aac agt ggc aac gcc gtc ata ccc agc gac gag aca     1298
Gly Gly Gly Gly Asn Ser Gly Asn Ala Val Ile Pro Ser Asp Glu Thr
                260                 265                 270 gtg ttc acg ccg gtg gag gac aag tgc agg tta gat gtg aac acc gag     1346
Val Phe Thr Pro Val Glu Asp Lys Cys Arg Leu Asp Val Asn Thr Glu
            275                 280                 285 ctc aac tcc agc atc gag gac ctt ctt gaa gca tcc atg cct tca agt     1394
Leu Asn Ser Ser Ile Glu Asp Leu Leu Glu Ala Ser Met Pro Ser Ser
        290                 295                 300 gac acg aca gtc act ttc aag tcc gaa gtc gcc gtc ctc tct ccg gaa     1442
Asp Thr Thr Val Thr Phe Lys Ser Glu Val Ala Val Leu Ser Pro Glu
    305                 310                 315 aag gcc gaa aat gac gac acc tac aaa gac gac gtc aat cat aat caa     1490
Lys Ala Glu Asn Asp Asp Thr Tyr Lys Asp Asp Val Asn His Asn Gln
320                 325                 330                 335 aag tgc aaa gaa aag atg gaa gct gaa gag gag gct tta gcg atc         1538
Lys Cys Lys Glu Lys Met Glu Ala Glu Glu Glu Ala Leu Ala Ile
                340                 345                 350 gcc atg gcg atg tca gcg tct cag gat gcc ctc ccc atc gtc cct cag     1586
Ala Met Ala Met Ser Ala Ser Gln Asp Ala Leu Pro Ile Val Pro Gln
            355                 360                 365 ctg cag gtg gaa aat gga gaa gat att atc atc att cag cag gac aca     1634
Leu Gln Val Glu Asn Gly Glu Asp Ile Ile Ile Ile Gln Gln Asp Thr
```

-continued

|  | 370 |  |  |  | 375 |  |  |  | 380 |  |  |  |  |
|---|---|---|---|---|---|---|---|---|---|---|---|---|---|
| cca | gaa | act | ctt | cca | gga | cat | acc | aaa | gcg | aaa | cag | cct | tac aga gaa | 1682 |
| Pro | Glu | Thr | Leu | Pro | Gly | His | Thr | Lys | Ala | Lys | Gln | Pro | Tyr Arg Glu |
|  | 385 |  |  |  | 390 |  |  |  | 395 |  |  |  |  |

| gac | gct | gag | tgg | ctg | aaa | ggc | cag | cag | ata | ggc | ctc | gga | gca ttt tct | 1730 |
| Asp | Ala | Glu | Trp | Leu | Lys | Gly | Gln | Gln | Ile | Gly | Leu | Gly | Ala Phe Ser |
| 400 |  |  |  |  | 405 |  |  |  | 410 |  |  |  | 415 |

| tcc | tgt | tac | caa | gca | cag | gat | gtg | ggg | act | ggg | act | tta | atg gct gtg | 1778 |
| Ser | Cys | Tyr | Gln | Ala | Gln | Asp | Val | Gly | Thr | Gly | Thr | Leu | Met Ala Val |
|  |  |  |  | 420 |  |  |  |  | 425 |  |  |  | 430 |

| aaa | cag | gtg | acg | tac | gtc | aga | aac | aca | tcc | tcc | gag | cag | gag gag gtg | 1826 |
| Lys | Gln | Val | Thr | Tyr | Val | Arg | Asn | Thr | Ser | Ser | Glu | Gln | Glu Glu Val |
|  |  |  | 435 |  |  |  | 440 |  |  |  |  | 445 |  |

| gtg | gaa | gcg | ttg | agg | gaa | gag | atc | cgg | atg | atg | ggt | cac | ctc aac cat | 1874 |
| Val | Glu | Ala | Leu | Arg | Glu | Glu | Ile | Arg | Met | Met | Gly | His | Leu Asn His |
|  |  | 450 |  |  |  |  | 455 |  |  |  | 460 |  |  |

| cca | aac | atc | atc | cgg | atg | ctg | ggg | gcc | acg | tgc | gag | aag | agc aac tac | 1922 |
| Pro | Asn | Ile | Ile | Arg | Met | Leu | Gly | Ala | Thr | Cys | Glu | Lys | Ser Asn Tyr |
|  | 465 |  |  |  |  | 470 |  |  |  | 475 |  |  |  |

| aac | ctc | ttc | att | gag | tgg | atg | gcg | gga | gga | tct | gtg | gct | cac ctc ttg | 1970 |
| Asn | Leu | Phe | Ile | Glu | Trp | Met | Ala | Gly | Gly | Ser | Val | Ala | His Leu Leu |
| 480 |  |  |  |  | 485 |  |  |  | 490 |  |  |  | 495 |

| agt | aaa | tac | gga | gct | ttc | aag | gag | tca | gtc | gtc | att | aac | tac act gag | 2018 |
| Ser | Lys | Tyr | Gly | Ala | Phe | Lys | Glu | Ser | Val | Val | Ile | Asn | Tyr Thr Glu |
|  |  |  |  | 500 |  |  |  |  | 505 |  |  |  | 510 |

| cag | tta | ctg | cgt | ggc | ctt | tcc | tat | ctc | cac | gag | aac | cag | atc att cac | 2066 |
| Gln | Leu | Leu | Arg | Gly | Leu | Ser | Tyr | Leu | His | Glu | Asn | Gln | Ile Ile His |
|  |  |  | 515 |  |  |  | 520 |  |  |  |  | 525 |  |

| aga | gac | gtc | aaa | ggt | gcc | aac | ctg | ctc | att | gac | agc | acc | ggt cag agg | 2114 |
| Arg | Asp | Val | Lys | Gly | Ala | Asn | Leu | Leu | Ile | Asp | Ser | Thr | Gly Gln Arg |
|  | 530 |  |  |  |  | 535 |  |  |  |  | 540 |  |  |

| ctg | aga | att | gca | gac | ttt | gga | gct | gct | gcc | agg | ttg | gca | tca aaa gga | 2162 |
| Leu | Arg | Ile | Ala | Asp | Phe | Gly | Ala | Ala | Ala | Arg | Leu | Ala | Ser Lys Gly |
|  | 545 |  |  |  |  | 550 |  |  |  |  | 555 |  |  |

| acc | ggt | gca | gga | gag | ttc | cag | gga | cag | tta | ctg | ggg | aca | att gca ttc | 2210 |
| Thr | Gly | Ala | Gly | Glu | Phe | Gln | Gly | Gln | Leu | Leu | Gly | Thr | Ile Ala Phe |
| 560 |  |  |  |  | 565 |  |  |  | 570 |  |  |  | 575 |

| atg | gcg | cct | gag | gtc | cta | aga | ggt | cag | cag | tat | ggt | agg | agc tgt gat | 2258 |
| Met | Ala | Pro | Glu | Val | Leu | Arg | Gly | Gln | Gln | Tyr | Gly | Arg | Ser Cys Asp |
|  |  |  | 580 |  |  |  |  | 585 |  |  |  |  | 590 |

| gta | tgg | agt | gtt | ggc | tgc | gcc | att | ata | gaa | atg | gct | tgt | gca aaa cca | 2306 |
| Val | Trp | Ser | Val | Gly | Cys | Ala | Ile | Ile | Glu | Met | Ala | Cys | Ala Lys Pro |
|  |  | 595 |  |  |  |  | 600 |  |  |  | 605 |  |  |

| cct | tgg | aat | gca | gaa | aaa | cac | tcc | aat | cat | ctc | gcc | ttg | ata ttt aag | 2354 |
| Pro | Trp | Asn | Ala | Glu | Lys | His | Ser | Asn | His | Leu | Ala | Leu | Ile Phe Lys |
|  |  |  | 610 |  |  |  | 615 |  |  |  |  | 620 |  |

| att | gct | agc | gca | act | act | gca | ccg | tcc | atc | ccg | tca | cac | ctg tcc ccg | 2402 |
| Ile | Ala | Ser | Ala | Thr | Thr | Ala | Pro | Ser | Ile | Pro | Ser | His | Leu Ser Pro |
|  | 625 |  |  |  |  | 630 |  |  |  |  | 635 |  |  |

| ggt | ctg | cgc | gac | gtg | gcc | gtg | cgc | tgc | tta | gaa | ctt | cag | cct cag gac | 2450 |
| Gly | Leu | Arg | Asp | Val | Ala | Val | Arg | Cys | Leu | Glu | Leu | Gln | Pro Gln Asp |
| 640 |  |  |  |  | 645 |  |  |  | 650 |  |  |  | 655 |

| cgg | cct | ccg | tcc | aga | gag | ctg | ctg | aaa | cat | ccg | gtc | ttc | cgt acc acg | 2498 |
| Arg | Pro | Pro | Ser | Arg | Glu | Leu | Leu | Lys | His | Pro | Val | Phe | Arg Thr Thr |
|  |  |  |  | 660 |  |  |  |  | 665 |  |  |  | 670 |

| tgg tagttaattg ttcagatcag ctctaatgga gacaggatat cgaaccggga | 2551 |
| Trp |

| gagagaaaag agaacttgtg ggcgaccatg ccgctaaccg cagccctcac gccactgaac | 2611 |

-continued

```
agccagaaac ggggccagcg gggaaccgta cctaagcatg tgattgacaa atcatgacct    2671
gtacctaagc tcgatatgca gacatctaca gctcgtgcag gaactgcaca ccgtgccttt    2731
cacaggactg gctctggggg accaggaagg cgatggagtt tgcatgacta agaacagaa    2791 gcataaattt attttttgga cacttttttca gctaatcagt attaccatgt acatcaacat   2851
gcccgccaca tttcaaactc agactgtccc agatgtcaag atccactgtg tttgagtttg    2911
tttgcagttc cctcagcttg ctggtaattg tggtgttttg ttttcgatgc aaatgtgatg    2971
taatattctt attttctttg gatcaaagct ggactgaaaa ttgtactgtg taattatttt    3031
tgtgttttta atgttatttg gtactcgaat tgtaaataac gtctactgct gtttattcca    3091
gtttctacta cctcaggtgt cctatagatt tttcttctac caaagttcac tctcagaatg    3151
aaattctacg tgctgtgtga ctatgactcc taagacttcc agggcttaag ggctaactcc    3211
tattagcacc ttactatgta agcaaatgct acaaaaaaaa aaaaaaaa                 3260
```

<210> SEQ ID NO 2
<211> LENGTH: 672
<212> TYPE: PRT
<213> ORGANISM: Mus musculus

<400> SEQUENCE: 2

```
Met Val Thr Ala Val Pro Ala Val Phe Ser Lys Leu Val Thr Met Leu
  1               5                  10                  15

Asn Ala Ser Gly Ser Thr His Phe Thr Arg Met Arg Arg Arg Leu Met
             20                  25                  30

Ala Ile Ala Asp Glu Val Glu Ile Ala Glu Val Ile Gln Leu Gly Val
         35                  40                  45

Glu Asp Thr Val Asp Gly His Gln Asp Ser Leu Gln Ala Val Ala Pro
     50                  55                  60

Thr Ser Cys Leu Glu Asn Ser Ser Leu Glu His Thr Val His Arg Glu
 65                  70                  75                  80

Lys Thr Gly Lys Gly Leu Ser Ala Thr Arg Leu Ser Ala Ser Ser Glu
                 85                  90                  95

Asp Ile Ser Asp Arg Leu Ala Gly Val Ser Val Gly Leu Pro Ser Ser
            100                 105                 110

Thr Thr Thr Glu Gln Pro Lys Pro Ala Val Gln Thr Lys Gly Arg Pro
        115                 120                 125

His Ser Gln Cys Leu Asn Ser Ser Pro Leu Ser His Ala Gln Leu Met
    130                 135                 140

Phe Pro Ala Pro Ser Ala Pro Cys Ser Ser Ala Pro Ser Val Pro Asp
145                 150                 155                 160

Ile Ser Lys His Arg Pro Gln Ala Phe Val Pro Cys Lys Ile Pro Ser
                165                 170                 175

Ala Ser Pro Gln Thr Gln Arg Lys Phe Ser Leu Gln Phe Gln Arg Asn
            180                 185                 190

Cys Ser Glu His Arg Asp Ser Asp Gln Leu Ser Pro Val Phe Thr Gln
        195                 200                 205

Ser Arg Pro Pro Ser Ser Asn Ile His Arg Pro Lys Pro Ser Arg
    210                 215                 220

Pro Val Pro Gly Ser Thr Ser Lys Leu Gly Asp Ala Thr Lys Ser Ser
225                 230                 235                 240

Met Thr Leu Asp Leu Gly Ser Ala Ser Arg Cys Asp Asp Ser Phe Gly
                245                 250                 255

Gly Gly Gly Asn Ser Gly Asn Ala Val Ile Pro Ser Asp Glu Thr Val
```

```
                    260                 265                 270
Phe Thr Pro Val Glu Asp Lys Cys Arg Leu Asp Val Asn Thr Glu Leu
            275                 280                 285
Asn Ser Ser Ile Glu Asp Leu Leu Glu Ala Ser Met Pro Ser Ser Asp
        290                 295                 300
Thr Thr Val Thr Phe Lys Ser Glu Val Ala Val Leu Ser Pro Glu Lys
305                 310                 315                 320
Ala Glu Asn Asp Asp Thr Tyr Lys Asp Val Asn His Asn Gln Lys
                325                 330                 335
Cys Lys Glu Lys Met Glu Ala Glu Glu Ala Leu Ala Ile Ala
            340                 345                 350
Met Ala Met Ser Ala Ser Gln Asp Ala Leu Pro Ile Val Pro Gln Leu
            355                 360                 365
Gln Val Glu Asn Gly Glu Asp Ile Ile Ile Gln Gln Asp Thr Pro
        370                 375                 380
Glu Thr Leu Pro Gly His Thr Lys Ala Lys Gln Pro Tyr Arg Glu Asp
385                 390                 395                 400
Ala Glu Trp Leu Lys Gly Gln Gln Ile Gly Leu Gly Ala Phe Ser Ser
                405                 410                 415
Cys Tyr Gln Ala Gln Asp Val Gly Thr Gly Thr Leu Met Ala Val Lys
            420                 425                 430
Gln Val Thr Tyr Val Arg Asn Thr Ser Ser Glu Gln Glu Glu Val Val
            435                 440                 445
Glu Ala Leu Arg Glu Glu Ile Arg Met Met Gly His Leu Asn His Pro
        450                 455                 460
Asn Ile Ile Arg Met Leu Gly Ala Thr Cys Glu Lys Ser Asn Tyr Asn
465                 470                 475                 480
Leu Phe Ile Glu Trp Met Ala Gly Gly Ser Val Ala His Leu Leu Ser
                485                 490                 495
Lys Tyr Gly Ala Phe Lys Glu Ser Val Val Ile Asn Tyr Thr Glu Gln
            500                 505                 510
Leu Leu Arg Gly Leu Ser Tyr Leu His Glu Asn Gln Ile Ile His Arg
            515                 520                 525
Asp Val Lys Gly Ala Asn Leu Leu Ile Asp Ser Thr Gly Gln Arg Leu
            530                 535                 540
Arg Ile Ala Asp Phe Gly Ala Ala Ala Arg Leu Ala Ser Lys Gly Thr
545                 550                 555                 560
Gly Ala Gly Glu Phe Gln Gly Gln Leu Leu Gly Thr Ile Ala Phe Met
                565                 570                 575
Ala Pro Glu Val Leu Arg Gly Gln Gln Tyr Gly Arg Ser Cys Asp Val
            580                 585                 590
Trp Ser Val Gly Cys Ala Ile Ile Glu Met Ala Cys Ala Lys Pro Pro
            595                 600                 605
Trp Asn Ala Glu Lys His Ser Asn His Leu Ala Leu Ile Phe Lys Ile
            610                 615                 620
Ala Ser Ala Thr Thr Ala Pro Ser Ile Pro His Leu Ser Pro Gly
625                 630                 635                 640
Leu Arg Asp Val Ala Val Arg Cys Leu Glu Leu Gln Pro Gln Asp Arg
                645                 650                 655
Pro Pro Ser Arg Glu Leu Leu Lys His Pro Val Phe Arg Thr Thr Trp
            660                 665                 670

<210> SEQ ID NO 3
```

-continued

```
<211> LENGTH: 5539
<212> TYPE: DNA
<213> ORGANISM: Mus musculus
<220> FEATURE:
<221> NAME/KEY: CDS
<222> LOCATION: (1)..(4779)

<400> SEQUENCE: 3
```

| gag ctc ccg ccg agc cgc tgc ccc gcc cgg tct cgc act acc tgg cgg | 48 |
|---|---|
| Glu Leu Pro Pro Ser Arg Cys Pro Ala Arg Ser Arg Thr Thr Trp Arg | |
| 1               5                   10                  15 | |

| cgg cct ggt tgc agc gca caa cgc ccg gcg ccc ggt tcc ccg cat tgc | 96 |
|---|---|
| Arg Pro Gly Cys Ser Ala Gln Arg Pro Ala Pro Gly Ser Pro His Cys | |
|         20                  25                  30 | |

| ccc tgc cct ccc acc tgc gcc gcg cgc ccg ccc gct ccg cgc tcc | 144 |
|---|---|
| Pro Cys Pro Pro Thr Cys Ala Ala Arg Pro Pro Ala Ala Pro Arg Ser | |
|     35                  40                  45 | |

| cgg gcc ccg gcc ggg agg cgc ggc ccc gct cgc gcc cgc gcc cgc gcc | 192 |
|---|---|
| Arg Ala Pro Ala Gly Arg Arg Gly Pro Ala Arg Ala Arg Ala Arg Ala | |
| 50                  55                  60 | |

| ctc ggc agc agc gcg cgc ccg ccc acc cgc cca ccg ctc cgc ccg ccc | 240 |
|---|---|
| Leu Gly Ser Ser Ala Arg Pro Pro Thr Arg Pro Pro Leu Arg Pro Pro | |
| 65                  70                  75                  80 | |

| ccc gcg ctc tcc ccg ccc cct ccc tcc cca gca ggc acg agc gaa tgt | 288 |
|---|---|
| Pro Ala Leu Ser Pro Pro Pro Ser Pro Ala Gly Thr Ser Glu Cys | |
|             85                  90                  95 | |

| agc ccg cga gag aaa atg gcg gcg gcg gcg ggc gat cgc gcc tcg tcg | 336 |
|---|---|
| Ser Pro Arg Glu Lys Met Ala Ala Ala Ala Gly Asp Arg Ala Ser Ser | |
|         100                 105                 110 | |

| tcg gga ttc ccg ggc gcc gcg gcg gcg agt ccc gag gcg ggc ggc ggc | 384 |
|---|---|
| Ser Gly Phe Pro Gly Ala Ala Ala Ala Ser Pro Glu Ala Gly Gly Gly | |
|     115                 120                 125 | |

| ggc gga gga gga gga gct ctc cag gga agc ggc gcg ccc gca gcg ggc | 432 |
|---|---|
| Gly Gly Gly Gly Gly Ala Leu Gln Gly Ser Gly Ala Pro Ala Ala Gly | |
| 130                 135                 140 | |

| gcg gcg ggg ctg ctg cgg gag cct ggc agc gcg ggg ccg agc gcg cgg | 480 |
|---|---|
| Ala Ala Gly Leu Leu Arg Glu Pro Gly Ser Ala Gly Pro Ser Ala Arg | |
| 145                 150                 155                 160 | |

| act ggc ggc ggc ggc acg tgc gca aag tgc gga gtg tgg agc tgg acc | 528 |
|---|---|
| Thr Gly Gly Gly Gly Thr Cys Ala Lys Cys Gly Val Trp Ser Trp Thr | |
|             165                 170                 175 | |

| agc tgc cgg agc agc cgc tct tcc tcg ccg ccg cct cgc cgc cct gcc | 576 |
|---|---|
| Ser Cys Arg Ser Ser Arg Ser Ser Pro Pro Pro Arg Arg Pro Ala | |
|         180                 185                 190 | |

| cat cta ctt ccc gtc gcc gga gcc cgc gga cgc ggc tgc agg agc gag | 624 |
|---|---|
| His Leu Leu Pro Val Ala Gly Ala Arg Gly Arg Gly Cys Arg Ser Glu | |
|     195                 200                 205 | |

| tcg ctt cca gcc cgc gcg gga ccg cca ccc ccg gga gcg gcg agt cgc | 672 |
|---|---|
| Ser Leu Pro Ala Arg Ala Gly Pro Pro Pro Gly Ala Ala Ser Arg | |
| 210                 215                 220 | |

| tgc ggc tcc cac tct gcc gag ctg gcg gcc gcg cgg gac agc ggc gcc | 720 |
|---|---|
| Cys Gly Ser His Ser Ala Glu Leu Ala Ala Ala Arg Asp Ser Gly Ala | |
| 225                 230                 235                 240 | |

| cgg agc ccc gcg ggg gcg gag ccg ccc tct gca gcg gcc ccc tcc ggt | 768 |
|---|---|
| Arg Ser Pro Ala Gly Ala Glu Pro Pro Ser Ala Ala Ala Pro Ser Gly | |
|             245                 250                 255 | |

| cga gag atg gag aat aaa gaa acc ctc aaa gga ctg cac aag atg gag | 816 |
|---|---|
| Arg Glu Met Glu Asn Lys Glu Thr Leu Lys Gly Leu His Lys Met Glu | |
|         260                 265                 270 | |

| gat cgc ccg gag gag aga atg atc cgg gag aag ctc aag gcg acc tgt | 864 |
|---|---|
| Asp Arg Pro Glu Glu Arg Met Ile Arg Glu Lys Leu Lys Ala Thr Cys | |

```
                275                 280                 285
atg ccg gcc tgg aag cac gag tgg ttg gag agg agg aac agg aga ggc      912
Met Pro Ala Trp Lys His Glu Trp Leu Glu Arg Arg Asn Arg Arg Gly
    290                 295                 300 cct gtg gtg gtg aag cca atc cct att aaa gga gat gga tct gaa gtg      960
Pro Val Val Val Lys Pro Ile Pro Ile Lys Gly Asp Gly Ser Glu Val
305                 310                 315                 320 aat aac ttg gca gct gag ccc cag gga gag ggc cag gca ggt tcc gct     1008
Asn Asn Leu Ala Ala Glu Pro Gln Gly Glu Gly Gln Ala Gly Ser Ala
                325                 330                 335 gca cca gcc ccc aag ggc cga cga agc cca tct cct ggc agc tct ccg     1056
Ala Pro Ala Pro Lys Gly Arg Arg Ser Pro Ser Pro Gly Ser Ser Pro
                340                 345                 350 tca ggg cgc tcg gtg aag ccg gaa tcc cca gga gta aga cgg aaa cga     1104
Ser Gly Arg Ser Val Lys Pro Glu Ser Pro Gly Val Arg Arg Lys Arg
            355                 360                 365 gtg tcc ccg gtg cct ttc cag agt ggc aga atc aca cca ccc cga aga     1152
Val Ser Pro Val Pro Phe Gln Ser Gly Arg Ile Thr Pro Pro Arg Arg
370                 375                 380 gcc cca tca ccg gat ggc ttc tcc ccg tac agc cca gag gag acg agc     1200
Ala Pro Ser Pro Asp Gly Phe Ser Pro Tyr Ser Pro Glu Glu Thr Ser
385                 390                 395                 400 cgc cgc gtg aac aaa gtg atg aga gcc agg ctg tac ctg ctg cag cag     1248
Arg Arg Val Asn Lys Val Met Arg Ala Arg Leu Tyr Leu Leu Gln Gln
                405                 410                 415 ata gga ccc aac tct ttc ctg att gga gga gac agt cca gac aat aaa     1296
Ile Gly Pro Asn Ser Phe Leu Ile Gly Gly Asp Ser Pro Asp Asn Lys
                420                 425                 430 tac cgg gtg ttt att ggg cca cag aac tgc agc tgt ggg cgt gga gca     1344
Tyr Arg Val Phe Ile Gly Pro Gln Asn Cys Ser Cys Gly Arg Gly Ala
                435                 440                 445 ttc tgt att cac ctc ttg ttt gtc atg ctc cgg gtg ttt cag cta gaa     1392
Phe Cys Ile His Leu Leu Phe Val Met Leu Arg Val Phe Gln Leu Glu
            450                 455                 460 ccc tct gac ccc atg tta tgg aga aaa act tta aaa aat ttc gag gtt     1440
Pro Ser Asp Pro Met Leu Trp Arg Lys Thr Leu Lys Asn Phe Glu Val
465                 470                 475                 480 gag agt ttg ttc cag aaa tac cac agt agg cgt agc tcg aga atc aaa     1488
Glu Ser Leu Phe Gln Lys Tyr His Ser Arg Arg Ser Ser Arg Ile Lys
                485                 490                 495 gct cca tcc cgg aac acc atc cag aag ttt gtg tca cgc atg tca aat     1536
Ala Pro Ser Arg Asn Thr Ile Gln Lys Phe Val Ser Arg Met Ser Asn
                500                 505                 510 tct cac aca ctg tca tcg tct agc aca tcc aca tct agt tca gaa aac     1584
Ser His Thr Leu Ser Ser Ser Ser Thr Ser Thr Ser Ser Ser Glu Asn
            515                 520                 525 agc atc aag gat gaa gag gag cag atg tgt ccc atc tgc ttg ctg ggc     1632
Ser Ile Lys Asp Glu Glu Glu Gln Met Cys Pro Ile Cys Leu Leu Gly
        530                 535                 540 atg ctg gat gag gag agc ctg act gtg tgt gaa gat ggc tgc agg aac     1680
Met Leu Asp Glu Glu Ser Leu Thr Val Cys Glu Asp Gly Cys Arg Asn
545                 550                 555                 560 aag ctg cac cac cat tgc atg tcc atc tgg gcg gaa gag tgt aga aga     1728
Lys Leu His His His Cys Met Ser Ile Trp Ala Glu Glu Cys Arg Arg
                565                 570                 575 aat aga gag cct tta ata tgt ccc ctt tgt aga tct aag tgg aga tcc     1776
Asn Arg Glu Pro Leu Ile Cys Pro Leu Cys Arg Ser Lys Trp Arg Ser
            580                 585                 590 cat gac ttc tac agc cat gag tta tca agc ccc gtg gag tcc ccc gcc    1824
```

```
                His Asp Phe Tyr Ser His Glu Leu Ser Ser Pro Val Glu Ser Pro Ala
                                595                 600                 605 tcc ctg cga gct gtc cag cag cca tcc tcc ccg cag cag ccc gtg gcc         1872
Ser Leu Arg Ala Val Gln Gln Pro Ser Ser Pro Gln Gln Pro Val Ala
610                 615                 620 gga tca cag cgg agg aat cag gag agc agt ttt aac ctt act cat ttt         1920
Gly Ser Gln Arg Arg Asn Gln Glu Ser Ser Phe Asn Leu Thr His Phe
625                 630                 635                 640 gga acc cag cag att cct tcc gct tac aaa gat ttg gcc gag cca tgg         1968
Gly Thr Gln Gln Ile Pro Ser Ala Tyr Lys Asp Leu Ala Glu Pro Trp
                645                 650                 655 att cag gtg ttt gga atg gaa ctc gtt ggc tgc tta ttc tct aga aac         2016
Ile Gln Val Phe Gly Met Glu Leu Val Gly Cys Leu Phe Ser Arg Asn
                660                 665                 670 tgg aac gta agg gaa atg gcc ctt agg cgt ctt tcc cac gac gtt agt         2064
Trp Asn Val Arg Glu Met Ala Leu Arg Arg Leu Ser His Asp Val Ser
                675                 680                 685 ggg gcc ctg ttg ttg gca aac ggg gag agc act gga aac tct gga ggc         2112
Gly Ala Leu Leu Leu Ala Asn Gly Glu Ser Thr Gly Asn Ser Gly Gly
690                 695                 700 ggc agt ggg ggc agc tta agc gcg gga gcg gcc agc ggg tcc tcc cag         2160
Gly Ser Gly Gly Ser Leu Ser Ala Gly Ala Ala Ser Gly Ser Ser Gln
705                 710                 715                 720 ccc agc atc tca ggg gat gtg gtg gag gcg tgc tgc agt gtc ctg tct         2208
Pro Ser Ile Ser Gly Asp Val Val Glu Ala Cys Cys Ser Val Leu Ser
                725                 730                 735 ata gtc tgc gct gac cct gtc tac aaa gtg tac gtt gct gct tta aaa         2256
Ile Val Cys Ala Asp Pro Val Tyr Lys Val Tyr Val Ala Ala Leu Lys
                740                 745                 750 aca ttg aga gcc atg ctg gta tac act cct tgc cac agt ctg gca gaa         2304
Thr Leu Arg Ala Met Leu Val Tyr Thr Pro Cys His Ser Leu Ala Glu
                755                 760                 765 aga atc aaa ctt cag aga ctc ctc cgg cca gtt gta gac act atc ctt         2352
Arg Ile Lys Leu Gln Arg Leu Leu Arg Pro Val Val Asp Thr Ile Leu
770                 775                 780 gtc aag tgt gca gat gcc aac agc cgc acg agt cag ctg tcc ata tct         2400
Val Lys Cys Ala Asp Ala Asn Ser Arg Thr Ser Gln Leu Ser Ile Ser
785                 790                 795                 800 aca gtg ctg gaa ctc tgc aag ggc caa gca gga gag ctg gcg gtt ggg         2448
Thr Val Leu Glu Leu Cys Lys Gly Gln Ala Gly Glu Leu Ala Val Gly
                805                 810                 815 aga gaa ata ctt aaa gct ggg tcc atc ggg gtt ggt ggt gtc gat tac         2496
Arg Glu Ile Leu Lys Ala Gly Ser Ile Gly Val Gly Gly Val Asp Tyr
                820                 825                 830 gtc tta agt tgt atc ctt gga aac caa gct gaa tca aac aac tgg caa         2544
Val Leu Ser Cys Ile Leu Gly Asn Gln Ala Glu Ser Asn Asn Trp Gln
                835                 840                 845 gaa ctg ctg ggt cgc ctc tgt ctt ata gac agg ttg ctg ttg gaa ttt         2592
Glu Leu Leu Gly Arg Leu Cys Leu Ile Asp Arg Leu Leu Leu Glu Phe
850                 855                 860 cct gct gaa ttc tat cct cat att gtc agt act gat gtc tca caa gct         2640
Pro Ala Glu Phe Tyr Pro His Ile Val Ser Thr Asp Val Ser Gln Ala
865                 870                 875                 880 gag cct gtt gaa atc agg tac aag aag ctg ctc tcc ctc tta acc ttt         2688
Glu Pro Val Glu Ile Arg Tyr Lys Lys Leu Leu Ser Leu Leu Thr Phe
                885                 890                 895 gcc ttg caa tcc att gac aat tcc cac tcg atg gtt ggc aag ctc tct         2736
Ala Leu Gln Ser Ile Asp Asn Ser His Ser Met Val Gly Lys Leu Ser
                900                 905                 910
```

-continued

```
cgg agg ata tat ctg agc tct gcc agg atg gtg acc gca gtg ccc gct    2784
Arg Arg Ile Tyr Leu Ser Ser Ala Arg Met Val Thr Ala Val Pro Ala
        915                 920                 925 gtg ttt tcc aag ctg gta acc atg ctt aat gct tct ggc tcc acc cac    2832
Val Phe Ser Lys Leu Val Thr Met Leu Asn Ala Ser Gly Ser Thr His
    930                 935                 940 ttc acc agg atg cgc cgg cgt ctg atg gct atc gcg gat gag gta gaa    2880
Phe Thr Arg Met Arg Arg Arg Leu Met Ala Ile Ala Asp Glu Val Glu
945                 950                 955                 960 att gcc gag gtc atc cag ctg ggt gtg gag gac act gtg gat ggg cat    2928
Ile Ala Glu Val Ile Gln Leu Gly Val Glu Asp Thr Val Asp Gly His
                965                 970                 975 cag gac agc tta cag gcc gtg gcc ccc acc agc tgt cta gaa aac agc    2976
Gln Asp Ser Leu Gln Ala Val Ala Pro Thr Ser Cys Leu Glu Asn Ser
            980                 985                 990 tcc ctt gag cac aca gtc cat aga gag aaa act gga aaa gga cta agt    3024
Ser Leu Glu His Thr Val His Arg Glu Lys Thr Gly Lys Gly Leu Ser
        995                 1000                1005 gct acg aga ctg agt gcc agc tcg gag gac att tct gac aga ctg gcc    3072
Ala Thr Arg Leu Ser Ala Ser Ser Glu Asp Ile Ser Asp Arg Leu Ala
    1010                1015                1020 ggc gtc tct gta gga ctt ccc agc tca aca aca aca gaa caa cca aag    3120
Gly Val Ser Val Gly Leu Pro Ser Ser Thr Thr Thr Glu Gln Pro Lys
1025                1030                1035                1040 cca gcg gtt caa aca aaa ggc aga ccc cac agt cag tgt ttg aac tcc    3168
Pro Ala Val Gln Thr Lys Gly Arg Pro His Ser Gln Cys Leu Asn Ser
                1045                1050                1055 tcc cct ttg tct cat gct caa tta atg ttc cca gca cca tca gcc cct    3216
Ser Pro Leu Ser His Ala Gln Leu Met Phe Pro Ala Pro Ser Ala Pro
            1060                1065                1070 tgt tcc tct gcc ccg tct gtc cca gat att tct aag cac aga ccc cag    3264
Cys Ser Ser Ala Pro Ser Val Pro Asp Ile Ser Lys His Arg Pro Gln
        1075                1080                1085 gca ttt gtt ccc tgc aaa ata cct tcc gca tct cct cag aca cag cgc    3312
Ala Phe Val Pro Cys Lys Ile Pro Ser Ala Ser Pro Gln Thr Gln Arg
    1090                1095                1100 aag ttc tct cta caa ttc cag agg aac tgc tct gaa cac cga gac tca    3360
Lys Phe Ser Leu Gln Phe Gln Arg Asn Cys Ser Glu His Arg Asp Ser
1105                1110                1115                1120 gac cag ctc tcc cca gtc ttc act cag tca aga ccc cca ccc tcc agt    3408
Asp Gln Leu Ser Pro Val Phe Thr Gln Ser Arg Pro Pro Pro Ser Ser
                1125                1130                1135 aac ata cac agg cca aag cca tcc cga ccc gtt ccg ggc agt aca agc    3456
Asn Ile His Arg Pro Lys Pro Ser Arg Pro Val Pro Gly Ser Thr Ser
            1140                1145                1150 aaa cta ggg gac gcc aca aaa agt agc atg aca ctt gat ctg ggc agt    3504
Lys Leu Gly Asp Ala Thr Lys Ser Ser Met Thr Leu Asp Leu Gly Ser
        1155                1160                1165 gct tcc agg tgt gac gac agc ttt ggc ggc ggc ggc aac agt ggc aac    3552
Ala Ser Arg Cys Asp Asp Ser Phe Gly Gly Gly Gly Asn Ser Gly Asn
    1170                1175                1180 gcc gtc ata ccc agc gac gag aca gtg ttc acg ccg gtg gag gac aag    3600
Ala Val Ile Pro Ser Asp Glu Thr Val Phe Thr Pro Val Glu Asp Lys
1185                1190                1195                1200 tgc agg tta gat gtg aac acc gag ctc aac tcc agc atc gag gac ctt    3648
Cys Arg Leu Asp Val Asn Thr Glu Leu Asn Ser Ser Ile Glu Asp Leu
                1205                1210                1215 ctt gaa gca tcc atg cct tca agt gac acg aca gtc act ttc aag tcc    3696
Leu Glu Ala Ser Met Pro Ser Ser Asp Thr Thr Val Thr Phe Lys Ser
            1220                1225                1230
```

-continued

```
gaa gtc gcc gtc ctc tct ccg gaa aag gcc gaa aat gac gac acc tac    3744
Glu Val Ala Val Leu Ser Pro Glu Lys Ala Glu Asn Asp Asp Thr Tyr
        1235                1240                1245 aaa gac gac gtc aat cat aat caa aag tgc aaa gaa aag atg gaa gct    3792
Lys Asp Asp Val Asn His Asn Gln Lys Cys Lys Glu Lys Met Glu Ala
1250                1255                1260 gaa gag gag gag gct tta gcg atc gcc atg gcg atg tca gcg tct cag    3840
Glu Glu Glu Glu Ala Leu Ala Ile Ala Met Ala Met Ser Ala Ser Gln
1265                1270                1275                1280 gat gcc ctc ccc atc gtc cct cag ctg cag gtg gaa aat gga gaa gat    3888
Asp Ala Leu Pro Ile Val Pro Gln Leu Gln Val Glu Asn Gly Glu Asp
            1285                1290                1295 att atc atc att cag cag gac aca cca gaa act ctt cca gga cat acc    3936
Ile Ile Ile Ile Gln Gln Asp Thr Pro Glu Thr Leu Pro Gly His Thr
        1300                1305                1310 aaa gcg aaa cag cct tac aga gaa gac gct gag tgg ctg aaa ggc cag    3984
Lys Ala Lys Gln Pro Tyr Arg Glu Asp Ala Glu Trp Leu Lys Gly Gln
        1315                1320                1325 cag ata ggc ctc gga gca ttt tct tcc tgt tac caa gca cag gat gtg    4032
Gln Ile Gly Leu Gly Ala Phe Ser Ser Cys Tyr Gln Ala Gln Asp Val
    1330                1335                1340 ggg act ggg act tta atg gct gtg aaa cag gtg acg tac gtc aga aac    4080
Gly Thr Gly Thr Leu Met Ala Val Lys Gln Val Thr Tyr Val Arg Asn
1345                1350                1355                1360 aca tcc tcc gag cag gag gag gtg gtg gaa gcg ttg agg gaa gag atc    4128
Thr Ser Ser Glu Gln Glu Glu Val Val Glu Ala Leu Arg Glu Glu Ile
            1365                1370                1375 cgg atg atg ggt cac ctc aac cat cca aac atc atc cgg atg ctg ggg    4176
Arg Met Met Gly His Leu Asn His Pro Asn Ile Ile Arg Met Leu Gly
        1380                1385                1390 gcc acg tgc gag aag agc aac tac aac ctc ttc att gag tgg atg gcg    4224
Ala Thr Cys Glu Lys Ser Asn Tyr Asn Leu Phe Ile Glu Trp Met Ala
        1395                1400                1405 gga gga tct gtg gct cac ctc ttg agt aaa tac gga gct ttc aag gag    4272
Gly Gly Ser Val Ala His Leu Leu Ser Lys Tyr Gly Ala Phe Lys Glu
    1410                1415                1420 tca gtc gtc att aac tac act gag cag tta ctg cgt ggc ctt tcc tat    4320
Ser Val Val Ile Asn Tyr Thr Glu Gln Leu Leu Arg Gly Leu Ser Tyr
1425                1430                1435                1440 ctc cac gag aac cag atc att cac aga gac gtc aaa ggt gcc aac ctg    4368
Leu His Glu Asn Gln Ile Ile His Arg Asp Val Lys Gly Ala Asn Leu
            1445                1450                1455 ctc att gac agc acc ggt cag agg ctg aga att gca gac ttt gga gct    4416
Leu Ile Asp Ser Thr Gly Gln Arg Leu Arg Ile Ala Asp Phe Gly Ala
        1460                1465                1470 gct gcc agg ttg gca tca aaa gga acc ggt gca gga gag ttc cag gga    4464
Ala Ala Arg Leu Ala Ser Lys Gly Thr Gly Ala Gly Glu Phe Gln Gly
        1475                1480                1485 cag tta ctg ggg aca att gca ttc atg gcg cct gag gtc cta aga ggt    4512
Gln Leu Leu Gly Thr Ile Ala Phe Met Ala Pro Glu Val Leu Arg Gly
    1490                1495                1500 cag cag tat ggt agg agc tgt gat gta tgg agt gtt ggc tgc gcc att    4560
Gln Gln Tyr Gly Arg Ser Cys Asp Val Trp Ser Val Gly Cys Ala Ile
1505                1510                1515                1520 ata gaa atg gct tgt gca aaa cca cct tgg aat gca gaa aaa cac tcc    4608
Ile Glu Met Ala Cys Ala Lys Pro Pro Trp Asn Ala Glu Lys His Ser
            1525                1530                1535 aat cat ctc gcc ttg ata ttt aag att gct agc gca act act gca ccg    4656
Asn His Leu Ala Leu Ile Phe Lys Ile Ala Ser Ala Thr Thr Ala Pro
```

-continued

```
                 1540                1545                1550
tcc atc ccg tca cac ctg tcc ccg ggt ctg cgc gac gtg gcc gtg cgc      4704
Ser Ile Pro Ser His Leu Ser Pro Gly Leu Arg Asp Val Ala Val Arg
         1555                1560                1565 tgc tta gaa ctt cag cct cag gac cgg cct ccg tcc aga gag ctg ctg      4752
Cys Leu Glu Leu Gln Pro Gln Asp Arg Pro Pro Ser Arg Glu Leu Leu
    1570                1575                1580 aaa cat ccg gtc ttc cgt acc acg tgg tagttaattg ttcagatcag            4799
Lys His Pro Val Phe Arg Thr Thr Trp
1585            1590 ctctaatgga gacaggatat gcaaccggga gagagaaaag agaacttgtg ggcgaccatg    4859
ccgctaaccg cagccctcac gccactgaac agccagaaac ggggccagcg gggaaccgta    4919
cctaagcatg tgattgacaa atcatgacct gtacctaagc tcgatatgca gacatctaca    4979
gctcgtgcag gaactgcaca ccgtgccttt cacaggactg gctctggggg accaggaagg    5039
cgatggagtt tgcatgacta agaacagaa gcataaattt attttttggag cacttttttca   5099 gctaatcagt attaccatgt acatcaacat gcccgccaca tttcaaactc agactgtccc    5159
agatgtcaag atccactgtg tttgagtttg tttgcagttc cctcagcttg ctggtaattg    5219
tggtgttttg ttttcgatgc aaatgtgatg taatattctt attttctttg gatcaaagct    5279
ggactgaaaa ttgtactgtg taattatttt tgtgttttta atgttatttg gtactcgaat    5339
tgtaaataac gtctactgct gtttattcca gtttctacta cctcaggtgt cctatagatt    5399
tttcttctac caaagttcac tctcagaatg aaattctacg tgctgtgtga ctatgactcc    5459
taagacttcc agggcttaag ggctaactcc tattagcacc ttactatgta agcaaatgct    5519
acaaaaaaaa aaaaaaaaa                                                 5539
```

<210> SEQ ID NO 4
<211> LENGTH: 1593
<212> TYPE: PRT
<213> ORGANISM: Mus musculus

<400> SEQUENCE: 4

```
Glu Leu Pro Pro Ser Arg Cys Pro Ala Arg Ser Arg Thr Thr Trp Arg
 1               5                  10                  15

Arg Pro Gly Cys Ser Ala Gln Arg Pro Ala Pro Gly Ser Pro His Cys
            20                  25                  30

Pro Cys Pro Pro Thr Cys Ala Ala Arg Pro Ala Ala Pro Arg Ser
        35                  40                  45

Arg Ala Pro Ala Gly Arg Arg Gly Pro Ala Arg Ala Arg Ala
    50                  55                  60

Leu Gly Ser Ser Ala Arg Pro Pro Thr Arg Pro Pro Leu Arg Pro Pro
 65                  70                  75                  80

Pro Ala Leu Ser Pro Pro Pro Ser Pro Ala Gly Thr Ser Glu Cys
                85                  90                  95

Ser Pro Arg Glu Lys Met Ala Ala Ala Ala Gly Asp Arg Ala Ser Ser
            100                 105                 110

Ser Gly Phe Pro Gly Ala Ala Ala Ser Pro Glu Ala Gly Gly Gly
        115                 120                 125

Gly Gly Gly Gly Gly Ala Leu Gln Gly Ser Gly Ala Pro Ala Ala Gly
    130                 135                 140

Ala Ala Gly Leu Leu Arg Glu Pro Gly Ser Ala Gly Pro Ser Ala Arg
145                 150                 155                 160

Thr Gly Gly Gly Gly Thr Cys Ala Lys Cys Gly Val Trp Ser Trp Thr
```

```
                165                 170                 175
Ser Cys Arg Ser Ser Arg Ser Ser Pro Pro Arg Pro Ala
            180                 185             190
His Leu Leu Pro Val Ala Gly Ala Arg Gly Arg Gly Cys Arg Ser Glu
            195                 200             205
Ser Leu Pro Ala Arg Ala Gly Pro Pro Pro Gly Ala Ala Ser Arg
    210                 215                 220
Cys Gly Ser His Ser Ala Glu Leu Ala Ala Arg Asp Ser Gly Ala
225                 230                 235                 240
Arg Ser Pro Ala Gly Ala Glu Pro Pro Ser Ala Ala Pro Ser Gly
                245                 250                 255
Arg Glu Met Glu Asn Lys Glu Thr Leu Lys Gly Leu His Lys Met Glu
            260                 265                 270
Asp Arg Pro Glu Glu Arg Met Ile Arg Glu Lys Leu Lys Ala Thr Cys
            275                 280                 285
Met Pro Ala Trp Lys His Glu Trp Leu Glu Arg Arg Asn Arg Gly
    290                 295                 300
Pro Val Val Lys Pro Ile Pro Ile Lys Gly Asp Gly Ser Glu Val
305                 310                 315                 320
Asn Asn Leu Ala Ala Glu Pro Gln Gly Glu Gly Gln Ala Gly Ser Ala
                325                 330                 335
Ala Pro Ala Pro Lys Gly Arg Arg Ser Pro Ser Pro Gly Ser Ser Pro
            340                 345                 350
Ser Gly Arg Ser Val Lys Pro Glu Ser Pro Gly Val Arg Arg Lys Arg
            355                 360                 365
Val Ser Pro Val Pro Phe Gln Ser Gly Arg Ile Thr Pro Pro Arg Arg
    370                 375                 380
Ala Pro Ser Pro Asp Gly Phe Ser Pro Tyr Ser Pro Glu Glu Thr Ser
385                 390                 395                 400
Arg Arg Val Asn Lys Val Met Arg Ala Arg Leu Tyr Leu Leu Gln Gln
                405                 410                 415
Ile Gly Pro Asn Ser Phe Leu Ile Gly Gly Asp Ser Pro Asp Asn Lys
            420                 425                 430
Tyr Arg Val Phe Ile Gly Pro Gln Asn Cys Ser Cys Gly Arg Gly Ala
            435                 440                 445
Phe Cys Ile His Leu Leu Phe Val Met Leu Arg Val Phe Gln Leu Glu
    450                 455                 460
Pro Ser Asp Pro Met Leu Trp Arg Lys Thr Leu Lys Asn Phe Glu Val
465                 470                 475                 480
Glu Ser Leu Phe Gln Lys Tyr His Ser Arg Arg Ser Arg Ile Lys
                485                 490                 495
Ala Pro Ser Arg Asn Thr Ile Gln Lys Phe Val Ser Arg Met Ser Asn
            500                 505                 510
Ser His Thr Leu Ser Ser Ser Thr Ser Thr Ser Ser Glu Asn
            515                 520                 525
Ser Ile Lys Asp Glu Glu Gln Met Cys Pro Ile Cys Leu Leu Gly
    530                 535                 540
Met Leu Asp Glu Glu Ser Leu Thr Val Cys Glu Asp Gly Cys Arg Asn
545                 550                 555                 560
Lys Leu His His His Cys Met Ser Ile Trp Ala Glu Glu Cys Arg Arg
                565                 570                 575
Asn Arg Glu Pro Leu Ile Cys Pro Leu Cys Arg Ser Lys Trp Arg Ser
            580                 585                 590
```

-continued

```
His Asp Phe Tyr Ser His Glu Leu Ser Ser Pro Val Glu Ser Pro Ala
            595                 600                 605

Ser Leu Arg Ala Val Gln Gln Pro Ser Ser Pro Gln Gln Pro Val Ala
        610                 615                 620

Gly Ser Gln Arg Arg Asn Gln Glu Ser Ser Phe Asn Leu Thr His Phe
625                 630                 635                 640

Gly Thr Gln Gln Ile Pro Ser Ala Tyr Lys Asp Leu Ala Glu Pro Trp
                645                 650                 655

Ile Gln Val Phe Gly Met Glu Leu Val Gly Cys Leu Phe Ser Arg Asn
                660                 665                 670

Trp Asn Val Arg Glu Met Ala Leu Arg Arg Leu Ser His Asp Val Ser
        675                 680                 685

Gly Ala Leu Leu Ala Asn Gly Glu Ser Thr Gly Asn Ser Gly Gly
690                 695                 700

Gly Ser Gly Gly Ser Leu Ser Ala Gly Ala Ser Gly Ser Ser Gln
705                 710                 715                 720

Pro Ser Ile Ser Gly Asp Val Val Glu Ala Cys Cys Ser Val Leu Ser
                725                 730                 735

Ile Val Cys Ala Asp Pro Val Tyr Lys Val Tyr Val Ala Ala Leu Lys
                740                 745                 750

Thr Leu Arg Ala Met Leu Val Tyr Thr Pro Cys His Ser Leu Ala Glu
        755                 760                 765

Arg Ile Lys Leu Gln Arg Leu Leu Arg Pro Val Val Asp Thr Ile Leu
        770                 775                 780

Val Lys Cys Ala Asp Ala Asn Ser Arg Thr Ser Gln Leu Ser Ile Ser
785                 790                 795                 800

Thr Val Leu Glu Leu Cys Lys Gly Gln Ala Gly Glu Leu Ala Val Gly
                805                 810                 815

Arg Glu Ile Leu Lys Ala Gly Ser Ile Gly Val Gly Val Asp Tyr
        820                 825                 830

Val Leu Ser Cys Ile Leu Gly Asn Gln Ala Glu Ser Asn Asn Trp Gln
        835                 840                 845

Glu Leu Leu Gly Arg Leu Cys Leu Ile Asp Arg Leu Leu Leu Glu Phe
850                 855                 860

Pro Ala Glu Phe Tyr Pro His Ile Val Ser Thr Asp Val Ser Gln Ala
865                 870                 875                 880

Glu Pro Val Glu Ile Arg Tyr Lys Lys Leu Leu Ser Leu Leu Thr Phe
                885                 890                 895

Ala Leu Gln Ser Ile Asp Asn Ser His Ser Met Val Gly Lys Leu Ser
                900                 905                 910

Arg Arg Ile Tyr Leu Ser Ser Ala Arg Met Val Thr Ala Val Pro Ala
        915                 920                 925

Val Phe Ser Lys Leu Val Thr Met Leu Asn Ala Ser Gly Ser Thr His
        930                 935                 940

Phe Thr Arg Met Arg Arg Arg Leu Met Ala Ile Ala Asp Glu Val Glu
945                 950                 955                 960

Ile Ala Glu Val Ile Gln Leu Gly Val Glu Asp Thr Val Asp Gly His
                965                 970                 975

Gln Asp Ser Leu Gln Ala Val Ala Pro Thr Ser Cys Leu Glu Asn Ser
        980                 985                 990

Ser Leu Glu His Thr Val His Arg Glu Lys Thr Gly Lys Gly Leu Ser
        995                 1000                1005
```

-continued

```
Ala Thr Arg Leu Ser Ala Ser Ser Glu Asp Ile Ser Asp Arg Leu Ala
    1010                1015                1020

Gly Val Ser Val Gly Leu Pro Ser Ser Thr Thr Thr Glu Gln Pro Lys
1025                1030                1035                1040

Pro Ala Val Gln Thr Lys Gly Arg Pro His Ser Gln Cys Leu Asn Ser
                1045                1050                1055

Ser Pro Leu Ser His Ala Gln Leu Met Phe Pro Ala Pro Ser Ala Pro
            1060                1065                1070

Cys Ser Ser Ala Pro Ser Val Pro Asp Ile Ser Lys His Arg Pro Gln
        1075                1080                1085

Ala Phe Val Pro Cys Lys Ile Pro Ser Ala Ser Pro Gln Thr Gln Arg
    1090                1095                1100

Lys Phe Ser Leu Gln Phe Gln Arg Asn Cys Ser Glu His Arg Asp Ser
1105                1110                1115                1120

Asp Gln Leu Ser Pro Val Phe Thr Gln Ser Arg Pro Pro Pro Ser Ser
                1125                1130                1135

Asn Ile His Arg Pro Lys Pro Ser Arg Pro Val Pro Gly Ser Thr Ser
            1140                1145                1150

Lys Leu Gly Asp Ala Thr Lys Ser Ser Met Thr Leu Asp Leu Gly Ser
        1155                1160                1165

Ala Ser Arg Cys Asp Asp Ser Phe Gly Gly Gly Asn Ser Gly Asn
    1170                1175                1180

Ala Val Ile Pro Ser Asp Glu Thr Val Phe Thr Pro Val Glu Asp Lys
1185                1190                1195                1200

Cys Arg Leu Asp Val Asn Thr Glu Leu Asn Ser Ser Ile Glu Asp Leu
                1205                1210                1215

Leu Glu Ala Ser Met Pro Ser Ser Asp Thr Thr Val Thr Phe Lys Ser
            1220                1225                1230

Glu Val Ala Val Leu Ser Pro Glu Lys Ala Glu Asn Asp Asp Thr Tyr
        1235                1240                1245

Lys Asp Asp Val Asn His Asn Gln Lys Cys Lys Glu Lys Met Glu Ala
    1250                1255                1260

Glu Glu Glu Glu Ala Leu Ala Ile Ala Met Ala Met Ser Ala Ser Gln
1265                1270                1275                1280

Asp Ala Leu Pro Ile Val Pro Gln Leu Gln Val Glu Asn Gly Glu Asp
                1285                1290                1295

Ile Ile Ile Ile Gln Gln Asp Thr Pro Glu Thr Leu Pro Gly His Thr
            1300                1305                1310

Lys Ala Lys Gln Pro Tyr Arg Glu Asp Ala Glu Trp Leu Lys Gly Gln
        1315                1320                1325

Gln Ile Gly Leu Gly Ala Phe Ser Ser Cys Tyr Gln Ala Gln Asp Val
    1330                1335                1340

Gly Thr Gly Thr Leu Met Ala Val Lys Gln Val Thr Tyr Val Arg Asn
1345                1350                1355                1360

Thr Ser Ser Glu Gln Glu Glu Val Val Glu Ala Leu Arg Glu Glu Ile
                1365                1370                1375

Arg Met Met Gly His Leu Asn His Pro Asn Ile Ile Arg Met Leu Gly
            1380                1385                1390

Ala Thr Cys Glu Lys Ser Asn Tyr Asn Leu Phe Ile Glu Trp Met Ala
        1395                1400                1405

Gly Gly Ser Val Ala His Leu Leu Ser Lys Tyr Gly Ala Phe Lys Glu
    1410                1415                1420

Ser Val Val Ile Asn Tyr Thr Glu Gln Leu Leu Arg Gly Leu Ser Tyr
```

```
                    1425                1430                1435                1440
Leu His Glu Asn Gln Ile Ile His Arg Asp Val Lys Gly Ala Asn Leu
                1445                1450                1455

Leu Ile Asp Ser Thr Gly Gln Arg Leu Arg Ile Ala Asp Phe Gly Ala
            1460                1465                1470

Ala Ala Arg Leu Ala Ser Lys Gly Thr Gly Ala Gly Glu Phe Gln Gly
        1475                1480                1485

Gln Leu Leu Gly Thr Ile Ala Phe Met Ala Pro Glu Val Leu Arg Gly
    1490                1495                1500

Gln Gln Tyr Gly Arg Ser Cys Asp Val Trp Ser Val Gly Cys Ala Ile
1505                1510                1515                1520

Ile Glu Met Ala Cys Ala Lys Pro Pro Trp Asn Ala Glu Lys His Ser
                1525                1530                1535

Asn His Leu Ala Leu Ile Phe Lys Ile Ala Ser Ala Thr Thr Ala Pro
            1540                1545                1550

Ser Ile Pro Ser His Leu Ser Pro Gly Leu Arg Asp Val Ala Val Arg
        1555                1560                1565

Cys Leu Glu Leu Gln Pro Gln Asp Arg Pro Pro Ser Arg Glu Leu Leu
    1570                1575                1580

Lys His Pro Val Phe Arg Thr Thr Trp
1585                1590
```

<210> SEQ ID NO 5
<211> LENGTH: 2503
<212> TYPE: DNA
<213> ORGANISM: Mus musculus
<220> FEATURE:
<221> NAME/KEY: CDS
<222> LOCATION: (466)..(2322)

<400> SEQUENCE: 5

```
ggtggcggcc gctctagaac tagtggatcc cccgggctgc aggaattcgg cacgagggac    60
gatccagcgg cagagtcgcc gcttccgctt cgctgcttct ccgtcggcg acgcgggccc    120 ggggcttcct tttcatcggc ccagcttatt ccgcgggccc cggggctgca gctacccaga   180
agcggcgaag aggccctggg ctgcgcgccc gctgtcccat gtgaagcagg ttgggcctgg   240
tccccggccc gtgcccggtt gtctgcggcc cttcaggcct cagggacccc cgcgaggcgc   300
tgctcctggg gggcgcggtg acaggccgtg cggggcgga ggggccagct cggtggcctc    360
ctctcggccc tcgcgtccgc gatcccgccc agcggccggg caataaagaa tgttgatggg   420
agaaccattt tcctaatttt caaattattg agctggtcgc gcata atg gat gat cag   477
                                               Met Asp Asp Gln
                                                 1 caa gct ttg aat tca atc atg caa gat ttg gct gtc ctt cat aag cca    525
Gln Ala Leu Asn Ser Ile Met Gln Asp Leu Ala Val Leu His Lys Pro
  5              10                  15                  20 gtc ggc cag cat tat ctt tac aag aaa cca gga aag caa aac ctt cat    573
Val Gly Gln His Tyr Leu Tyr Lys Lys Pro Gly Lys Gln Asn Leu His
             25                  30                  35 cac caa aaa aac aga atg atg ttc gag tca aat ttg aac ata gag gag    621
His Gln Lys Asn Arg Met Met Phe Glu Ser Asn Leu Asn Ile Glu Glu
         40                  45                  50 gaa aaa agg atc ctg cag gtt act aga cca gtt aaa cta gaa gac ctg    669
Glu Lys Arg Ile Leu Gln Val Thr Arg Pro Val Lys Leu Glu Asp Leu
     55                  60                  65 aga tct aag tct aag atc gcc ttt ggg cag tct atg gat cta cac tat    717
Arg Ser Lys Ser Lys Ile Ala Phe Gly Gln Ser Met Asp Leu His Tyr
 70                  75                  80
```

-continued

|  |  |
|---|---|
| acc aac aat gag ttg gta att ccg tta act acc caa gat gac ttg gac<br>Thr Asn Asn Glu Leu Val Ile Pro Leu Thr Thr Gln Asp Asp Leu Asp<br>85                              90                          95                          100 | 765 |
| aaa gct gtg gaa ctg ctg gat cgc agt att cac atg aag agt ctc aag<br>Lys Ala Val Glu Leu Leu Asp Arg Ser Ile His Met Lys Ser Leu Lys<br>                            105                          110                          115 | 813 |
| ata tta ctt gta gta aat ggg agt aca cag gct act aat tta gaa cca<br>Ile Leu Leu Val Val Asn Gly Ser Thr Gln Ala Thr Asn Leu Glu Pro<br>                   120                          125                          130 | 861 |
| tca ccg tca cca gaa gat ttg aat aat aca cca ctt ggt gca gag agg<br>Ser Pro Ser Pro Glu Asp Leu Asn Asn Thr Pro Leu Gly Ala Glu Arg<br>          135                          140                          145 | 909 |
| aaa aag cgg cta tct gta gta ggt ccc cct aat agg gat aga agt tcc<br>Lys Lys Arg Leu Ser Val Val Gly Pro Pro Asn Arg Asp Arg Ser Ser<br>150                            155                          160 | 957 |
| cct cct cca gga tac att cca gac ata cta cac cag att gcc cgg aat<br>Pro Pro Pro Gly Tyr Ile Pro Asp Ile Leu His Gln Ile Ala Arg Asn<br>165                            170                          175                          180 | 1005 |
| ggg tca ttc act agc atc aac agt gaa gga gag ttc att cca gag agc<br>Gly Ser Phe Thr Ser Ile Asn Ser Glu Gly Glu Phe Ile Pro Glu Ser<br>                            185                          190                          195 | 1053 |
| atg gac caa atg ctg gat cca ttg tct tta agc agc cct gaa aat tct<br>Met Asp Gln Met Leu Asp Pro Leu Ser Leu Ser Ser Pro Glu Asn Ser<br>                 200                          205                          210 | 1101 |
| ggc tca gga agc tgt ccg tca ctt gat agt cct ttg gat gga gaa agc<br>Gly Ser Gly Ser Cys Pro Ser Leu Asp Ser Pro Leu Asp Gly Glu Ser<br>                            215                          220                        225 | 1149 |
| tac cca aaa tca cgg atg cct agg gca cag agc tac cca gat aat cat<br>Tyr Pro Lys Ser Arg Met Pro Arg Ala Gln Ser Tyr Pro Asp Asn His<br>230                            235                          240 | 1197 |
| cag gag ttt aca gac tat gat aac ccc att ttt gag aaa ttt gga aaa<br>Gln Glu Phe Thr Asp Tyr Asp Asn Pro Ile Phe Glu Lys Phe Gly Lys<br>245                            250                          255                          260 | 1245 |
| gga gga aca tat cca aga agg tac cac gtt tcc tat cat cac cag gag<br>Gly Gly Thr Tyr Pro Arg Arg Tyr His Val Ser Tyr His His Gln Glu<br>                            265                          270                          275 | 1293 |
| tat aat gac ggt cgg aag act ttt cca aga gct aga agg acc cag ggc<br>Tyr Asn Asp Gly Arg Lys Thr Phe Pro Arg Ala Arg Arg Thr Gln Gly<br>                 280                          285                          290 | 1341 |
| acc agt ttc cgg tct cct gtg agc ttc agt cct act gat cac tcc tta<br>Thr Ser Phe Arg Ser Pro Val Ser Phe Ser Pro Thr Asp His Ser Leu<br>                            295                          300                          305 | 1389 |
| agc act agt agt gga agc agt gtc ttt acc cca gag tat gac gac agt<br>Ser Thr Ser Ser Gly Ser Ser Val Phe Thr Pro Glu Tyr Asp Asp Ser<br>310                            315                          320 | 1437 |
| cga ata aga aga cgg ggg agt gac ata gac aat cct act ttg act gtc<br>Arg Ile Arg Arg Arg Gly Ser Asp Ile Asp Asn Pro Thr Leu Thr Val<br>325                            330                          335                          340 | 1485 |
| aca gac atc agc cca ccc agc cgt tca cct cga gct ccg acc aac tgg<br>Thr Asp Ile Ser Pro Pro Ser Arg Ser Pro Arg Ala Pro Thr Asn Trp<br>                   345                          350                          355 | 1533 |
| aga ctg ggc aag ctg ctt ggc caa gga gct ttt ggt agg gtc tac ctc<br>Arg Leu Gly Lys Leu Leu Gly Gln Gly Ala Phe Gly Arg Val Tyr Leu<br>                            360                          365                          370 | 1581 |
| tgc tat gat gtt gat acc gga aga gag ctg gct gtt aag caa gtt cag<br>Cys Tyr Asp Val Asp Thr Gly Arg Glu Leu Ala Val Lys Gln Val Gln<br>375                            380                          385 | 1629 |
| ttt aac cct gag agc cca gag acc agc aag gaa gta aat gca ctt gag | 1677 |

```
tgt gaa att cag ttg ttg aaa aac ttg ttg cat gag cga att gtt cag      1725
Cys Glu Ile Gln Leu Leu Lys Asn Leu Leu His Glu Arg Ile Val Gln
405                 410                 415                 420 tat tat ggc tgt ttg agg gat cct cag gag aaa aca ctt tcc atc ttt      1773
Tyr Tyr Gly Cys Leu Arg Asp Pro Gln Glu Lys Thr Leu Ser Ile Phe
                425                 430                 435 atg gag ctc tcg cca ggg ggt tca att aag gac caa cta aaa gcc tac      1821
Met Glu Leu Ser Pro Gly Gly Ser Ile Lys Asp Gln Leu Lys Ala Tyr
            440                 445                 450 gga gct ctt act gag aac gtg acg agg aag tac acc cgt cag att ctg      1869
Gly Ala Leu Thr Glu Asn Val Thr Arg Lys Tyr Thr Arg Gln Ile Leu
        455                 460                 465 gag ggg gtc cat tat ttg cat agt aat atg att gtc cat aga gat atc      1917
Glu Gly Val His Tyr Leu His Ser Asn Met Ile Val His Arg Asp Ile
    470                 475                 480 aaa gga gca aat atc tta agg gat tcc aca ggc aat atc aag tta gga      1965
Lys Gly Ala Asn Ile Leu Arg Asp Ser Thr Gly Asn Ile Lys Leu Gly
485                 490                 495                 500 gac ttt ggg gct agt aaa cgg ctt cag acc atc tgt ctc tca ggc aca      2013
Asp Phe Gly Ala Ser Lys Arg Leu Gln Thr Ile Cys Leu Ser Gly Thr
                505                 510                 515 gga atg aag tct gtc aca ggc acg cca tac tgg atg agt cct gag gtc      2061
Gly Met Lys Ser Val Thr Gly Thr Pro Tyr Trp Met Ser Pro Glu Val
            520                 525                 530 atc agt gga gaa ggc tat gga aga aaa gca gac atc tgg agt gta gca      2109
Ile Ser Gly Glu Gly Tyr Gly Arg Lys Ala Asp Ile Trp Ser Val Ala
        535                 540                 545 tgt act gtg gta gaa atg cta act gaa aag cca cct tgg gct gaa ttt      2157
Cys Thr Val Val Glu Met Leu Thr Glu Lys Pro Pro Trp Ala Glu Phe
    550                 555                 560 gaa gca atg gct gcc atc ttt aag atc gcc act cag cca acg aac cca      2205
Glu Ala Met Ala Ala Ile Phe Lys Ile Ala Thr Gln Pro Thr Asn Pro
565                 570                 575                 580 aag ctg cca cct cat gtc tca gac tat act cgg gac ttc ctc aaa cgg      2253
Lys Leu Pro Pro His Val Ser Asp Tyr Thr Arg Asp Phe Leu Lys Arg
                585                 590                 595 att ttt gta gag gcc aaa ctt cga cct tca gcg gag gag ctc ttg cgg      2301
Ile Phe Val Glu Ala Lys Leu Arg Pro Ser Ala Glu Glu Leu Leu Arg
            600                 605                 610 cac atg ttt gtg cat tat cac tagcagcggc ggcttcggtc ctccaccagc         2352
His Met Phe Val His Tyr His
        615 tccatcctcg cggccacctt ctctcttact gcactttcct tttttataaa aaagagagat    2412 ggggagaaaa agacaagagg gaaatatttt ctcttgattc ttggttaaat ttgtttaata    2472 ataatagtaa actaaaaaaa aaaaaaaaaa a                                    2503

<210> SEQ ID NO 6
<211> LENGTH: 619
<212> TYPE: PRT
<213> ORGANISM: Mus musculus

<400> SEQUENCE: 6

Met Asp Asp Gln Gln Ala Leu Asn Ser Ile Met Gln Asp Leu Ala Val
 1               5                  10                  15

Leu His Lys Pro Val Gly Gln His Tyr Leu Tyr Lys Lys Pro Gly Lys
            20                  25                  30
```

-continued

```
Gln Asn Leu His His Gln Lys Asn Arg Met Met Phe Glu Ser Asn Leu
             35                  40                  45

Asn Ile Glu Glu Glu Lys Arg Ile Leu Gln Val Thr Arg Pro Val Lys
         50                  55                  60

Leu Glu Asp Leu Arg Ser Lys Ser Lys Ile Ala Phe Gly Gln Ser Met
 65                  70                  75                  80

Asp Leu His Tyr Thr Asn Asn Glu Leu Val Ile Pro Leu Thr Thr Gln
                 85                  90                  95

Asp Asp Leu Asp Lys Ala Val Glu Leu Leu Asp Arg Ser Ile His Met
            100                 105                 110

Lys Ser Leu Lys Ile Leu Leu Val Val Asn Gly Ser Thr Gln Ala Thr
            115                 120                 125

Asn Leu Glu Pro Ser Pro Ser Pro Glu Asp Leu Asn Asn Thr Pro Leu
        130                 135                 140

Gly Ala Glu Arg Lys Lys Arg Leu Ser Val Val Gly Pro Pro Asn Arg
145                 150                 155                 160

Asp Arg Ser Ser Pro Pro Pro Gly Tyr Ile Pro Asp Ile Leu His Gln
                165                 170                 175

Ile Ala Arg Asn Gly Ser Phe Thr Ser Ile Asn Ser Glu Gly Glu Phe
            180                 185                 190

Ile Pro Glu Ser Met Asp Gln Met Leu Asp Pro Leu Ser Leu Ser Ser
        195                 200                 205

Pro Glu Asn Ser Gly Ser Gly Ser Cys Pro Ser Leu Asp Ser Pro Leu
    210                 215                 220

Asp Gly Glu Ser Tyr Pro Lys Ser Arg Met Pro Arg Ala Gln Ser Tyr
225                 230                 235                 240

Pro Asp Asn His Gln Glu Phe Thr Asp Tyr Asp Asn Pro Ile Phe Glu
                245                 250                 255

Lys Phe Gly Lys Gly Gly Thr Tyr Pro Arg Arg Tyr His Val Ser Tyr
            260                 265                 270

His His Gln Glu Tyr Asn Asp Gly Arg Lys Thr Phe Pro Arg Ala Arg
        275                 280                 285

Arg Thr Gln Gly Thr Ser Phe Arg Ser Pro Val Ser Phe Ser Pro Thr
    290                 295                 300

Asp His Ser Leu Ser Thr Ser Ser Gly Ser Ser Val Phe Thr Pro Glu
305                 310                 315                 320

Tyr Asp Asp Ser Arg Ile Arg Arg Gly Ser Asp Ile Asp Asn Pro
                325                 330                 335

Thr Leu Thr Val Thr Asp Ile Ser Pro Pro Ser Arg Ser Pro Arg Ala
            340                 345                 350

Pro Thr Asn Trp Arg Leu Gly Lys Leu Leu Gly Gln Gly Ala Phe Gly
        355                 360                 365

Arg Val Tyr Leu Cys Tyr Asp Val Asp Thr Gly Arg Glu Leu Ala Val
    370                 375                 380

Lys Gln Val Gln Phe Asn Pro Glu Ser Pro Glu Thr Ser Lys Glu Val
385                 390                 395                 400

Asn Ala Leu Glu Cys Glu Ile Gln Leu Leu Lys Asn Leu Leu His Glu
                405                 410                 415

Arg Ile Val Gln Tyr Tyr Gly Cys Leu Arg Asp Pro Gln Glu Lys Thr
            420                 425                 430

Leu Ser Ile Phe Met Glu Leu Ser Pro Gly Gly Ser Ile Lys Asp Gln
        435                 440                 445

Leu Lys Ala Tyr Gly Ala Leu Thr Glu Asn Val Thr Arg Lys Tyr Thr
```

```
                    450                  455                  460
Arg Gln Ile Leu Glu Gly Val His Tyr Leu His Ser Asn Met Ile Val
465                 470                 475                 480

His Arg Asp Ile Lys Gly Ala Asn Ile Leu Arg Asp Ser Thr Gly Asn
                485                 490                 495

Ile Lys Leu Gly Asp Phe Gly Ala Ser Lys Arg Leu Gln Thr Ile Cys
            500                 505                 510

Leu Ser Gly Thr Gly Met Lys Ser Val Thr Gly Thr Pro Tyr Trp Met
        515                 520                 525

Ser Pro Glu Val Ile Ser Glu Gly Tyr Gly Arg Lys Ala Asp Ile
    530                 535                 540

Trp Ser Val Ala Cys Thr Val Val Glu Met Leu Thr Glu Lys Pro Pro
545                 550                 555                 560

Trp Ala Glu Phe Glu Ala Met Ala Ala Ile Phe Lys Ile Ala Thr Gln
                565                 570                 575

Pro Thr Asn Pro Lys Leu Pro Pro His Val Ser Asp Tyr Thr Arg Asp
            580                 585                 590

Phe Leu Lys Arg Ile Phe Val Glu Ala Lys Leu Arg Pro Ser Ala Glu
        595                 600                 605

Glu Leu Leu Arg His Met Phe Val His Tyr His
    610                 615

<210> SEQ ID NO 7
<211> LENGTH: 2503
<212> TYPE: DNA
<213> ORGANISM: Mus musculus
<220> FEATURE:
<221> NAME/KEY: CDS
<222> LOCATION: (466)..(2322)

<400> SEQUENCE: 7
ggtggcggcc gctctagaac tagtggatcc cccgggctgc aggaattcgg cacgagggac      60
gatccagcgg cagagtcgcc gcttccgctt cgctgcttct ccgtcggcg acgcgggccc      120 ggggcttcct tttcatcggc ccagcttatt ccgcgggccc cggggctgca gctacccaga     180
agcggcgaag aggccctggg ctgcgcgccc gctgtcccat gtgaagcagg ttgggcctgg     240
tccccggccc gtgcccggtt gtctgcgcc cttcaggcct cagggacccc cgcgaggcgc      300
tgctcctggg gggcgcggtg acaggccgtg cggggcgga ggggccagct cggtggcctc      360
ctctcggccc tcgcgtccgc gatcccgccc agcggccggg caataaagaa tgttgatggg     420
agaaccattt tcctaatttt caaattattg agctggtcgc gcata atg gat gat cag    477
                                             Met Asp Asp Gln
                                               1 caa gct ttg aat tca atc atg caa gat ttg gct gtc ctt cat aag gcc     525
Gln Ala Leu Asn Ser Ile Met Gln Asp Leu Ala Val Leu His Lys Ala
  5                 10                  15                  20 agt cgg cca gca tta tct tta caa gaa acc agg aaa gca aaa cct tca    573
Ser Arg Pro Ala Leu Ser Leu Gln Glu Thr Arg Lys Ala Lys Pro Ser
            25                  30                  35 tca cca aaa aaa cag aat gat gtt cga gtc aaa ttt gaa cat aga gga    621
Ser Pro Lys Lys Gln Asn Asp Val Arg Val Lys Phe Glu His Arg Gly
        40                  45                  50 gaa aaa agg atc ctg cag gtt act aga cca gtt aaa cta gaa gac ctg    669
Glu Lys Arg Ile Leu Gln Val Thr Arg Pro Val Lys Leu Glu Asp Leu
    55                  60                  65 aga tct aag tct aag atc gcc ttt ggg cag tct atg gat cta cac tat    717
Arg Ser Lys Ser Lys Ile Ala Phe Gly Gln Ser Met Asp Leu His Tyr
```

```
          70                    75                      80
acc aac aat gag ttg gta att ccg tta act acc caa gat gac ttg gac    765
Thr Asn Asn Glu Leu Val Ile Pro Leu Thr Thr Gln Asp Asp Leu Asp
 85                      90                      95                     100 aaa gct gtg gaa ctg ctg gat cgc agt att cac atg aag agt ctc aag    813
Lys Ala Val Glu Leu Leu Asp Arg Ser Ile His Met Lys Ser Leu Lys
                        105                     110                     115 ata tta ctt gta gta aat ggg agt aca cag gct act aat tta gaa cca    861
Ile Leu Leu Val Val Asn Gly Ser Thr Gln Ala Thr Asn Leu Glu Pro
                120                     125                     130 tca ccg tca cca gaa gat ttg aat aat aca cca ctt ggt gca gag agg    909
Ser Pro Ser Pro Glu Asp Leu Asn Asn Thr Pro Leu Gly Ala Glu Arg
        135                     140                     145 aaa aag cgg cta tct gta gta ggt ccc cct aat agg gat aga agt tcc    957
Lys Lys Arg Leu Ser Val Val Gly Pro Pro Asn Arg Asp Arg Ser Ser
150                     155                     160 cct cct cca gga tac att cca gac ata cta cac cag att gcc cgg aat   1005
Pro Pro Pro Gly Tyr Ile Pro Asp Ile Leu His Gln Ile Ala Arg Asn
165                     170                     175                     180 ggg tca ttc act agc atc aac agt gaa gga gag ttc att cca gag agc   1053
Gly Ser Phe Thr Ser Ile Asn Ser Glu Gly Glu Phe Ile Pro Glu Ser
                185                     190                     195 atg gac caa atg ctg gat cca ttg tct tta agc agc cct gaa aat tct   1101
Met Asp Gln Met Leu Asp Pro Leu Ser Leu Ser Ser Pro Glu Asn Ser
        200                     205                     210 ggc tca gga agc tgt ccg tca ctt gat agt cct ttg gat gga gaa agc   1149
Gly Ser Gly Ser Cys Pro Ser Leu Asp Ser Pro Leu Asp Gly Glu Ser
        215                     220                     225 tac cca aaa tca cgg atg cct agg gca cag agc tac cca gat aat cat   1197
Tyr Pro Lys Ser Arg Met Pro Arg Ala Gln Ser Tyr Pro Asp Asn His
230                     235                     240 cag gag ttt aca gac tat gat aac ccc att ttt gag aaa ttt gga aaa   1245
Gln Glu Phe Thr Asp Tyr Asp Asn Pro Ile Phe Glu Lys Phe Gly Lys
245                     250                     255                     260 gga gga aca tat cca aga agg tac cac gtt tcc tat cat cac cag gag   1293
Gly Gly Thr Tyr Pro Arg Arg Tyr His Val Ser Tyr His His Gln Glu
                265                     270                     275 tat aat gac ggt cgg aag act ttt cca aga gct aga agg acc cag ggc   1341
Tyr Asn Asp Gly Arg Lys Thr Phe Pro Arg Ala Arg Arg Thr Gln Gly
        280                     285                     290 acc agt ttc cgg tct cct gtg agc ttc agt cct act gat cac tcc tta   1389
Thr Ser Phe Arg Ser Pro Val Ser Phe Ser Pro Thr Asp His Ser Leu
        295                     300                     305 agc act agt agt gga agc agt gtc ttt acc cca gag tat gac gac agt   1437
Ser Thr Ser Ser Gly Ser Ser Val Phe Thr Pro Glu Tyr Asp Asp Ser
310                     315                     320 cga ata aga aga cgg ggg agt gac ata gac aat cct act ttg act gtc   1485
Arg Ile Arg Arg Arg Gly Ser Asp Ile Asp Asn Pro Thr Leu Thr Val
325                     330                     335                     340 aca gac atc agc cca ccc agc cgt tca cct cga gct ccg acc aac tgg   1533
Thr Asp Ile Ser Pro Pro Ser Arg Ser Pro Arg Ala Pro Thr Asn Trp
                345                     350                     355 aga ctg ggc aag ctg ctt ggc caa gga gct ttt ggt agg gtc tac ctc   1581
Arg Leu Gly Lys Leu Leu Gly Gln Gly Ala Phe Gly Arg Val Tyr Leu
        360                     365                     370 tgc tat gat gtt gat acc gga aga gag ctg gct gtt aag caa gtt cag   1629
Cys Tyr Asp Val Asp Thr Gly Arg Glu Leu Ala Val Lys Gln Val Gln
        375                     380                     385 ttt aac cct gag agc cca gag acc agc aag gaa gta aat gca ctt gag   1677
```

```
                                          -continued

Phe Asn Pro Glu Ser Pro Glu Thr Ser Lys Glu Val Asn Ala Leu Glu
        390                 395                 400 tgt gaa att cag ttg ttg aaa aac ttg ttg cat gag cga att gtt cag      1725
Cys Glu Ile Gln Leu Leu Lys Asn Leu Leu His Glu Arg Ile Val Gln
405                 410                 415                 420 tat tat ggc tgt ttg agg gat cct cag gag aaa aca ctt tcc atc ttt      1773
Tyr Tyr Gly Cys Leu Arg Asp Pro Gln Glu Lys Thr Leu Ser Ile Phe
                425                 430                 435 atg gag tat atg cca ggg ggt tca att aag gac caa cta aaa gcc tac      1821
Met Glu Tyr Met Pro Gly Gly Ser Ile Lys Asp Gln Leu Lys Ala Tyr
        440                 445                 450 gga gct ctt act gag aac gtg acg agg aag tac acc cgt cag att ctg      1869
Gly Ala Leu Thr Glu Asn Val Thr Arg Lys Tyr Thr Arg Gln Ile Leu
            455                 460                 465 gag ggg gtc cat tat ttg cat agt aat atg att gtc cat aga gat atc      1917
Glu Gly Val His Tyr Leu His Ser Asn Met Ile Val His Arg Asp Ile
470                 475                 480 aaa gga gca aat atc tta agg gat tcc aca ggc aat atc aag tta gga      1965
Lys Gly Ala Asn Ile Leu Arg Asp Ser Thr Gly Asn Ile Lys Leu Gly
485                 490                 495                 500 gac ttt ggg gct agt aaa cgg ctt cag acc atc tgt ctc tca ggc aca      2013
Asp Phe Gly Ala Ser Lys Arg Leu Gln Thr Ile Cys Leu Ser Gly Thr
                505                 510                 515 gga atg aag tct gtc aca ggc acg cca tac tgg atg agt cct gag gtc      2061
Gly Met Lys Ser Val Thr Gly Thr Pro Tyr Trp Met Ser Pro Glu Val
        520                 525                 530 atc agt gga gaa ggc tat gga aga aaa gca gac atc tgg agt gta gca      2109
Ile Ser Gly Glu Gly Tyr Gly Arg Lys Ala Asp Ile Trp Ser Val Ala
            535                 540                 545 tgt act gtg gta gaa atg cta act gaa aag cca cct tgg gct gaa ttt      2157
Cys Thr Val Val Glu Met Leu Thr Glu Lys Pro Pro Trp Ala Glu Phe
550                 555                 560 gaa gca atg gct gcc atc ttt aag atc gcc act cag cca acg aac cca      2205
Glu Ala Met Ala Ala Ile Phe Lys Ile Ala Thr Gln Pro Thr Asn Pro
565                 570                 575                 580 aag ctg cca cct cat gtc tca gac tat act cgg gac ttc ctc aaa cgg      2253
Lys Leu Pro Pro His Val Ser Asp Tyr Thr Arg Asp Phe Leu Lys Arg
                585                 590                 595 att ttt gta gag gcc aaa ctt cga cct tca gcg gag gag ctc ttg cgg      2301
Ile Phe Val Glu Ala Lys Leu Arg Pro Ser Ala Glu Glu Leu Leu Arg
        600                 605                 610 cac atg ttt gtg cat tat cac tagcagcggc ggcttcggtc ctccaccagc         2352
His Met Phe Val His Tyr His
            615 tccatcctcg cggccacctt ctctcttact gcactttcct tttttataaa aaagagagat    2412 ggggagaaaa agacaagagg gaaaatattt ctcttgattc ttggttaaat ttgtttaata    2472 ataatagtaa actaaaaaaa aaaaaaaaaa a                                   2503

<210> SEQ ID NO 8
<211> LENGTH: 619
<212> TYPE: PRT
<213> ORGANISM: Mus musculus

<400> SEQUENCE: 8

Met Asp Asp Gln Gln Ala Leu Asn Ser Ile Met Gln Asp Leu Ala Val
1               5                   10                  15

Leu His Lys Ala Ser Arg Pro Ala Leu Ser Leu Gln Glu Thr Arg Lys
            20                  25                  30
```

-continued

```
Ala Lys Pro Ser Ser Pro Lys Lys Gln Asn Asp Val Arg Val Lys Phe
             35                  40                  45

Glu His Arg Gly Glu Lys Arg Ile Leu Gln Val Thr Arg Pro Val Lys
         50                  55                  60

Leu Glu Asp Leu Arg Ser Lys Ser Lys Ile Ala Phe Gly Gln Ser Met
 65                  70                  75                  80

Asp Leu His Tyr Thr Asn Asn Glu Leu Val Ile Pro Leu Thr Thr Gln
                 85                  90                  95

Asp Asp Leu Asp Lys Ala Val Glu Leu Leu Asp Arg Ser Ile His Met
                100                 105                 110

Lys Ser Leu Lys Ile Leu Leu Val Val Asn Gly Ser Thr Gln Ala Thr
            115                 120                 125

Asn Leu Glu Pro Ser Pro Ser Pro Glu Asp Leu Asn Asn Thr Pro Leu
        130                 135                 140

Gly Ala Glu Arg Lys Lys Arg Leu Ser Val Val Gly Pro Pro Asn Arg
145                 150                 155                 160

Asp Arg Ser Ser Pro Pro Gly Tyr Ile Pro Asp Ile Leu His Gln
                165                 170                 175

Ile Ala Arg Asn Gly Ser Phe Thr Ser Ile Asn Ser Glu Gly Glu Phe
                180                 185                 190

Ile Pro Glu Ser Met Asp Gln Met Leu Asp Pro Leu Ser Leu Ser Ser
            195                 200                 205

Pro Glu Asn Ser Gly Ser Gly Ser Cys Pro Ser Leu Asp Ser Pro Leu
        210                 215                 220

Asp Gly Glu Ser Tyr Pro Lys Ser Arg Met Pro Arg Ala Gln Ser Tyr
225                 230                 235                 240

Pro Asp Asn His Gln Glu Phe Thr Asp Tyr Asp Asn Pro Ile Phe Glu
                245                 250                 255

Lys Phe Gly Lys Gly Gly Thr Tyr Pro Arg Arg Tyr His Val Ser Tyr
            260                 265                 270

His His Gln Glu Tyr Asn Asp Gly Arg Lys Thr Phe Pro Arg Ala Arg
        275                 280                 285

Arg Thr Gln Gly Thr Ser Phe Arg Ser Pro Val Ser Phe Ser Pro Thr
290                 295                 300

Asp His Ser Leu Ser Thr Ser Ser Gly Ser Ser Val Phe Thr Pro Glu
305                 310                 315                 320

Tyr Asp Asp Ser Arg Ile Arg Arg Arg Gly Ser Asp Ile Asp Asn Pro
                325                 330                 335

Thr Leu Thr Val Thr Asp Ile Ser Pro Pro Ser Arg Ser Pro Arg Ala
            340                 345                 350

Pro Thr Asn Trp Arg Leu Gly Lys Leu Leu Gly Gln Gly Ala Phe Gly
        355                 360                 365

Arg Val Tyr Leu Cys Tyr Asp Val Asp Thr Gly Arg Glu Leu Ala Val
370                 375                 380

Lys Gln Val Gln Phe Asn Pro Glu Ser Pro Glu Thr Ser Lys Glu Val
385                 390                 395                 400

Asn Ala Leu Glu Cys Glu Ile Gln Leu Leu Lys Asn Leu Leu His Glu
                405                 410                 415

Arg Ile Val Gln Tyr Tyr Gly Cys Leu Arg Asp Pro Gln Glu Lys Thr
            420                 425                 430

Leu Ser Ile Phe Met Glu Tyr Met Pro Gly Gly Ser Ile Lys Asp Gln
        435                 440                 445

Leu Lys Ala Tyr Gly Ala Leu Thr Glu Asn Val Thr Arg Lys Tyr Thr
```

```
             450              455              460
Arg Gln Ile Leu Glu Gly Val His Tyr Leu His Ser Asn Met Ile Val
465              470              475              480

His Arg Asp Ile Lys Gly Ala Asn Ile Leu Arg Asp Ser Thr Gly Asn
                485              490              495

Ile Lys Leu Gly Asp Phe Gly Ala Ser Lys Arg Leu Gln Thr Ile Cys
            500              505              510

Leu Ser Gly Thr Gly Met Lys Ser Val Thr Gly Thr Pro Tyr Trp Met
        515              520              525

Ser Pro Glu Val Ile Ser Glu Gly Tyr Gly Arg Lys Ala Asp Ile
    530              535              540

Trp Ser Val Ala Cys Thr Val Val Glu Met Leu Thr Glu Lys Pro Pro
545              550              555              560

Trp Ala Glu Phe Glu Ala Met Ala Ala Ile Phe Lys Ile Ala Thr Gln
                565              570              575

Pro Thr Asn Pro Lys Leu Pro Pro His Val Ser Asp Tyr Thr Arg Asp
            580              585              590

Phe Leu Lys Arg Ile Phe Val Glu Ala Lys Leu Arg Pro Ser Ala Glu
        595              600              605

Glu Leu Leu Arg His Met Phe Val His Tyr His
    610              615

<210> SEQ ID NO 9
<211> LENGTH: 3089
<212> TYPE: DNA
<213> ORGANISM: Mus musculus
<220> FEATURE:
<221> NAME/KEY: CDS
<222> LOCATION: (400)..(2277)

<400> SEQUENCE: 9
agggaacaaa agctggagct ccaccgcggt ggcggccgct ctagaactag tggatccccc     60
gggctgcagg aattcggcac gaggaacagt ggccggtcgg agcgtcttct ggacttcagg    120
actcgcaggc ggcccggtcg agtggcgccg ccgaggccgg gttgggccga gcctgggagc    180
gccggggatg tagcgggcca acctgctcat gccacagcgc ccggccgcgg ccgagccgga    240
gcctggggag gcggcggggg ccccgagcgc agcccacggc ccccgcgcgg agccaggccc    300
gctgccgtcc ccgccgcccg ctcccccggc atgcagcccc ggctgcggag gtgacacttc    360
tgggctgtag tcgccaccgc cgcctccgcc atcgccacc atg gat gaa caa gag       414
                                           Met Asp Glu Gln Glu
                                             1               5 gca tta gac tcg atc atg aag gac ctg gtg gcc ctc cag atg agc cga     462
Ala Leu Asp Ser Ile Met Lys Asp Leu Val Ala Leu Gln Met Ser Arg
             10                  15                  20 cga acc cgg ttg tct gga tat gag acc atg aag aat aag gac aca ggt     510
Arg Thr Arg Leu Ser Gly Tyr Glu Thr Met Lys Asn Lys Asp Thr Gly
         25                  30                  35 cac cca aac agg cag agt gac gtc aga atc aag ttt gaa cac aat ggg     558
His Pro Asn Arg Gln Ser Asp Val Arg Ile Lys Phe Glu His Asn Gly
     40                  45                  50 gag aga cga att ata gca ttc agc cgg cct gtg aga tac gaa gat gtg     606
Glu Arg Arg Ile Ile Ala Phe Ser Arg Pro Val Arg Tyr Glu Asp Val
 55                  60                  65 gag cac aag gtg aca aca gtc ttt ggg cag cct ctt gat ttg cat tat     654
Glu His Lys Val Thr Thr Val Phe Gly Gln Pro Leu Asp Leu His Tyr
 70                  75                  80                  85
```

| | | |
|---|---|---|
| atg aat aat gag ctc tcc atc ctg ttg aaa aac caa gat gat ctc gat<br>Met Asn Asn Glu Leu Ser Ile Leu Leu Lys Asn Gln Asp Asp Leu Asp<br>                     90                  95                 100 | 702 |
| aaa gcc att gac att ttg gat aga agc tca agt atg aaa agc ctt agg<br>Lys Ala Ile Asp Ile Leu Asp Arg Ser Ser Ser Met Lys Ser Leu Arg<br>           105                 110                 115 | 750 |
| ata cta ctg tta tcc caa gac aga aac cat act agt tcc tct ccc cac<br>Ile Leu Leu Leu Ser Gln Asp Arg Asn His Thr Ser Ser Ser Pro His<br>           120                 125                 130 | 798 |
| tct gga gtg tcc agg cag gtt cgg atc aag cct tcc cag tct gca ggg<br>Ser Gly Val Ser Arg Gln Val Arg Ile Lys Pro Ser Gln Ser Ala Gly<br>135                  140                 145 | 846 |
| gat ata aat acc atc tac caa gct cct gag ccc aga agc agg cac ctg<br>Asp Ile Asn Thr Ile Tyr Gln Ala Pro Glu Pro Arg Ser Arg His Leu<br>150                  155                 160                 165 | 894 |
| tct gtc agc tcc cag aac cct ggc cga agc tct cct ccc ccg gga tat<br>Ser Val Ser Ser Gln Asn Pro Gly Arg Ser Ser Pro Pro Pro Gly Tyr<br>           170                 175                 180 | 942 |
| gta cct gag cga caa cag cac att gcc cgg caa gga tcc tat acg agc<br>Val Pro Glu Arg Gln Gln His Ile Ala Arg Gln Gly Ser Tyr Thr Ser<br>               185                 190                 195 | 990 |
| atc aac agc gaa ggt gaa ttc atc cca gag acc agc gaa cag tgt atg<br>Ile Asn Ser Glu Gly Glu Phe Ile Pro Glu Thr Ser Glu Gln Cys Met<br>           200                 205                 210 | 1038 |
| cta gat ccc ctc agc agt gcc gaa aat tcc ttg tca gga agc tgc caa<br>Leu Asp Pro Leu Ser Ser Ala Glu Asn Ser Leu Ser Gly Ser Cys Gln<br>215                  220                 225 | 1086 |
| tcc ttg gac agg tca gca gac agc cca tcc ttc agg aaa tca caa atg<br>Ser Leu Asp Arg Ser Ala Asp Ser Pro Ser Phe Arg Lys Ser Gln Met<br>230                  235                 240                 245 | 1134 |
| tcc cga gcc cgg agc ttc cca gac aac aga aag gaa tgc tca gat cgg<br>Ser Arg Ala Arg Ser Phe Pro Asp Asn Arg Lys Glu Cys Ser Asp Arg<br>           250                 255                 260 | 1182 |
| gag acc cag ctc tat gat aaa ggt gtc aaa ggt gga acc tat ccc agg<br>Glu Thr Gln Leu Tyr Asp Lys Gly Val Lys Gly Gly Thr Tyr Pro Arg<br>               265                 270                 275 | 1230 |
| cgc tac cat gtg tct gtg cat cac aaa gac tac aat gat ggc aga aga<br>Arg Tyr His Val Ser Val His His Lys Asp Tyr Asn Asp Gly Arg Arg<br>           280                 285                 290 | 1278 |
| aca ttt ccc cga ata cga cgg cat caa ggc aac cta ttc act ctg gtg<br>Thr Phe Pro Arg Ile Arg Arg His Gln Gly Asn Leu Phe Thr Leu Val<br>295                  300                 305 | 1326 |
| ccc tca agt cgc tcc ttg agc aca aat ggc gag aac atg ggt gta gct<br>Pro Ser Ser Arg Ser Leu Ser Thr Asn Gly Glu Asn Met Gly Val Ala<br>310                  315                 320                 325 | 1374 |
| gtg caa tac ctg gac ccc cgt ggg cgc cta cgg agt gca gac agt gag<br>Val Gln Tyr Leu Asp Pro Arg Gly Arg Leu Arg Ser Ala Asp Ser Glu<br>           330                 335                 340 | 1422 |
| aat gcc ctc act gtg cag gaa agg aat gtg cca acc aaa tct cct agt<br>Asn Ala Leu Thr Val Gln Glu Arg Asn Val Pro Thr Lys Ser Pro Ser<br>               345                 350                 355 | 1470 |
| gct ccc atc aat tgg cgt cgg ggg aag ctc ctg ggt caa ggt gcc ttc<br>Ala Pro Ile Asn Trp Arg Arg Gly Lys Leu Leu Gly Gln Gly Ala Phe<br>           360                 365                 370 | 1518 |
| ggc agg gtc tac ttg tgc tat gat gtg gac aca gga cgt gaa ctt gct<br>Gly Arg Val Tyr Leu Cys Tyr Asp Val Asp Thr Gly Arg Glu Leu Ala<br>               375                 380                 385 | 1566 |
| tct aag cag gtc cag ttt gac cca gat agt cct gag aca agc aag gag<br>Ser Lys Gln Val Gln Phe Asp Pro Asp Ser Pro Glu Thr Ser Lys Glu<br>390                  395                 400                 405 | 1614 |

```
gtg agt gct ctg gag tgt gag atc cag ttg ctg aag aac ctg cag cat      1662
Val Ser Ala Leu Glu Cys Glu Ile Gln Leu Leu Lys Asn Leu Gln His
            410                 415                 420 gag cgc att gtg cag tac tac ggc tgc ctg cgg gac cgt gct gag aag      1710
Glu Arg Ile Val Gln Tyr Tyr Gly Cys Leu Arg Asp Arg Ala Glu Lys
                425                 430                 435 atc ctc acc atc ttt atg gag tat atg cca ggg ggc tct gta aaa gac      1758
Ile Leu Thr Ile Phe Met Glu Tyr Met Pro Gly Gly Ser Val Lys Asp
        440                 445                 450 cag ttg aag gcc tac gga gct ctg aca gag agt gtg acc cgc aag tac      1806
Gln Leu Lys Ala Tyr Gly Ala Leu Thr Glu Ser Val Thr Arg Lys Tyr
    455                 460                 465 acc cgg cag att ctg gag ggc atg tca tac ctg cac agc aac atg att      1854
Thr Arg Gln Ile Leu Glu Gly Met Ser Tyr Leu His Ser Asn Met Ile
470                 475                 480                 485 gtg cat cgg gac atc aag gga gcc aat atc ctc cga gac tca gct ggg      1902
Val His Arg Asp Ile Lys Gly Ala Asn Ile Leu Arg Asp Ser Ala Gly
                490                 495                 500 aat gtg aag ctt ggg gat ttt ggg gcc agc aaa cgc cta cag acc atc      1950
Asn Val Lys Leu Gly Asp Phe Gly Ala Ser Lys Arg Leu Gln Thr Ile
            505                 510                 515 tgc atg tca ggg aca ggc att cgc tct gtc act ggc aca ccc tac tgg      1998
Cys Met Ser Gly Thr Gly Ile Arg Ser Val Thr Gly Thr Pro Tyr Trp
        520                 525                 530 atg agt cct gaa gtc atc agt ggc gag ggc tat gga aga aag gca gac      2046
Met Ser Pro Glu Val Ile Ser Gly Glu Gly Tyr Gly Arg Lys Ala Asp
    535                 540                 545 gtg tgg agc ctg ggc tgt act gtg gtg gaa atg ctg aca gag aaa cca      2094
Val Trp Ser Leu Gly Cys Thr Val Val Glu Met Leu Thr Glu Lys Pro
550                 555                 560                 565 cct tgg gca gag tat gaa gct atg gct gcc att ttc aag att gcc acc      2142
Pro Trp Ala Glu Tyr Glu Ala Met Ala Ala Ile Phe Lys Ile Ala Thr
                570                 575                 580 cag cct acc aat cct cag ctg ccc tct cac atc tca gaa cac ggc agg      2190
Gln Pro Thr Asn Pro Gln Leu Pro Ser His Ile Ser Glu His Gly Arg
            585                 590                 595 gac ttc ctg agg cgc ata ttt gtg gaa gct cgt cag aga ccc tca gct      2238
Asp Phe Leu Arg Arg Ile Phe Val Glu Ala Arg Gln Arg Pro Ser Ala
        600                 605                 610 gag gag ctg ctc aca cac cac ttt gca cag cta gtg tac tgagctctca      2287
Glu Glu Leu Leu Thr His His Phe Ala Gln Leu Val Tyr
    615                 620                 625 aggctatcag gctgccagct gccacctgct gagcaggcaa ggggctgctg tcaggctcag   2347
tgaagttgct gcttcttcca ggcaaggcta tgaccagtgg agcatcggtc cagccattgt   2407
ttgtctgtgc cccatctgcc actgggactc aaagccagga tgggatagct ctggcatcaa   2467
gactgggagc tccagcctgt aagacccaag agctttagca ccttaagctc agtatggcgg   2527
gaagggctgg aaacagtatg caagactgcc atgggtcctg cctaccctca gatgtgtcct   2587
aacactgcag acagcactga agtcaagagg gactggggca caggaggtcc tcaagggtat   2647
gaatagtgtt acttcattca gagtgttact ttgtttctct cccaatgttt ggagaccacc   2707
agcctgtctc tgggctgcaa gcctgaggta agcccagca tcccccagcc aacagaaggt    2767
agaggtttgg gctaccccac tatagcttcc aggtattcgg tgtcagtcct gtcttaccaa   2827
agatgaatga agcaaatgtt acactgcctt attctgggaa ggaggagcta ctcggataag   2887
cagggcctga gagatggagc tgcctccaga aactggggag acccagtctt gtcaatgcaa   2947
```

```
ttgtctctgt tttacaagtt ggagtcactc ttatgctgtt cccagtttta aaactggaga    3007
ctttgccctc tgagctctgg agacccatgt gggcttaggc ttggactgga tggaagagct    3067
gatggcctct gcccctggcc tg                                              3089
```

<210> SEQ ID NO 10
<211> LENGTH: 626
<212> TYPE: PRT
<213> ORGANISM: Mus musculus

<400> SEQUENCE: 10

```
Met Asp Glu Gln Glu Ala Leu Asp Ser Ile Met Lys Asp Leu Val Ala
 1               5                  10                  15

Leu Gln Met Ser Arg Arg Thr Arg Leu Ser Gly Tyr Glu Thr Met Lys
            20                  25                  30

Asn Lys Asp Thr Gly His Pro Asn Arg Gln Ser Asp Val Arg Ile Lys
        35                  40                  45

Phe Glu His Asn Gly Glu Arg Arg Ile Ile Ala Phe Ser Arg Pro Val
    50                  55                  60

Arg Tyr Glu Asp Val Glu His Lys Val Thr Thr Val Phe Gly Gln Pro
65                  70                  75                  80

Leu Asp Leu His Tyr Met Asn Asn Glu Leu Ser Ile Leu Lys Asn
                85                  90                  95

Gln Asp Asp Leu Asp Lys Ala Ile Asp Ile Leu Asp Arg Ser Ser Ser
            100                 105                 110

Met Lys Ser Leu Arg Ile Leu Leu Leu Ser Gln Asp Arg Asn His Thr
        115                 120                 125

Ser Ser Ser Pro His Ser Gly Val Ser Arg Gln Val Arg Ile Lys Pro
    130                 135                 140

Ser Gln Ser Ala Gly Asp Ile Asn Thr Ile Tyr Gln Ala Pro Glu Pro
145                 150                 155                 160

Arg Ser Arg His Leu Ser Val Ser Ser Gln Asn Pro Gly Arg Ser Ser
                165                 170                 175

Pro Pro Pro Gly Tyr Val Pro Glu Arg Gln Gln His Ile Ala Arg Gln
            180                 185                 190

Gly Ser Tyr Thr Ser Ile Asn Ser Glu Gly Glu Phe Ile Pro Glu Thr
        195                 200                 205

Ser Glu Gln Cys Met Leu Asp Pro Leu Ser Ser Ala Glu Asn Ser Leu
    210                 215                 220

Ser Gly Ser Cys Gln Ser Leu Asp Arg Ser Ala Asp Ser Pro Ser Phe
225                 230                 235                 240

Arg Lys Ser Gln Met Ser Arg Ala Arg Ser Phe Pro Asp Asn Arg Lys
                245                 250                 255

Glu Cys Ser Asp Arg Glu Thr Gln Leu Tyr Asp Lys Gly Val Lys Gly
            260                 265                 270

Gly Thr Tyr Pro Arg Arg Tyr His Val Ser Val His Lys Asp Tyr
        275                 280                 285

Asn Asp Gly Arg Arg Thr Phe Pro Arg Ile Arg Arg His Gln Gly Asn
    290                 295                 300

Leu Phe Thr Leu Val Pro Ser Ser Arg Ser Leu Ser Thr Asn Gly Glu
305                 310                 315                 320

Asn Met Gly Val Ala Val Gln Tyr Leu Asp Pro Arg Gly Arg Leu Arg
                325                 330                 335

Ser Ala Asp Ser Glu Asn Ala Leu Thr Val Gln Glu Arg Asn Val Pro
            340                 345                 350
```

```
Thr Lys Ser Pro Ser Ala Pro Ile Asn Trp Arg Arg Gly Lys Leu Leu
        355                 360                 365
Gly Gln Gly Ala Phe Gly Arg Val Tyr Leu Cys Tyr Asp Val Asp Thr
    370                 375                 380
Gly Arg Glu Leu Ala Ser Lys Gln Val Gln Phe Asp Pro Asp Ser Pro
385                 390                 395                 400
Glu Thr Ser Lys Glu Val Ser Ala Leu Glu Cys Glu Ile Gln Leu Leu
                405                 410                 415
Lys Asn Leu Gln His Glu Arg Ile Val Gln Tyr Tyr Gly Cys Leu Arg
            420                 425                 430
Asp Arg Ala Glu Lys Ile Leu Thr Ile Phe Met Glu Tyr Met Pro Gly
        435                 440                 445
Gly Ser Val Lys Asp Gln Leu Lys Ala Tyr Gly Ala Leu Thr Glu Ser
    450                 455                 460
Val Thr Arg Lys Tyr Thr Arg Gln Ile Leu Glu Gly Met Ser Tyr Leu
465                 470                 475                 480
His Ser Asn Met Ile Val His Arg Asp Ile Lys Gly Ala Asn Ile Leu
                485                 490                 495
Arg Asp Ser Ala Gly Asn Val Lys Leu Gly Asp Phe Gly Ala Ser Lys
            500                 505                 510
Arg Leu Gln Thr Ile Cys Met Ser Gly Thr Gly Ile Arg Ser Val Thr
        515                 520                 525
Gly Thr Pro Tyr Trp Met Ser Pro Glu Val Ile Ser Gly Glu Gly Tyr
    530                 535                 540
Gly Arg Lys Ala Asp Val Trp Ser Leu Gly Cys Thr Val Val Glu Met
545                 550                 555                 560
Leu Thr Glu Lys Pro Pro Trp Ala Glu Tyr Glu Ala Met Ala Ala Ile
                565                 570                 575
Phe Lys Ile Ala Thr Gln Pro Thr Asn Pro Gln Leu Pro Ser His Ile
            580                 585                 590
Ser Glu His Gly Arg Asp Phe Leu Arg Arg Ile Phe Val Glu Ala Arg
        595                 600                 605
Gln Arg Pro Ser Ala Glu Glu Leu Leu Thr His His Phe Ala Gln Leu
    610                 615                 620
Val Tyr
625
```

```
<210> SEQ ID NO 11
<211> LENGTH: 3913
<212> TYPE: DNA
<213> ORGANISM: Mus musculus
<220> FEATURE:
<221> NAME/KEY: CDS
<222> LOCATION: (747)..(3416)
<220> FEATURE:
<223> OTHER INFORMATION: At postion 116 of the CDS region, Xaa = any
      amino acid

<400> SEQUENCE: 11
aattcggcac gagaacctat cagacattgg ctggccagtg tttgaaatcc cctcccctcg      60
gccgtccaag ggctacgagc cagaggacga ggtcgaggac acggaggttg agctgaggga     120
gctggagagc gggacggagg agagtgacga ggagccaacc cccagtccga gggtgccaga     180
gctcaggctg tccacagaca ccatcttgga cagtcgctcc cagggctgcg tctccaggaa     240
gctggagagg ctcgagtcag aggaagattc cataggctgg gggacagcgg actgtggccc     300
```

-continued

```
tgaagccagc aggcattgtt tgacttctat ctatagacca ttcgtggaca aagcactgaa      360
gcaaatgggg ctaagaaagt taattttacg acttcataag cttatgaatg ggtccttgca      420
aagagctcgt gtagctctgg tgaaggacga ccgtcagtgg agttctctga ctttccaggt      480
cccatgtggg gctcggatta tgtgcagttg tcgggaacac ctccttcctc agagcagaag      540
tgtagcgctg tgtcctggga agaactgaga gccatggacc tgccttcctt tgagcccgcc      600
ttcctggtgc tctgtcgggt cctgctgaac gtgatccacg agtgcctgaa gctgcggctg      660
gaacagaggc tgccggggag ccttccctct tgagtatcaa acagctagtg cgagagtgta      720
aagaggtcct aaaggcggg ctcctg atg aag cag tat tac cag ttc atg ctg        773
                              Met Lys Gln Tyr Tyr Gln Phe Met Leu
                                1               5
```

| Codons | Amino acids | Pos |
|---|---|---|
| cag gag gtc ctg ggc gga ctg gag aag acc gac tgc aac atg gat gcc | Gln Glu Val Leu Gly Gly Leu Glu Lys Thr Asp Cys Asn Met Asp Ala<br>10              15                  20                  25 | 821 |
| ttt gag gag gac ctg cag aag atg ctg atg gtg tat ttt gat tac atg | Phe Glu Glu Asp Leu Gln Lys Met Leu Met Val Tyr Phe Asp Tyr Met<br>    30                  35                  40 | 869 |
| aga agc tgg atc caa atg cta cag cag tta cct cag gct tcc cat agc | Arg Ser Trp Ile Gln Met Leu Gln Gln Leu Pro Gln Ala Ser His Ser<br>        45                  50                  55 | 917 |
| tta aaa aac ctg cta gaa gag gaa tgg aat ttc acc aaa gaa ata acc | Leu Lys Asn Leu Leu Glu Glu Glu Trp Asn Phe Thr Lys Glu Ile Thr<br>    60                  65                  70 | 965 |
| cat tat atc cgt ggc gga gaa gcg cag gct gga aag ctt ttc tgt gac | His Tyr Ile Arg Gly Gly Glu Ala Gln Ala Gly Lys Leu Phe Cys Asp<br>75                  80                  85 | 1013 |
| atc gca ggg atg ctg ctg aaa tcc aca ggg agc ttt ctg gaa tcc ggc | Ile Ala Gly Met Leu Leu Lys Ser Thr Gly Ser Phe Leu Glu Ser Gly<br>90                  95                  100                 105 | 1061 |
| ctg cag gag agc tgt gct gag ctg tgg acc agn gcc gac gac aac ggt | Leu Gln Glu Ser Cys Ala Glu Leu Trp Thr Xaa Ala Asp Asp Asn Gly<br>            110                 115                 120 | 1109 |
| gct gcc gac gag cta agg aga tct gtc atc gag atc agc cga gca ctc | Ala Ala Asp Glu Leu Arg Arg Ser Val Ile Glu Ile Ser Arg Ala Leu<br>            125                 130                 135 | 1157 |
| aag gag ctc ttc cac gaa gcc agg gaa aga gcc tcc aag gcc ctg ggc | Lys Glu Leu Phe His Glu Ala Arg Glu Arg Ala Ser Lys Ala Leu Gly<br>        140                 145                 150 | 1205 |
| ttt gct aaa atg ctg agg aag gac cta gaa ata gca gca gag ttc gtg | Phe Ala Lys Met Leu Arg Lys Asp Leu Glu Ile Ala Ala Glu Phe Val<br>    155                 160                 165 | 1253 |
| cta tct gca tca gcc cga gag ctc ctg gac gct ctg aaa gca aag cag | Leu Ser Ala Ser Ala Arg Glu Leu Leu Asp Ala Leu Lys Ala Lys Gln<br>170                 175                 180                 185 | 1301 |
| tat gtt aag gta cag att ccc ggg tta gag aat ttg cac gtg ttt gtc | Tyr Val Lys Val Gln Ile Pro Gly Leu Glu Asn Leu His Val Phe Val<br>            190                 195                 200 | 1349 |
| ccc gac agc ctc gct gag gag aag aaa att att ttg cag cta ctc aat | Pro Asp Ser Leu Ala Glu Glu Lys Lys Ile Ile Leu Gln Leu Leu Asn<br>        205                 210                 215 | 1397 |
| gct gcc aca gga aag gac tgc tca aag gat cca gac gac gtc ttc atg | Ala Ala Thr Gly Lys Asp Cys Ser Lys Asp Pro Asp Asp Val Phe Met<br>    220                 225                 230 | 1445 |
| gat gcc ttc ctg ctc ctg acc aag cat ggg gac cga gcc cgt gac tca | Asp Ala Phe Leu Leu Leu Thr Lys His Gly Asp Arg Ala Arg Asp Ser<br>235                 240                 245 | 1493 |
| gaa gat ggc tgg ggc aca tgg gaa gct cgg gct gtc aaa att gtg cct |  | 1541 |

```
                                                                                -continued Glu Asp Gly Trp Gly Thr Trp Glu Ala Arg Ala Val Lys Ile Val Pro
250                 255                 260                 265 cag gtg gag act gtg gac acc ctg aga agc atg cag gtg gac aac ctt       1589
Gln Val Glu Thr Val Asp Thr Leu Arg Ser Met Gln Val Asp Asn Leu
                    270                 275                 280 ctg ctg gtt gtc atg gag tct gct cac ctc gta ctt cag aga aaa gcc       1637
Leu Leu Val Val Met Glu Ser Ala His Leu Val Leu Gln Arg Lys Ala
                285                 290                 295 ttc cag cag tcc att gag ggg ctg atg act gta cgc cat gag cag aca       1685
Phe Gln Gln Ser Ile Glu Gly Leu Met Thr Val Arg His Glu Gln Thr
            300                 305                 310 tct agc cag ccc atc atc gcc aaa ggt ttg cag cag ctc aag aac gat       1733
Ser Ser Gln Pro Ile Ile Ala Lys Gly Leu Gln Gln Leu Lys Asn Asp
        315                 320                 325 gca ctt gag cta tgc aac aga atc agc gat gcc atc gac cgt gtg gac       1781
Ala Leu Glu Leu Cys Asn Arg Ile Ser Asp Ala Ile Asp Arg Val Asp
330                 335                 340                 345 cac atg ttc acc ctg gag ttc gat gct gag gtc gag gag tct gag tcg       1829
His Met Phe Thr Leu Glu Phe Asp Ala Glu Val Glu Glu Ser Glu Ser
                350                 355                 360 gcc acg ctg cag cag tac tac cga gaa gcc atg att cag ggc tac aac       1877
Ala Thr Leu Gln Gln Tyr Tyr Arg Glu Ala Met Ile Gln Gly Tyr Asn
                365                 370                 375 ttt ggg ttt gag tat cat aaa gaa gtt gtt cgt ttg atg tct ggg gaa       1925
Phe Gly Phe Glu Tyr His Lys Glu Val Val Arg Leu Met Ser Gly Glu
            380                 385                 390 ttc agg cag aag ata gga gac aaa tat ata acg ttc gcc cag aag tgg       1973
Phe Arg Gln Lys Ile Gly Asp Lys Tyr Ile Thr Phe Ala Gln Lys Trp
        395                 400                 405 atg aat tac gtg ctg acc aaa tgc gag agc ggc aga ggc aca aga ccc       2021
Met Asn Tyr Val Leu Thr Lys Cys Glu Ser Gly Arg Gly Thr Arg Pro
410                 415                 420                 425 aga tgg gcc acc caa gga ttt gat ttc cta caa gcc att gaa cct gcc       2069
Arg Trp Ala Thr Gln Gly Phe Asp Phe Leu Gln Ala Ile Glu Pro Ala
                430                 435                 440 ttt att tca gct tta cca gaa gat gac ttc ttg agt ttg caa gcc ctg       2117
Phe Ile Ser Ala Leu Pro Glu Asp Asp Phe Leu Ser Leu Gln Ala Leu
                445                 450                 455 atg aat gag tgc atc ggg cac gtc ata gga aag cca cac agc cct gtc       2165
Met Asn Glu Cys Ile Gly His Val Ile Gly Lys Pro His Ser Pro Val
            460                 465                 470 aca gct atc cat cgg aac agc ccc cgc cct gtg aag gtg ccc cga tgc       2213
Thr Ala Ile His Arg Asn Ser Pro Arg Pro Val Lys Val Pro Arg Cys
        475                 480                 485 cac agt gac cct cct aac cct cac ctc atc atc ccg act cca gag gga       2261
His Ser Asp Pro Pro Asn Pro His Leu Ile Ile Pro Thr Pro Glu Gly
490                 495                 500                 505 ttc agg ggt tcc agt gtc cct gaa aac gac cgc ttg gcc tcc ata gct       2309
Phe Arg Gly Ser Ser Val Pro Glu Asn Asp Arg Leu Ala Ser Ile Ala
                510                 515                 520 gca gaa ctg cag ttc agg tct ctg agt cgg cac tca agc ccc acg gaa       2357
Ala Glu Leu Gln Phe Arg Ser Leu Ser Arg His Ser Ser Pro Thr Glu
                525                 530                 535 gag cga gac gag cca gcg tat cct cgg agt gac tca agt gga tca act       2405
Glu Arg Asp Glu Pro Ala Tyr Pro Arg Ser Asp Ser Ser Gly Ser Thr
            540                 545                 550 cgg aga agc tgg gaa ctt cga aca ctc atc agc cag acc aaa gac tcg       2453
Arg Arg Ser Trp Glu Leu Arg Thr Leu Ile Ser Gln Thr Lys Asp Ser
        555                 560                 565
```

```
gcc tct aag cag ggg ccc ata gaa gct atc cag aag tca gtc cga ctg      2501
Ala Ser Lys Gln Gly Pro Ile Glu Ala Ile Gln Lys Ser Val Arg Leu
570             575                 580                 585 ttt gaa gag agg agg tat cga gag atg agg aga aag aat atc atc ggc      2549
Phe Glu Glu Arg Arg Tyr Arg Glu Met Arg Arg Lys Asn Ile Ile Gly
                590                 595                 600 caa gtg tgc gat acc cct aag tcc tat gat aac gtc atg cat gtt gga      2597
Gln Val Cys Asp Thr Pro Lys Ser Tyr Asp Asn Val Met His Val Gly
            605                 610                 615 ctg agg aag gtg aca ttt aag tgg caa aga gga aac aaa att gga gaa      2645
Leu Arg Lys Val Thr Phe Lys Trp Gln Arg Gly Asn Lys Ile Gly Glu
        620                 625                 630 gga cag tat gga aaa gta tac acc tgc atc agt gtt gac aca ggg gag      2693
Gly Gln Tyr Gly Lys Val Tyr Thr Cys Ile Ser Val Asp Thr Gly Glu
    635                 640                 645 ctg atg gcc atg aag gag att cga ttt cag cct aac gac cac aag act      2741
Leu Met Ala Met Lys Glu Ile Arg Phe Gln Pro Asn Asp His Lys Thr
650                 655                 660                 665 atc aag gag act gca gac gag ttg aaa ata ttt gaa ggc atc aag cac      2789
Ile Lys Glu Thr Ala Asp Glu Leu Lys Ile Phe Glu Gly Ile Lys His
                670                 675                 680 ccc aac ctg gtc cgg tat ttt ggc gtg gag ctt cac agg gaa gag atg      2837
Pro Asn Leu Val Arg Tyr Phe Gly Val Glu Leu His Arg Glu Glu Met
            685                 690                 695 tac atc ttc atg gag tac tgt gat gag ggt aca cta gag gag gtg tca      2885
Tyr Ile Phe Met Glu Tyr Cys Asp Glu Gly Thr Leu Glu Glu Val Ser
        700                 705                 710 cga ctg ggc ctg cag gag cac gtc atc agg tta tat acc aag cag atc      2933
Arg Leu Gly Leu Gln Glu His Val Ile Arg Leu Tyr Thr Lys Gln Ile
    715                 720                 725 act gtc gcc atc aac gtc ctc cat gag cac ggc atc gtt cac cga gac      2981
Thr Val Ala Ile Asn Val Leu His Glu His Gly Ile Val His Arg Asp
730                 735                 740                 745 atc aaa ggt gcc aat atc ttc ctt acg tca tct gga cta atc aag ctg      3029
Ile Lys Gly Ala Asn Ile Phe Leu Thr Ser Ser Gly Leu Ile Lys Leu
                750                 755                 760 gga gat ttt gga tgc tct gta aaa ctt aaa aac aac gcc cag acc atg      3077
Gly Asp Phe Gly Cys Ser Val Lys Leu Lys Asn Asn Ala Gln Thr Met
            765                 770                 775 ccc gga gag gtg aac agc acc cta ggg aca gca gct tac atg gcc cct      3125
Pro Gly Glu Val Asn Ser Thr Leu Gly Thr Ala Ala Tyr Met Ala Pro
        780                 785                 790 gaa gtt att acc cga gcc aaa gga gaa ggc cac gga cgt gcg gca gat      3173
Glu Val Ile Thr Arg Ala Lys Gly Glu Gly His Gly Arg Ala Ala Asp
    795                 800                 805 atc tgg agt ctg ggg tgc gtc gtc ata gag atg gtg act ggc aag cgg      3221
Ile Trp Ser Leu Gly Cys Val Val Ile Glu Met Val Thr Gly Lys Arg
810                 815                 820                 825 cct tgg cat gag tat gaa cac aac ttt cag att atg tac aag gtg ggg      3269
Pro Trp His Glu Tyr Glu His Asn Phe Gln Ile Met Tyr Lys Val Gly
                830                 835                 840 atg gga cac aag cca cca atc ccg gaa agg cta agc cct gaa gga aag      3317
Met Gly His Lys Pro Pro Ile Pro Glu Arg Leu Ser Pro Glu Gly Lys
            845                 850                 855 gcc ttt ctc tcg cac tgc ctg gaa agt gac ccg aag ata cgg tgg aca      3365
Ala Phe Leu Ser His Cys Leu Glu Ser Asp Pro Lys Ile Arg Trp Thr
        860                 865                 870 gcc agc cag ctc ctc gac cac gct ttt gtc aag gtt tgc aca gat gaa      3413
Ala Ser Gln Leu Leu Asp His Ala Phe Val Lys Val Cys Thr Asp Glu
    875                 880                 885
```

-continued

```
gag tgaagtgaac cagtccgtgg cctagtagtg tgtggacaga atcccgtgat    3466
Glu
890 cactactgta tgtaatattt acataaagac tgcagcgcag gcggccttcc taacctccca    3526 ggactgaaga ctacaggggt gacaagcctc acttctgctg ctcctgtcgc ctgctgagtg    3586 acagtgctga ggttaaagga gccgcacgtt aagtgccatt actactgtac acggccaccg    3646 cctctgtccc ctccgaccct ctcgtgactg agaaccaacc gtgtcatcag cacagtgttt    3706 ttgagctcct ggggttcaga agaacatgta gtgttcccgg gtgtccggga cgtttatttc    3766 aacctcctgg tcgttggctc tgactgtgga gcctccttgt tcgaaagctg caggtttgtt    3826 atgcaaaggc tcgtaagtga agctgaagaa aaggttcttt ttcaataaat ggtttatttt    3886 aggaaagcga aaaaaaaaaa aaaaaaa    3913
```

<210> SEQ ID NO 12
<211> LENGTH: 890
<212> TYPE: PRT
<213> ORGANISM: Mus musculus
<220> FEATURE:
<223> OTHER INFORMATION: At postion 116, Xaa = any amino acid

<400> SEQUENCE: 12

```
Met Lys Gln Tyr Tyr Gln Phe Met Leu Gln Glu Val Leu Gly Gly Leu
  1               5                  10                  15

Glu Lys Thr Asp Cys Asn Met Asp Ala Phe Glu Glu Asp Leu Gln Lys
             20                  25                  30

Met Leu Met Val Tyr Phe Asp Tyr Met Arg Ser Trp Ile Gln Met Leu
         35                  40                  45

Gln Gln Leu Pro Gln Ala Ser His Ser Leu Lys Asn Leu Leu Glu Glu
     50                  55                  60

Glu Trp Asn Phe Thr Lys Glu Ile Thr His Tyr Ile Arg Gly Gly Glu
 65                  70                  75                  80

Ala Gln Ala Gly Lys Leu Phe Cys Asp Ile Ala Gly Met Leu Leu Lys
                 85                  90                  95

Ser Thr Gly Ser Phe Leu Glu Ser Gly Leu Gln Glu Ser Cys Ala Glu
                100                 105                 110

Leu Trp Thr Xaa Ala Asp Asp Asn Gly Ala Ala Asp Glu Leu Arg Arg
            115                 120                 125

Ser Val Ile Glu Ile Ser Arg Ala Leu Lys Glu Leu Phe His Glu Ala
    130                 135                 140

Arg Glu Arg Ala Ser Lys Ala Leu Gly Phe Ala Lys Met Leu Arg Lys
145                 150                 155                 160

Asp Leu Glu Ile Ala Ala Glu Phe Val Leu Ser Ala Ser Ala Arg Glu
                165                 170                 175

Leu Leu Asp Ala Leu Lys Ala Lys Gln Tyr Val Lys Val Gln Ile Pro
            180                 185                 190

Gly Leu Glu Asn Leu His Val Phe Val Pro Asp Ser Leu Ala Glu Glu
        195                 200                 205

Lys Lys Ile Ile Leu Gln Leu Leu Asn Ala Ala Thr Gly Lys Asp Cys
    210                 215                 220

Ser Lys Asp Pro Asp Asp Val Phe Met Asp Ala Phe Leu Leu Leu Thr
225                 230                 235                 240

Lys His Gly Asp Arg Ala Arg Asp Ser Glu Asp Gly Trp Gly Thr Trp
                245                 250                 255
```

-continued

```
Glu Ala Arg Ala Val Lys Ile Val Pro Gln Val Glu Thr Val Asp Thr
            260                 265                 270
Leu Arg Ser Met Gln Val Asp Asn Leu Leu Val Val Met Glu Ser
        275                 280                 285
Ala His Leu Val Leu Gln Arg Lys Ala Phe Gln Gln Ser Ile Glu Gly
    290                 295                 300
Leu Met Thr Val Arg His Glu Gln Thr Ser Ser Gln Pro Ile Ile Ala
305                 310                 315                 320
Lys Gly Leu Gln Gln Leu Lys Asn Asp Ala Leu Glu Leu Cys Asn Arg
                325                 330                 335
Ile Ser Asp Ala Ile Asp Arg Val Asp His Met Phe Thr Leu Glu Phe
            340                 345                 350
Asp Ala Glu Val Glu Glu Ser Glu Ser Ala Thr Leu Gln Gln Tyr Tyr
        355                 360                 365
Arg Glu Ala Met Ile Gln Gly Tyr Asn Phe Gly Phe Glu Tyr His Lys
    370                 375                 380
Glu Val Val Arg Leu Met Ser Glu Phe Arg Gln Lys Ile Gly Asp
385                 390                 395                 400
Lys Tyr Ile Thr Phe Ala Gln Lys Trp Met Asn Tyr Val Leu Thr Lys
                405                 410                 415
Cys Glu Ser Gly Arg Gly Thr Arg Pro Arg Trp Ala Thr Gln Gly Phe
            420                 425                 430
Asp Phe Leu Gln Ala Ile Glu Pro Ala Phe Ile Ser Ala Leu Pro Glu
        435                 440                 445
Asp Asp Phe Leu Ser Leu Gln Ala Leu Met Asn Glu Cys Ile Gly His
    450                 455                 460
Val Ile Gly Lys Pro His Ser Pro Val Thr Ala Ile His Arg Asn Ser
465                 470                 475                 480
Pro Arg Pro Val Lys Val Pro Arg Cys His Ser Asp Pro Pro Asn Pro
                485                 490                 495
His Leu Ile Ile Pro Thr Pro Glu Gly Phe Arg Gly Ser Ser Val Pro
            500                 505                 510
Glu Asn Asp Arg Leu Ala Ser Ile Ala Ala Glu Leu Gln Phe Arg Ser
        515                 520                 525
Leu Ser Arg His Ser Ser Pro Thr Glu Glu Arg Asp Glu Pro Ala Tyr
    530                 535                 540
Pro Arg Ser Asp Ser Ser Gly Ser Thr Arg Arg Ser Trp Glu Leu Arg
545                 550                 555                 560
Thr Leu Ile Ser Gln Thr Lys Asp Ser Ala Ser Lys Gln Gly Pro Ile
                565                 570                 575
Glu Ala Ile Gln Lys Ser Val Arg Leu Phe Glu Glu Arg Arg Tyr Arg
            580                 585                 590
Glu Met Arg Arg Lys Asn Ile Ile Gly Gln Val Cys Asp Thr Pro Lys
        595                 600                 605
Ser Tyr Asp Asn Val Met His Val Gly Leu Arg Lys Val Thr Phe Lys
    610                 615                 620
Trp Gln Arg Gly Asn Lys Ile Gly Glu Gly Gln Tyr Gly Lys Val Tyr
625                 630                 635                 640
Thr Cys Ile Ser Val Asp Thr Gly Glu Leu Met Ala Met Lys Glu Ile
                645                 650                 655
Arg Phe Gln Pro Asn Asp His Lys Thr Ile Lys Glu Thr Ala Asp Glu
            660                 665                 670
```

-continued

```
Leu Lys Ile Phe Glu Gly Ile Lys His Pro Asn Leu Val Arg Tyr Phe
            675                 680                 685
Gly Val Glu Leu His Arg Glu Met Tyr Ile Phe Met Glu Tyr Cys
        690                 695                 700
Asp Glu Gly Thr Leu Glu Val Ser Arg Leu Gly Leu Gln Glu His
705                 710                 715                 720
Val Ile Arg Leu Tyr Thr Lys Gln Ile Thr Val Ala Ile Asn Val Leu
                725                 730                 735
His Glu His Gly Ile Val His Arg Asp Ile Lys Gly Ala Asn Ile Phe
            740                 745                 750
Leu Thr Ser Ser Gly Leu Ile Lys Leu Gly Asp Phe Gly Cys Ser Val
            755                 760                 765
Lys Leu Lys Asn Asn Ala Gln Thr Met Pro Gly Glu Val Asn Ser Thr
        770                 775                 780
Leu Gly Thr Ala Ala Tyr Met Ala Pro Glu Val Ile Thr Arg Ala Lys
785                 790                 795                 800
Gly Glu Gly His Gly Arg Ala Ala Asp Ile Trp Ser Leu Gly Cys Val
                805                 810                 815
Val Ile Glu Met Val Thr Gly Lys Arg Pro Trp His Glu Tyr Glu His
            820                 825                 830
Asn Phe Gln Ile Met Tyr Lys Val Gly Met Gly His Lys Pro Pro Ile
        835                 840                 845
Pro Glu Arg Leu Ser Pro Glu Gly Lys Ala Phe Leu Ser His Cys Leu
    850                 855                 860
Glu Ser Asp Pro Lys Ile Arg Trp Thr Ala Ser Gln Leu Leu Asp His
865                 870                 875                 880
Ala Phe Val Lys Val Cys Thr Asp Glu Glu
                885                 890

<210> SEQ ID NO 13
<211> LENGTH: 5414
<212> TYPE: DNA
<213> ORGANISM: Mus musculus
<220> FEATURE:
<221> NAME/KEY: CDS
<222> LOCATION: (127)..(4917)

<400> SEQUENCE: 13
acggctcctg cggcgggcta gaggcggagg cggagtcgag tcactccctc accccgcggc      60
tcctggtctt cccgcaccag gctgcagctg acgacccgcc gcggtcatgc gaagcttgat     120 gcacgg atg aga gac gcc atc gcc gag ccg gtg ccc cct cct gcc ctc       168
       Met Arg Asp Ala Ile Ala Glu Pro Val Pro Pro Pro Ala Leu
        1               5                  10 gcc gac acc cct gca gcc gcc atg gag gag ctg cgg cca gca ccg ccg       216
Ala Asp Thr Pro Ala Ala Ala Met Glu Glu Leu Arg Pro Ala Pro Pro
 15                  20                  25                  30 cca cag ccc gag ccg gat ccg gag tgc tgc cca gcg gcg agg cag gag       264
Pro Gln Pro Glu Pro Asp Pro Glu Cys Cys Pro Ala Ala Arg Gln Glu
                35                  40                  45 tgc atg ttg gga gag tcg gct cgc aaa agt atg gaa tcc gat cca gag       312
Cys Met Leu Gly Glu Ser Ala Arg Lys Ser Met Glu Ser Asp Pro Glu
            50                  55                  60 gac ttt tct gat gaa aca aat aca gag act ctc tac ggc acc tca ccc       360
Asp Phe Ser Asp Glu Thr Asn Thr Glu Thr Leu Tyr Gly Thr Ser Pro
        65                  70                  75 cca agc aca cct cga cag atg aaa cgc ctg tca gcc aag cac cag agg       408
Pro Ser Thr Pro Arg Gln Met Lys Arg Leu Ser Ala Lys His Gln Arg
```

```
              80                    85                    90
aac agc gca ggg agg ccg gcc agc cga tcg aac ttg aaa gaa aaa atg    456
Asn Ser Ala Gly Arg Pro Ala Ser Arg Ser Asn Leu Lys Glu Lys Met
 95                 100                 105                 110 aac aca ccg agt cag tct cca cat aaa gat ttg ggg aag gga gtg gag    504
Asn Thr Pro Ser Gln Ser Pro His Lys Asp Leu Gly Lys Gly Val Glu
                115                 120                 125 acc gtg gaa gaa tac agc tac aag cag gag aag aag att cga gca act    552
Thr Val Glu Glu Tyr Ser Tyr Lys Gln Glu Lys Lys Ile Arg Ala Thr
                    130                 135                 140 ctg aga aca acg gag cga gac cat aag aaa aat gca cag tgc tca ttc    600
Leu Arg Thr Thr Glu Arg Asp His Lys Lys Asn Ala Gln Cys Ser Phe
                145                 150                 155 atg ttg gac tcg gtg gct ggg tct ttg cca aaa aaa tcg att cca gat    648
Met Leu Asp Ser Val Ala Gly Ser Leu Pro Lys Lys Ser Ile Pro Asp
160                 165                 170 gtg gat ctc aat aag cct tac ctc agt ctc ggc tgt agc aat gcc aag    696
Val Asp Leu Asn Lys Pro Tyr Leu Ser Leu Gly Cys Ser Asn Ala Lys
175                 180                 185                 190 ctg ccc gtc tcg atg ccc atg ccg ata gcc aga act gca cgg cag act    744
Leu Pro Val Ser Met Pro Met Pro Ile Ala Arg Thr Ala Arg Gln Thr
                    195                 200                 205 tcc cgg act gac tgc ccc gca gat cgc tta aag ttc ttt gaa aca ctg    792
Ser Arg Thr Asp Cys Pro Ala Asp Arg Leu Lys Phe Phe Glu Thr Leu
                210                 215                 220 cgc ctt ttg cta aag ctt acc tca gtc tcg aag aag aag gac agg gag    840
Arg Leu Leu Leu Lys Leu Thr Ser Val Ser Lys Lys Lys Asp Arg Glu
                225                 230                 235 cag agg gga caa gaa aac acg gct gct ttc tgg ttc aac cga tcg aac    888
Gln Arg Gly Gln Glu Asn Thr Ala Ala Phe Trp Phe Asn Arg Ser Asn
240                 245                 250 gaa ctg atc tgg tta gaa ctg cag gcc tgg cac gcg ggc cgc acc atc    936
Glu Leu Ile Trp Leu Glu Leu Gln Ala Trp His Ala Gly Arg Thr Ile
255                 260                 265                 270 aat gac cag gac ctc ttt ctc tac aca gcc cgc cag gcc atc cca gac    984
Asn Asp Gln Asp Leu Phe Leu Tyr Thr Ala Arg Gln Ala Ile Pro Asp
                275                 280                 285 atc atc aat gag atc ctc acc ttc aaa gtt aac tac ggg agc att gcc   1032
Ile Ile Asn Glu Ile Leu Thr Phe Lys Val Asn Tyr Gly Ser Ile Ala
                290                 295                 300 ttc tcc agc aat gga gcc ggt ttc aac ggg ccc ttg gta gaa ggc cag   1080
Phe Ser Ser Asn Gly Ala Gly Phe Asn Gly Pro Leu Val Glu Gly Gln
                305                 310                 315 tgc aga acc cct cag gag aca aac cgt gtg ggc tgc tca tcg tac cac   1128
Cys Arg Thr Pro Gln Glu Thr Asn Arg Val Gly Cys Ser Ser Tyr His
320                 325                 330 gag cac ctc cag cgc cag agg gtc tcg ttt gag cag gtg aag cgg ata   1176
Glu His Leu Gln Arg Gln Arg Val Ser Phe Glu Gln Val Lys Arg Ile
335                 340                 345                 350 atg gag ctg ctg gag tac atg gag gca ctt tac cca tcc ttg cag gct   1224
Met Glu Leu Leu Glu Tyr Met Glu Ala Leu Tyr Pro Ser Leu Gln Ala
                355                 360                 365 ctg cag aag gac tat gaa cgg tac gcc gcc aag gac ttt gag gac aga   1272
Leu Gln Lys Asp Tyr Glu Arg Tyr Ala Ala Lys Asp Phe Glu Asp Arg
                370                 375                 380 gtg cag gcg ctc tgc ctg tgg ctc aac atc acg aaa gat cta aat cag   1320
Val Gln Ala Leu Cys Leu Trp Leu Asn Ile Thr Lys Asp Leu Asn Gln
                385                 390                 395 aag ctc cgg atc atg ggc acc gtg ctg ggc atc aag aac cta tca gac   1368
```

```
                                                              -continued

Lys Leu Arg Ile Met Gly Thr Val Leu Gly Ile Lys Asn Leu Ser Asp
    400                 405                 410 att ggc tgg cca gtg ttt gaa atc ccc tcc cct cgg ccg tcc aag ggc      1416
Ile Gly Trp Pro Val Phe Glu Ile Pro Ser Pro Arg Pro Ser Lys Gly
415                 420                 425                 430 tac gag cca gag gac gag gtc gag gac acg gag gtt gag ctg agg gag      1464
Tyr Glu Pro Glu Asp Glu Val Glu Asp Thr Glu Val Glu Leu Arg Glu
                435                 440                 445 ctg gag agc ggg acg gag gag agt gac gag gag cca acc ccc agt ccg      1512
Leu Glu Ser Gly Thr Glu Glu Ser Asp Glu Glu Pro Thr Pro Ser Pro
            450                 455                 460 agg gtg cca gag ctc agg ctg tcc aca gac acc atc ttg gac agt cgc      1560
Arg Val Pro Glu Leu Arg Leu Ser Thr Asp Thr Ile Leu Asp Ser Arg
        465                 470                 475 tcc cag ggc tgc gtc tcc agg aag ctg gag agg ctc gag tca gag gaa      1608
Ser Gln Gly Cys Val Ser Arg Lys Leu Glu Arg Leu Glu Ser Glu Glu
    480                 485                 490 gat tcc ata ggc tgg ggg aca gcg gac tgt ggc cct gaa gcc agc agg      1656
Asp Ser Ile Gly Trp Gly Thr Ala Asp Cys Gly Pro Glu Ala Ser Arg
495                 500                 505                 510 cat tgt ttg act tct atc tat aga cca ttc gtg gac aaa gca ctg aag      1704
His Cys Leu Thr Ser Ile Tyr Arg Pro Phe Val Asp Lys Ala Leu Lys
                515                 520                 525 caa atg ggg cta aga aag tta att tta cga ctt cat aag ctt atg aat      1752
Gln Met Gly Leu Arg Lys Leu Ile Leu Arg Leu His Lys Leu Met Asn
            530                 535                 540 ggg tcc ttg caa aga gct cgt gta gct ctg gtg aag gac gac cgt cca      1800
Gly Ser Leu Gln Arg Ala Arg Val Ala Leu Val Lys Asp Asp Arg Pro
        545                 550                 555 gtg gag ttc tct gac ttt cca ggt ccc atg tgg ggc tcg gat tat gtg      1848
Val Glu Phe Ser Asp Phe Pro Gly Pro Met Trp Gly Ser Asp Tyr Val
    560                 565                 570 cag ttg tcg gga aca cct cct tcc tca gag cag aag tgt agc gct gtg      1896
Gln Leu Ser Gly Thr Pro Pro Ser Ser Glu Gln Lys Cys Ser Ala Val
575                 580                 585                 590 tcc tgg gaa gaa ctg aga gcc atg gac ctg cct tcc ttt gag ccc gcc      1944
Ser Trp Glu Glu Leu Arg Ala Met Asp Leu Pro Ser Phe Glu Pro Ala
                595                 600                 605 ttc ctg gtg ctc tgt cgg gtc ctg ctg aac gtg atc cac gag tgc ctg      1992
Phe Leu Val Leu Cys Arg Val Leu Leu Asn Val Ile His Glu Cys Leu
            610                 615                 620 aag ctg cgg ctg gaa cag agg cct gcc ggg gag cct tcc ctc ttg agt      2040
Lys Leu Arg Leu Glu Gln Arg Pro Ala Gly Glu Pro Ser Leu Leu Ser
        625                 630                 635 atc aaa cag cta gtg cga gag tgt aaa gag gtc cta aag ggc ggg ctc      2088
Ile Lys Gln Leu Val Arg Glu Cys Lys Glu Val Leu Lys Gly Gly Leu
    640                 645                 650 ctg atg aag cag tat tac cag ttc atg ctg cag gag gtc ctg ggc gga      2136
Leu Met Lys Gln Tyr Tyr Gln Phe Met Leu Gln Glu Val Leu Gly Gly
655                 660                 665                 670 ctg gag aag acc gac tgc aac atg gat gcc ttt gag gag gac ctg cag      2184
Leu Glu Lys Thr Asp Cys Asn Met Asp Ala Phe Glu Glu Asp Leu Gln
                675                 680                 685 aag atg ctg atg gtg tat ttt gat tac atg aga agc tgg atc caa atg      2232
Lys Met Leu Met Val Tyr Phe Asp Tyr Met Arg Ser Trp Ile Gln Met
            690                 695                 700 cta cag cag tta cct cag gct tcc cat agc tta aaa aac ctg cta gaa      2280
Leu Gln Gln Leu Pro Gln Ala Ser His Ser Leu Lys Asn Leu Leu Glu
        705                 710                 715
```

-continued

| | |
|---|---|
| gag gaa tgg aat ttc acc aaa gaa ata acc cat tat atc cgt ggc gga<br>Glu Glu Trp Asn Phe Thr Lys Glu Ile Thr His Tyr Ile Arg Gly Gly<br>720                            725                            730 | 2328 |
| gaa gcg cag gct gga aag ctt ttc tgt gac atc gca ggg atg ctg ctg<br>Glu Ala Gln Ala Gly Lys Leu Phe Cys Asp Ile Ala Gly Met Leu Leu<br>735                            740                            745                     750 | 2376 |
| aaa tcc aca ggg agc ttt ctg gaa tcc ggc ctg cag gag agc tgt gct<br>Lys Ser Thr Gly Ser Phe Leu Glu Ser Gly Leu Gln Glu Ser Cys Ala<br>                    755                            760                          765 | 2424 |
| gag ctg tgg acc agc gcc gac gac aac ggt gct gcc gac gag cta agg<br>Glu Leu Trp Thr Ser Ala Asp Asp Asn Gly Ala Ala Asp Glu Leu Arg<br>            770                            775                          780 | 2472 |
| aga tct gtc atc gag atc agc cga gca ctc aag gag ctc ttc cac gaa<br>Arg Ser Val Ile Glu Ile Ser Arg Ala Leu Lys Glu Leu Phe His Glu<br>785                            790                            795 | 2520 |
| gcc agg gaa aga gcc tcc aag gcc ctg ggc ttt gct aaa atg ctg agg<br>Ala Arg Glu Arg Ala Ser Lys Ala Leu Gly Phe Ala Lys Met Leu Arg<br>800                            805                            810 | 2568 |
| aag gac cta gaa ata gca gca gag ttc gtg cta tct gca tca gcc cga<br>Lys Asp Leu Glu Ile Ala Ala Glu Phe Val Leu Ser Ala Ser Ala Arg<br>815                            820                            825                     830 | 2616 |
| gag ctc ctg gac gct ctg aaa gca aag cag tat gtt aag gta cag att<br>Glu Leu Leu Asp Ala Leu Lys Ala Lys Gln Tyr Val Lys Val Gln Ile<br>                     835                          840                          845 | 2664 |
| ccc ggg tta gag aat ttg cac gtg ttt gtc ccc gac agc ctc gct gag<br>Pro Gly Leu Glu Asn Leu His Val Phe Val Pro Asp Ser Leu Ala Glu<br>            850                            855                          860 | 2712 |
| gag aag aaa att att ttg cag cta ctc aat gct gcc aca gga aag gac<br>Glu Lys Lys Ile Ile Leu Gln Leu Leu Asn Ala Ala Thr Gly Lys Asp<br>865                            870                            875 | 2760 |
| tgc tca aag gat cca gac gac gtc ttc atg gat gcc ttc ctg ctc ctg<br>Cys Ser Lys Asp Pro Asp Asp Val Phe Met Asp Ala Phe Leu Leu Leu<br>880                            885                            890 | 2808 |
| acc aag cat ggg gac cga gcc cgt gac tca gaa gat ggc tgg ggc aca<br>Thr Lys His Gly Asp Arg Ala Arg Asp Ser Glu Asp Gly Trp Gly Thr<br>895                            900                            905                     910 | 2856 |
| tgg gaa gct cgg gct gtc aaa att gtg cct cag gtg gag act gtg gac<br>Trp Glu Ala Arg Ala Val Lys Ile Val Pro Gln Val Glu Thr Val Asp<br>                     915                          920                          925 | 2904 |
| acc ctg aga agc atg cag gtg gac aac ctt ctg ctg gtt gtc atg gag<br>Thr Leu Arg Ser Met Gln Val Asp Asn Leu Leu Leu Val Val Met Glu<br>            930                            935                          940 | 2952 |
| tct gct cac ctc gta ctt cag aga aaa gcc ttc cag cag tcc att gag<br>Ser Ala His Leu Val Leu Gln Arg Lys Ala Phe Gln Gln Ser Ile Glu<br>            945                            950                          955 | 3000 |
| ggg ctg atg act gta cgc cat gag cag aca tct agc cag ccc atc atc<br>Gly Leu Met Thr Val Arg His Glu Gln Thr Ser Ser Gln Pro Ile Ile<br>960                            965                            970 | 3048 |
| gcc aaa ggt ttg cag cag ctc aag aac gat gca ctt gag cta tgc aac<br>Ala Lys Gly Leu Gln Gln Leu Lys Asn Asp Ala Leu Glu Leu Cys Asn<br>975                            980                            985                     990 | 3096 |
| aga atc agc gat gcc atc gac cgt gtg gac cac atg ttc acc ctg gag<br>Arg Ile Ser Asp Ala Ile Asp Arg Val Asp His Met Phe Thr Leu Glu<br>                     995                        1000                        1005 | 3144 |
| ttc gat gct gag gtc gag gag tct gag tcg gcc acg ctg cag cag tac<br>Phe Asp Ala Glu Val Glu Glu Ser Glu Ser Ala Thr Leu Gln Gln Tyr<br>            1010                        1015                        1020 | 3192 |
| tac cga gaa gcc atg att cag ggc tac aac ttt ggg ttt gag tat cat<br>Tyr Arg Glu Ala Met Ile Gln Gly Tyr Asn Phe Gly Phe Glu Tyr His<br>                     1025                        1030                        1035 | 3240 |

```
aaa gaa gtt gtt cgt ttg atg tct ggg gaa ttc agg cag aag ata gga      3288
Lys Glu Val Val Arg Leu Met Ser Gly Glu Phe Arg Gln Lys Ile Gly
    1040                1045                1050 gac aaa tat ata agc ttc gcc cag aag tgg atg aat tac gtg ctg acc      3336
Asp Lys Tyr Ile Ser Phe Ala Gln Lys Trp Met Asn Tyr Val Leu Thr
1055                1060                1065                1070 aaa tgc gag agc ggc aga ggc aca aga ccc aga tgg gcc acc caa gga      3384
Lys Cys Glu Ser Gly Arg Gly Thr Arg Pro Arg Trp Ala Thr Gln Gly
            1075                1080                1085 ttt gat ttc cta caa gcc att gaa cct gcc ttt att tca gct tta cca      3432
Phe Asp Phe Leu Gln Ala Ile Glu Pro Ala Phe Ile Ser Ala Leu Pro
                1090                1095                1100 gaa gat gac ttc ttg agt ttg caa gcc ctg atg aat gag tgc atc ggg      3480
Glu Asp Asp Phe Leu Ser Leu Gln Ala Leu Met Asn Glu Cys Ile Gly
    1105                1110                1115 cac gtc ata gga aag cca cac agc cct gtc aca gct atc cat cgg aac      3528
His Val Ile Gly Lys Pro His Ser Pro Val Thr Ala Ile His Arg Asn
1120                1125                1130 agc ccc cgc cct gtg aag gtg ccc cga tgc cac agt gac cct cct aac      3576
Ser Pro Arg Pro Val Lys Val Pro Arg Cys His Ser Asp Pro Pro Asn
1135                1140                1145                1150 cct cac ctc atc atc ccg act cca gag gga ttc agc acc cgg agc gtg      3624
Pro His Leu Ile Ile Pro Thr Pro Glu Gly Phe Ser Thr Arg Ser Val
            1155                1160                1165 cct tcc gac gct cgg acc cat ggc aac tct gtt gct gct gct gct gct      3672
Pro Ser Asp Ala Arg Thr His Gly Asn Ser Val Ala Ala Ala Ala Ala
                1170                1175                1180 gtt cgt gcc gcc gcc acc act gct gct ggc cgc cct ggc cca ggt ggt      3720
Val Arg Ala Ala Ala Thr Thr Ala Ala Gly Arg Pro Gly Pro Gly Gly
    1185                1190                1195 ggt gac tct gtg cca gcc aaa cct gtc aac act gcc cct gat acc agg      3768
Gly Asp Ser Val Pro Ala Lys Pro Val Asn Thr Ala Pro Asp Thr Arg
1200                1205                1210 ggt tcc agt gtc cct gaa aac gac cgc ttg gcc tcc ata gct gca gaa      3816
Gly Ser Ser Val Pro Glu Asn Asp Arg Leu Ala Ser Ile Ala Ala Glu
1215                1220                1225                1230 ctg cag ttc agg tct ctg agt cgg cac tca agc ccc acg gaa gag cga      3864
Leu Gln Phe Arg Ser Leu Ser Arg His Ser Ser Pro Thr Glu Glu Arg
            1235                1240                1245 gac gag cca gcg tat cct cgg agt gac tca agt gga tca act cgg aga      3912
Asp Glu Pro Ala Tyr Pro Arg Ser Asp Ser Ser Gly Ser Thr Arg Arg
                1250                1255                1260 agc tgg gaa ctt cga aca ctc atc agc cag acc aaa gac tcg gcc tct      3960
Ser Trp Glu Leu Arg Thr Leu Ile Ser Gln Thr Lys Asp Ser Ala Ser
    1265                1270                1275 aag cag ggg ccc ata gaa gct atc cag aag tca gtc cga ctg ttt gaa      4008
Lys Gln Gly Pro Ile Glu Ala Ile Gln Lys Ser Val Arg Leu Phe Glu
1280                1285                1290 gag agg agg tat cga gag atg agg aga aag aat atc atc ggc caa gtg      4056
Glu Arg Arg Tyr Arg Glu Met Arg Arg Lys Asn Ile Ile Gly Gln Val
1295                1300                1305                1310 tgc gat acc cct aag tcc tat gat aac gtc atg cat gtt gga ctg agg      4104
Cys Asp Thr Pro Lys Ser Tyr Asp Asn Val Met His Val Gly Leu Arg
            1315                1320                1325 aag gtg aca ttt aag tgg caa aga gga aac aaa att gga gaa gga cag      4152
Lys Val Thr Phe Lys Trp Gln Arg Gly Asn Lys Ile Gly Glu Gly Gln
                1330                1335                1340 tat gga aaa gta tac acc tgc atc agt gtt gac aca ggg gag ctg atg      4200
Tyr Gly Lys Val Tyr Thr Cys Ile Ser Val Asp Thr Gly Glu Leu Met
```

```
       1345              1350              1355
gcc atg aag gag att cga ttt cag cct aac gac cac aag act atc aag    4248
Ala Met Lys Glu Ile Arg Phe Gln Pro Asn Asp His Lys Thr Ile Lys
    1360              1365              1370 gag act gca gac gag ttg aaa ata ttt gaa ggc atc aag cac ccc aac    4296
Glu Thr Ala Asp Glu Leu Lys Ile Phe Glu Gly Ile Lys His Pro Asn
1375              1380              1385              1390 ctg gtc cgg tat ttt ggc gtg gag ctt cac agg gaa gag atg tac atc    4344
Leu Val Arg Tyr Phe Gly Val Glu Leu His Arg Glu Glu Met Tyr Ile
        1395              1400              1405 ttc atg gag tac tgt gat gag ggt aca cta gag gag gtg tca cga ctg    4392
Phe Met Glu Tyr Cys Asp Glu Gly Thr Leu Glu Glu Val Ser Arg Leu
    1410              1415              1420 ggc ctg cag gag cac gtc atc agg tta tat acc aag cag atc act gtc    4440
Gly Leu Gln Glu His Val Ile Arg Leu Tyr Thr Lys Gln Ile Thr Val
        1425              1430              1435 gcc atc aac gtc ctc cat gag cac ggc atc gtt cac cga gac atc aaa    4488
Ala Ile Asn Val Leu His Glu His Gly Ile Val His Arg Asp Ile Lys
    1440              1445              1450 ggt gcc aat atc ttc ctt acg tca tct gga cta atc aag ctg gga gat    4536
Gly Ala Asn Ile Phe Leu Thr Ser Ser Gly Leu Ile Lys Leu Gly Asp
1455              1460              1465              1470 ttt gga tgc tct gta aaa ctt aaa aac aac gcc cag acc atg ccc gga    4584
Phe Gly Cys Ser Val Lys Leu Lys Asn Asn Ala Gln Thr Met Pro Gly
        1475              1480              1485 gag gtg aac agc acc cta ggg aca gca gct tac atg gcc cct gaa gtt    4632
Glu Val Asn Ser Thr Leu Gly Thr Ala Ala Tyr Met Ala Pro Glu Val
    1490              1495              1500 att acc cga gcc aaa gga gaa ggc cac gga cgt gcg gca gat atc tgg    4680
Ile Thr Arg Ala Lys Gly Glu Gly His Gly Arg Ala Ala Asp Ile Trp
        1505              1510              1515 agt ctg ggg tgc gtc gtc ata gag atg gtg act ggc aag cgg cct tgg    4728
Ser Leu Gly Cys Val Val Ile Glu Met Val Thr Gly Lys Arg Pro Trp
    1520              1525              1530 cat gag tat gaa cac aac ttt cag att atg tac aag gtg ggg atg gga    4776
His Glu Tyr Glu His Asn Phe Gln Ile Met Tyr Lys Val Gly Met Gly
1535              1540              1545              1550 cac aag cca cca atc ccg gaa agg cta agc cct gaa gga aag gcc ttt    4824
His Lys Pro Pro Ile Pro Glu Arg Leu Ser Pro Glu Gly Lys Ala Phe
        1555              1560              1565 ctc tcg cac tgc ctg gaa agt gac ccg aag ata cgg tgg aca gcc agc    4872
Leu Ser His Cys Leu Glu Ser Asp Pro Lys Ile Arg Trp Thr Ala Ser
    1570              1575              1580 cag ctc ctc gac cac gct ttt gtc aag gtt tgc aca gat gaa gag         4917
Gln Leu Leu Asp His Ala Phe Val Lys Val Cys Thr Asp Glu Glu
        1585              1590              1595 tgaagtgaac cagtccgtgg cctagtagtg tgtggacaga atcccgtgat cactactgta    4977
tgtaatattt acataaagac tgcagcgcag gcggccttcc taacctccca ggactgaaga    5037
ctacaggggt gacaagcctc acttctgctg ctcctgtcgc ctgctgagtg acagtgctga    5097
ggttaaagga gccgcacgtt aagtgccatt actactgtac acgggccacc gcctctgtcc    5157
cctccgaccc tctcgtgact gagaaccaac cgtgtcatca gcacagtgtt tttgagctcc    5217
tggggttcag aagaacatgt agtgttcccg ggtgtccggg acgtttattt caacctcctg    5277
gtcgttggct ctgactgtgg agcctccttg ttcgaaagct gcaggtttgt tatgcaaagg    5337
ctcgtaagtg aagctgaaga aaaggttctt tttcaataat ggtttatttt aggaaagcga    5397
aaaaaaaaaa aaaaaaa                                                   5414
```

```
<210> SEQ ID NO 14
<211> LENGTH: 1597
<212> TYPE: PRT
<213> ORGANISM: Mus musculus

<400> SEQUENCE: 14

Met Arg Asp Ala Ile Ala Glu Pro Val Pro Pro Ala Leu Ala Asp
 1               5                  10                  15

Thr Pro Ala Ala Ala Met Glu Glu Leu Arg Pro Ala Pro Pro Gln
                20                  25                  30

Pro Glu Pro Asp Pro Glu Cys Cys Pro Ala Ala Arg Gln Glu Cys Met
                35                  40                  45

Leu Gly Glu Ser Ala Arg Lys Ser Met Glu Ser Asp Pro Glu Asp Phe
 50                  55                  60

Ser Asp Glu Thr Asn Thr Glu Thr Leu Tyr Gly Thr Ser Pro Pro Ser
 65                  70                  75                  80

Thr Pro Arg Gln Met Lys Arg Leu Ser Ala Lys His Gln Arg Asn Ser
                85                  90                  95

Ala Gly Arg Pro Ala Ser Arg Ser Asn Leu Lys Glu Lys Met Asn Thr
                100                 105                 110

Pro Ser Gln Ser Pro His Lys Asp Leu Gly Lys Gly Val Glu Thr Val
                115                 120                 125

Glu Glu Tyr Ser Tyr Lys Gln Glu Lys Lys Ile Arg Ala Thr Leu Arg
 130                 135                 140

Thr Thr Glu Arg Asp His Lys Lys Asn Ala Gln Cys Ser Phe Met Leu
145                  150                 155                 160

Asp Ser Val Ala Gly Ser Leu Pro Lys Lys Ser Ile Pro Asp Val Asp
                165                 170                 175

Leu Asn Lys Pro Tyr Leu Ser Leu Gly Cys Ser Asn Ala Lys Leu Pro
                180                 185                 190

Val Ser Met Pro Met Pro Ile Ala Arg Thr Ala Arg Gln Thr Ser Arg
                195                 200                 205

Thr Asp Cys Pro Ala Asp Arg Leu Lys Phe Phe Glu Thr Leu Arg Leu
 210                 215                 220

Leu Leu Lys Leu Thr Ser Val Ser Lys Lys Asp Arg Glu Gln Arg
225                  230                 235                 240

Gly Gln Glu Asn Thr Ala Ala Phe Trp Phe Asn Arg Ser Asn Glu Leu
                245                 250                 255

Ile Trp Leu Glu Leu Gln Ala Trp His Ala Gly Arg Thr Ile Asn Asp
                260                 265                 270

Gln Asp Leu Phe Leu Tyr Thr Ala Arg Gln Ala Ile Pro Asp Ile Ile
                275                 280                 285

Asn Glu Ile Leu Thr Phe Lys Val Asn Tyr Gly Ser Ile Ala Phe Ser
 290                 295                 300

Ser Asn Gly Ala Gly Phe Asn Gly Pro Leu Val Glu Gly Gln Cys Arg
305                  310                 315                 320

Thr Pro Gln Glu Thr Asn Arg Val Gly Cys Ser Ser Tyr His Glu His
                325                 330                 335

Leu Gln Arg Gln Arg Val Ser Phe Glu Gln Val Lys Arg Ile Met Glu
                340                 345                 350

Leu Leu Glu Tyr Met Glu Ala Leu Tyr Pro Ser Leu Gln Ala Leu Gln
                355                 360                 365

Lys Asp Tyr Glu Arg Tyr Ala Ala Lys Asp Phe Glu Asp Arg Val Gln
```

```
                    370                 375                 380
     Ala Leu Cys Leu Trp Leu Asn Ile Thr Lys Asp Leu Asn Gln Lys Leu
     385                 390                 395                 400
     Arg Ile Met Gly Thr Val Leu Gly Ile Lys Asn Leu Ser Asp Ile Gly
                         405                 410                 415
     Trp Pro Val Phe Glu Ile Pro Ser Pro Arg Pro Ser Lys Gly Tyr Glu
                     420                 425                 430
     Pro Glu Asp Glu Val Glu Asp Thr Glu Val Glu Leu Arg Glu Leu Glu
                 435                 440                 445
     Ser Gly Thr Glu Glu Ser Asp Glu Glu Pro Thr Pro Ser Pro Arg Val
             450                 455                 460
     Pro Glu Leu Arg Leu Ser Thr Asp Thr Ile Leu Asp Ser Arg Ser Gln
     465                 470                 475                 480
     Gly Cys Val Ser Arg Lys Leu Glu Arg Leu Glu Ser Glu Glu Asp Ser
                         485                 490                 495
     Ile Gly Trp Gly Thr Ala Asp Cys Gly Pro Glu Ala Ser Arg His Cys
                     500                 505                 510
     Leu Thr Ser Ile Tyr Arg Pro Phe Val Asp Lys Ala Leu Lys Gln Met
                 515                 520                 525
     Gly Leu Arg Lys Leu Ile Leu Arg Leu His Lys Leu Met Asn Gly Ser
             530                 535                 540
     Leu Gln Arg Ala Arg Val Ala Leu Val Lys Asp Asp Arg Pro Val Glu
     545                 550                 555                 560
     Phe Ser Asp Phe Pro Gly Pro Met Trp Gly Ser Asp Tyr Val Gln Leu
                         565                 570                 575
     Ser Gly Thr Pro Pro Ser Ser Glu Gln Lys Cys Ser Ala Val Ser Trp
                     580                 585                 590
     Glu Glu Leu Arg Ala Met Asp Leu Pro Ser Phe Glu Pro Ala Phe Leu
                 595                 600                 605
     Val Leu Cys Arg Val Leu Leu Asn Val Ile His Glu Cys Leu Lys Leu
             610                 615                 620
     Arg Leu Glu Gln Arg Pro Ala Gly Glu Pro Ser Leu Leu Ser Ile Lys
     625                 630                 635                 640
     Gln Leu Val Arg Glu Cys Lys Glu Val Leu Lys Gly Gly Leu Leu Met
                         645                 650                 655
     Lys Gln Tyr Tyr Gln Phe Met Leu Gln Glu Val Leu Gly Gly Leu Glu
                     660                 665                 670
     Lys Thr Asp Cys Asn Met Asp Ala Phe Glu Glu Asp Leu Gln Lys Met
                 675                 680                 685
     Leu Met Val Tyr Phe Asp Tyr Met Arg Ser Trp Ile Gln Met Leu Gln
             690                 695                 700
     Gln Leu Pro Gln Ala Ser His Ser Leu Lys Asn Leu Leu Glu Glu Glu
     705                 710                 715                 720
     Trp Asn Phe Thr Lys Glu Ile Thr His Tyr Ile Arg Gly Gly Glu Ala
                         725                 730                 735
     Gln Ala Gly Lys Leu Phe Cys Asp Ile Ala Gly Met Leu Leu Lys Ser
                     740                 745                 750
     Thr Gly Ser Phe Leu Glu Ser Gly Leu Gln Glu Ser Cys Ala Glu Leu
                 755                 760                 765
     Trp Thr Ser Ala Asp Asp Asn Gly Ala Ala Asp Glu Leu Arg Arg Ser
             770                 775                 780
     Val Ile Glu Ile Ser Arg Ala Leu Lys Glu Leu Phe His Glu Ala Arg
     785                 790                 795                 800
```

-continued

```
Glu Arg Ala Ser Lys Ala Leu Gly Phe Ala Lys Met Leu Arg Lys Asp
            805                 810                 815
Leu Glu Ile Ala Ala Glu Phe Val Leu Ser Ala Ser Ala Arg Glu Leu
            820                 825                 830
Leu Asp Ala Leu Lys Ala Lys Gln Tyr Val Lys Val Gln Ile Pro Gly
            835                 840                 845
 Leu Glu Asn Leu His Val Phe Val Pro Asp Ser Leu Ala Glu Glu Lys
            850                 855                 860
ys Ile Ile Leu Gln Leu Leu Asn Ala Ala Thr Gly Lys Asp Cys Ser
865                 870                 875                 880
Lys Asp Pro Asp Asp Val Phe Met Asp Ala Phe Leu Leu Leu Thr Lys
            885                 890                 895
His Gly Asp Arg Ala Arg Asp Ser Glu Asp Gly Trp Gly Thr Trp Glu
            900                 905                 910
Ala Arg Ala Val Lys Ile Val Pro Gln Val Glu Thr Val Asp Thr Leu
            915                 920                 925
Arg Ser Met Gln Val Asp Asn Leu Leu Leu Val Val Met Glu Ser Ala
            930                 935                 940
His Leu Val Leu Gln Arg Lys Ala Phe Gln Gln Ser Ile Glu Gly Leu
945                 950                 955                 960
Met Thr Val Arg His Glu Gln Thr Ser Ser Gln Pro Ile Ile Ala Lys
            965                 970                 975
Gly Leu Gln Gln Leu Lys Asn Asp Ala Leu Glu Leu Cys Asn Arg Ile
            980                 985                 990
Ser Asp Ala Ile Asp Arg Val Asp His Met Phe Thr Leu Glu Phe Asp
            995                 1000                1005
Ala Glu Val Glu Glu Ser Glu Ser Ala Thr Leu Gln Gln Tyr Tyr Arg
    1010                1015                1020
Glu Ala Met Ile Gln Gly Tyr Asn Phe Gly Phe Glu Tyr His Lys Glu
025                 1030                1035                1040
Val Val Arg Leu Met Ser Gly Glu Phe Arg Gln Lys Ile Gly Asp Lys
            1045                1050                1055
Tyr Ile Ser Phe Ala Gln Lys Trp Met Asn Tyr Val Leu Thr Lys Cys
            1060                1065                1070
Glu Ser Gly Arg Gly Thr Arg Pro Arg Trp Ala Thr Gln Gly Phe Asp
            1075                1080                1085
Phe Leu Gln Ala Ile Glu Pro Ala Phe Ile Ser Ala Leu Pro Glu Asp
            1090                1095                1100
Asp Phe Leu Ser Leu Gln Ala Leu Met Asn Glu Cys Ile Gly His Val
105                 1110                1115                1120
Ile Gly Lys Pro His Ser Pro Val Thr Ala Ile His Arg Asn Ser Pro
            1125                1130                1135
Arg Pro Val Lys Val Pro Arg Cys His Ser Asp Pro Asn Pro His
            1140                1145                1150
Leu Ile Ile Pro Thr Pro Glu Gly Phe Ser Thr Arg Ser Val Pro Ser
            1155                1160                1165
Asp Ala Arg Thr His Gly Asn Ser Val Ala Ala Ala Ala Val Arg
    1170                1175                1180
Ala Ala Ala Thr Thr Ala Ala Gly Arg Pro Gly Pro Gly Gly Gly Asp
185                 1190                1195                1200
Ser Val Pro Ala Lys Pro Val Asn Thr Ala Pro Asp Thr Arg Gly Ser
            1205                1210                1215
```

```
Ser Val Pro Glu Asn Asp Arg Leu Ala Ser Ile Ala Ala Glu Leu Gln
        1220                1225                1230

Phe Arg Ser Leu Ser Arg His Ser Ser Pro Thr Glu Glu Arg Asp Glu
        1235                1240                1245

Pro Ala Tyr Pro Arg Ser Asp Ser Ser Gly Ser Thr Arg Arg Ser Trp
    1250                1255                1260

Glu Leu Arg Thr Leu Ile Ser Gln Thr Lys Asp Ser Ala Ser Lys Gln
265                 1270                1275                1280

Gly Pro Ile Glu Ala Ile Gln Lys Ser Val Arg Leu Phe Glu Glu Arg
            1285                1290                1295

Arg Tyr Arg Glu Met Arg Arg Lys Asn Ile Ile Gly Gln Val Cys Asp
        1300                1305                1310

Thr Pro Lys Ser Tyr Asp Asn Val Met His Val Gly Leu Arg Lys Val
    1315                1320                1325

Thr Phe Lys Trp Gln Arg Gly Asn Lys Ile Gly Glu Gly Gln Tyr Gly
    1330                1335                1340

Lys Val Tyr Thr Cys Ile Ser Val Asp Thr Gly Glu Leu Met Ala Met
345                 1350                1355                1360

Lys Glu Ile Arg Phe Gln Pro Asn Asp His Lys Thr Ile Lys Glu Thr
            1365                1370                1375

Ala Asp Glu Leu Lys Ile Phe Glu Gly Ile Lys His Pro Asn Leu Val
        1380                1385                1390

Arg Tyr Phe Gly Val Glu Leu His Arg Glu Glu Met Tyr Ile Phe Met
    1395                1400                1405

Glu Tyr Cys Asp Glu Gly Thr Leu Glu Glu Val Ser Arg Leu Gly Leu
    1410                1415                1420

Gln Glu His Val Ile Arg Leu Tyr Thr Lys Gln Ile Thr Val Ala Ile
425                 1430                1435                1440

Asn Val Leu His Glu His Gly Ile Val His Arg Asp Ile Lys Gly Ala
            1445                1450                1455

Asn Ile Phe Leu Thr Ser Ser Gly Leu Ile Lys Leu Gly Asp Phe Gly
        1460                1465                1470

Cys Ser Val Lys Leu Lys Asn Asn Ala Gln Thr Met Pro Gly Glu Val
    1475                1480                1485

Asn Ser Thr Leu Gly Thr Ala Ala Tyr Met Ala Pro Glu Val Ile Thr
    1490                1495                1500

Arg Ala Lys Gly Glu Gly His Gly Arg Ala Ala Asp Ile Trp Ser Leu
505                 1510                1515                1520

Gly Cys Val Val Ile Glu Met Val Thr Gly Lys Arg Pro Trp His Glu
            1525                1530                1535

Tyr Glu His Asn Phe Gln Ile Met Tyr Lys Val Gly Met Gly His Lys
        1540                1545                1550

Pro Pro Ile Pro Glu Arg Leu Ser Pro Glu Gly Lys Ala Phe Leu Ser
    1555                1560                1565

His Cys Leu Glu Ser Asp Pro Lys Ile Arg Trp Thr Ala Ser Gln Leu
    1570                1575                1580

Leu Asp His Ala Phe Val Lys Val Cys Thr Asp Glu Glu
585                 1590                1595
```

<210> SEQ ID NO 15
<211> LENGTH: 20
<212> TYPE: DNA
<213> ORGANISM: synthetic construct
<220> FEATURE:
<223> OTHER INFORMATION: N at postion 4 = c or t

```
<220> FEATURE:
<223> OTHER INFORMATION: N at postions 6,12,and 15 = Iosine

<400> SEQUENCE: 15
garntnatgg cngtnaarca                                            20

<210> SEQ ID NO 16
<211> LENGTH: 23
<212> TYPE: DNA
<213> ORGANISM: synthetic construct
<220> FEATURE:
<223> OTHER INFORMATION: N at postions 3,6,12,and 18 = Iosine
<220> FEATURE:
<223> OTHER INFORMATION: N at postion 9 = t or c
<220> FEATURE:
<223> OTHER INFORMATION: N at postion 20 = g or t

<400> SEQUENCE: 16
ttngcnccnt tnatrtcncn rtg                                        23

<210> SEQ ID NO 17
<211> LENGTH: 11
<212> TYPE: PRT
<213> ORGANISM: synthetic construct

<400> SEQUENCE: 17

Gly Tyr Pro Tyr Asp Val Pro Asp Tyr Ala Ser
 1               5                  10

<210> SEQ ID NO 18
<211> LENGTH: 56
<212> TYPE: DNA
<213> ORGANISM: synthetic construct

<400> SEQUENCE: 18
atggggtacc cgtacgacgt gccggactac gcttccgatg atcagcaagc tttgaa    56

<210> SEQ ID NO 19
<211> LENGTH: 56
<212> TYPE: DNA
<213> ORGANISM: synthetic construct

<400> SEQUENCE: 19
atggggtacc cgtacgacgt gccggactac gcttccgatg aacaagaggc attaga    56

<210> SEQ ID NO 20
<211> LENGTH: 21
<212> TYPE: DNA
<213> ORGANISM: synthetic construct

<400> SEQUENCE: 20
agacttagat ctcaggtctt c                                          21

<210> SEQ ID NO 21
<211> LENGTH: 21
<212> TYPE: DNA
<213> ORGANISM: synthetic construct

<400> SEQUENCE: 21
gattctgacg tcactctgcc t                                          21

<210> SEQ ID NO 22
<211> LENGTH: 35
<212> TYPE: DNA
<213> ORGANISM: synthetic construct
```

```
<400> SEQUENCE: 22
tcacgttcta gagccaccat ggggtacccg tacga                          35

<210> SEQ ID NO 23
<211> LENGTH: 19
<212> TYPE: PRT
<213> ORGANISM: synthetic construct

<400> SEQUENCE: 23

Cys Glu Ala Arg Gln Arg Pro Ser Ala Glu Glu Leu Leu Thr His His
  1               5                  10                  15

Phe Ala Gln

<210> SEQ ID NO 24
<211> LENGTH: 14
<212> TYPE: PRT
<213> ORGANISM: synthetic construct

<400> SEQUENCE: 24

Cys Phe Val Phe Pro Pro Leu Asp Gln Glu Glu Met Glu Ser
  1               5                  10

<210> SEQ ID NO 25
<211> LENGTH: 20
<212> TYPE: PRT
<213> ORGANISM: synthetic construct

<400> SEQUENCE: 25

Thr Thr Tyr Ala Asp Phe Ile Ala Ser Gly Arg Thr Gly Arg Arg Asn
  1               5                  10                  15

Ala Ile His Asp
             20
```